United States Patent
Engelhardt et al.

(10) Patent No.: US 8,637,549 B2
(45) Date of Patent: Jan. 28, 2014

(54) PYRIDONS AS PDK1 INHIBITORS

(75) Inventors: Harald Engelhardt, Ebreichsdorf (AT);
Guido Boehmelt, Gaaden (AT);
Christiane Kofink, Vienna (AT); Daniel Kuhn, Rossdorf (DE); Darryl McConnell, Vienna (AT); Heinz Stadtmueller, Vienna (AT)

(73) Assignee: Boehringer Ingelheim International GmbH, Ingelhem am Rhein (DE)

( * ) Notice: Subject to any disclaimer, the term of this patent is extended or adjusted under 35 U.S.C. 154(b) by 0 days.

(21) Appl. No.: 13/054,245

(22) PCT Filed: Jul. 15, 2009

(86) PCT No.: PCT/EP2009/059114
§ 371 (c)(1),
(2), (4) Date: Apr. 15, 2011

(87) PCT Pub. No.: WO2010/007116
PCT Pub. Date: Jan. 21, 2010

(65) Prior Publication Data
US 2011/0269958 A1    Nov. 3, 2011

(30) Foreign Application Priority Data

Jul. 16, 2008  (EP) .................................... 08160567
May 20, 2009  (EP) .................................... 09160842

(51) Int. Cl.
*A01N 43/40*    (2006.01)
*A61K 31/44*    (2006.01)
*C07D 487/00*   (2006.01)

(52) U.S. Cl.
USPC .......................................... 514/333; 546/256

(58) Field of Classification Search
None
See application file for complete search history.

(56) References Cited

FOREIGN PATENT DOCUMENTS

| WO | 2008005457 A2 | 1/2008 |
| WO | 2008079371 A2 | 7/2008 |

OTHER PUBLICATIONS

International Search Report, Form PCT/ISA/210, for corresponding PCT/EP2009/09114; date of mailing: Mar. 29, 2010.

*Primary Examiner* — Jeffrey Murray
(74) *Attorney, Agent, or Firm* — Michael P. Morris; Mary-Ellen M. Devlin

(57) ABSTRACT

The present invention encompasses compounds of general formula (1) while the groups $R^4$ to $R^7$ and the units W, L, $Q^a$ and $Q^H$ are defined as in claim 1, which are suitable for the treatment of diseases characterized by excessive or abnormal cell proliferation, and their use as medicaments having the above-mentioned properties.

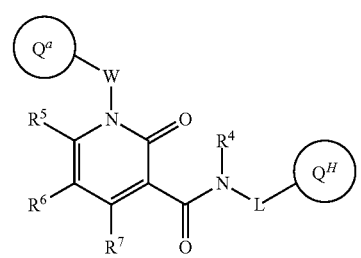

(1)

17 Claims, No Drawings

PYRIDONS AS PDK1 INHIBITORS

The present invention relates to new compounds of general formula (1)

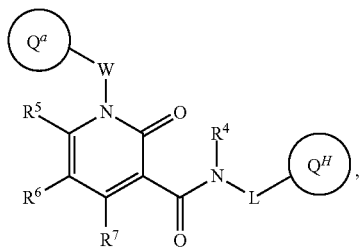
(1)

wherein the groups $R^4$ to $R^7$ and the units W, L, $Q^a$ and $Q^H$ have the meanings given in the claims and specification, as well as the tautomers, racemates, enantiomers, diastereomers, mixtures and the salts of all these forms, and their use as medicaments with an antiproliferative activity.

BACKGROUND TO THE INVENTION

Substituted pyridinonecarboxylic acid amides are described in WO 2008/005457 as inhibitors of PDK1.

The aim of the present invention is to discover new active substances which can be used for the prevention and/or treatment of diseases characterised by excessive or abnormal cell proliferation.

DETAILED DESCRIPTION OF THE INVENTION

It has now been found that, surprisingly, compounds of general formula (1), wherein the groups $R^4$ to $R^7$ and the units W, L, $Q^a$ and $Q^H$ have the meanings given hereinafter act as inhibitors of specific signal enzymes which are involved in controlling cell proliferation. Thus, the compounds according to the invention may be used for example for the treatment of diseases connected with the activity of these signal enzymes and characterised by excessive or abnormal cell proliferation.

The present invention therefore relates to compounds of general formula (1)

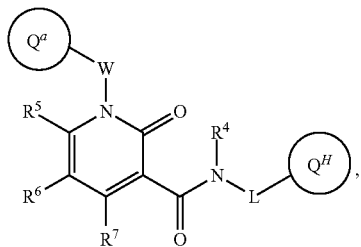
(1)

while:
$Q^a$ is a ring system optionally substituted by one or more, identical or different $R^a$ and/or $R^b$, selected from among $C_{3-10}$cycloalkyl, $C_{6-10}$aryl, 5-12 membered heteroaryl and 3-14 membered heterocycloalkyl;
W is selected from among —$CR^1R^2$—, —$NR^3$—, and —O—;
  $R^1$ and $R^2$ independently of one another are selected from among $R^a$ and $R^b$,
  $R^3$ denotes $R^a$;
the group $Q^a$-W— is not an unsubstituted or substituted benzyl;

$R^4$ denotes hydrogen or $C_{1-6}$-alkyl;
$R^5$, $R^6$ and $R^7$ independently of one another are selected from among $R^a$ and $R^b$;
L denotes the group -$L^1$-$L^2$-$L^3$-, wherein $L^1$ binds to the unit —$NR^4$— and $L^3$ binds to the ring system $Q^H$;
  $L^1$, $L^2$ and $L^3$ are selected independently of one another from among $C_{1-6}$alkylene, 2-6 membered heteroalkylene, $C_{1-6}$haloalkylene, $C_{3-10}$cycloalkylene, $C_{6-10}$arylene, 5-12 membered heteroarylene, 3-14 membered heterocycloalkylene,
    while all the above-mentioned bivalent units may each optionally be substituted independently of one another by one or more, identical or different $R^a$ and/or $R^b$,
    —O—, —S—, —$NR^g$—, —$N(OR^g)$—, —C(O)—, —C(O)O—, —C(O)$NR^g$—, —OS(O)$_2$—, —OS(O)$_2NR^g$—, —OC(O)—, —OC(O)O—, —OC(O)$NR^g$—, —S(O)$_2$—, —S(O)$_2$O—, —S(O)$_2NR^g$—, —$NR^g$C(O)—, —$NR^g$C(O)O—, —$NR^g$C(O)$NR^g$—, —$NR^g$S(O)$_2$—, —$NR^g$S(O)$_2$O— and —$NR^g$S(O)$_2NR^g$—,
  and/or
  $L^1$, $L^2$ and $L^3$ each independently of one another denotes a bond,
    while at least one of the units $L^1$, $L^2$ or $L^3$ must be other than a bond;
the ring system $Q^H$ is selected from among

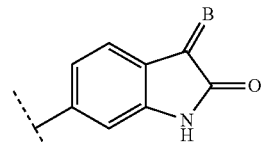
$Q^H$-1a

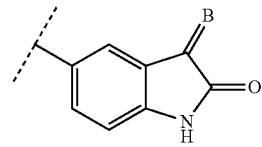
$Q^H$-1b

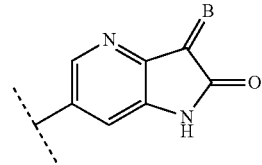
$Q^H$-1c

$Q^H$-1d

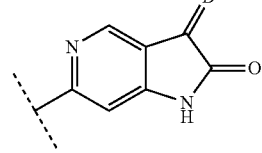
$Q^H$-1e

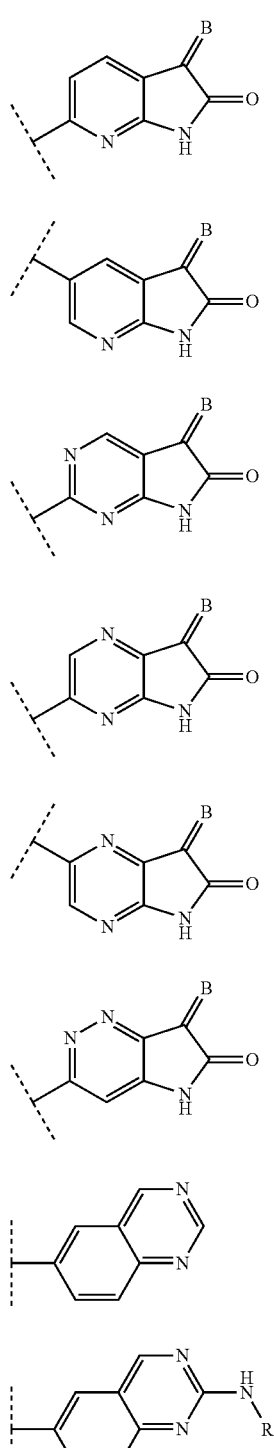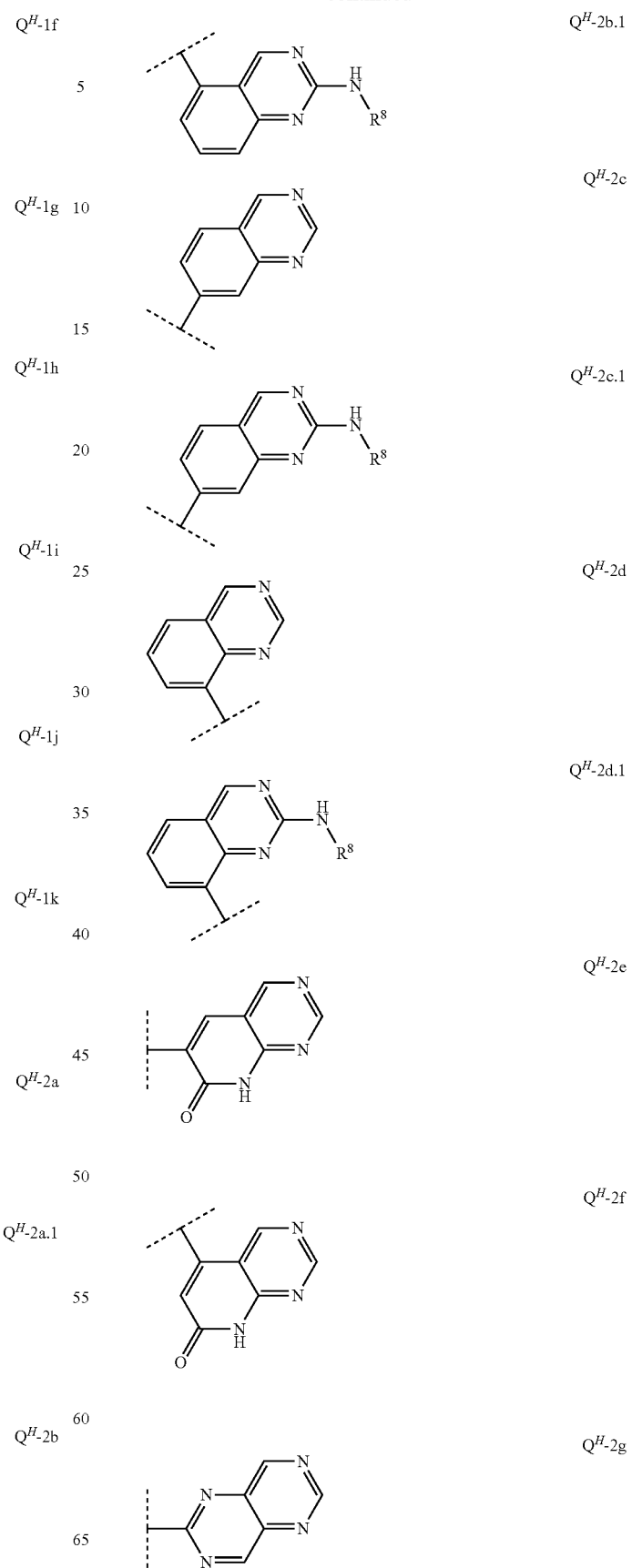

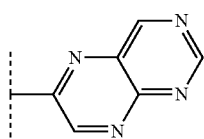
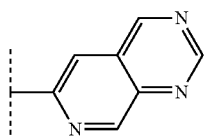
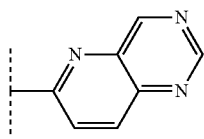
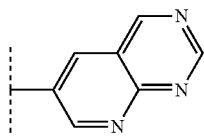
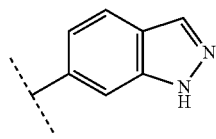
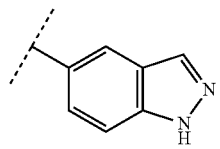
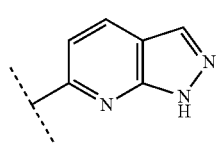
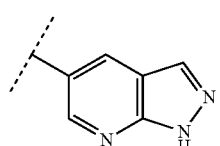
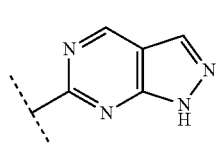
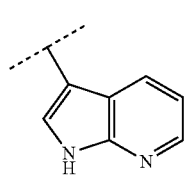
$Q^H$-2h
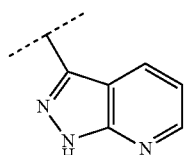
$Q^H$-2i
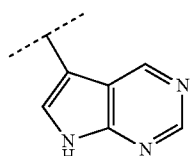
$Q^H$-2j
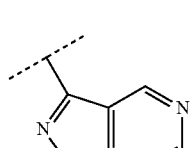
$Q^H$-2k
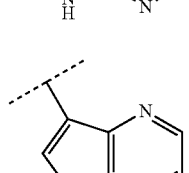
$Q^H$-3a
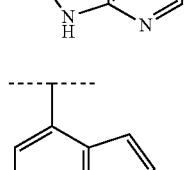
$Q^H$-3b
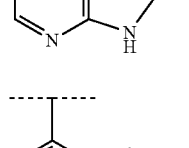
$Q^H$-3c
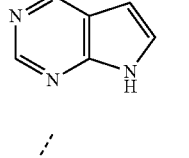
$Q^H$-3d
$Q^H$-3e
$Q^H$-4a
$Q^H$-4b
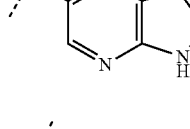
$Q^H$-4c
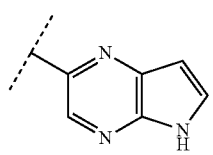
$Q^H$-4d
$Q^H$-4e
$Q^H$-5a
$Q^H$-5b
$Q^H$-6a
$Q^H$-6b
$Q^H$-6c
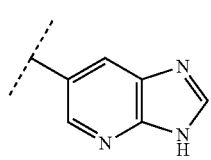

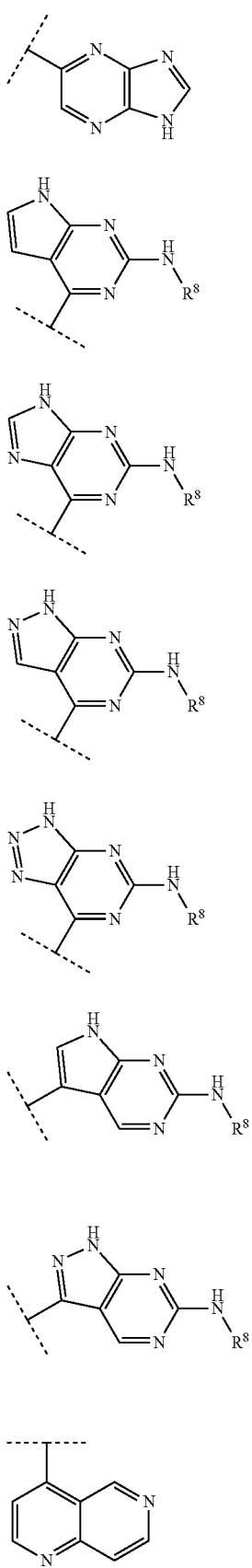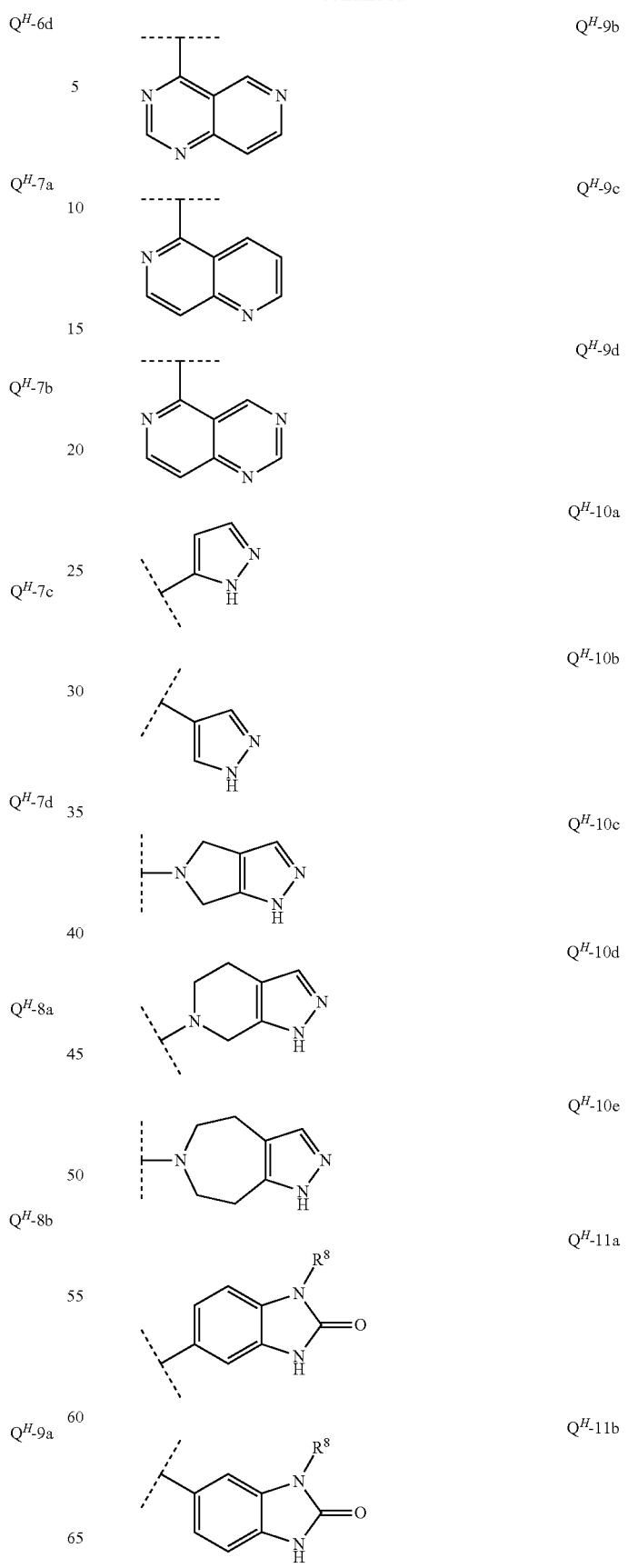

-continued

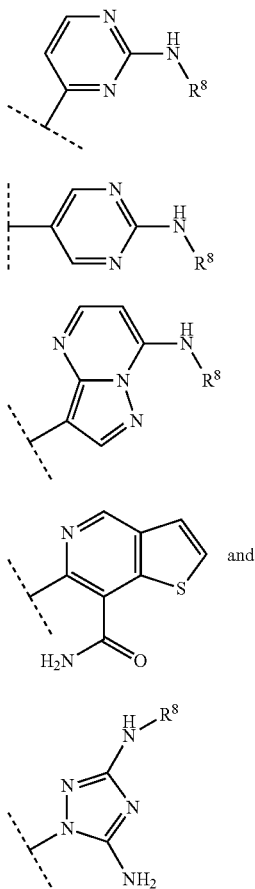

$Q^H$-12a $Q^H$-12b $Q^H$-13

$Q^H$-14 and $Q^H$-15 while
the above mentioned ring systems $Q^H$ may each optionally be substituted independently of one another at one or more hydrogen-carrying ring atom(s) by $R^a$ and/or $R^b$,
$R^8$ denotes $R^a$,
B denotes =$CR^9R^{10}$ or =$NR^{11}$,
$R^9$ denotes a group $R^{a1}$ and $R^{10}$ denotes a group $R^{a2}$
or
=$CR^9R^{10}$ denotes a 5-12 membered heteroaryl or 5-14 membered heterocycloalkyl, optionally substituted by one or more, identical or different $R^a$ and/or $R^b$,
$R^{11}$ denotes a group $R^{a3}$;
$R^{a1}$ denotes a group optionally substituted by one or more, identical or different $R^b$ and/or
$R^c$ selected from among $C_{1-6}$alkyl, $C_{1-6}$haloalkyl, 2-6 membered heteroalkyl, $C_{3-10}$cycloalkyl, $C_{6-10}$aryl, 5-12 membered heteroaryl and 3-14 membered heterocycloalkyl,
or
a suitable substituent, selected from among —$OR^c$, —$SR^c$, —$NR^cR^c$, —$ONR^cR^c$, —$N(OR^c)R^c$, —$NR^gNR^cR^c$, —$NR^gC(O)R^c$, —$NR^gC(O)OR^c$, —$NR^gC(O)NR^cR^c$, —$NR^gC(O)NR^gNR^cR^c$, —$NR^gC(NR^g)R^c$, —$NR^gC(NR^g)OR^c$, —$NR^gC(NR^g)NR^cR^c$, —$NR^gC(NOR^c)R^c$, —$NR^gS(O)_2R^c$, —$NR^gNR^gC(O)R^c$, —$NR^gNR^gC(O)NR^cR^c$ and —$NR^gNR^gC(NR^g)R^c$;
$R^{a2}$ is hydrogen or a group optionally substituted by one or more identical or different $R^b$ and/or $R^c$, selected from among $C_{1-6}$alkyl, $C_{1-6}$haloalkyl, 2-6 membered heteroalkyl, $C_{3-10}$cycloalkyl, $C_{6-10}$aryl, 5-12 membered heteroaryl and 3-14 membered heterocycloalkyl, or
a suitable substituent, selected from among —CN, —C(O)$R^c$, —C(O)$OR^c$, —C(O)$NR^cR^c$, —C(O)$SR^c$, —C(O)$NR^gNR^cR^c$ and —C(O)$NR^gOR^c$;
$R^{a3}$ is a group optionally substituted by one or more identical or different $R^b$ and/or $R^c$, selected from among $C_{1-6}$alkyl, $C_{1-6}$haloalkyl, 2-6 membered heteroalkyl, $C_{3-10}$cycloalkyl, $C_{6-10}$aryl, 5-12 membered heteroaryl and 3-14 membered heterocycloalkyl,
or
a suitable substituent, selected from among —$OR^c$ and —$NR^cR^c$;
each $R^a$ independently of one another is hydrogen or a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;
each $R^b$ denotes a suitable substituent and each is selected independently of one another from among —$OR^c$, —$NR^cR^c$, halogen, —CN, —$NO_2$, —C(O)$R^c$, —C(O)$OR^c$, —C(O)$NR^cR^c$, —OC(O)$R^c$, —OC(O)$OR^c$, —OC(O)$NR^cR^c$, —S(O)$_2R^c$, —S(O)$_2OR^c$, —S(O)$_2NR^cR^c$, —$NR^gC(O)R^c$, —$NR^gC(O)OR^c$, —$NR^gC(O)NR^cR^c$, —$NR^gS(O)_2R^c$, —$NR^gS(O)_2OR^c$ and —$NR^gS(O)_2NR^cR^c$, and the bivalent substituent =O, while the latter may only be a substituent in non-aromatic ring systems;
each $R^c$ independently of one another is hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{6-10}$ aryl, 5-12 membered heteroaryl and 3-14 membered heterocycloalkyl;
each $R^d$ is a suitable substituent and each is selected independently of one another from among —$OR^e$, —$NR^eR^e$, halogen, —CN, —$NO_2$, —C(O)$R^e$, —C(O)$OR^e$, —C(O)$NR^eR^e$, —OC(O)$R^e$, —OC(O)$OR^e$, —OC(O)$NR^eR^e$, —S(O)$_2R^e$, —S(O)$_2OR^e$, —S(O)$_2NR^eR^e$, —$NR^gC(O)R^e$, —$NR^gC(O)OR^e$, —$NR^gC(O)NR^eR^e$, —$NR^gS(O)_2R^e$, —$NR^gS(O)_2OR^e$ and —$NR^gS(O)_2NR^eR^e$, and the bivalent substituent =O, while the latter may only be a substituent in non-aromatic ring systems;
each $R^e$ independently of one another is hydrogen or a group optionally substituted by one or more identical or different $R^f$ and/or $R^g$, selected from among $C_{1-6}$alkyl, 2-6 membered heteroalkyl, $C_{1-6}$haloalkyl, $C_{3-10}$cycloalkyl, $C_{6-10}$ aryl, 5-12 membered heteroaryl and 3-14 membered heterocycloalkyl;
each $R^f$ is a suitable substituent and each is selected independently of one another from among —$OR^g$, —$NR^gR^g$, halogen, —CN, —$NO_2$, —C(O)$R^g$, —C(O)$OR^g$, —C(O)$NR^gR^g$, —OC(O)$R^g$, —OC(O)$OR^g$, —OC(O)$NR^gR^g$, —S(O)$_2R^g$, —S(O)$_2OR^g$, —S(O)$_2NR^gR^g$, —$NR^hC(O)R^g$, —$NR^hC(O)OR^g$, —$NR^hC(O)NR^gR^g$, —$NR^hS(O)_2R^g$, —$NR^hS(O)_2OR^g$ and —$NR^hS(O)_2NR^gR^g$, and the bivalent substituent =O, while the latter may only be a substituent in non-aromatic ring systems;
each $R^g$ independently of one another is hydrogen or a group optionally substituted by one or more identical or different $R^h$, selected from among $C_{1-6}$alkyl, 2-6 membered heteroalkyl, $C_{1-6}$haloalkyl, $C_{3-10}$cycloalkyl, $C_{6-10}$ aryl, 5-12 membered heteroaryl and 3-14 membered heterocycloalkyl,
and
each $R^h$ independently of one another is selected from among hydrogen, $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl In one aspect (A1) the invention relates to compounds (1), wherein $Q^a$ is a ring system optionally substituted by one or more identical or different $R^a$ and/or $R^b$, selected from among $C_{6-10}$aryl and 5-12 membered heteroaryl, and $R^a$ and $R^b$ are as hereinbefore defined.

In another aspect (A2) the invention relates to compounds (1), wherein $Q^a$ is a ring system optionally substituted by one or more identical or different $R^a$ and/or $R^b$, selected from among phenyl, naphthyl, indanyl, 1,2,3,4-tetrahydronaphthyl, furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, indolyl, isoindolyl, benzofuryl, benzothienyl, benzoxazolyl, benzothiazolyl, benzisoxazolyl, benzisothiazolyl, benzimidazolyl, indazolyl, isoquinolinyl and quinolinyl, and $R^a$ and $R^b$ are as hereinbefore defined.

In another aspect (A3) the invention relates to compounds (1), wherein $Q^a$ is a ring system optionally substituted by one or more identical or different $R^a$ and/or $R^b$, selected from among phenyl, furyl, thienyl, oxazolyl, thiazolyl, isoxazolyl, isothiazolyl, pyrimidyl and pyridyl, and $R^a$ and $R^b$ are as hereinbefore defined.

In another aspect (A4) the invention relates to compounds (1), wherein $Q^a$ is a ring system optionally substituted by one or more identical or different $R^a$ and/or $R^b$, selected from among phenyl and pyridyl, and $R^a$ and $R^b$ are as hereinbefore defined.

In another aspect (B1) the invention relates to compounds (1), wherein the ring system $Q^a$ may be substituted by one or more identical or different substituents, selected from among $C_{1-6}$alkyl, $C_{1-6}$haloalkyl, —$OR^{h1}$, —$NR^{h1}R^{h1}$, halogen, —CN, —C(O)$R^{h1}$, —C(O)O$R^{h1}$, —C(O)N$R^{h1}R^{h1}$—S(O)$_2$N$R^{h1}R^{h1}$, —N$R^{h1}$C(O)$R^{h1}$, —N$R^{h1}$C(O)O$R^{h1}$, —N$R^{h1}$C(O)N$R^{h1}R^{h1}$, —N$R^{h1}$S(O)$_2R^{h1}$ and =O, while the latter may only be a substituent in non-aromatic ring systems, and $R^{h1}$ is in each case selected independently of one another from among hydrogen, $C_{1-6}$alkyl, 2-6 membered heteroalkyl and $C_{1-6}$haloalkyl.

In another aspect (B2) the invention relates to compounds (1), wherein the ring system $Q^a$ may be substituted by up to three identical or different substituents, selected from among methyl, trifluoromethyl, —$OCH_3$, —$NH_2$, —$NH(CH_3)$, —$N(CH_3)_2$, fluorine, chlorine and bromine.

In another aspect (C1) the invention relates to compounds (1), wherein

W is selected from among —NH—, —N($C_{1-6}$alkyl)-, —$CH_2$—, —CH($C_{1-6}$alkyl)-, —C($C_{1-6}$alkyl)$_2$- and —O—.

In another aspect (C2) the invention relates to compounds (1), wherein

W is selected from among —$CH_2$—, —CH($CH_3$)—, —NH— and —N($CH_3$)—.

In another aspect (C3) the invention relates to compounds (1), wherein

W is selected from among —$CH_2$— and —CH($CH_3$)—.

The above-mentioned structural aspects A1 to A4, B1, B2 and C1 to C3 may be permuted with one another as desired to form 24 different combinations ABC (=D) which characterise the partial range $Q^a$-W of compounds (1) according to the invention. All these embodiments (D1 to D24) are expressly included, while those compounds in which the group $Q^a$-W— denotes an unsubstituted or substituted benzyl are not included;

In another aspect (D25) the invention relates to compounds (1), wherein $Q^a$ denotes phenyl, while this phenyl may be substituted by one or more identical or different substituents, selected from among $C_{1-6}$alkyl, $C_{1-6}$haloalkyl, —$OR^{h1}$, —$NR^{h1}R^{h1}$, halogen, —CN, —C(O)$R^{h1}$, —C(O)O$R^{h1}$, —C(O)N$R^{h1}R^{h1}$, —S(O)$_2$N$R^{h1}R^{h1}$, —N$R^{h1}$C(O)$R^{h1}$, —N$R^{h1}$C(O)O$R^{h1}$, —N$R^{h1}$C(O)N$R^{h1}R^{h1}$ and —N$R^{h1}$S(O)$_2R^{h1}$, $R^{h1}$ is selected in each case independently of one another from among hydrogen, $C_{1-6}$alkyl, 2-6 membered heteroalkyl and $C_{1-6}$haloalkyl, and W is selected from among —NH—, —N($C_{1-6}$alkyl)- and —O—.

In another aspect (D26) the invention relates to compounds (1), wherein $Q^a$ is selected from among furyl, thienyl, oxazolyl, thiazolyl, isoxazolyl, isothiazolyl, pyrimidyl and pyridyl, while the ring system $Q^a$ may be substituted by one or more, identical or different substituents, selected from among $C_{1-6}$alkyl, $C_{1-6}$haloalkyl, —$OR^{h1}$, —$NR^{h1}R^{h1}$, halogen, —CN, —C(O)$R^{h1}$, —C(O)O$R^{h1}$, —C(O)N$R^{h1}R^{h1}$, —S(O)$_2$N$R^{h1}R^{h1}$, —N$R^{h1}$C(O)$R^{h1}$, —N$R^{h1}$C(O)O$R^{h1}$, —N$R^{h1}$C(O)N$R^{h1}R^{h1}$ and —N$R^{h1}$S(O)$_2R^{h1}$, $R^{h1}$ is selected independently of one another in each case from among hydrogen, $C_{1-6}$alkyl, 2-6 membered heteroalkyl and $C_{1-6}$haloalkyl, and W is selected from among —NH—, —N($C_{1-6}$alkyl)-, —$CH_2$—, —CH($C_{1-6}$alkyl)-, —C($C_{1-6}$alkyl)$_2$- and —O—.

In another aspect (D27) the invention relates to compounds (1), wherein $Q^a$ denotes phenyl, while this phenyl may be substituted by up to three identical or different substituents, selected independently of one another from among methyl, trifluoromethyl, —$OCH_3$, —$NH_2$, —$NH(CH_3)$, —$N(CH_3)_2$, fluorine, chlorine and bromine, and W is selected from among —NH—, —N($C_{1-6}$alkyl)- and —O—.

In another aspect (D28) the invention relates to compounds (1), wherein $Q^a$ is selected from among furyl, thienyl, oxazolyl, thiazolyl, isoxazolyl, isothiazolyl, pyrimidyl and pyridyl, while the ring system $Q^a$ may be substituted by up to three identical or different substituents, selected independently of one another from among methyl, trifluoromethyl, —$OCH_3$, —$NH_2$, —$NH(CH_3)$, —$N(CH_3)_2$, fluorine, chlorine and bromine, and W is selected from among —NH—, —N($C_{1-6}$alkyl)-, —$CH_2$—, —CH($C_{1-6}$alkyl), —C($C_{1-6}$alkyl)$_2$- and —O—.

In another aspect (D29) the invention relates to compounds (1), wherein $Q^a$ denotes phenyl, while this phenyl may be substituted by up to three identical or different substituents, selected independently of one another from among methyl, trifluoromethyl, —$OCH_3$, —$NH_2$, —$NH(CH_3)$, —$N(CH_3)_2$, fluorine, chlorine and bromine, may be substituted, and W is selected from among —NH— and —N($CH_3$)—.

In another aspect (D30) the invention relates to compounds (1), wherein $Q^a$ is selected from among furyl, thienyl, oxazolyl, thiazolyl, isoxazolyl, isothiazolyl, pyrimidyl and pyridyl, while
- the ring system $Q^a$ may be substituted by up to three identical or different substituents, selected independently of one another from among methyl, trifluoromethyl, —OCH$_3$, —NH$_2$, —NH(CH$_3$), —N(CH$_3$)$_2$, fluorine, chlorine and bromine, may be substituted, and W is selected from among —CH$_2$—, —CH(CH$_3$)—, —NH— and —N(CH$_3$)—.

In another aspect (D31) the invention relates to compounds (1), wherein $Q^a$ is selected from among furyl, thienyl, oxazolyl, thiazolyl, isoxazolyl, isothiazolyl, pyrimidyl and pyridyl, while
- the ring system $Q^a$ may be substituted by up to three identical or different substituents, selected independently of one another from among methyl, trifluoromethyl, —OCH$_3$, —NH$_2$, —NH(CH$_3$), —N(CH$_3$)$_2$, fluorine, chlorine and bromine, and W is selected from among —CH$_2$— and —CH(CH$_3$)—.

In another aspect (D32) the invention relates to compounds (1), wherein $Q^a$ denotes pyridyl, while
- this pyridyl may be substituted by up to three identical or different substituents, selected independently of one another from among methyl, trifluoromethyl, —OCH$_3$, —NH$_2$, —NH(CH$_3$), —N(CH$_3$)$_2$, fluorine, chlorine and bromine, and W is selected from among —CH$_2$— and —CH(CH$_3$)—.

In another aspect (E1) the invention relates to compounds (1), wherein $R^4$ denotes hydrogen.

In another aspect (F1) the invention relates to compounds (1), wherein $R^5$, $R^6$ and $R^7$ independently of one another are selected from among hydrogen, $C_{1-6}$alkyl, $C_{1-6}$haloalkyl, —OR$^{h2}$, —NR$^{h2}$R$^{h2}$, halogen, —CN, —C(O)R$^{h2}$, —C(O)OR$^{h2}$, —C(O)NR$^{h2}$R$^{h2}$, —S(O)$_2$NR$^{h2}$R$^{h2}$, —NR$^{h2}$C(O)R$^{h2}$, —NR$^{h2}$C(O)OR$^{h2}$, —NR$^{h2}$C(O)NR$^{h2}$R$^{h2}$ and —NR$^{h2}$S(O)$_2$R$^{h2}$ and
- $R^{h2}$ is selected independently of one another in each case from among hydrogen, $C_{1-6}$alkyl, 2-6 membered heteroalkyl and $C_{1-6}$haloalkyl.

In another aspect (F2) the invention relates to compounds (1), wherein $R^5$, $R^6$ and $R^7$ in each case denotes hydrogen.

In another aspect (G1) the invention relates to compounds (1), wherein

L is selected from among

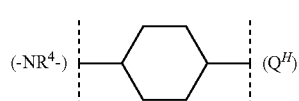

L-1

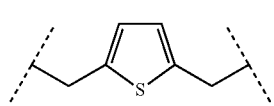

L-2

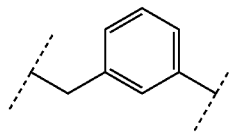

L-3

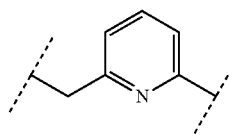

L-4

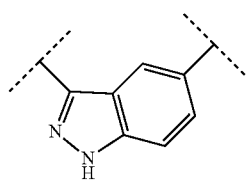

L-5

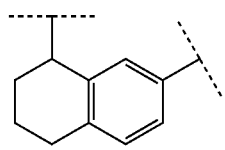

L-6

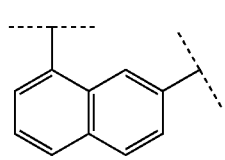

L-7

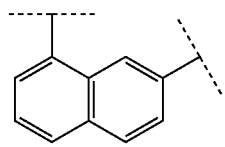

L-8

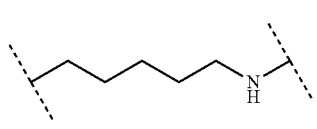

L-9

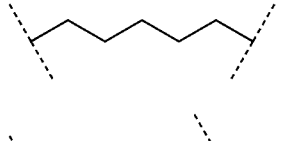

L-10

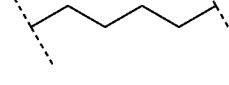

L-11

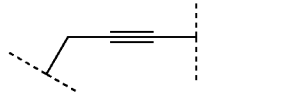

L-12

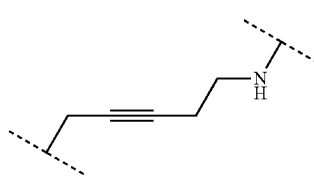

L-13

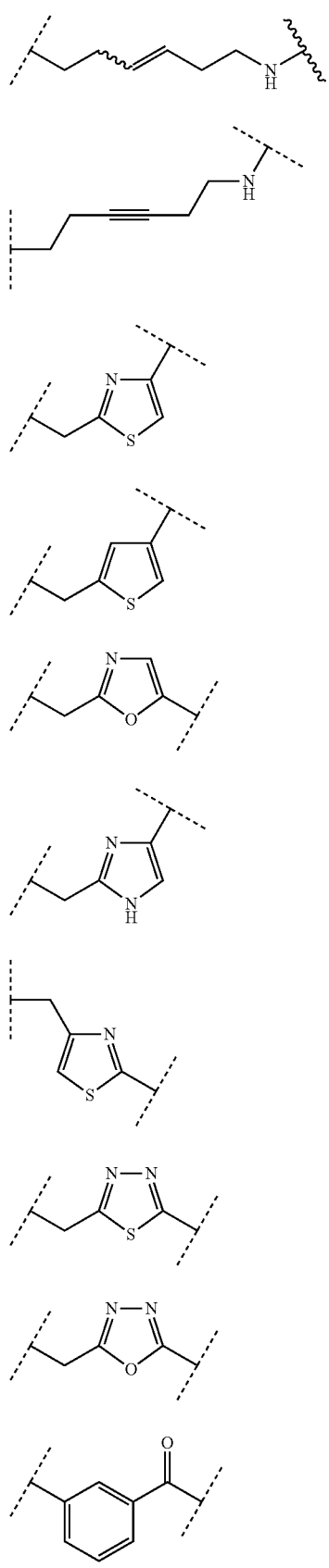
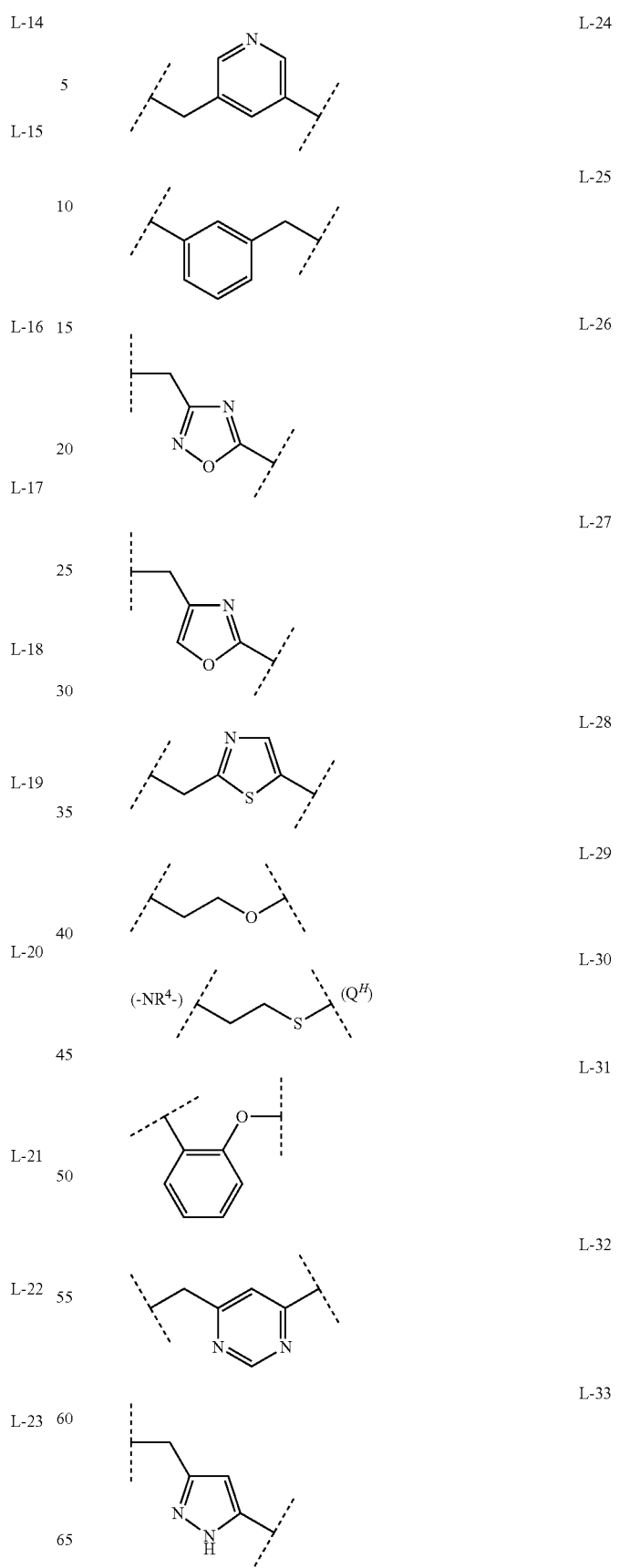

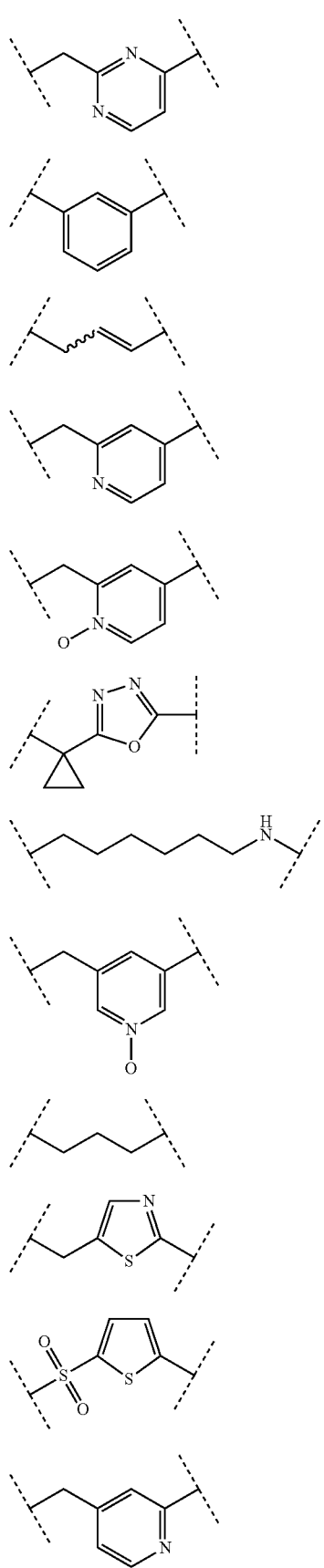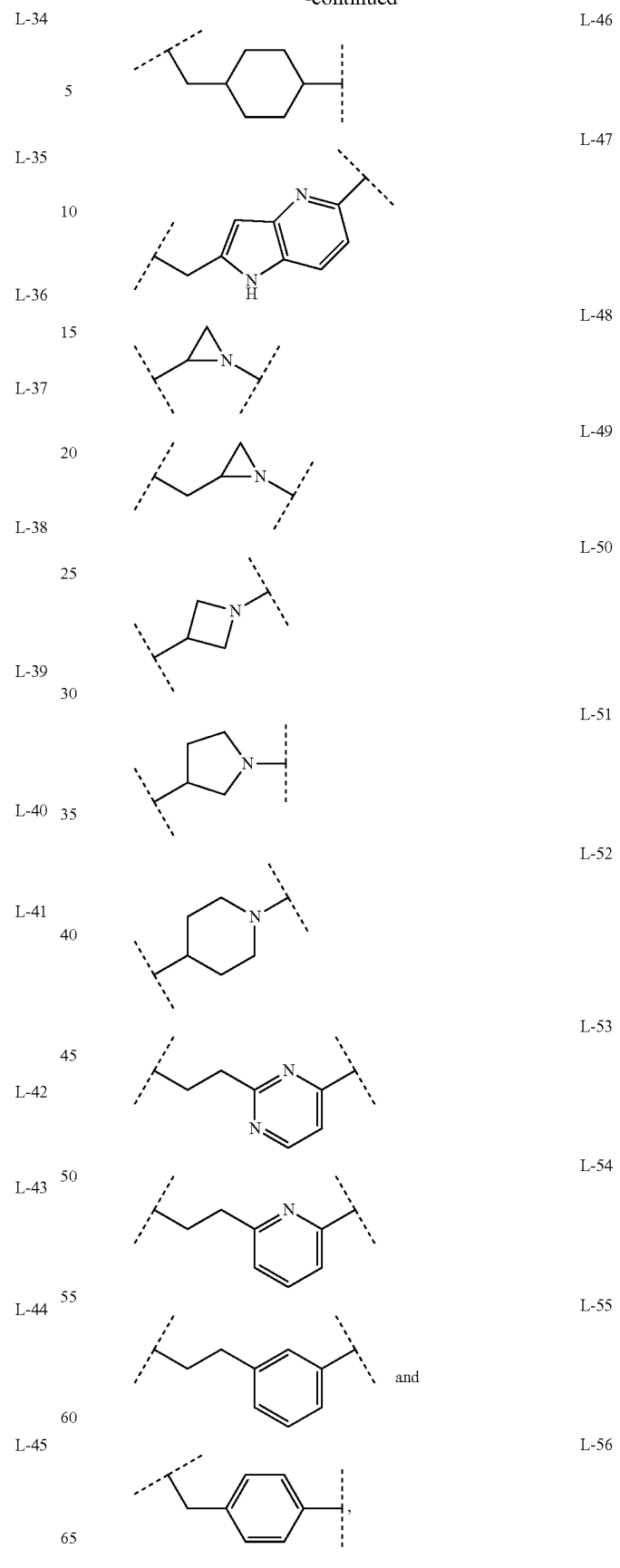

the bivalent units L shown bind on the right to the ring system $Q^H$ and on the left to the amide nitrogen —NR$^4$— according to formula (1) and may optionally each be substituted independently of one another by one or more identical or different $R^a$ and/or $R^b$ and $R^a$ and $R^b$ are as hereinbefore defined.

In another aspect (G2) the invention relates to compounds (1), wherein

L is selected from among L-1 to L-47 and L-53 to L-56,
the bivalent units L bind on the right to the ring system $Q^H$ and on the left to the amide nitrogen —NR$^4$— according to formula (1) and may optionally each be substituted independently of one another by one or more identical or different $R^a$ and/or $R^b$ and $R^a$ and $R^b$ are as hereinbefore defined.

In another aspect (G3) the invention relates to compounds (1), wherein

L is selected from among

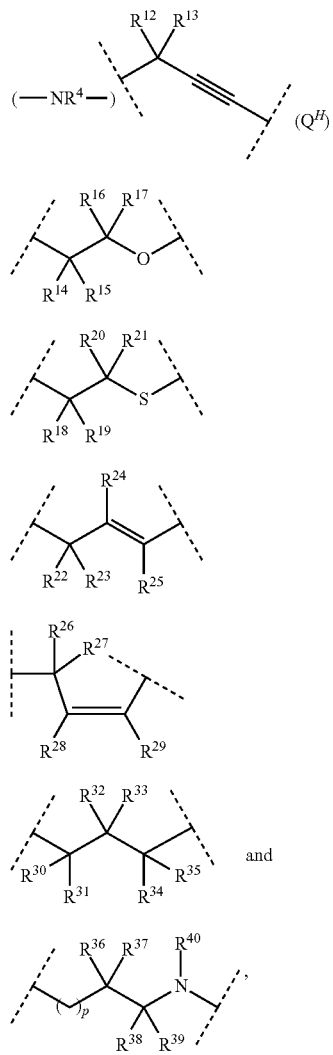

L-I

L-II

L-III

L-IV

L-V

L-VI and

L-VII while the bivalent units L shown bind on the right to the ring system $Q^H$ and on the left to the amide nitrogen —NR$^4$— according to formula (1);

p denotes 0 or 1;

$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$ and $R^{39}$ is selected in each case independently of one another from among $R^a$ and $R^b$, and $R^{40}$ denotes $R^a$; or $R^{15}$ and $R^{17}$ are each selected independently of one another from among $R^a$ and $R^b$, $R^{14}$ and $R^{16}$ together with the carbon atoms to which they are bound form a $C_{3-7}$cycloalkylene or a 3-7 membered heterocycloalkylene, while the above-mentioned ring systems may optionally each be substituted independently of one another by one or more identical or different $R^a$ and/or $R^b$; or $R^{19}$ and $R^{21}$ are each selected independently of one another from among $R^a$ and $R^b$, $R^{18}$ and $R^{20}$ together with the carbon atoms to which they are bound form a $C_{3-7}$cycloalkylene or a 3-7 membered heterocycloalkylene, while the above-mentioned ring systems may optionally each be substituted independently of one another by one or more identical or different $R^a$ and/or $R^b$; or $R^{23}$ and $R^{24}$ are each selected independently of one another from among $R^a$ and $R^b$, $R^{22}$ and $R^{25}$ together with the carbon atoms to which they are bound form an unsaturated $C_{4-7}$cycloalkylene or an unsaturated 4-7 membered heterocycloalkylene, while the above-mentioned ring systems may optionally each be substituted independently of one another by one or more identical or different $R^a$ and/or $R^b$; or $R^{30}$, $R^{31}$, $R^{33}$ and $R^{35}$ are each selected independently of one another from among $R^a$ and $R^b$, $R^{32}$ and $R^{35}$ together with the carbon atoms to which they are bound form a $C_{3-7}$cycloalkylene or a 3-7 membered heterocycloalkylene, while the above-mentioned ring systems may optionally each be substituted independently of one another by one or more identical or different $R^a$ and/or $R^b$; or $R^{37}$, $R^{38}$ and $R^{39}$ are each selected independently of one another from among $R^a$ and $R^b$, $R^{36}$ and $R^{40}$ together with the atoms to which they are bound form a 3-7 membered heterocycloalkylene, while this heterocycloalkylene may optionally be substituted independently of one another in each case by one or more identical or different $R^a$ and/or $R^b$; or $R^{36}$, $R^{37}$ and $R^{39}$ are each selected independently of one another from among $R^a$ and $R^b$, $R^{38}$ and $R^{40}$ together with the atoms to which they are bound form a 3-7 membered heterocycloalkylene, while this heterocycloalkylene may optionally be substituted independently of one another in each case by one or more identical or different $R^a$ and/or $R^b$; and $R^a$ and $R^b$ are as hereinbefore defined.

In another aspect (G4) the invention relates to compounds (1), wherein

L is selected from among

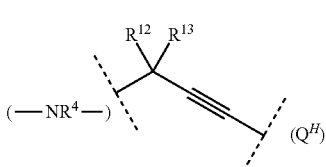

L-I

-continued

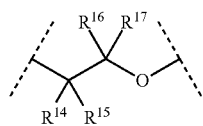
L-II

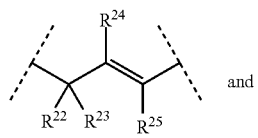
and
L-IV

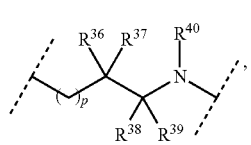
L-VII while
the bivalent units L shown bind on the right to the ring system $Q^H$ and on the left to the amide nitrogen —$NR^4$— according to formula (1);

p denotes 0 or 1;

$R^{12}, R^{13}, R^{14}, R^{15}, R^{16}, R^{17}, R^{22}, R^{23}, R^{24}, R^{25}, R^{36}, R^{37}, R^{38}$ and $R^{39}$ are each selected independently of one another from among $R^a$ and $R^b$, and $R^{40}$ denotes $R^a$; or $R^{37}, R^{38}$ and $R^{39}$ are each selected independently of one another from among $R^a$ and $R^b$, $R^{36}$ and $R^{40}$ together with the atoms to which they are bound form a 3-7 membered heterocycloalkylene, while this heterocycloalkylene may optionally be substituted independently of one another in each case by one or more identical or different $R^a$ and/or $R^b$; or $R^{36}, R^{37}$ and $R^{39}$ are each selected independently of one another from among $R^a$ and $R^b$, $R^{38}$ and $R^{40}$ together with the atoms to which they are bound form a 3-7 membered heterocycloalkylene, while this heterocycloalkylene may optionally be substituted independently of one another in each case by one or more identical or different $R^a$ and/or $R^b$; and $R^a$ and $R^b$ are as hereinbefore defined.

In another aspect (G5) the invention relates to compounds (1), wherein

L is selected from among

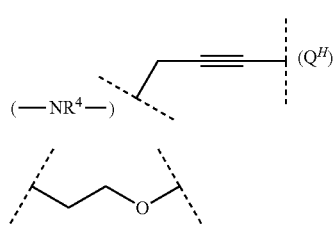
L-12

L-29

-continued

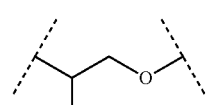
L-29a

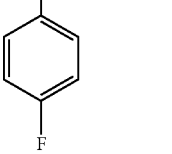
L-29b

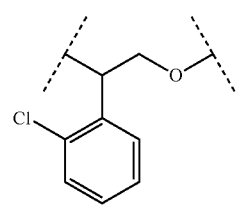
L-29c

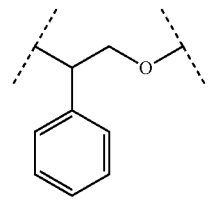
L-29d

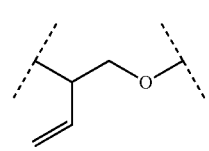
L-29e

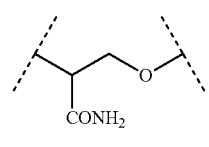
L-29f

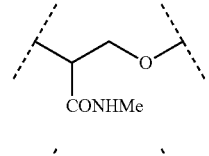
L-29g

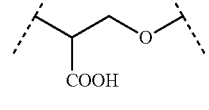
L-29h

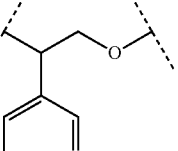
L-29i

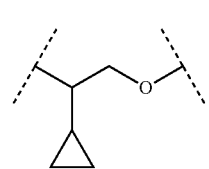

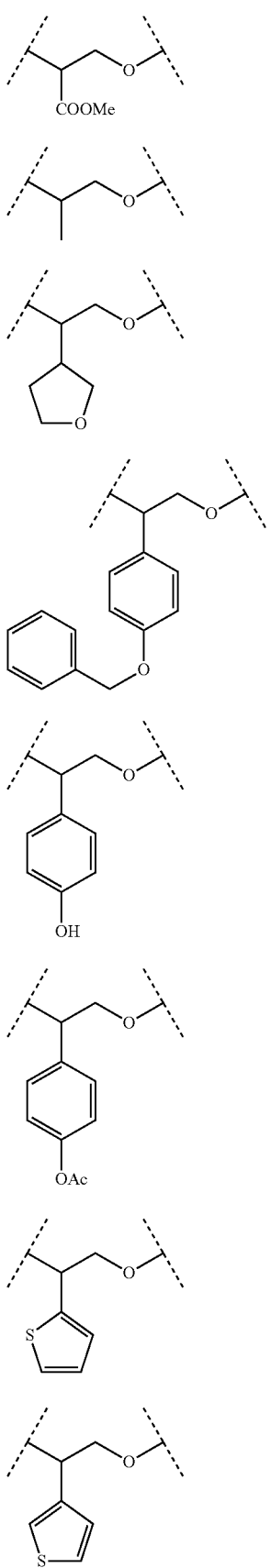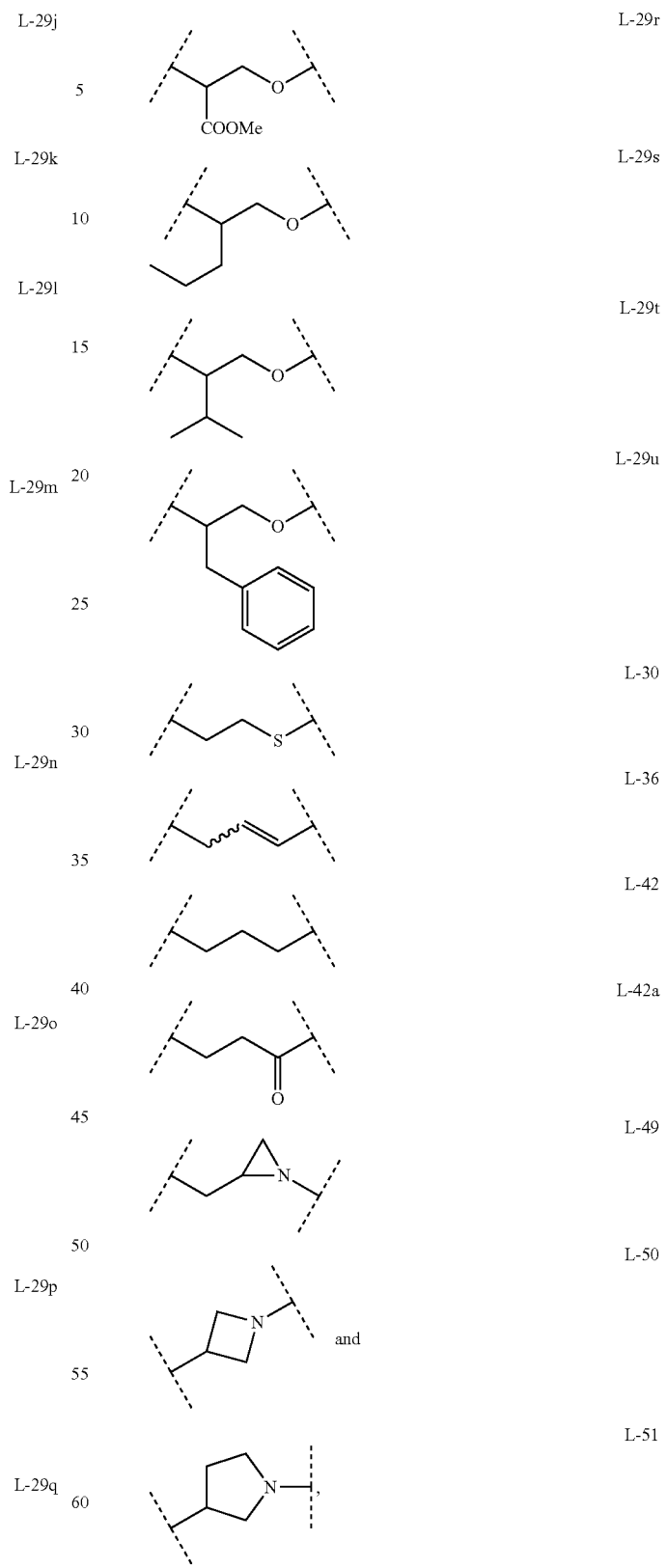
and the bivalent units L shown bind on the right to the ring system $Q^H$ and on the left to the amide nitrogen —$NR^4$— according to formula (1).

In another aspect (G6) the invention relates to compounds (1), wherein

L is selected from among

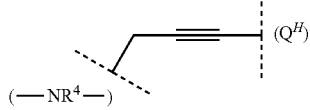

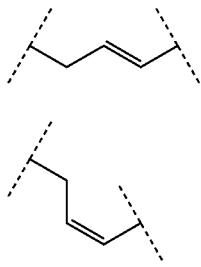

L-12

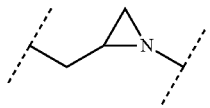

L-36

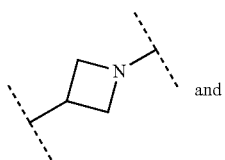

L-36

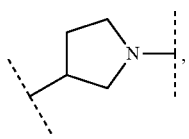

L-49

L-50 and

L-51 and the bivalent units L shown bind on the right to the ring system $Q^H$ and on the left to the amide nitrogen —NR$^4$— according to formula (1).

In another aspect (G7) the invention relates to compounds (1), wherein

L is selected from among

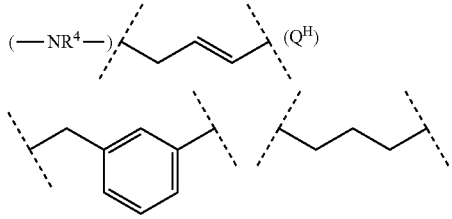

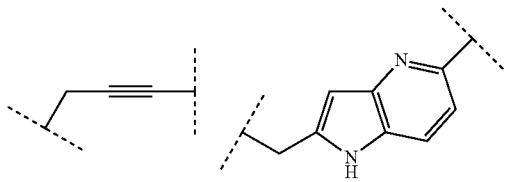

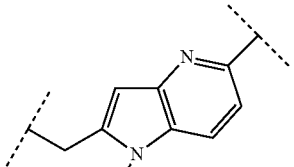

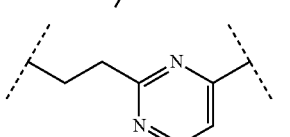

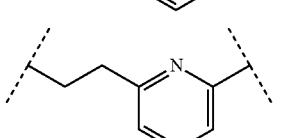

and

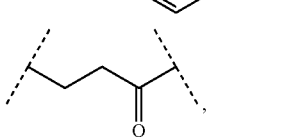

and the bivalent units L shown bind on the right to the ring system $Q^H$ and on the left to the amide nitrogen —NR$^4$— according to formula (1).

In another aspect (H1) the invention relates to compounds (1), wherein $Q^H$ is selected from among $Q^H$-1a

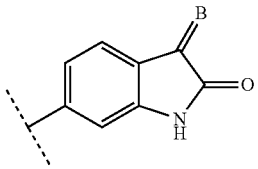

$Q^H$-1c

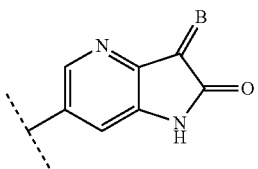

$Q^H$-1e

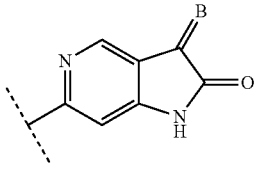

$Q^H$-1f

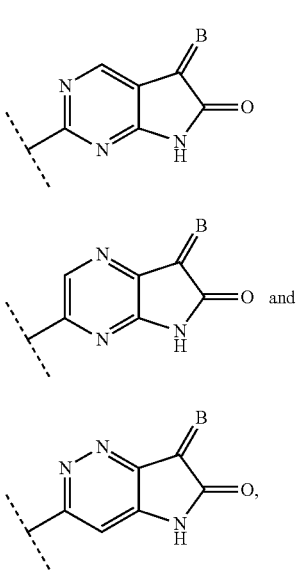

the ring systems $Q^H$ shown may each optionally be substituted independently of one another at one or more hydrogen-carrying carbon atom(s) by $R^a$ and/or $R^b$ and B, $R^a$ and $R^b$ are as hereinbefore defined.

In another aspect (H2) the invention relates to compounds (1) with the structural aspect H1, wherein B denotes $=CR^{a1}R^{a2}$;

$R^{a1}$ is a group optionally substituted by one or more identical or different $R^b$ and/or $R^c$, selected from among $C_{6-10}$aryl and 5-12 membered heteroaryl;

$R^{a2}$ is selected from among hydrogen, $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl and $R^b$ and $R^c$ are as hereinbefore defined.

In another aspect (H3) the invention relates to compounds (1) with the structural aspect H2, wherein $R^{a1}$ is a group optionally substituted by one or more identical or different $R^b$ and/or $R^c$, selected from among phenyl, naphthyl, 1,2,3,4-tetrahydronaphthyl, thienyl, pyrrolyl, pyrazolyl, imidazolyl, 1,2,3-triazolyl, 1,2,4-triazolyl, oxazolyl, isoxazolyl, thiazolyl, isothiazolyl, furyl, 1,2,3-oxadiazolyl, 1,2,4-oxadiazolyl, 1,2,5-oxadiazolyl, 1,3,4-oxadiazolyl, 1,2,3,4-oxatriazolyl, 1,2,3,5-oxatriazolyl, 1,2,3-thiadiazolyl, 1,2,4-thiadiazolyl, 1,2,5-thiadiazolyl, 1,3,4-thiadiazolyl, 1,2,3,4-thiatriazolyl, 1,2,3,5-thiatriazolyl, tetrazolyl, indolyl, isoindolyl, azaindolyl, benzothienyl, benzofuryl, 4,5,6,7-tetrahydro-1H-indolyl, 1,4,5,6-tetrahydro-cyclopenta[b]pyrrolyl and 1-benzopyran-4-on-yl, and $R^b$ and $R^c$ are as hereinbefore defined.

In another aspect (H4) the invention relates to compounds (1) with the structural aspect H3, wherein $R^{a1}$ is a group optionally substituted by one or more identical or different $R^b$ and/or $R^c$, selected from among pyrrolyl, pyrazolyl and imidazolyl, and $R^b$ and $R^c$ are as hereinbefore defined.

In another aspect (H5) the invention relates to compounds (1) with one of the structural aspects H1 to H4, wherein $R^{a2}$ is hydrogen, methyl or ethyl.

In another aspect (H6) the invention relates to compounds (1) with one of the structural aspects H1 to H5, wherein $R^{a1}$ is substituted by one or more, identical or different $R^{b2}$ and/or $R^{c1}$;

each $R^{b1}$ is a suitable substituent and is selected in each case independently of one another from among $-OR^c$, $-SR^c$, $-NR^cR^c$, halogen, $-CN$, $-NO_2$, $-C(O)R^c$, $-C(O)OR^c$, $-C(O)NR^cR^c$, $-OC(O)R^c$, $-OC(O)OR^c$, $-OC(O)NR^cR^c$, $-S(O)_2R^c$, $-S(O)_2OR^c$, $-S(O)_2NR^cR^c$, $-NR^gC(O)R^c$, $-NR^gC(O)OR^c$, $-NR^gC(O)NR^cR^c$, $-NR^gS(O)_2R^c$, $-NR^gS(O)_2OR^c$ and $-NR^gS(O)_2NR^cR^c$ and the bivalent substituent $=O$, while the latter may only be a substituent in non-aromatic ring systems;

each $R^{c1}$ independently denotes a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl, and $R^c$, $R^d$, $R^e$ and $R^g$ are as hereinbefore defined.

In another aspect (H7) the invention relates to compounds (1), wherein

B denotes $=CR^{a1}R^{a2}$ or $=NR^{a3}$;

$R^{a1}$ and $R^{a1}$ are selected independently of one another from among $-NHR^{c2}$ or $-N(C_{1-6}$alkyl$)R^{c2}$;

$R^{a2}$ is selected from among hydrogen, methyl and ethyl;

$R^{c2}$ is selected from among phenyl, pyridyl, pyrimidyl, piperidyl, cyclohexyl and benzyl, all the above-mentioned groups optionally being substituted by one or more identical or different $R^d$ and/or $R^e$ and $R^d$ and $R^e$ are as hereinbefore defined.

In another aspect (H8) the invention relates to compounds (1), wherein $Q^H$ is selected from among

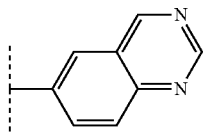

$Q^H$-2a

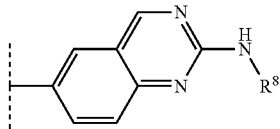

$Q^H$-2a.1

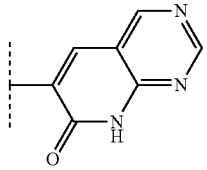

$Q^H$-2e

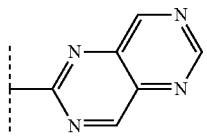

$Q^H$-2g

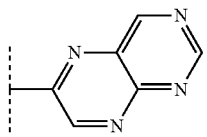

$Q^H$-2h

-continued

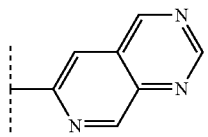
Q^H-2i

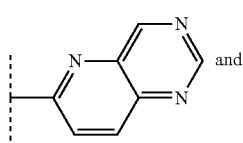
Q^H-2j
and

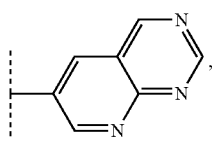
Q^H-2k
, the ring systems $Q^H$ shown may each optionally be substituted independently of one another at one or more hydrogen-carrying ring atom(s) by $R^a$ and/or $R^b$ and
$R^8$, $R^a$ and $R^b$ are as hereinbefore defined.

In another aspect (H9) the invention relates to compounds (1), wherein
$Q^H$ is selected from among

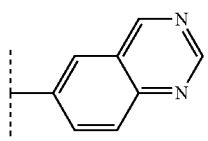
Q^H-2a

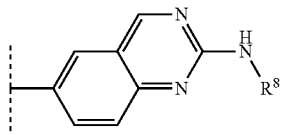
Q^H-2a.1

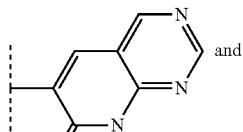
and

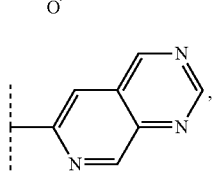
Q^H-2i
, the ring systems $Q^H$ shown may each optionally be substituted independently of one another at one or more hydrogen-carrying ring atom(s) by $R^a$ and/or $R^b$ and
$R^8$, $R^a$ and $R^b$ are as hereinbefore defined.

In another aspect (H10) the invention relates to compounds (1), wherein
$Q^H$ is selected from among

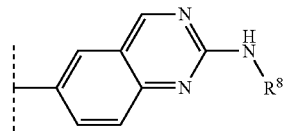
Q^H-2a.1

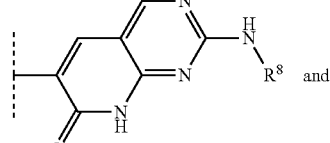
and

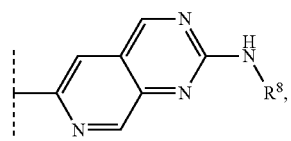
, the ring systems $Q^H$ shown may each optionally be substituted independently of one another at one or more hydrogen-carrying ring atom(s) by $R^a$ and/or $R^b$,
$R^8$ denotes $R^c$ and
$R^a$, $R^b$ and $R^c$ are as hereinbefore defined.

In another aspect (H11) the invention relates to compounds (1), wherein
$Q^H$ is selected from among

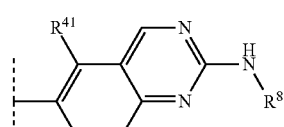

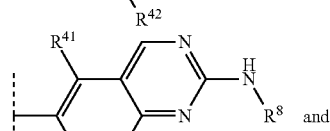
and

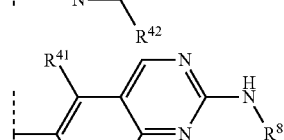
, while
$R^{41}$ is selected from among hydrogen, halogen, methyl, ethyl, trifluoromethyl and methoxy,
$R^{42}$ is selected from among hydrogen, $R^a$ and $R^b$,
$R^{43}$ denotes hydrogen or $R^a$,
$R^8$ denotes $R^c$ and
$R^a$, $R^b$ and $R^c$ are as hereinbefore defined.

In another aspect (H12) the invention relates to compounds (1), wherein
$Q^H$ is selected from among

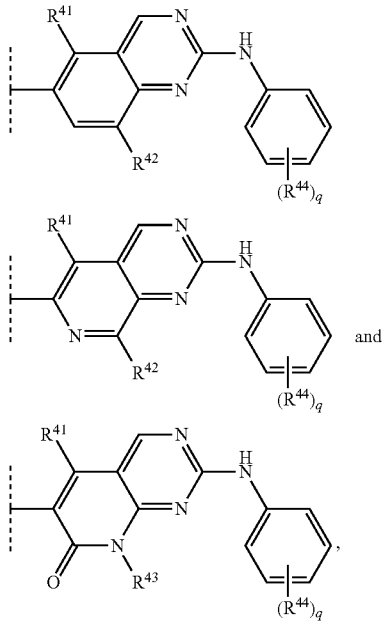

while $R^{41}$ is selected from among hydrogen, halogen, methyl, ethyl, trifluoromethyl and methoxy, $R^{42}$ is selected from among hydrogen, $R^a$ and $R^b$, $R^{43}$ denotes hydrogen or $R^a$, $R^{44}$ is selected from among $R^d$ and $R^e$, q denotes 0, 1, 2 or 3 and $R^a$, $R^b$, $R^d$ and $R^e$ are as hereinbefore defined.

In another aspect (H13) the invention relates to compounds (1), wherein
$Q^H$ is selected from among

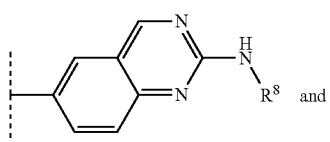

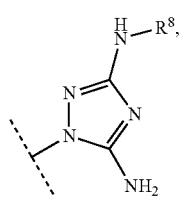

$R^8$ denotes a phenyl, optionally substituted by one or more, identical or different $R^b$ and/or $R^c$, and $R^b$ and $R^c$ are as hereinbefore defined.

In another aspect (H14) the invention relates to compounds (1), wherein
$Q^H$ is selected from among

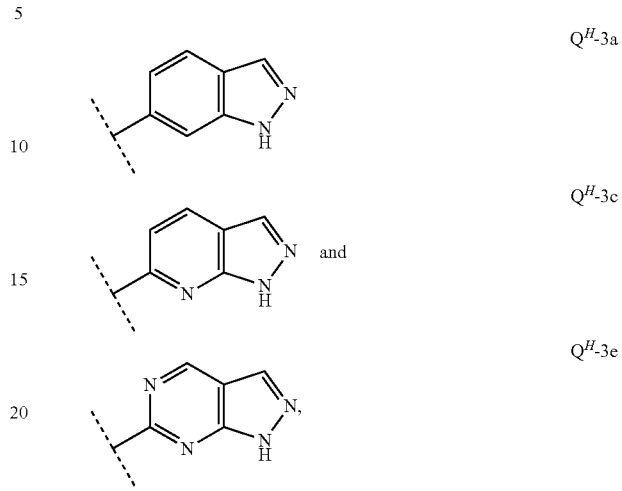

$Q^H$-3a $Q^H$-3c $Q^H$-3e the ring systems $Q^H$ shown may each optionally be substituted independently of one another at one or more hydrogen-carrying ring atom(s) by $R^a$ and/or $R^b$ and $R^a$ and $R^b$ are as hereinbefore defined.

In another aspect (H15) the invention relates to compounds (1), wherein
$Q^H$ is selected from among

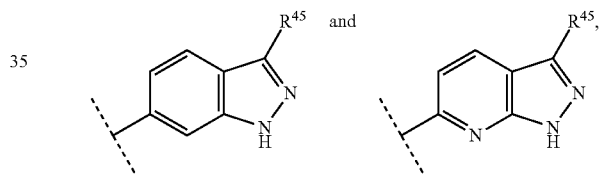

$R^{45}$ independently of one another denotes hydrogen or a group optionally substituted by one or more identical or different $R^b$ and/or $R^c$, selected from among $C_{3-7}$-cycloalkyl, phenyl, 5-10 membered heteroaryl, particularly 1H-benzimidazolyl, 1H-indolyl, pyrrolyl, imidazolyl or pyrazolyl, and 3-10 membered heterocycloalkyl, and $R^b$ and $R^c$ are as hereinbefore defined.

In another aspect (H16) the invention relates to compounds (1), wherein
$Q^H$ is selected from among

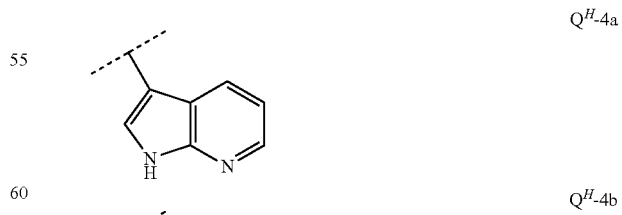

$Q^H$-4a

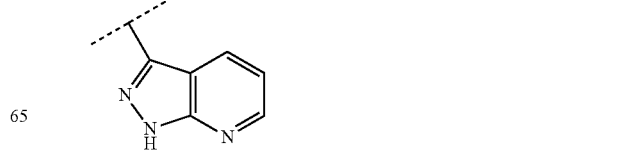

$Q^H$-4b

-continued

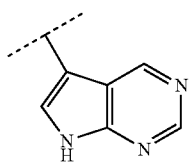
Q^H-4c

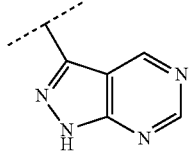
Q^H-4d

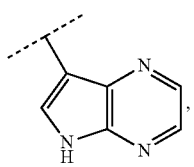
Q^H-4e the ring systems Q^H shown may each optionally be substituted independently of one another at one or more hydrogen-carrying ring atom(s) by $R^a$ and/or $R^b$ and $R^a$ and $R^b$ are as hereinbefore defined.

In another aspect (H17) the invention relates to compounds (1), wherein

Q^H is selected from among

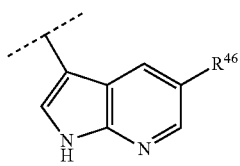

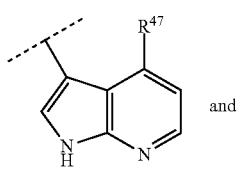

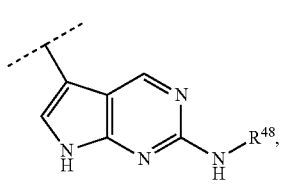

$R^{46}$ and $R^{47}$ in each case independently of one another denote hydrogen or a group optionally substituted by one or more, identical or different $R^b$ and/or $R^c$, selected from among $C_{3-7}$cycloalkyl, phenyl, 5-10 membered heteroaryl, particularly pyridyl, and 3-10 membered heterocycloalkyl, $R^{48}$ denotes $R^c$ and $R^b$ and $R^c$ are as hereinbefore defined.

In another aspect (H18) the invention relates to compounds (1), wherein

Q^H denotes

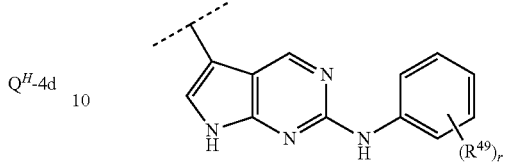

$R^{49}$ is selected from among $R^d$ and $R^e$, r denotes 0, 1, 2 or 3 and $R^d$ and $R^e$ are as hereinbefore defined.

In another aspect (H19) the invention relates to compounds (1), wherein

Q^H is selected from among

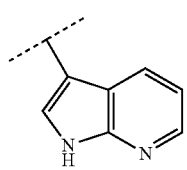
Q^H-4a

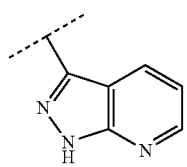
Q^H-4b

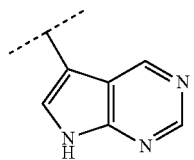
Q^H-4c

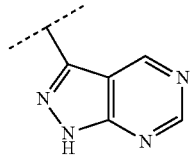
Q^H-4d

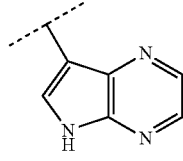
Q^H-4e

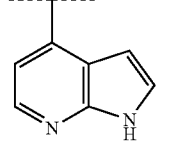
Q^H-5a

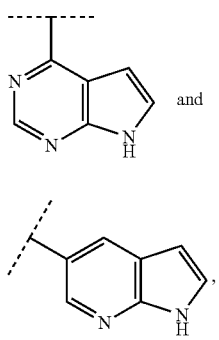

Q$^H$-5b and

Q$^H$-6a the above mentioned ring systems Q$^H$ may each optionally be substituted independently of one another at one or more hydrogen-carrying carbon atom(s) by R$^a$ and/or R$^b$ and R$^a$ and R$^b$ are as hereinbefore defined.

In another aspect (H20) the invention relates to compounds (1) with the structural aspect H19, wherein Q$^H$ may each optionally be substituted independently of one another at one or more hydrogen-carrying ring atom(s) by a substituent selected from among —NH$_2$, —NH(C$_{1-6}$alkyl), —N(C$_{1-6}$alkyl)$_2$, —C$_{1-6}$alkylene-OH, halogen, —C(O)OH, —C(O)NH$_2$, —C(O)NH(C$_{1-6}$alkyl), —C(O)N(C$_{1-6}$alkyl)$_2$, —C$_{1-6}$alkylene-NH$_2$, heteroaryl, phenyl, —C(O)NH—C$_{1-6}$alkylene-O—C$_{1-6}$alkyl, —C$_{1-6}$alkylene-NH(C$_{1-6}$alkyl), —CN, —OC$_{1-6}$alkyl, —C(O)morpholinyl, —C$_{1-6}$alkylene-N(C$_{1-6}$ alkyl)$_2$, —C(O)piperazinyl, C$_{1-6}$ alkyl, —CF$_3$, —C(O)NH(C$_{3-10}$cycloalkyl) and —OH.

In another aspect (H21) the invention relates to compounds (1), wherein

Q$^H$ is selected from among

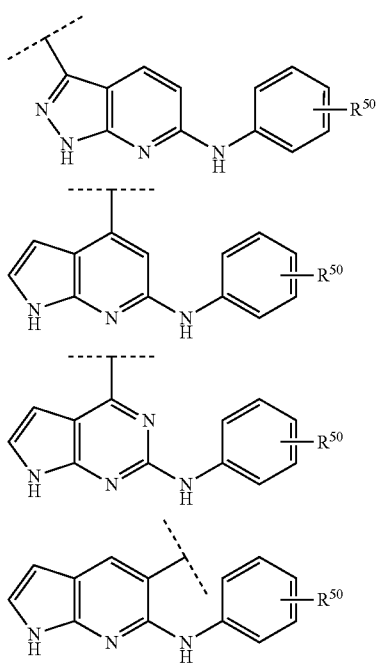

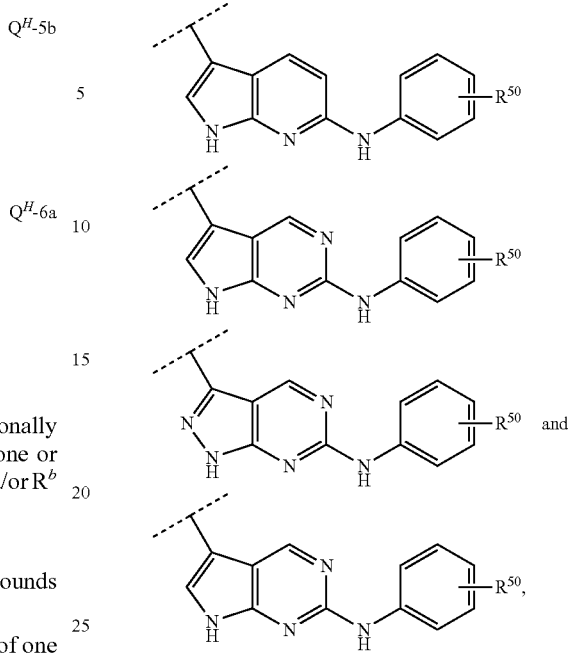

R$^{50}$ is selected from among R$^d$ and R$^e$ and

R$^d$ and R$^e$ are as hereinbefore defined.

All the above listed structural aspects D, E, F, G and H relating to different molecular parts of the compounds according to the invention (1) may be combined with one another in any desired permutation to form combinations DEFGH, resulting in preferred compounds (1). Each combination DEFGH represents and defines individual embodiments or generic partial quantities of compounds according to the invention. Each individual embodiment or partial quantity fixed by this combination is expressly included and forms part of the subject-matter of the invention.

In another aspect the invention relates to compounds selected from among

I-1 1-[(6-chloropyridin-3-yl)methyl]-N-{(2E)-3-[(3Z)-3-(1H-imidazol-5-ylmethylidene)-2-oxo-2,3-dihydro-1H-indol-6-yl]prop-2-en-1-yl}-2-oxo-1,2-dihydropyridine-3-carboxamide I-2 1-[(6-chloropyridin-3-yl)methyl]-2-oxo-N-{(2E)-3-[(3Z)-2-oxo-3-(1H-pyrrol-2-ylmethylidene)-2,3-dihydro-1H-indol-6-yl]prop-2-en-1-yl}-1,2-dihydropyridine-3-carboxamide;

I-3 1-[(6-chloropyridin-3-yl)methyl]-N-{(2E)-3-[(3Z)-3-{[4-(3-{[2-(dimethylamino)-ethyl]carbamoyl}phenyl)-1H-pyrrol-2-yl]methylidene}-2-oxo-2,3-dihydro-1H-indol-6-yl]prop-2-en-1-yl}-2-oxo-1,2-dihydropyridine-3-carboxamide;

I-4 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyridin-3-ylmethyl)-1,2-dihydropyridine-3-carboxamide;

I-5 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyridin-4-ylmethyl)-1,2-dihydropyridine-3-carboxamide;

I-6 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyridin-2-ylmethyl)-1,2-dihydropyridine-3-carboxamide;

I-7 N-{(2E)-3-[(3Z)-3-(1H-imidazol-5-ylmethylidene)-2-oxo-2,3-dihydro-1H-indol-6-yl]prop-2-en-1-yl}-2-oxo-1-(pyridin-3-ylmethyl)-1,2-dihydropyridine-3-carboxamide;

I-8 N-{(2E)-3-[(3Z)-3-(1H-imidazol-5-ylmethylidene)-2-oxo-2,3-dihydro-1H-indol-6-yl]prop-2-en-1-yl}-2-oxo-1-(pyridin-4-ylmethyl)-1,2-dihydropyridine-3-carboxamide;

I-9 N-{(2E)-3-[(3Z)-3-(1H-imidazol-5-ylmethylidene)-2-oxo-2,3-dihydro-1H-indol-6-yl]prop-2-en-1-yl}-2-oxo-1-(pyridin-2-ylmethyl)-1,2-dihydropyridine-3-carboxamide;

I-10 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyrimidin-5-ylmethyl)-1,2-dihydropyridine-3-carboxamide;

I-11 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyrimidin-4-ylmethyl)-1,2-dihydropyridine-3-carboxamide;

I-12 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyrimidin-2-ylmethyl)-1,2-dihydropyridine-3-carboxamide;

I-13 1-(cyclo hexylmethyl)-2-oxo-N-{(2E)-3-[(3Z)-2-oxo-3-(1H-pyrrol-2-ylmethylidene)-2,3-dihydro-1H-indol-6-yl]prop-2-en-1-yl}-1,2-dihydropyridine-3-carboxamide;

I-14 2-oxo-N-{(2E)-3-[(3Z)-2-oxo-3-(1H-pyrrol-2-ylmethylidene)-2,3-dihydro-1H-indol-6-yl]prop-2-en-1-yl}-1-(tetrahydro-2H-pyran-4-ylmethyl)-1,2-dihydropyridine-3-carboxamide;

I-15 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyridazin-4-ylmethyl)-1,2-dihydropyridine-3-carboxamide;

I-16 2-oxo-N-{(2E)-3-[(3Z)-2-oxo-3-(1H-pyrrol-2-ylmethylidene)-2,3-dihydro-1H-indol-6-yl]prop-2-en-1-yl}-1-(phenylamino)-1,2-dihydropyridine-3-carboxamide;

I-17 1-[methyl(phenyl)amino]-2-oxo-N-{(2E)-3-[(3Z)-2-oxo-3-(1H-pyrrol-2-ylmethylidene)-2,3-dihydro-1H-indol-6-yl]prop-2-en-1-yl}-1,2-dihydropyridine-3-carboxamide;

I-18 1-[(3,4-difluorophenyl)amino]-2-oxo-N-{(2E)-3-[(3Z)-2-oxo-3-(1H-pyrrol-2-ylmethylidene)-2,3-dihydro-1H-indol-6-yl]prop-2-en-1-yl}-1,2-dihydropyridine-3-carboxamide;

I-19 1-[(3,4-difluorophenyl)(methyl)amino]-2-oxo-N-{(2E)-3-[(3Z)-2-oxo-3-(1H-pyrrol-2-ylmethylidene)-2,3-dihydro-1H-indol-6-yl]prop-2-en-1-yl}-1,2-dihydropyridine-3-carboxamide;

I-20 N-{(2E)-3-[(3Z)-3-{6-[(dimethylamino)methyl]-3,4-dihydroquinazolin-2(1H)-yliden}-2-oxo-2,3-dihydro-1H-indol-6-yl]prop-2-en-1-yl}-2-oxo-1-(pyridin-3-ylmethyl)-1,2-dihydropyridine-3-carboxamide;

I-21 N-[(2E)-3-{(3Z)-3-[({4-[(dimethylamino)methyl]phenyl}amino)(phenyl)methylidene]-2-oxo-2,3-dihydro-1H-indol-6-yl}prop-2-en-1-yl]-2-oxo-1-(pyridin-3-ylmethyl)-1,2-dihydropyridine-3-carboxamide;

I-22 N-{(2E)-3-[(3Z)-3-(2-{4-[(dimethylamino)methyl]phenyl}hydrazinyliden)-2-oxo-2,3-dihydro-1H-indol-6-yl]prop-2-en-1-yl}-2-oxo-1-(pyridin-3-ylmethyl)-1,2-dihydropyridine-3-carboxamide;

I-23 2-oxo-N-{(2E)-3-[(3Z)-2-oxo-3-(quinoline-2(1H)-yliden)-2,3-dihydro-1H-indol-6-yl]prop-2-en-1-yl}-1-(pyridin-3-ylmethyl)-1,2-dihydropyridine-3-carboxamide;

I-24 N-{(2E)-3-[(3Z)-3-(1H-imidazol-5-ylmethylidene)-2-oxo-2,3-dihydro-1H-indol-6-yl]prop-2-en-1-yl}-1-[(6-methylpyridin-3-yl)methyl]-2-oxo-1,2-dihydropyridine-3-carboxamide;

I-25 1-(cyclo hexylmethyl)-N-{(2E)-3-[(3Z)-3-(1H-imidazol-5-ylmethylidene)-2-oxo-2,3-dihydro-1H-indol-6-yl]prop-2-en-1-yl}-2-oxo-1,2-dihydropyridine-3-carboxamide;

I-26 N-{(2E)-3-[(3Z)-3-(1H-imidazol-5-ylmethylidene)-2-oxo-2,3-dihydro-1H-indol-6-yl]prop-2-en-1-yl}-1-[(1-methyl-1H-imidazol-5-yl)methyl]-2-oxo-1,2-dihydropyridine-3-carboxamide;

I-27 N-{(2E)-3-[(3Z)-3-(1H-imidazol-5-ylmethylidene)-2-oxo-2,3-dihydro-1H-indol-6-yl]prop-2-en-1-yl}-1-[(1-methyl-1H-imidazol-4-yl)methyl]-2-oxo-1,2-dihydropyridine-3-carboxamide;

II-1 2-oxo-1-(pyridin-3-ylmethyl)-N-[3-(1H-pyrrolo[2,3-b]pyridin-3-yl)benzyl]-1,2-dihydropyridine-3-carboxamide;

II-2 2-oxo-N-{3-[2-(phenylamino)quinazolin-6-yl]prop-2-yn-1-yl}-1-(pyridin-3-ylmethyl)-1,2-dihydropyridine-3-carboxamide;

II-3 1-[(6-chloropyridin-3-yl)methyl]-2-oxo-N-[3-(1H-pyrrolo[2,3-b]pyridin-3-yl)benzyl]-1,2-dihydropyridine-3-carboxamide;

II-4 1-[(6-chloropyridin-3-yl)methyl]-2-oxo-N-{3-[2-(phenylamino)quinazolin-6-yl]prop-2-yn-1-yl}-1,2-dihydropyridine-3-carboxamide;

II-5 N-{3-[2-({4-[(dimethylamino)methyl]phenyl}amino)quinazolin-6-yl]prop-2-yn-1-yl}-2-oxo-1-(pyridin-3-ylmethyl)-1,2-dihydropyridine-3-carboxamide;

II-6 N-{3-[2-({4-[(dimethylamino)methyl]phenyl}amino)quinazolin-6-yl]prop-2-yn-1-yl}-2-oxo-1-{[6-(trifluoromethyl)pyridin-3-yl]methyl}-1,2-dihydropyridine-3-carboxamide;

II-7 N-{3-[2-({3-fluoro-4-[(1-methylpiperidin-4-yl)amino]phenyl}amino)quinazolin-6-yl]prop-2-yn-1-yl}-2-oxo-1-{[6-(trifluoromethyl)pyridin-3-yl]methyl}-1,2-dihydropyridine-3-carboxamide;

II-8 N-{3-[2-({4-[methyl(1-methylpiperidin-4-yl)amino]phenyl}amino)quinazolin-6-yl]prop-2-yn-1-yl}-2-oxo-1-{[6-(trifluoromethyl)pyridin-3-yl]methyl}-1,2-dihydropyridine-3-carboxamide;

II-9 N-{3-[8-(3-aminopropoxy)-2-{[4-(morpholin-4-yl)phenyl]amino}quinazolin-6-yl]prop-2-yn-1-yl}-2-oxo-1-(pyridin-3-ylmethyl)-1,2-dihydropyridine-3-carboxamide;

II-10 N-{3-[8-(3-aminopropoxy)-2-{[4-(morpholin-4-yl)phenyl]amino}quinazolin-6-yl]prop-2-yn-1-yl}-1-[(6-chlorpyridin-3-yl)methyl]-2-oxo-1,2-dihydropyridine-3-carboxamide;

II-11 N-{3-[2-({4-[(dimethylamino)methyl]phenyl}amino)-5-fluoroquinazolin-6-yl]prop-2-yn-1-yl}-2-oxo-1-(pyridin-3-ylmethyl)-1,2-dihydropyridine-3-carboxamide;

II-12 1-[(6-chloropyridin-3-yl)methyl]-N-{3-[2-({4-[(dimethylamino)methyl]phenyl}-amino)-5-fluoroquinazolin-6-yl]prop-2-yn-1-yl}-2-oxo-1,2-dihydropyridine-3-carboxamide;

II-13 N-{3-[5-methyl-2-{[4-(morpholin-4-yl)phenyl]amino}-7-oxo-8-(propane-2-yl)-7,8-dihydropyrido[2,3-d]pyrimidin-6-yl]prop-2-yn-1-yl}-2-oxo-1-(pyridin-3-ylmethyl)-1,2-dihydropyridine-3-carboxamide;

II-14 1-[(6-chloropyridin-3-yl)methyl]-N-{3-[5-methyl-2-{[4-(morpholin-4-yl)phenyl]-amino}-7-oxo-8-(propane-2-yl)-7,8-dihydropyrido[2,3-d]pyrimidin-6-yl]prop-2-yn-1-yl}-2-oxo-1,2-dihydropyridine-3-carboxamide;

II-15 N-{3-[2-({4-[(dimethylamino)methyl]phenyl}amino)pyrido[3,4-c]pyrimidin-6-yl]prop-2-yn-1-yl}-2-oxo-1-(pyridin-3-ylmethyl)-1,2-dihydropyridine-3-carboxamide;

II-16 1-[(6-chloropyridin-3-yl)methyl]-N-{3-[2-({4-[(dimethylamino)methyl]phenyl}-amino)pyrido[3,4-c]pyrimidin-6-yl]prop-2-yn-1-yl}-2-oxo-1,2-dihydropyridine-3-carboxamide;

II-17 N-{3-[2-({4-[(dimethylamino)methyl]phenyl}amino)pyrido[2,3-c]pyrimidin-6-yl]prop-2-yn-1-yl}-2-oxo-1-(pyridin-3-ylmethyl)-1,2-dihydropyridine-3-carboxamide;

II-18 1-[(6-chloropyridin-3-yl)methyl]-N-{3-[2-({4-[(dimethylamino)methyl]phenyl}-amino)pyrido[2,3-c]pyrimidin-6-yl]prop-2-yn-1-yl}-2-oxo-1,2-dihydropyridine-3-carboxamide;

III-1 2-oxo-N-{(2E)-3-[2-(phenylamino)quinazolin-6-yl]prop-2-en-1-yl}-1-(pyridin-3-ylmethyl)-1,2-dihydropyridine-3-carboxamide;

III-2 1-[(6-chloropyridin-3-yl)methyl]-2-oxo-N-{(2E)-3-[2-(phenylamino)quinazolin-6-yl]prop-2-en-1-yl}-1,2-dihydropyridine-3-carboxamide;

III-3 N-[(2E)-3-{4-[5-amino-3-(phenylamino)-1H-1,2,4-triazol-1-yl]-5-methoxypyrimidin-2-yl}prop-2-en-1-yl]-2-oxo-1-(pyridin-3-ylmethyl)-1,2-dihydropyridine-3-carboxamide;

III-4 N-{(2E)-3-[4-(5-amino-3-{[4-(4-methylpiperazin-1-yl)phenyl]amino}-1H-1,2,4-triazol-1-yl)-5-methoxypyrimidin-2-yl]prop-2-en-1-yl}-2-oxo-1-(pyridin-3-ylmethyl)-1,2-dihydropyridine-3-carboxamide;

III-5 N-[(2E)-3-{4-[5-amino-3-(phenylamino)-1H-1,2,4-triazol-1-yl]-5-methoxy-6-(piperidin-3-ylamino)pyrimidin-2-yl}prop-2-en-1-yl]-2-oxo-1-(pyridin-3-ylmethyl)-1,2-dihydropyridine-3-carboxamide;

III-6 N-({5-[5-amino-3-({4-[(dimethylamino)methyl]phenyl}amino)-1H-1,2,4-triazol-1-yl]-1H-pyrrolo[3,2-b]pyridin-2-yl}methyl)-2-oxo-1-(pyridin-3-ylmethyl)-1,2-dihydropyridine-3-carboxamide;

III-7 N-({5-[5-amino-3-({4-[(dimethylamino)methyl]phenyl}amino)-1H-1,2,4-triazol-1-yl]-1-methyl-1H-pyrrolo[3,2-b]pyridin-2-yl}methyl)-2-oxo-1-(pyridin-3-ylmethyl)-1,2-dihydropyridine-3-carboxamide;

III-8 N-(2-{6-[5-amino-3-({4-[(dimethylamino)methyl]phenyl}amino)-1H-1,2,4-triazol-1-yl]pyridin-2-yl}ethyl)-2-oxo-1-(pyridin-3-ylmethyl)-1,2-dihydropyridine-3-carboxamide;

III-9 N-{2-[6-(5-amino-3-{[4-(4-methylpiperazin-1-yl)phenyl]amino}-1H-1,2,4-triazol-1-yl)pyridin-2-yl]ethyl}-2-oxo-1-(pyridin-3-ylmethyl)-1,2-dihydropyridine-3-carboxamide;

III-10 N-(2-{4-[5-amino-3-({4-[(dimethylamino)methyl]phenyl}amino)-1H-1,2,4-triazol-1-yl]pyrimidin-2-yl}ethyl)-2-oxo-1-(pyridin-3-ylmethyl)-1,2-dihydropyridine-3-carboxamide;

III-11 N-{2-[4-(5-amino-3-{[4-(4-methylpiperazin-1-yl)phenyl]amino}-1H-1,2,4-triazol-1-yl)pyrimidin-2-yl]ethyl}-2-oxo-1-(pyridin-3-ylmethyl)-1,2-dihydropyridine-3-carboxamide;

III-12 N-{(2E)-3-[2-({4-[(dimethylamino)methyl]phenyl}amino)quinazolin-6-yl]prop-2-en-1-yl}-2-oxo-1-(pyridin-3-ylmethyl)-1,2-dihydropyridine-3-carboxamide;

III-13 1-[(6-chloropyridin-3-yl)methyl]-N-{(2E)-3-[2-({4-[(dimethylamino)methyl]-phenyl}amino)quinazolin-6-yl]prop-2-en-1-yl}-2-oxo-1,2-dihydropyridine-3-carboxamide;

III-14 N-{(2E)-3-[2-({3-fluoro-4-[(1-methylpiperidin-4-yl)amino]phenyl}amino)quinazolin-6-yl]prop-2-en-1-yl}-2-oxo-1-{[6-(trifluoromethyl)pyridin-3-yl]methyl}-1,2-dihydropyridine-3-carboxamide;

III-15 N-{(2E)-3-[2-({4-[methyl(1-methylpiperidin-4-yl)amino]phenyl}amino)quinazolin-6-yl]prop-2-en-1-yl}-2-oxo-1-{[6-(trifluoromethyl)pyridin-3-yl]methyl}-1,2-dihydropyridine-3-carboxamide;

III-16 N-{(2E)-3-[2-({4-[(dimethylamino)methyl]phenyl}amino)quinazolin-6-yl]prop-2-en-1-yl}-2-oxo-1-{[6-(trifluoromethyl)pyridin-3-yl]methyl}-1,2-dihydropyridine-3-carboxamide;

III-17 N-{(2E)-3-[8-(3-aminoprop oxy)-2-{[4-(morpholin-4-yl)phenyl]amino}quinazolin-6-yl]prop-2-en-1-yl}-2-oxo-1-(pyridin-3-ylmethyl)-1,2-dihydropyridine-3-carboxamide;

III-18 N-{(2E)-3-[8-(3-aminoprop oxy)-2-{[4-(morpholin-4-yl)phenyl]amino}quinazolin-6-yl]prop-2-en-1-yl}-1-[(6-chlorpyridin-3-yl)methyl]-2-oxo-1,2-dihydropyridine-3-carboxamide;

III-19 N-{(2E)-3-[2-({4-[(dimethylamino)methyl]phenyl}amino)-5-fluoroquinazolin-6-yl]prop-2-en-1-yl}-2-oxo-1-(pyridin-3-ylmethyl)-1,2-dihydropyridine-3-carboxamide;

III-20 1-[(6-chloropyridin-3-yl)methyl]-N-{(2E)-3-[2-({4-[(dimethylamino)methyl]-phenyl}amino)-5-fluoroquinazolin-6-yl]prop-2-en-1-yl}-2-oxo-1,2-dihydropyridine-3-carboxamide;

III-21 N-{(2E)-3-[5-methyl-2-{[4-(morpholin-4-yl)phenyl]amino}-7-oxo-8-(propane-2-yl)-7,8-dihydropyrido[2,3-d]pyrimidin-6-yl]prop-2-en-1-yl}-2-oxo-1-(pyridin-3-ylmethyl)-1,2-dihydropyridine-3-carboxamide;

III-22 1-[(6-chloropyridin-3-yl)methyl]-N-{(2E)-3-[5-methyl-2-{[4-(morpholin-4-yl)-phenyl]amino}-7-oxo-8-(propane-2-yl)-7,8-dihydropyrido[2,3-d]pyrimidin-6-yl]prop-2-en-1-yl}-2-oxo-1,2-dihydropyridine-3-carboxamide;

III-23 N-{(2E)-3-[2-({4-[(dimethylamino)methyl]phenyl}amino)pyrido[3,4-d]pyrimidin-6-yl]prop-2-en-1-yl}-2-oxo-1-(pyridin-3-ylmethyl)-1,2-dihydropyridine-3-carboxamide;

III-24 1-[(6-chloropyridin-3-yl)methyl]-N-{(2E)-3-[2-({4-[(dimethylamino)methyl]-phenyl}amino)pyrido[3,4-d]pyrimidin-6-yl]prop-2-en-1-yl}-2-oxo-1,2-dihydropyridine-3-carboxamide;

III-25 N-{(2E)-3-[2-({4-[(dimethylamino)methyl]phenyl}amino)pyrido[2,3-d]pyrimidin-6-yl]prop-2-en-1-yl}-2-oxo-1-(pyridin-3-ylmethyl)-1,2-dihydropyridine-3-carboxamide;

III-26 1-[(6-chloropyridin-3-yl)methyl]-N-{(2E)-3-[2-({4-[(dimethylamino)methyl]-phenyl}amino)pyrido[2,3-d]pyrimidin-6-yl]prop-2-en-1-yl}-2-oxo-1,2-dihydropyridine-3-carboxamide;

III-27 2-oxo-1-(pyridin-3-ylmethyl)-N-{(2E)-3-[3-(1H-pyrrol-2-yl)-1H-indazol-6-yl]prop-2-en-1-yl}-1,2-dihydropyridine-3-carboxamide;

III-28 1-[(6-chloropyridin-3-yl)methyl]-2-oxo-N-{(2E)-3-[3-(1H-pyrrol-2-yl)-1H-indazol-6-yl]prop-2-en-1-yl}-1,2-dihydropyridine-3-carboxamide;

III-29 2-oxo-1-(pyridin-3-ylmethyl)-N-{3-[3-(1H-pyrrol-2-yl)-1H-indazol-6-yl]prop-2-yn-1-yl}-1,2-dihydropyridine-3-carboxamide;

III-30 1-[(6-chloropyridin-3-yl)methyl]-2-oxo-N-{3-[3-(1H-pyrrol-2-yl)-1H-indazol-6-yl]prop-2-yn-1-yl}-1,2-dihydropyridine-3-carboxamide;

III-31 N-[(2E)-3-(3-{4-[(dimethylamino)methyl]phenyl}-1H-indazol-6-yl)prop-2-en-1-yl]-2-oxo-1-(pyridin-3-ylmethyl)-1,2-dihydropyridine-3-carboxamide;

III-32 1-[(6-chloropyridin-3-yl)methyl]-N-[(2E)-3-(3-{4-[(dimethylamino)methyl]-phenyl}-1H-indazol-6-yl)prop-2-en-1-yl]-2-oxo-1,2-dihydropyridine-3-carboxamide;

III-33 N-[3-(3-{4-[(dimethylamino)methyl]phenyl}-1H-indazol-6-yl)prop-2-yn-1-yl]-2-oxo-1-(pyridin-3-ylmethyl)-1,2-dihydropyridine-3-carboxamide;

III-34 1-[(6-chloropyridin-3-yl)methyl]-N-[3-(3-{4-[(dimethylamino)methyl]phenyl}-1H-indazol-6-yl)prop-2-yn-1-yl]-2-oxo-1,2-dihydropyridine-3-carboxamide;

III-35 N-{1-[2-({4-[(dimethylamino)methyl]phenyl}amino)quinazolin-6-yl]pyrrolidin-3-yl}-2-oxo-1-(pyridin-3-ylmethyl)-1,2-dihydropyridine-3-carboxamide;

III-36 1-[(6-chloropyridin-3-yl)methyl]-N-{1-[2-({4-[(dimethylamino)methyl]phenyl}-amino)quinazolin-6-yl]pyrrolidin-3-yl}-2-oxo-1,2-dihydropyridine-3-carboxamide;

IV-1 N-{3-[3-(1H-indole-2-yl)-4,6-dihydropyrrolo[3,4-c]pyrazol-5(1H)-yl]-3-oxopropyl}-2-oxo-1-(pyridin-3-ylmethyl)-1,2-dihydropyridine-3-carboxamide;

IV-2 1-[(6-chloropyridin-3-yl)methyl]-N-{3-[3-(1H-indol-2-yl)-4,6-dihydropyrrolo[3,4-c]pyrazol-5(1H)-yl]-3-oxopropyl}-2-oxo-1,2-dihydropyridine-3-carboxamide;

IV-3 N-{3-[3-({[4-(4-methylpiperazin-1-yl)phenyl]carbonyl}amino)-4,6-dihydropyrrolo[3,4-c]pyrazol-5(1H)-yl]-3-oxopropyl}-2-oxo-1-(pyridin-3-ylmethyl)-1,2-dihydropyridine-3-carboxamide;

In another aspect the invention relates to compounds—or the pharmacologically acceptable salts thereof—of general formula (1) as pharmaceutical compositions.

In another aspect the invention relates to compounds—or the pharmacologically acceptable salts thereof—of general formula (1) for the treatment and/or prevention of cancer, infections, inflammations and autoimmune diseases.

In another aspect the invention relates to compounds—or the pharmacologically acceptable salts thereof—of general formula (1) for the treatment and/or prevention of cancer.

In another aspect the invention relates to pharmaceutical preparations, containing as active substance one or more compounds of general formula (1) or the pharmacologically acceptable salts thereof, optionally in combination with conventional excipients and/or carriers.

In another aspect the invention relates to a pharmaceutical preparation comprising a compound of general formula (1), while the compounds (1) may optionally also be in the form of the tautomers, racemates, enantiomers, diastereomers, mixtures thereof or as the respective pharmacologically acceptable salts of all the above-mentioned forms, and at least one other cytostatic or cytotoxic active substance different from formula (1).

DEFINITIONS

As used herein, the following definitions apply, unless stated otherwise:

The use of the prefix $C_{x-y}$, where x and y in each case denote a natural number (x<y), indicates that the chain or cyclic structure or combination of chain and cyclic structure referred to and mentioned in direction connection may consist in total of a maximum of y and a minimum of x carbon atoms.

The information as to the number of members in groups containing one or more hetero atom(s) (hetero alkyl, heteroaryl, heteroarylalkyl, heterocycloalkyl, heterocycloalkyl) refers to the total atomic number of all the ring members or chain members or the total of all the ring and chain members.

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl at least one triple bond. If a hydrocarbon chain should have both at least one double bond and at least one triple bond, by definition it belongs to the alkynyl sub-group. All the above-mentioned sub-groups may be further subdivided into straight-chain (unbranched) and branched. If an alkyl is substituted, it may be mono- or polysubstituted independently of one another at all the hydrogen-carrying carbon atoms.

Examples of individual sub-groups are listed below.

Straight-Chain (Unbranched) or Branched, Saturated Hydrocarbon Chains:
methyl; ethyl; n-propyl; isopropyl (1-methylethyl); n-butyl; 1-methylpropyl; isobutyl (2-methylpropyl); sec.-butyl (1-methylpropyl); tert.-butyl (1.1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chained (Unbranched) or Branched Alkenyl:
vinyl (ethenyl); prop-1-enyl; allyl (prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methylprop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:
ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. unless otherwise stated are meant saturated hydrocarbon groups with the corresponding number of carbon atoms, including all the isomeric forms.

By the terms propenyl, butenyl, pentenyl, hexenyl, heptenyl, octenyl, nonenyl, decenyl etc. unless otherwise stated are meant unsaturated hydrocarbon groups with the corresponding number of carbon atoms and a double bond, including all the isomeric forms, also (Z)/(E)-isomers, where applicable.

By the terms butadienyl, pentadienyl, hexadienyl, heptadienyl, octadienyl, nonadienyl, decadienyl etc. unless otherwise stated are meant unsaturated hydrocarbon groups with the corresponding number of carbon atoms and two double bonds, including all the isomeric forms, also (Z)/(E)-isomers, where applicable.

By the terms propynyl, butynyl, pentynyl, hexynyl, heptynyl, octynyl, nonynyl, decynyl etc. unless otherwise stated are meant unsaturated hydrocarbon groups with the corresponding number of carbon atoms and a triple bond, including all the isomeric forms.

From alkyl as hereinbefore defined and its subgroups the term alkylene can also be derived. Alkylene unlike alkyl is bivalent and requires two bonding partners. Formally the second valency is produced by removing a hydrogen atom from an alkyl. Corresponding groups are for example —CH$_3$ and —CH$_2$, —CH$_2$CH$_3$ and —CH$_2$CH$_2$ or >CHCH$_3$ etc. For all the subgroups of alkyl there are correspondences for alkylene.

By heteroatoms are meant oxygen, nitrogen and sulphur atoms.

By the term heteroalkyl are meant groups which are derived from the alkyl as hereinbefore defined in its widest sense by replacing, in the hydrocarbon chains, one or more of the groups —CH$_3$ independently of one another by the groups —OH, —SH or —NH$_2$, one or more of the groups —CH$_2$— independently of one another by the groups —O—, —S— or —NH—, one or more of the groups >CH— by the group >N, one or more of the groups =CH— by the group =N, one or more of the groups =CH$_2$ by the group =NH or one or more of the groups ≡CH by the group ≡N, while a total of not more than three heteroatoms may be present in one heteroalkyl, there must be at least one carbon atom between two oxygen atoms and between two sulphur atoms or between one oxygen and one sulphur atom and the group as a whole must have chemical stability.

A direct result of the indirect definition/derivation from alkyl is that heteroalkyl is made up of the sub-groups saturated hydrocarbon chains with heteroatom(s), heteroalkenyl and heteroalkynyl, and it may be further subdivided into straight-chain (unbranched) and branched. If a heteroalkyl is substituted, it may be mono- or polysubstituted independently of one another at all the hydrogen-carrying oxygen, sulphur, nitrogen and/or carbon atoms. Heteroalkyl itself as a substituent may be attached to the molecule both through a carbon atom and through a heteroatom.

The following are listed by way of example:
dimethylaminomethyl; dimethylaminoethyl (1-dimethylaminoethyl; 2-dimethylaminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylamino ethyl (1-diisopropylamino ethyl, 2-diisopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

From heteroalkyl as hereinbefore defined and its subgroups the term heteroalkylene can also be derived. Heteroalkylene unlike heteroalkyl is bivalent and requires two bonding partners. Formally the second valency is produced by removing a hydrogen atom from a heteroalkyl. Corresponding groups are for example —CH$_2$NH$_2$ and —CH$_2$NH or >CHNH$_2$, —NHCH$_3$ and >NCH$_3$ or —NHCH$_2$, —CH$_2$OCH$_3$ and —CH$_2$OCH$_2$ or >CHOCH$_3$ etc. For all the subgroups of heteroalkyl there are correspondences for heteroalkylene.

Haloalkyl is derived from alkyl as hereinbefore defined in its broadest sense, by replacing one or more hydrogen atoms of the hydrocarbon chain independently of one another by halogen atoms, which may be identical or different. A direct result of the indirect definition/derivation from alkyl is that haloalkyl is made up of the sub-groups saturated hydrohalogen chains, haloalkenyl and haloalkynyl, and it may be further subdivided into straight-chain (unbranched) and branched. If a haloalkyl is substituted, it may be mono- or polysubstituted independently of one another at all the hydrogen-carrying carbon atoms.

Typical examples are listed below:
—CF$_3$; —CHF$_2$; —CH$_2$F; —CF$_2$CF$_3$; —CHFCF$_3$; —CH$_2$CF$_3$; —CF$_2$CH$_3$; —CHFCH$_3$; —CF$_2$CF$_2$CF$_3$; —CF$_2$CH$_2$CH$_3$; —CF=CF$_2$; —CCl=CH$_2$; —CBr=CH$_2$; —CI=CH$_2$; —C≡C—CF$_3$; —CHFCH$_2$CH$_3$; —CHFCH$_2$CF$_3$ etc.

From haloalkyl as hereinbefore defined and its subgroups the term haloalkylene can also be derived. Haloalkylene unlike haloalkyl is bivalent and requires two bonding partners.

Formally the second valency is produced by removing a hydrogen atom from a haloalkyl. Corresponding groups are for example —CH$_2$F and —CHF, —CHFCH$_2$F and —CHFCHF or >CFCH$_2$F etc. For all the subgroups of haloalkyl there are correspondences for haloalkylene.

Halogen encompasses fluorine, chlorine, bromine and/or iodine atoms.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). By unsaturated is meant that there is at least one double bond in the ring system, but no aromatic system is formed. In bicyclic hydrocarbon rings two rings are linked such that they share at least two carbon atoms. In spirohydrocarbon rings one carbon atom (spiroatom) is shared by two rings. If a cycloalkyl is substituted, it may be mono- or polysubstituted independently of one another at all the hydrogen-carrying carbon atoms. Cycloalkyl itself as a substituent may be attached to the molecule through any suitable position of the ring system.

The following individual sub-groups are listed by way of example:

Monocyclic Hydrocarbon Rings, Saturated:

cyclopropyl; cyclobutyl; cyclopentyl; cyclohexyl; cycloheptyl etc.

Monocyclic Hydrocarbon Rings, Unsaturated:

cycloprop-1-enyl; cycloprop-2-enyl; cyclo but-1-enyl; cyclobut-2-enyl; cyclopent-1-enyl; cyclopent-2-enyl; cyclopent-3-enyl; cyclo hex-1-enyl; cyclohex-2-enyl; cyclo hex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.

Bicyclic Hydrocarbon Rings (Saturated and Unsaturated):

bicyclo[2.2.0]hexyl; bicyclo[3.2.0]heptyl; bicyclo[3.2.1]octyl; bicyclo[2.2.2]octyl; bicyclo[4.3.0]nonyl (octahydroindenyl); bicyclo[4.4.0]decyl (decahydronaphthalene); bicyclo[2.2.1]heptyl (norbornyl); (bicyclo[2.2.1]hepta-2,5-dienyl (norborna-2,5-dienyl); bicyclo[2.2.1]hept-2-enyl (norbornenyl); bicyclo[4.1.0]heptyl (norcaranyl); bicyclo-[3.1.1]heptyl (pinanyl) etc.

Spirohydrocarbon Rings (Saturated and Unsaturated):

spiro[2.5]octyl, spiro[3.3]heptyl, spiro[4.5]dec-2-ene, etc.

If the free valency of a cycloalkyl is saturated off, an alicyclic ring is obtained.

From cycloalkyl as hereinbefore defined and its subgroups the term cycloalkylene can also be derived. Cycloalkylene unlike cycloalkyl is bivalent and requires two bonding partners. Formally the second valency is produced by removing a hydrogen atom from a cycloalkyl. Corresponding groups are for example cyclohexyl and

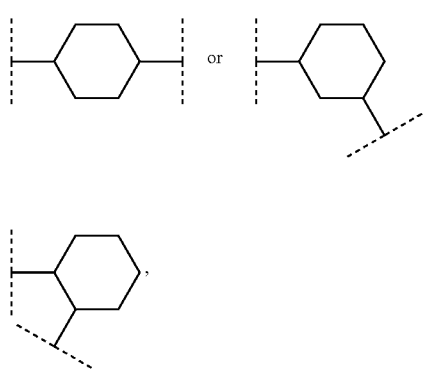

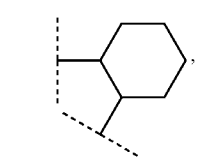

cyclopentenyl and

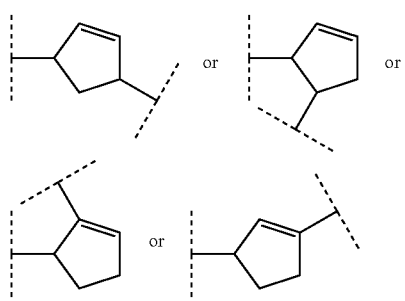

etc.

For all the subgroups of cycloalkyl there are correspondences for cycloalkylene.

Cycloalkylalkyl refers to the combination of the alkyl in question, as hereinbefore defined, with cycloalkyl, both in their widest sense. Alternatively cycloalkylalkyl may also be regarded as a combination of cycloalkyl with alkylene. Formally, cycloalkylalkyl is obtained by first linking an alkyl as substituent directly with the molecule and then substituting with a cycloalkyl. The linking of alkyl and cycloalkyl may be carried out in both groups using carbon atoms that are suitable for this purpose. The respective subgroups of alkyl (alkylene) and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system.

Typical examples are listed below:

phenyl, naphthyl, indanyl (2,3-dihydroindenyl), 1,2,3,4-tetrahydronaphthyl; fluorenyl, etc.

If the free valency of an aryl is saturated off, an aromatic group is obtained.

From aryl as hereinbefore defined the term arylene can also be derived. Arylene unlike aryl is bivalent and requires two bonding partners. Formally the second valency is produced by removing a hydrogen atom from an aryl. Corresponding groups are for example phenyl and

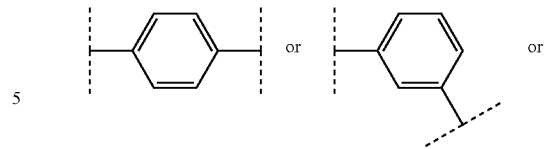

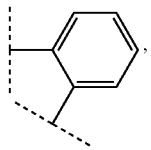

naphthyl and

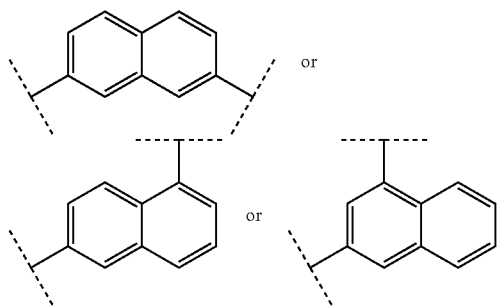

etc. For all the subgroups of aryl there are correspondences for arylene.

Arylalkyl denotes the combination of the groups alkyl and aryl as hereinbefore defined, in each case in their broadest sense. Alternatively arylalkyl may also be regarded as a combination of aryl with alkylene. Formally, arylalkyl is obtained by first linking an alkyl as substituent directly to the molecule and substituting it with an aryl group. The alkyl and aryl may be linked in both groups via any carbon atoms suitable for this purpose. The respective sub-groups of alkyl (alkylene) and aryl are also included in the combination of the two groups.

Typical examples are listed below:

benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. The prerequisite for the presence of heteroaryl is a heteroatom and an aromatic system, although it need not necessarily be a heteroaromatic system. Thus 2,3-dihydro-1H-indol-6-yl

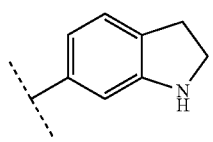

may according to the definition be a heteroaryl.

If a heteroaryl is substituted, the substitution may be mono- or polysubstitution in each case, at all the hydrogen-carrying carbon and/or nitrogen atoms, independently of one another.

Heteroaryl itself as substituent may be linked to the molecule via any suitable position of the ring system, both carbon and nitrogen.

Typical examples are listed below.

Monocyclic Heteroaryls:

furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.

Polycyclic Heteroaryls indolyl; isoindolyl; benzofuryl; benzothienyl; benzoxazolyl; benzothiazolyl; benzisoxazolyl; benzisothiazolyl; dihydroindolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydro-thienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; coumarinyl; isocoumarinyl; chromonyl; chromanonyl; tetrahydro quinolinyl; dihydro quinolinyl; dihydroquinolinonyl; dihydroisoquinolinonyl; dihydro coumarinyl; dihydroisocoumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzothiopyranyl-S-oxide and benzothiopyranyl-S,S-dioxide etc.

If the free valency of a heteroaryl is saturated off, a heteroaromatic group is obtained.

From heteroaryl as hereinbefore defined the term heteroarylene can also be derived. Heteroarylene unlike heteroaryl is bivalent and requires two bonding partners. Formally the second valency is produced by removing a hydrogen atom from a heteroaryl.

Corresponding groups are for example pyrrolyl and

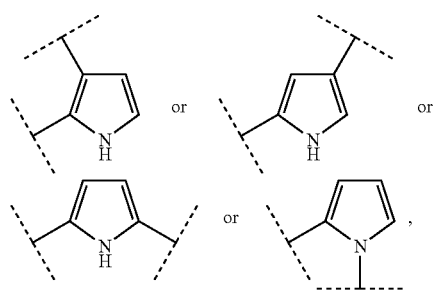

2,3-dihydro-1H-indolyl and

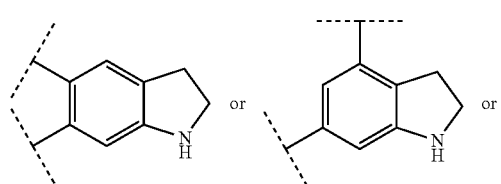

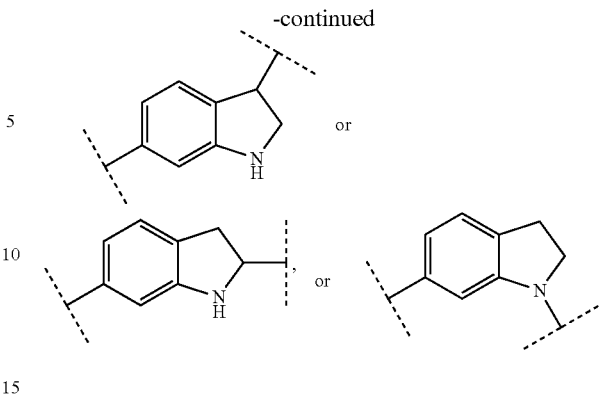

etc.

For all the subgroups of heteroaryl there are correspondences for heteroarylene.

Heteroarylalkyl denotes the combination of the alkyl in question as hereinbefore defined with heteroaryl, both in their broadest sense. Alternatively heteroarylalkyl may also be regarded as a combination of heteroaryl with alkylene. Formally heteroarylalkyl is obtained by first linking an alkyl as substituent directly with the molecule and then substituting it with a heteroaryl. The linking of the alkyl and heteroaryl may be achieved on the alkyl side via any carbon atoms suitable for this purpose and on the heteroaryl side via any carbon or nitrogen atoms suitable for this purpose. The respective subgroups of alkyl (alkylene) and heteroaryl are also included in the combination of the two groups.

By the term heterocycloalkyl are meant groups which are derived from the cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —SO$_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.

Monocyclic Heterorings (Saturated and Unsaturated):

tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-S-oxide; thio morpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydropyrimidinyl; dihydrofuryl; dihydropyranyl; tetrahydrothienyl-S-oxide; tetrahydrothienyl-S,S-dioxide; homothiomorpholinyl-5-oxide; 2,3-dihydroazet; 2H-pyrrolyl; 4H-pyranyl; 1,4-dihydropyridinyl etc.
Bicyclic Heterorings (Saturated and Unsaturated):
8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3,8-diaza-bicyclo[3.2.1]octyl; 2,5-diaza-bicyclo-[2.2.1]heptyl; 1-aza-bicyclo[2.2.2]octyl; 3,8-diaza-bicyclo[3.2.1]octyl; 3,9-diaza-bicyclo[4.2.1]nonyl; 2,6-diaza-bicyclo[3.2.2]nonyl etc.
Spiro-Heterorings (Saturated and Unsaturated):
1,4-dioxa-spiro[4.5]decyl; 1-oxa-3,8-diaza-spiro[4.5]decyl; and 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

If the free valency of a heterocycloalkyl is saturated off, then a heterocyclic ring is obtained.

From heterocycloalkyl as hereinbefore defined the term heterocycloalkylene can also be derived. Heterocycloalkylene unlike heterocycloalkyl is bivalent and requires two bonding partners. Formally the second valency is produced by removing a hydrogen atom from a heterocycloalkyl. Corresponding groups are for example piperidinyl and

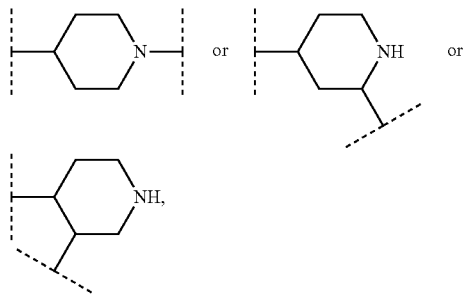

2,3-dihydro-1H-pyrrolyl and

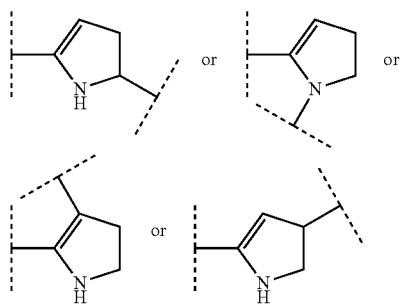

etc. For all the subgroups of heterocycloalkyl there are correspondences for heterocycloalkylene.

Heterocycloalkylalkyl denotes the combination of the alkyl in question as hereinbefore defined with heterocycloalkyl, both in their broadest sense. Alternatively heterocycloalkylalkyl may also be regarded as a combination of heterocycloalkyl with alkylene. Formally heterocycloalkyl is obtained by first linking an alkyl as substituent directly with the molecule and then substituting it with a heterocycloalkyl. The linking of the alkyl and heterocycloalkyl may be achieved on the alkyl side via any carbon atoms suitable for this purpose and on the heterocycloalkyl side via any carbon or nitrogen atoms suitable for this purpose. The respective sub-groups of alkyl and heterocycloalkyl are also included in the combination of the two groups.

By is substituted is meant that a hydrogen atom that is bound directly to the atom under consideration is replaced by another atom or another group of atoms (substituent). Depending on the starting conditions (number of hydrogen atoms) mono- or polysubstitution may take place at an atom.

Bivalent substituents such as for example =S, =NR, =NOR, =NNRR, =NN(R)C(O)NRR, =N$_2$ or the like may only be substituents at carbon atoms, while the bivalent substituent =O may also be a substituent of sulphur. Generally speaking, substitution by a bivalent substituent may only take place at ring systems and requires exchange for two geminal hydrogen atoms, i.e. hydrogen atoms that are bound to the same carbon atom saturated before the substitution. Substitution by a bivalent substituent is therefore only possible at the group —CH$_2$— or sulphur atoms of a ring system.

In addition to this, the term "suitable substituent" denotes a substituent which on the one hand is suitable on account of its valency and on the other hand leads to a system with chemical stability.

The following are some abbreviated notations and their structural correspondences:

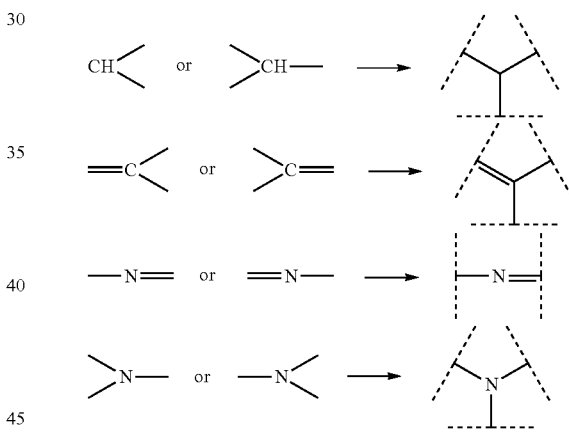

If for example in the sequence A-B-C the member B were to correspond to the structural detail —N=, this is to be understood as both A=N—C and A-N=C.

If for example in the sequence

the member A were to correspond to the structural detail >C=
this is to be understood as being

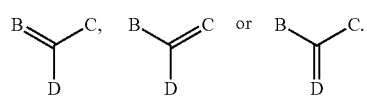

In a diagram such as for example

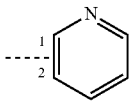

the dotted line indicates that the ring system may be attached to the molecule via the carbon 1 or 2, i.e. is equivalent to the following diagram

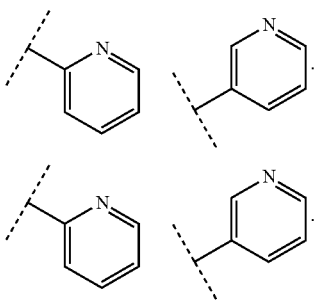

Groups or substituents are frequently selected from among alternative groups/substituents with a corresponding group designation (e.g. $R^a$, $R^b$ etc). If a group of this kind is used repeatedly to define a compound according to the invention in different parts of the molecule, it should always be borne in mind that the respective uses are to be regarded as being totally independent of one another.

List of Abbreviations

| | |
|---|---|
| aa | amino acid |
| Ac | acetyl |
| AIBN | azo-bis-(isobutyronitrile) |
| ATP | adenosine triphosphate |
| BINAP | 2,2'-bis(diphenylphosphino)-1,1'-binaphthyl |
| Boc | tert.-butyloxycarbonyl |
| BSA | bovine serum albumin |
| Bu | butyl |
| d | day(s) |
| DC, TLC | thin layer chromatography |
| DCC | dicyclohexylcarbodiimide |
| DCM | dichloromethane |
| DEA | diethylamine |
| DIC | diisopropylcarbodiimide |
| DIPEA | N-ethyl-N,N-diisopropylamine (Hünig base) |
| DMF | N,N-dimethylformamide |
| DMSO | dimethylsulphoxide |
| EDC | N-(3-dimethylaminopropyl)-N4-ethylcarbodiimide hydrochloride |
| ESI | electron spray ionization |
| Et | ethyl |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| Hünig base | N-ethyl-N,N-diisopropylamine |
| i | iso |
| cat. | catalyst, catalytic |
| conc. | concentrated |
| LC | liquid chromatography |
| sln. | solution |
| mCPBA | meta-chloro-perbenzoic acid |
| Me | methyl |
| MeOH | methanol |
| min | minutes |
| MPLC | medium pressure liquid chromatography |
| MS | mass spectrometry |
| NBS | N-bromosuccinimide |
| NMP | N-methylpyrrolidone |
| PBS | phosphate-buffered saline |
| $Pd_2dba_3$ | tris(dibenzylideneacetone)dipalladium(0) |
| $Pd(dppf)Cl_2$ | 1,1'-bis(diphenylphosphino)ferrocene palladium(II)-dichloride |
| PDK1 | phosphoinositide-dependent kinase 1 |
| Ph | phenyl |
| PI3K | phosphatidylinositol-3-kinase |
| PKT | protein kinase B |
| Pr | propyl |
| $R_f$ (Rf) | retention factor |
| RP | reversed phase |
| RT | ambient temperature |
| s | second |
| TBTU | O-(benzotriazol-1-yl)-N,N,N',N'-tetramethyl-uronium tetrafluoroborate |
| TEA | triethylamine |
| tert | tertiary |
| Tf | triflate |
| TFA | trifluoroacetic acid |
| THF | tetrahydrofuran |
| TMEDA | N,N,N,N-tetramethylethylenediamine |
| TMS | trimethylsilyl |
| Tos | tosyl |
| $t_{Ret.}$ | retention time (HPLC) |
| TRIS | tris(hydroxymethyl)-aminomethane |
| UV | ultraviolet |
| X-Phos | dicyclohexyl-(2',4',6'-triisopropylbiphenyl-2-yl)phosphane |

Features and advantages of the present invention will become apparent from the following detailed Examples, which illustrate the fundamentals of the invention by way of example, without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

Microwave reactions are carried out in an initiator made by Biotage or in an Explorer made by CEM in sealed containers (preferably 2, 5 or 20 mL), preferably with stirring.

Chromatography

The thin layer chromatography is carried out on ready-made TLC silica gel 60 plates on glass (with fluorescence indicator F-254) made by Merck.

The preparative high pressure chromatography (HPLC) is carried out using columns made by Waters (named: Sunfire C18, 5 µm, 30×100 mm Part. No. 186002572; X-Bridge C18, 5 µm, 30×100 mm Part. No. 186002982), the analytical HPLC (reaction control) using columns made by Agilent (named: Zorbax Extend C18, 3.5 µm, 2.1×50 mm, Part. No. 735700-902; Zorbax SB-C8, 3.5 µm, 2.1×50 mm, Part. No. 871700-906) and Phenomenex (named: Mercury Gemini C18, 3 µm, 2×20 mm, Part. No. 00M-4439-B0-CE).

HPLC Mass Spectroscopy/UV Spectrometry

The retention times/MS-ESI$^+$ for characterising the examples are obtained using an HPLC-MS apparatus (high performance liquid chromatography with mass detector)

made by Agilent. Compounds that elute at the injection peak have the retention time $t_{Ret.}$=0.00.

HPLC-Methods

Preparative

Prep. HPLC1:

| | |
|---|---|
| HPLC: | 333 and 334 Pumps |
| column: | Waters X-Bridge C18, 5 µm, 30 × 100 mm Part. No. 186002982 |
| eluant: | A: 10 mM NH$_4$HCO$_3$ in H$_2$O; B: acetonitrile (HPLC grade) |
| detection: | UV/Vis-155 |
| flow: | 50 mL/min |
| gradient: | 0.00 min: 5% B |
| | 3.00-15.00 min: variable (see individual methods) |
| | 15.00-17.00 min: 100% B |

Prep. HPLC2:

| | |
|---|---|
| HPLC: | 333 and 334 Pumps |
| column: | Waters Sunfire C18, 5 µm, 30 × 100 mm Part. No. 186002572 |
| eluant: | A: H$_2$O + 0.2% HCOOH; B: acetonitrile (HPLC grade) + 0.2% HCOOH |
| detection: | UV/Vis-155 |
| flow: | 50 mL/min |
| gradient: | 0.00 min: 5% B |
| | 3.00-15.00 min: variable (see individual methods) |
| | 15.00-17.00 min: 100% B |

Analytical

LCMSBAS1:

| | |
|---|---|
| HPLC: | Agilent 1100 Series |
| MS: | Agilent LC/MSD SL |
| column: | Phenomenex Mercury Gemini C18, 3 µm, 2 × 20 mm, Part. No. 00M-4439-B0-CE |
| eluant: | A: 5 mM NH$_4$HCO$_3$/20 mM NH$_3$ in H$_2$O; B: acetonitrile (HPLC grade) |
| detection: | MS: Positive and negative mode |
| mass range: | 120-700 m/z |
| flow: | 1.00 mL/min |
| column temp.: | 40° C. |
| gradient: | 0.00 min: 5% B |
| | 0.00-2.50 min: 5% → 95% B |
| | 2.50-2.80 min: 95% B |
| | 2.81-3.10 min: 95% → 5% B |

FECB3:

| | |
|---|---|
| HPLC: | Agilent 1100 Series |
| MS: | Agilent LC/MSD SL |
| column: | WatersXBridgeC18 2.1 × 50 mm, 3.5µ |
| eluant: | A: 5 mM NH$_4$HCO$_3$/20 mM NH$_3$ in H$_2$O; B: acetonitrile (HPLC grade) |
| detection: | MS: Positive and negative mode |
| mass range: | 105-1200 m/z |
| flow: | 1.20 mL/min |
| column temp.: | 35° C. |
| gradient: | 0.01 min: 5% B |
| | 0.01-1.25 min: 5% → 95% B |
| | 1.25-2.00 min: 95% B |
| | 2.00-2.01 min: 95% → 5% B |

FECB4/FECBM2:

| | |
|---|---|
| HPLC: | Agilent 1100 Series |
| MS: | Agilent LC/MSD SL |
| column: | Agilent Zorbax Extend C18, 3.5 µm, 2.1 × 50 mm, Part. No. 735700-902 |
| eluant: | A: 5 mM NH$_4$HCO$_3$/20 mM NH$_3$ in H$_2$O; B: acetonitrile (HPLC grade) |
| detection: | MS: Positive and negative mode |
| mass range: | 105-1200 m/z |
| flow: | 1.20 mL/min |
| column temp.: | 35° C. |
| gradient: | 0.01 min: 5% B |
| | 0.01-1.25 min: 5% → 95% B |
| | 1.25-2.00 min: 95% B |
| | 2.00-2.01 min: 95% → 5% B |

FECS:

| | |
|---|---|
| HPLC: | Agilent 1100 Series |
| MS: | Agilent LC/MSD SL |
| column: | Agilent Zorbax Zorbax SB-C8, 3.5 µm, 2.1 × 50 mm, Part. No. 871700-906 |
| eluant: | A: H$_2$O + 0.2% HCOOH; B: acetonitrile (HPLC grade) + 0.2% HCOOH |
| detection: | MS: Positive and negative mode |
| mass range: | 105-1200 m/z |
| flow: | 1.20 mL/min |
| column temp.: | 35° C. |
| gradient: | 0.01 min: 5% B |
| | 0.01-1.25 min: 5% → 95% B |
| | 1.25-2.00 min: 95% B |
| | 2.00-2.01 min: 95% → 5% B |

FSUN, FECSUNFIRE, FECS1:

| | |
|---|---|
| HPLC: | Agilent 1100 Series |
| MS: | Agilent LC/MSD SL |
| column: | Waters Sunfire, 2.1 × 50 mm, 3.5 µm |
| eluant: | A: H$_2$O + 0.2% HCOOH; B: acetonitrile (HPLC grade) + 0.2% HCOOH |
| detection: | MS: Positive and negative mode |
| mass range: | 105-1200 m/z |
| flow: | 1.20 mL/min |
| column temp.: | 35° C. |
| gradient: | 0.01 min: 5% B |
| | 0.01-1.50 min: 5% → 100% B |
| | 1.50-2.00 min: 100% B |
| | 2.00-2.01 min: 100% → 5% B |

FECB5:

| | |
|---|---|
| HPLC: | Agilent 1100 Series |
| MS: | Agilent LC/MSD SL |
| column: | WatersXBridge C18 2.1 × 50 mm, 5.0 µm |
| eluant: | A: 5 mM NH$_4$HCO$_3$/20 mM NH$_3$ in H$_2$O; B: acetonitrile (HPLC grade) |
| detection: | MS: Positive and negative mode |
| mass range: | 105-1200 m/z |
| flow: | 1.20 mL/min |
| column temp.: | 35° C. |
| gradient: | 0.01 min: 5% B |
| | 0.01-1.25 min: 5% → 95% B |
| | 1.25-2.00 min: 95% B |
| | 2.00-2.01 min: 95% → 5% B |

AFEC:

| | |
|---|---|
| HPLC: | Agilent 1100 Series |
| MS: | Agilent LC/MSD |
| column: | Waters Sunfire, 21 × 50 mm, 3.5 µm |
| eluant: | A: H$_2$O + 1% HCOOH; B: acetonitrile (HPLC grade) |
| detection: | MS: Positive and negative mode; UV: 254 as well as 210 nm |
| mass range: | 100-750 m/z |
| flow: | 1.00 mL/min (0.9 mL H$_2$O/MeCN, 0.1 mL formic acid buffer) |
| column temp.: | 35° C. |
| gradient: | 0.1 min: 5% B |
| | 0.1-1.50 min: 5% → 100% B |
| | 1.50-2.10 min: 100% B |
| | 2.10-2.20 min: 100% → 5% B |
| | 2.20-2.70 min: 5% B |

FEC3:

| | |
|---|---|
| HPLC: | Agilent 1100 Series |
| MS: | Agilent LC/MSD SL |
| column: | Agilent Zorbax SBC8, 2.1 × 50 mm, 3.5 µm |
| eluant: | A: H$_2$O + 0.2% HCOOH; B: acetonitrile (HPLC grade) + 0.2% HCOOH |
| detection: | MS: Positive and negative mode |
| mass range: | 105-1200 m/z |
| flow: | 1.20 mL/min |
| column temp.: | 35° C. |
| gradient: | 0.01 min: 5% B |
| | 0.01-1.50 min: 5% → 100% B |
| | 1.50-2.00 min: 100% B |
| | 2.00-2.01 min: 100% → 5% B |

The compounds according to the invention are prepared by the methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Reaction scheme A-1

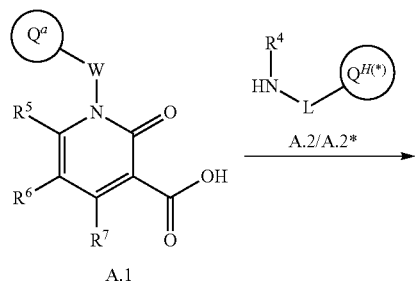

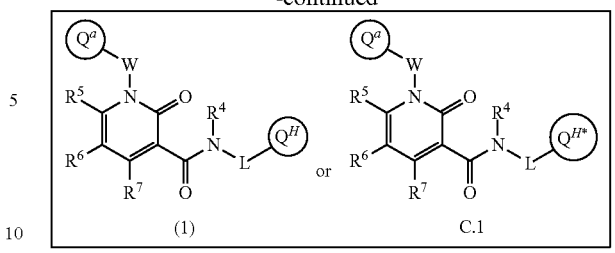

A key intermediate in the synthesis of compounds (1) according to the invention are the pyridinonecarboxylic acids A.1. Starting from compounds A.1, compounds (1) are obtained directly by amide coupling with amines A.2, while A.1 is activated by coupling reagents such as for example DCC, DIC, TBTU, HATU, EDC or the like. Carrying out this reaction requires aminic synthesis components A.2 which contain both the linker unit L and the grouping $Q^H$.

Alternatively under the same coupling conditions, synthesis components A.2* may also be coupled, by means of which first of all a precursor $Q^{H*}$ of the final grouping $Q^H$ is introduced. The intermediate C.1 obtained is then reacted in later steps to obtain compounds (1) (cf. Reaction scheme C).

In Reaction scheme A-1 and the following schemes the term $Q^{H(*)}$ is used as an abbreviation for these two alternatives, $Q^H$ and $Q^{H*}$.

Reaction scheme A-2

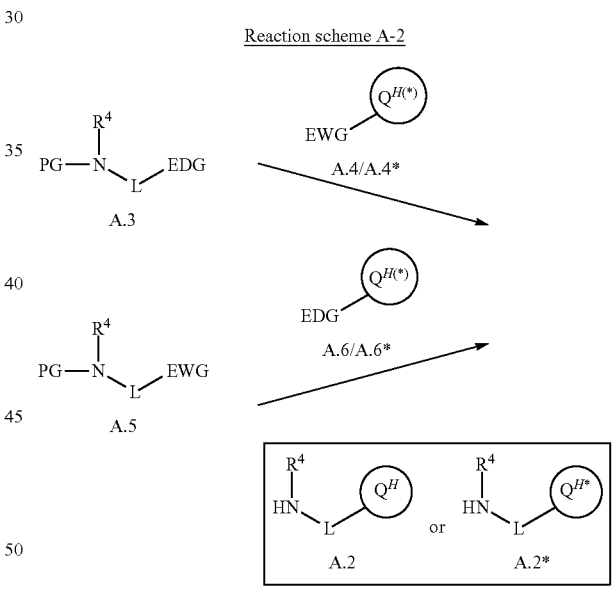

EWG = electron-attracting group, e.g. halogen, triflate, mesylate, but also —OH or a leaving group —X in an (activated) carboxyl group —C(O)OH/ —C(O)X [e.g. where L$^3$ = —C(O)—]

EDG = electron-repelling group, e.g.. —B(OH)$_2$/ —B(OR')$_2$, —MgHal, —ZnHal, SnR'$_3$ or hydrogen PG = protecting group The synthesis of the components A.2/A.2* proceeds via the incorporation of the ring system $Q^{H(*)}$ into the amines A.3 or A.5 provided with protective groups, while $Q^{H(*)}$ is introduced in the form of the activated species A.4/A.4* or A.6/A.6* (Reaction scheme A-2). These are simple reactions of substitution between nucleophils or electrophils activated by electron-attracting and -pushing groups, or transition metal-catalysed cross-coupling reactions, e.g. the BUCHWALD- HARTWIG, SUZUKI, KUMADA, STILLE, NEGISHI, HECK or SONOGASH-IRA reaction. The activating groups EWG and EDG suitable for these reactions are generally known in the art. Electron-pulling groups EWG are particularly halogen, triflate, mesylate, but also —OH or a leaving group —X in an (activated) carboxyl group —C(O)OH/—C(O)X [e.g. at $L^3$=—C(O)—]. Electron-pushing groups EDG are, in particular, boric acid and boric acid ester derivatives —B(OH)$_2$/—B(OR')$_2$, —MgHal, —ZnHal and —SnR'$_3$, but this term may also include hydrogen. Suitable groups R' are known to the skilled man. The activating groups act as leaving groups in all the types of reaction mentioned above. After the reaction of A.3 with A.4/A.4* or A.5 with A.6/A.6* the product obtained still contains the protective group PG (intermediate product A.2-PG or A.2*-PG), which is cleaved in order to obtain A.2/A.2*. Any of the amino protecting groups common in organic synthesis may be used as the protective group PG.

Optionally a component A.2* may also be converted into a component A.2, the final grouping $Q^H$ being formed from the grouping $Q^{H*}$.

Alternatively, compounds (1) according to the invention may also be synthesised stepwise (Reaction scheme A-3). To do this, first of all an amine A.7 or A.8, which in each case contains only the linker unit L, is coupled to the carboxylic acid A.1 (→A.9 or A.10) and only then is the grouping $Q^H$ introduced via the components A.4 or A.6. The linking of the linker unit L and the grouping $Q^H$ are carried out from a chemical-method point of view analogously to that described under Reaction scheme A-2. The amide coupling in the first reaction step is assisted by coupling reagents such as for example DCC, DIC, TBTU, HATU, EDC or the like.

Here too, alternatively, as in Reaction scheme A-1 and A-2, instead of A.4 and A.6 and consequently A.2, a comparable component A.4* and A.6* may be used, which introduces only one precursor $Q^{H*}$ of the final grouping $Q^H$ (intermediate stages C.1, cf. Reaction scheme C).

The synthesis components to be used in the foregoing reaction schemes are optionally provided with the customary protective groups when used. Therefore, additional intermediate steps may be needed to remove these protective groups.

Reaction scheme A-3

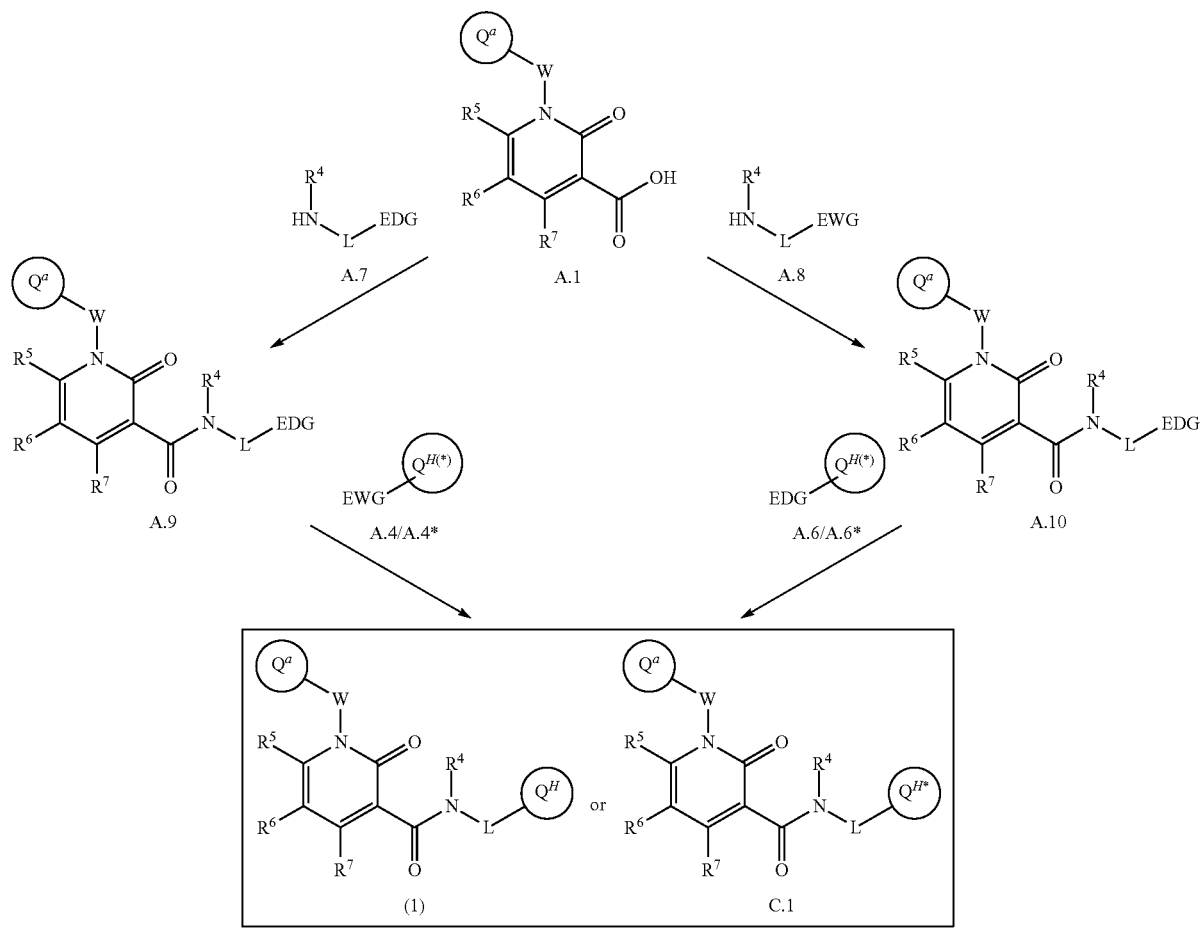

EWG = electron-attracting group, e.g. halogen, triflate, mesylate, but also —OH or a leaving group —X in an (activated) carboxyl group —C(O)OH/—C(O)X [e.g. where $L^3$ = —C(O)—]

EDG = electron-repelling group, e.g., —B(OH)$_2$/—B(OR')$_2$, —MgHal, —ZnHal, SnR'$_3$ or hydrogen The compounds (1) which may be obtained directly or stepwise according to the foregoing reaction schemes may optionally be modified by associated synthesis steps (e.g. Substitutions, acylations etc.) to obtain further compounds according to the invention (1).

With regard to the feasibility of the reaction methods described and illustrated in the foregoing reaction schemes reference is made to WO 2008/005457. In the cited specification, pyridinonecarboxylic acids 2s are amidated in various ways. The methods and variants used therein for synthesising the example compounds I-196 correspond substantially to those shown in reaction schemes A-1, A-2 and A-3, while the synthesis of intermediates that are comparable with the components A.2 to A.10 is disclosed in particular.

coupling, esterification, carbamate or urea formation (Reaction scheme A-4). This is possible if the linker fragment $L^3$ in the target compounds (1) is selected from among —C(O)O—, —C(O)NR$^g$—, —OS(O)$_2$—, —OS(O)$_2$NR$^g$—, —OC(O)—, —OC(O)O—, —OC(O)NR$^g$—, —S(O)$_2$O—, —S(O)$_2$NR$^g$—, —NR$^g$C(O)—, —NR$^g$C(O)O—, —NR$^g$C(O)NR$^g$—, —NR$^g$S(O)$_2$—, —NR$^g$S(O)$_2$O— and —NR$^g$S(O)$_2$NR$^g$—. In these cases, one of the groups R* or R** of the components A.11, A.12/A.12* or A.13 is an optionally activated carbon, sulphone, sulphur or carbonic acid function, while an alcohol or amine, is present as the other group in each case. A urea or carbamate unit for $L^3$ may also be syn-

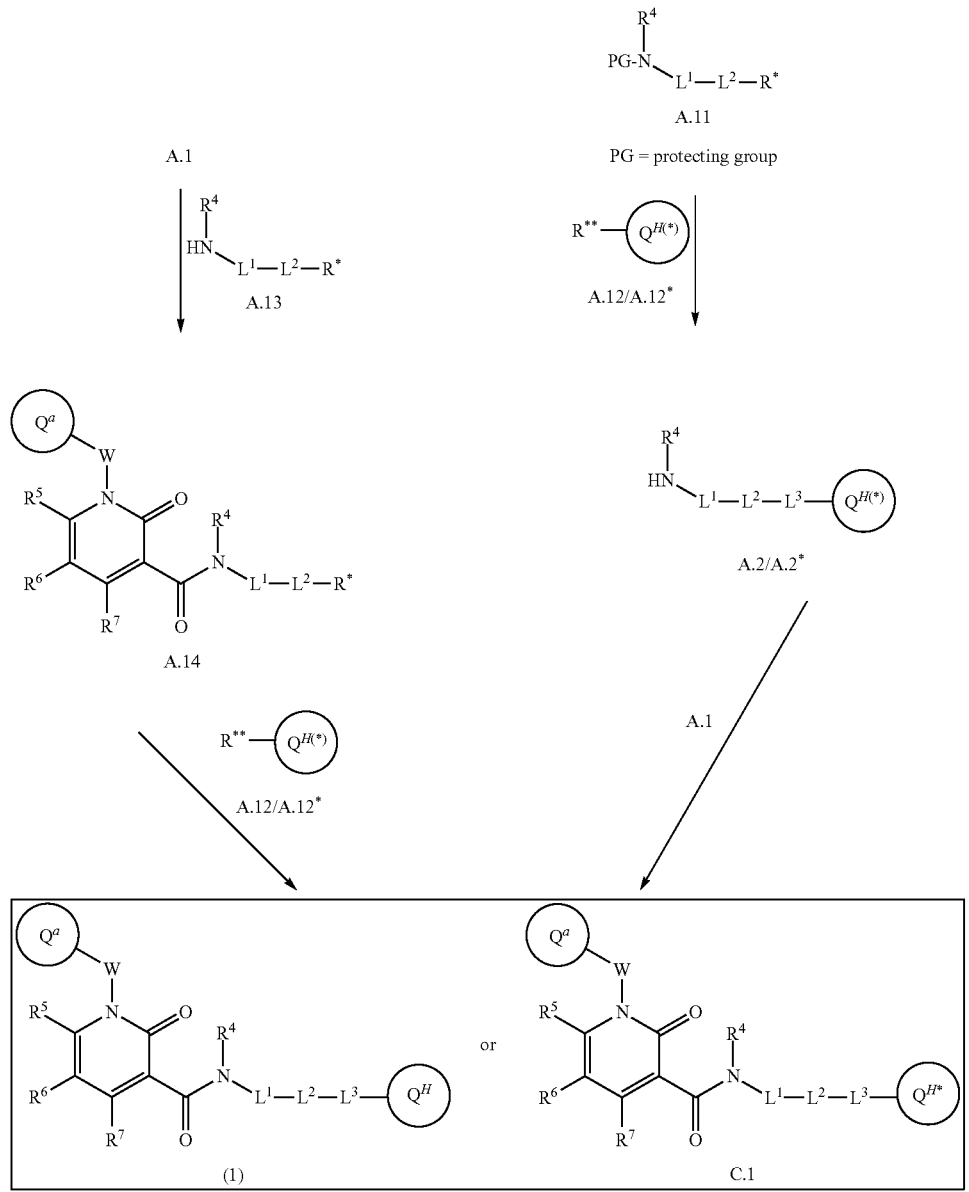

Reaction scheme A-4

In a departure from the cases shown in reaction schemes A-1 to A-3 the incorporation of the grouping $Q^H$ or a corresponding precursor $Q^{H*}$ may also be carried out by amide thesised by reacting an isocyanate A.11/A.14 or A.12/A.12* (R* or R**=—N=C=O) with an alcohol/amine A.12/A.12* or A.11/A.14.

Reaction scheme B

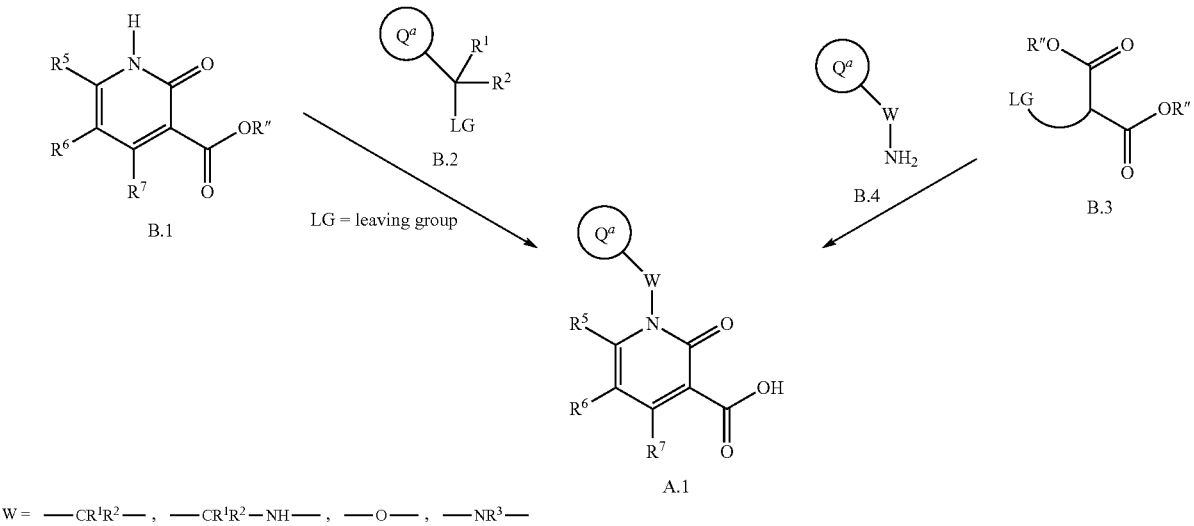

The method of synthesising pyridinonecarboxylic acids A.1 depends on the bridge unit W that joins together the ring systems $Q^a$ and $Q^b$:

Starting from the esters B.1 the grouping $Q^a$-$CR^1R^2$— may be incorporated by nucleophilic substitution at component B.2, which is activated by an electron-attracting leaving group LG, e.g. a halogen, triflate or mesylate. B.1 is optionally deprotonated for this purpose by the addition of a base.

The synthesis of a pyridinone ring system is carried out starting from malonic acid diester derivatives B.3. The derivatives used are di- or trielectrophils, which cyclise during the reaction with amines, hydroxylamines or hydrazines B.4. It is not absolutely essential for a leaving group LG to be present in compounds B.3. Instead of an electrophilic carbon activated by a leaving group, an electrophilic carbonylcarbon is also possible.

Using the synthesis methods described above, and starting from the cyclic carboxylic acid esters B.1 or their precursor B.3, after reaction with B.2 or B.4 carboxylic acid esters A.1* are obtained first of all. These are saponified in each case to form the free acid A.1. In the grouping —COOR" it is possible to have groups R" which enable this saponification to take place easily and gently. These include in particular methyl, ethyl, tert-butyl and benzyl esters, while others are known to the skilled man from his general knowledge of the art.

The educts B.1 and B.3 needed are commercially obtainable, have already been described in the literature or may be prepared according to published methods.

Reaction scheme C

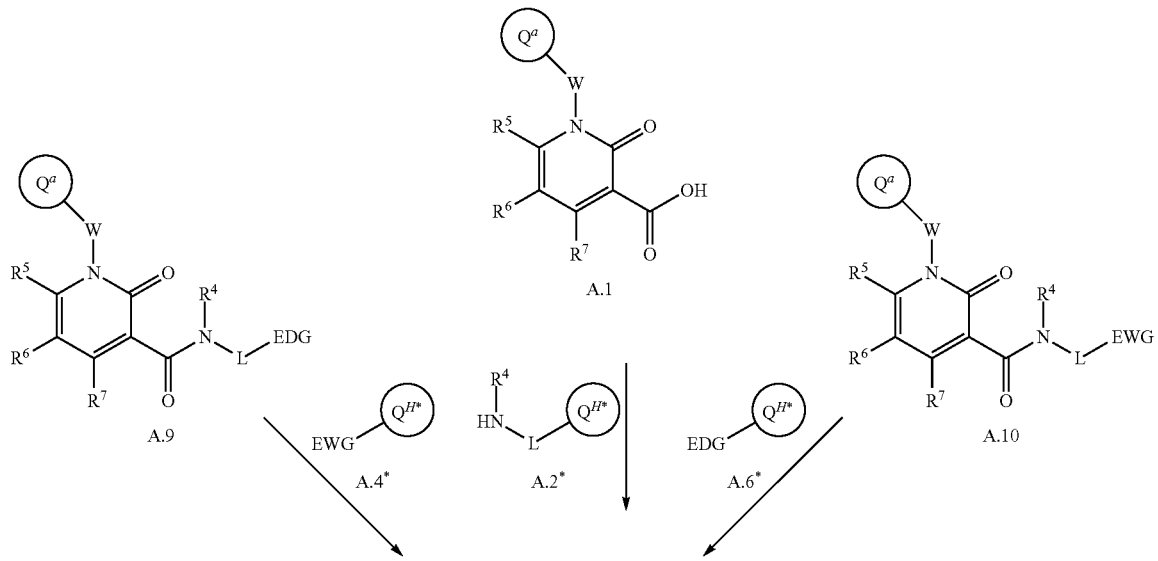

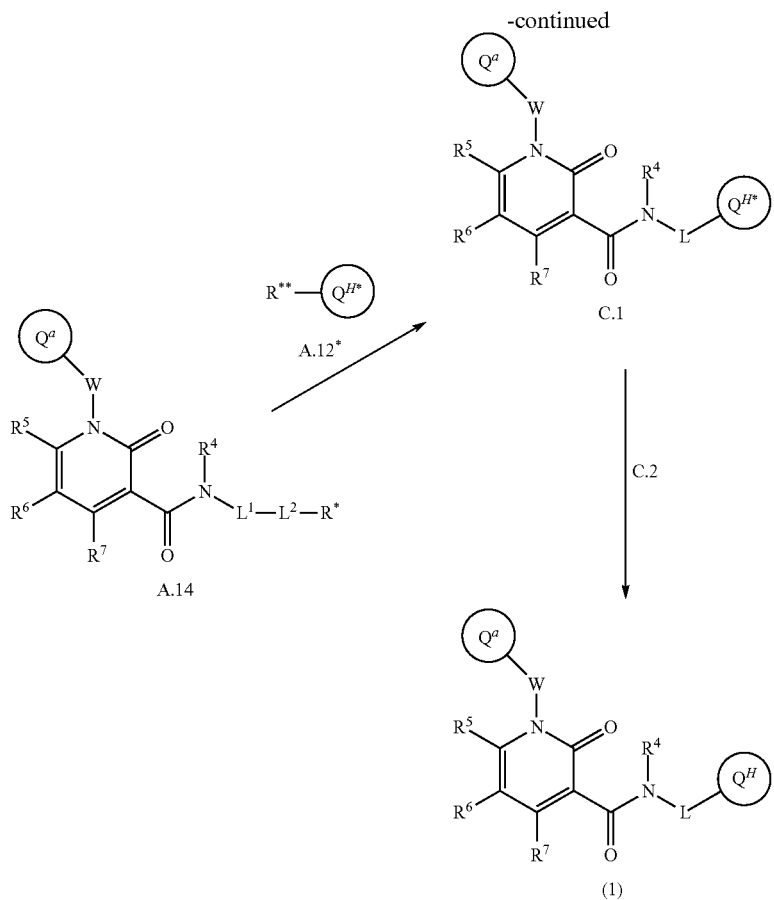

EWG = electron-attracting group, e.g. halogen, triflate, mesylate, but also —OH or a leaving group —X in an (activated) carboxyl group —C(O)OH/ —C(O)X [e.g. where L³ = —C(O)— ]

EDG = electron-repelling group, e.g.. —B(OH)₂/ —B(OR')₂, —MgHal, SnR'₃ or hydrogen The syntheses via the intermediates C.1 described hereinbefore, wherein compounds (1) according to the invention are finally obtained in one or more steps by converting $Q^{H*}$ into $Q^H$ (e.g. by reaction with compounds C.2; reaction scheme C), are used mainly for the following embodiments of $Q^H$

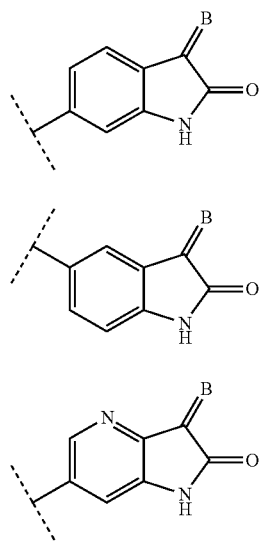

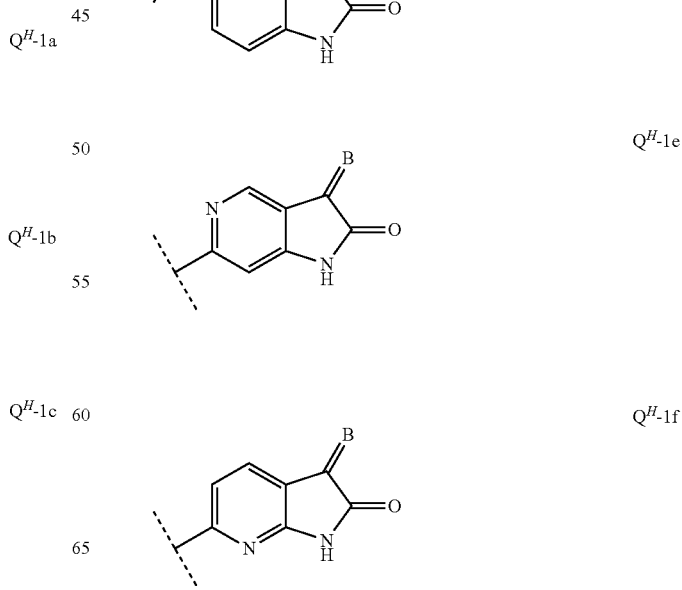

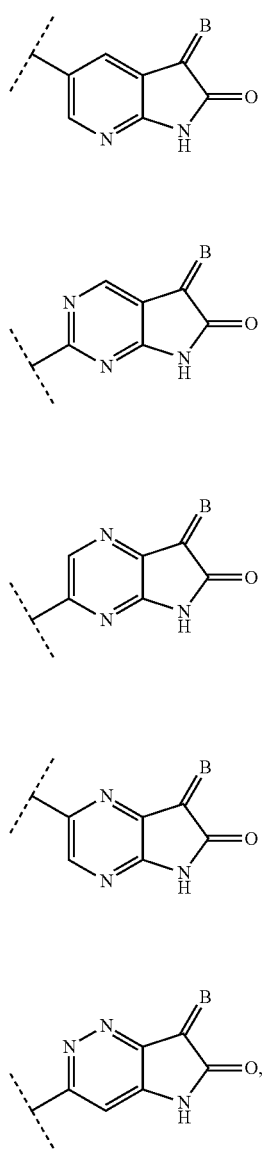

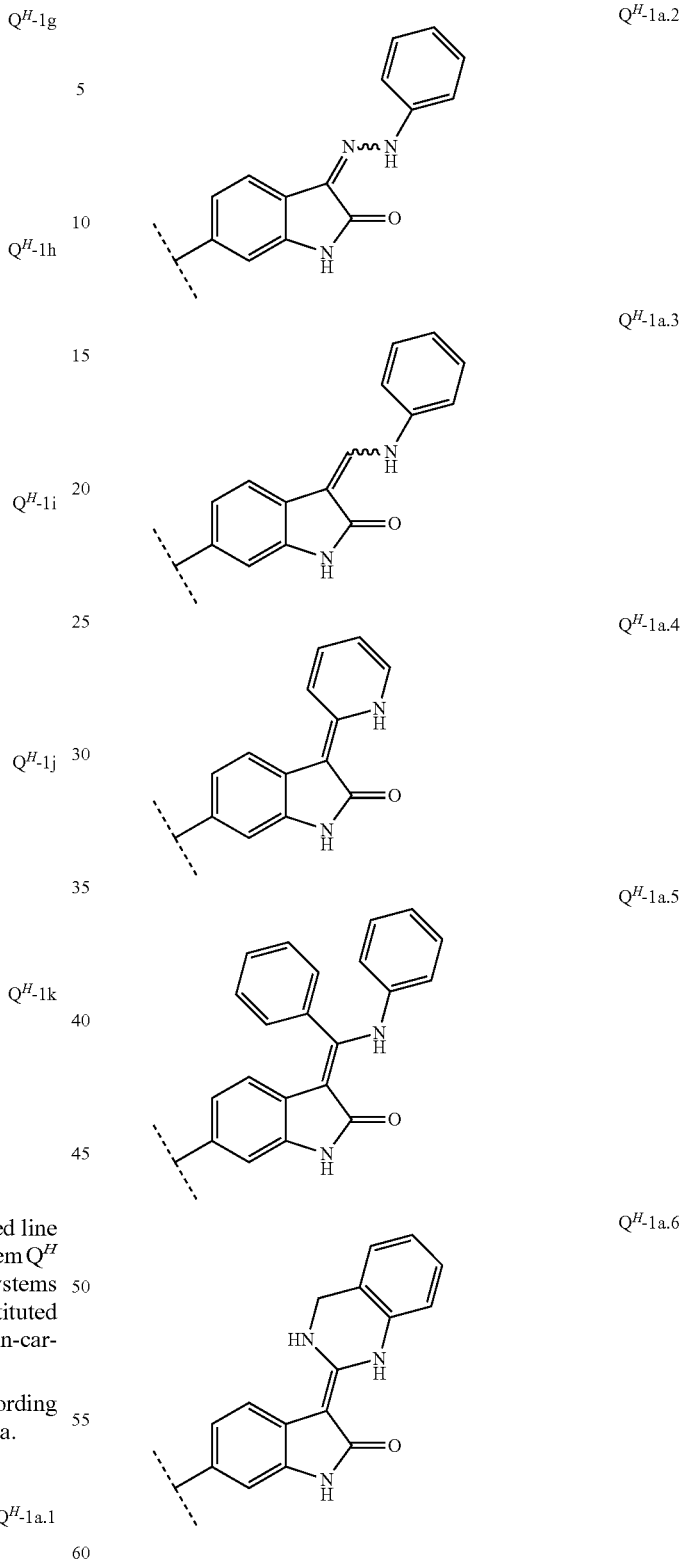

wherein B denotes =CR$^9$R$^{10}$ or =NR$^{11}$ and the dotted line indicates the cyclic atom(s) through which the ring system Q$^H$ may be attached to the linker group L. The ring systems Q$^H$-1a to Q$^H$-1k shown may each optionally be substituted independently of one another at one or more hydrogen-carrying carbon atom(s) by R$^a$ and/or R$^b$.

Typical embodiments of B in the compounds (1) according to the invention are shown below on the basis of Q$^H$-1a.

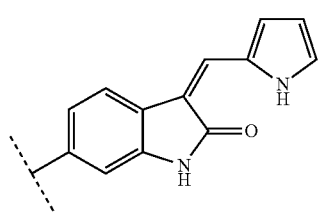

In addition, within the scope of the definitions for =CR$^9$R$^{10}$ or =NR$^{11}$ many more embodiments are possible, and in particular, unlike Q$^H$-1a.1 to Q$^H$-1a.6, in grouping B other ring systems may occur or these ring systems may also be mono- or polysubstituted within the scope of the definitions. Corresponding embodiments are also possible starting from Q$^H$-1b to Q$^H$-1k (Q$^H$-1b.1 to Q$^H$-1b.6, Q$^H$-1c.1 to $Q^H$-1c.6 etc.). Embodiments $Q^H$-1a to $Q^H$-1k or more especially $Q^H$-1a.1 to $Q^H$-1a.6 for example can be synthesised via the following key intermediates $Q^{H*}$-1a.1 to $Q^{H*}$-1a.3 (prepared on the basis of $Q^H$-1a, also analogously for $Q^H$-1b to $Q^H$-1k)

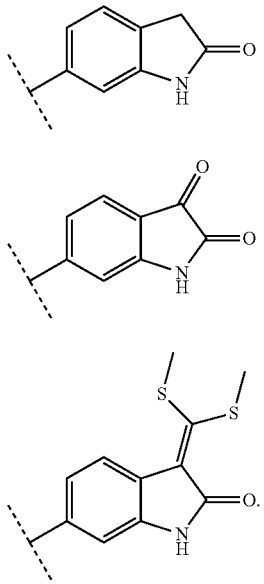

$Q^{H*}$-1a.1

$Q^{H*}$-1a.2

$Q^{H*}$-1a.3

The use of these intermediates for synthesising the embodiments $Q^H$-1a.1 to $Q^H$-1a.6 or for synthesising a plurality of embodiments analogous to $Q^H$-1a.1 to $Q^H$-1a.6, the synthesis of reactants C.2 and the preparation of the intermediates themselves are described in detail in the literature.

$Q^H$-1a.1 or analogous embodiment:
WO 96/40116, WO 98/07695, WO 98/50356, WO 00/35908, US 2005/0090541, WO 2008/005457

$Q^H$-1a.2, $Q^H$-1a.3 or analogous embodiment:
WO 99/15500, WO 00/56710

$Q^H$-1a.4 or analogous embodiment:
WO 02/094809, WO 03/053330, WO 03/082853, WO 2005/061519

$Q^H$-1a.5 or analogous embodiment:
WO 2005/087726, WO 2008/152013

$Q^H$-1a.6 or analogous embodiment:
WO 2008/152014

In order to be able to incorporate ring systems $Q^H$ or $Q^{H*}$, which are derived from the above-mentioned $Q^H$-1a to $Q^H$-1k, in the target structures according to reaction schemes A-1 to A-4 and reaction scheme C, the corresponding reactants A.2 ($R^4$—NH-L-$Q^H$) or A.2* ($R^4$—NH-L-$Q^{H*}$),
A.4 (EWG-$Q^H$) or A.4* (EWG-$Q^{H*}$),
A.6 (EDG-$Q^H$) or A.6* (EDG-$Q^{H*}$) and
A.12 ($R^{**}$-$Q^H$) or A.12* ($R^{**}$-$Q^{H*}$)

may be used, while the activating substituents EWG and EDG or the linker fragment $R^{**}$ are located at $Q^H/Q^{H*}$ in such a way that their position corresponds to the later linkage point to the linker unit L. Numerous examples of the synthesis of such components can also be found in the literature referred to hereinbefore and additionally in EP 0 436 333. Other components of this kind are also directly commercially obtainable.

In addition to the embodiments $Q^H$-1a to $Q^H$-1k there is also the possibility of incorporating further ring systems $Q^H$ via the reactants A.2/A.2*, A.4/A.4*, A.6/A.6* or A.12/A.12* in compounds (1) according to the invention. These include in particular the following systems $Q^H$:

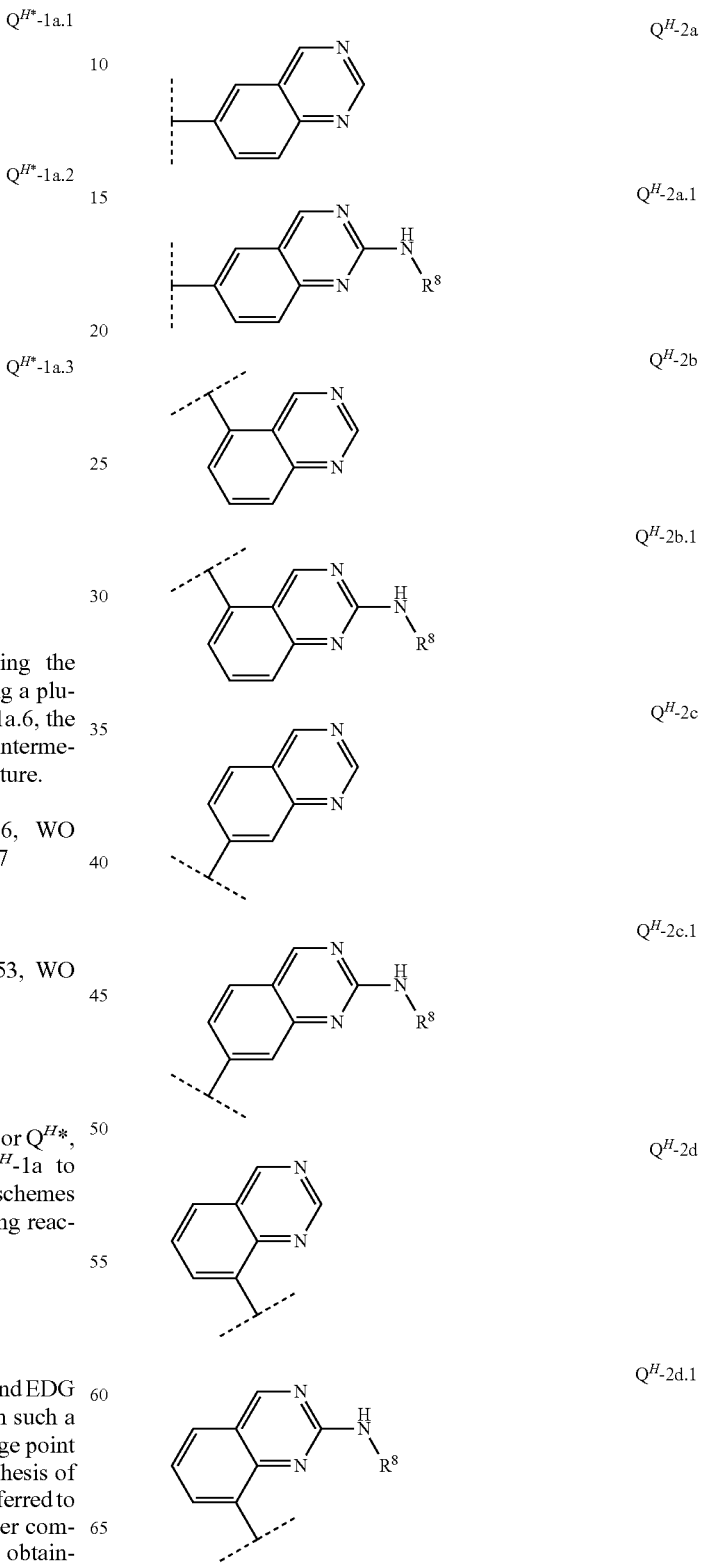

$Q^H$-2a $Q^H$-2a.1

$Q^H$-2b $Q^H$-2b.1

$Q^H$-2c $Q^H$-2c.1

$Q^H$-2d $Q^H$-2d.1

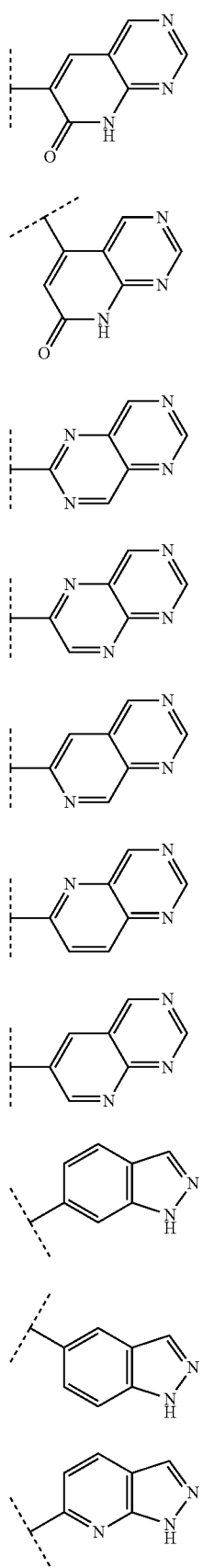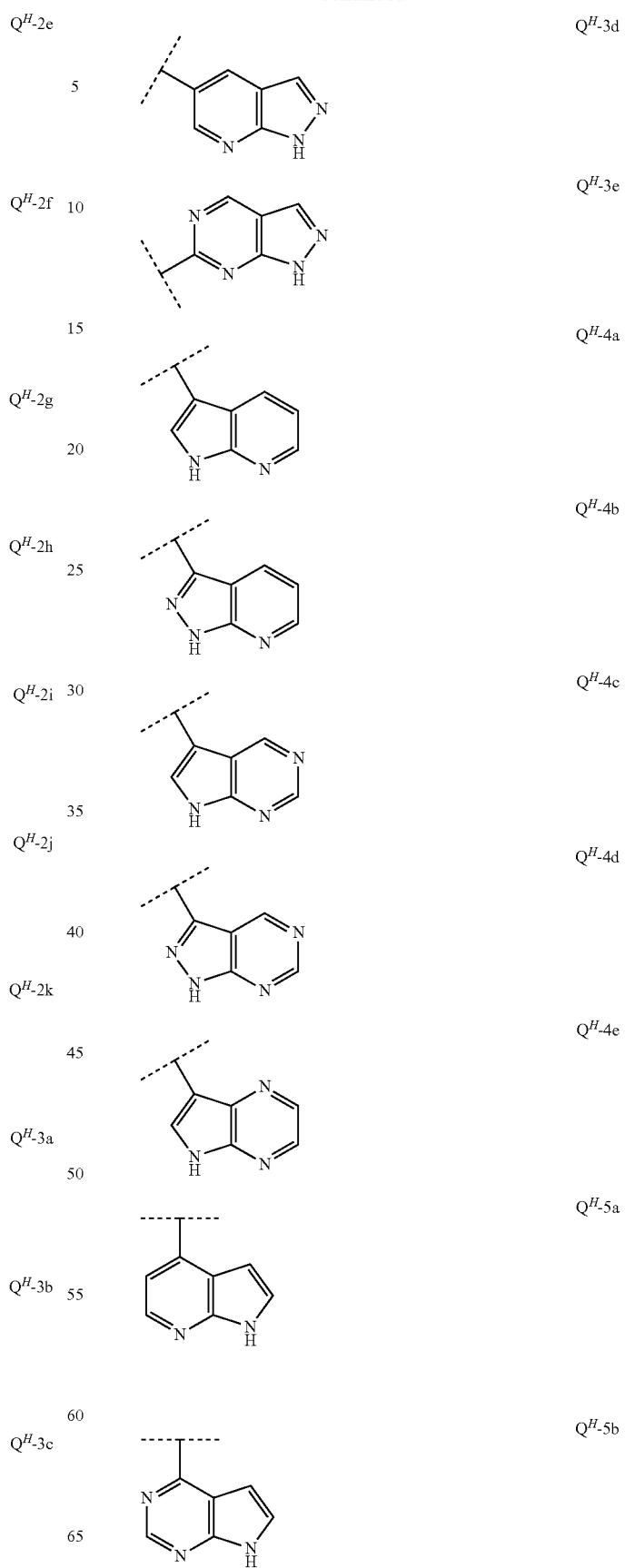

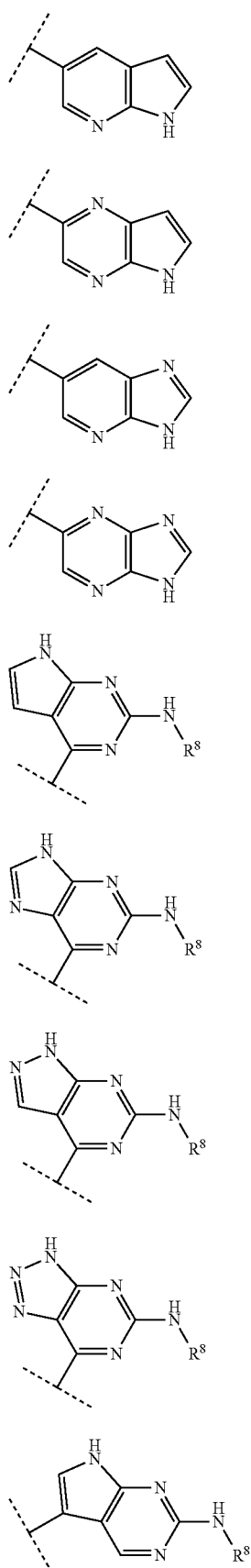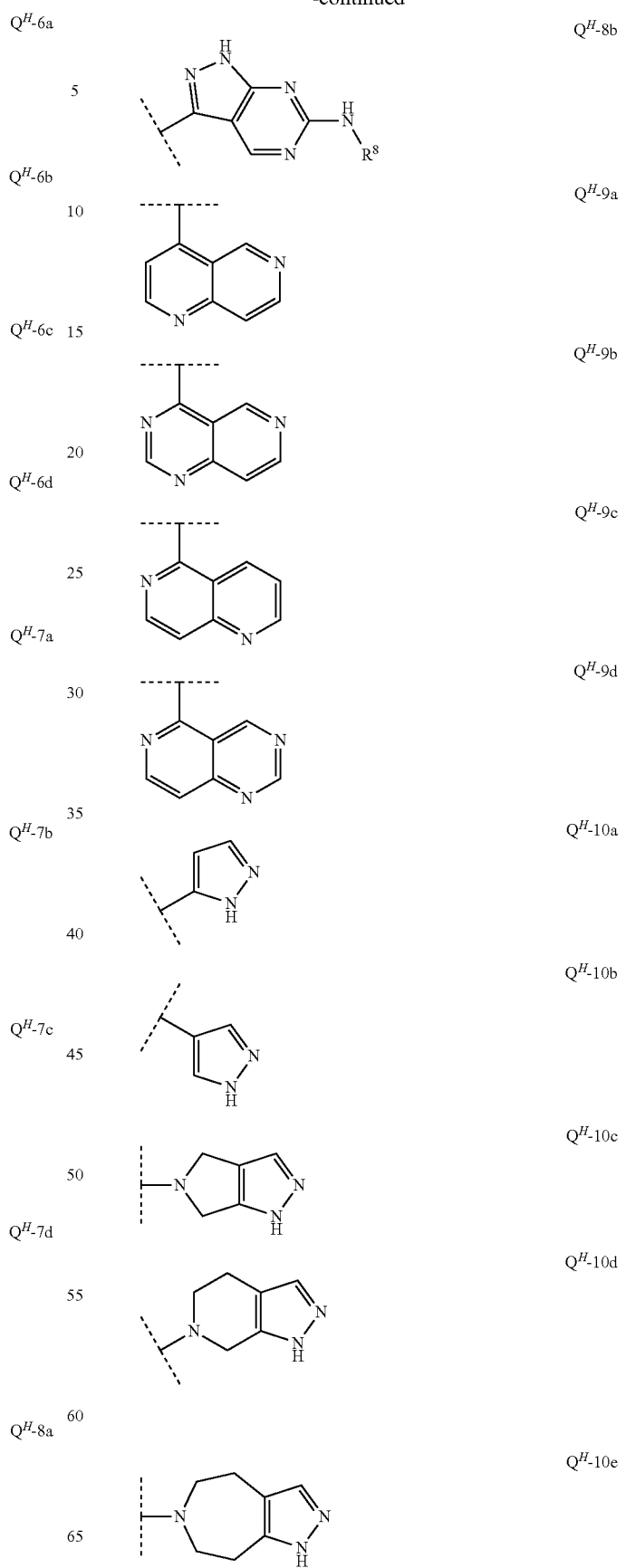

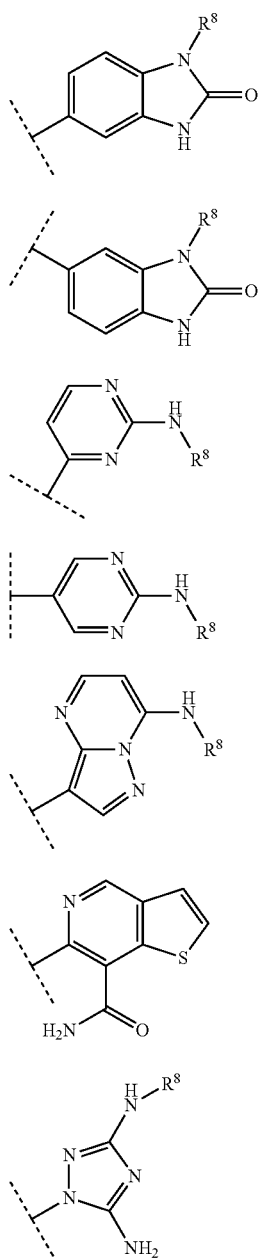

$Q^H$-7a, $Q^H$-7b, $Q^H$-7c, $Q^H$-7d: WO 2008/107444
$Q^H$-9a, $Q^H$-9b, $Q^H$-9c, $Q^H$-9d: WO 03/057695
$Q^H$-10a, $Q^H$-10b: WO 2006/134318, WO 2007/077435
$Q^H$-10c, $Q^H$-10d, $Q^H$-10e: WO 2007/099171, WO 2006/108488, WO 2007/068619, WO 2004/013144; *J. Med. Chem.* 2006, 7247
$Q^H$-11a, $Q^H$-11b: WO 2008/005457
$Q^H$-12a, $Q^H$-12b: WO 2008/003766
$Q^H$-13: WO 2004/087707
$Q^H$-14: WO 2006/106326
$Q^H$-15: WO 2004/046120, WO 2006/050249

Typical embodiments of the linker unit L which may be incorporated or synthesised according to methods described in reaction schemes A-1 to A-4 and reaction scheme C are as follows (the notation in each case being such that the bond to the amide nitrogen —NR$^4$— is shown on the left and the bond to the ring system $Q^H$ is shown on the right):

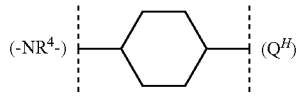
L-1

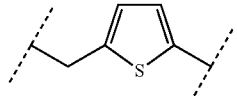
L-2

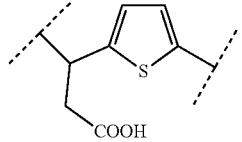
L-2a

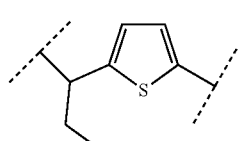
L-2b

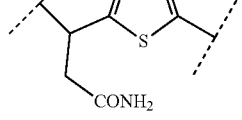
L-2c

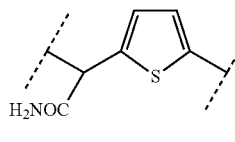
L-2d

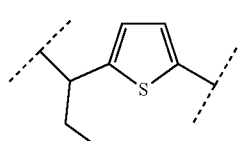
L-2e

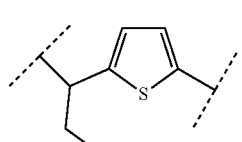
L-2f

The above-mentioned ring systems $Q^H$ may each optionally be substituted independently of one another at one or more hydrogen-carrying ring atom(s) by $R^a$ and/or $R^b$, while $R^8$, B, $R^a$ and $R^b$ are as hereinbefore defined.

The synthesis of corresponding reactants that are suitable for such incorporation is described in the literature or may be carried out analogously to published methods:

$Q^H$-2a, $Q^H$-2b, $Q^H$-2c, $Q^H$-2d: WO 2007/117607, WO 2008/079988
$Q^H$-2e, $Q^H$-2f: *J. Med. Chem.* 2000, 4606; *J. Med. Chem.* 2005, 2371
$Q^H$-3a, $Q^H$-3b, $Q^H$-3c, $Q^H$-3d, $Q^H$-3e: WO 01/53268, WO 03/035065, WO 03/024969, WO 2008/005457
$Q^H$-4a, $Q^H$-4b, $Q^H$-4c, $Q^H$-4d, $Q^H$-4e: WO 2008/005457
$Q^H$-5a, $Q^H$-5b: WO 2008/005457
$Q^H$-6a, $Q^H$-6b, $Q^H$-6c, $Q^H$-6d: WO 2008/005457

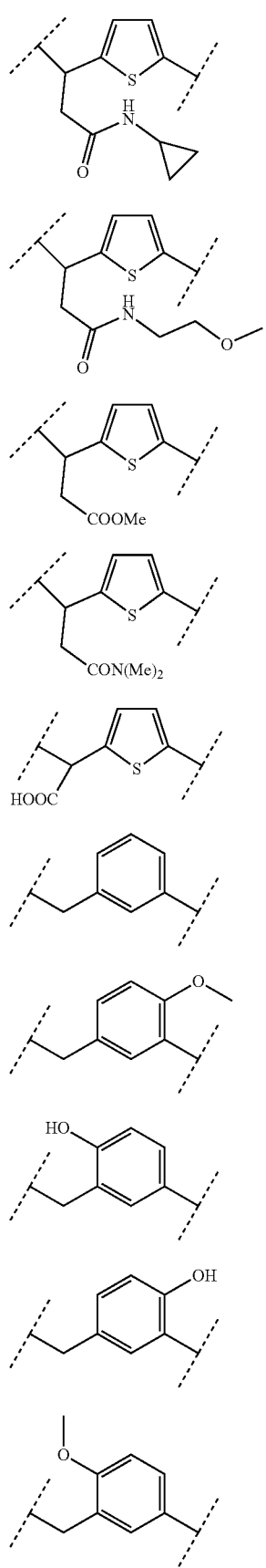
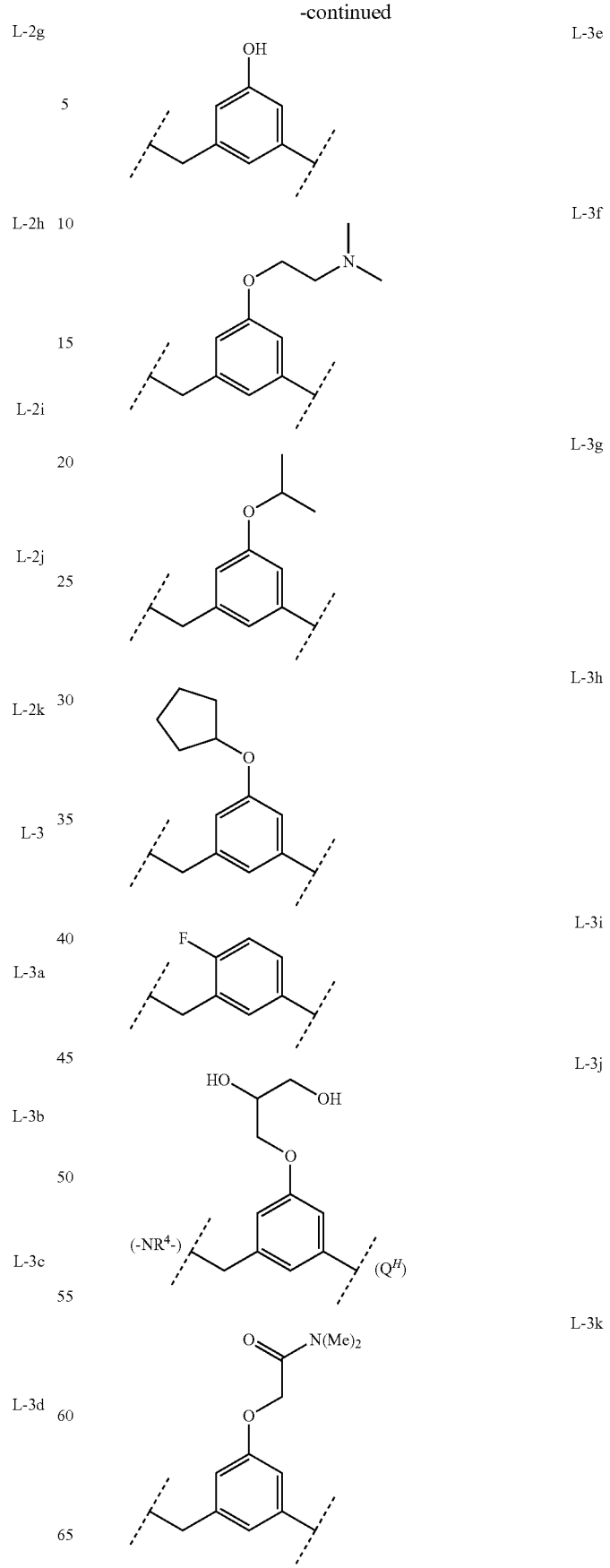

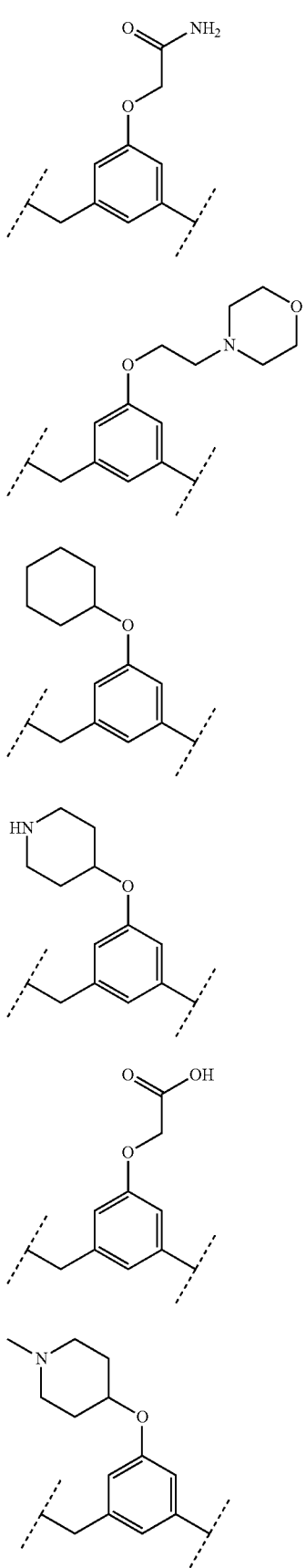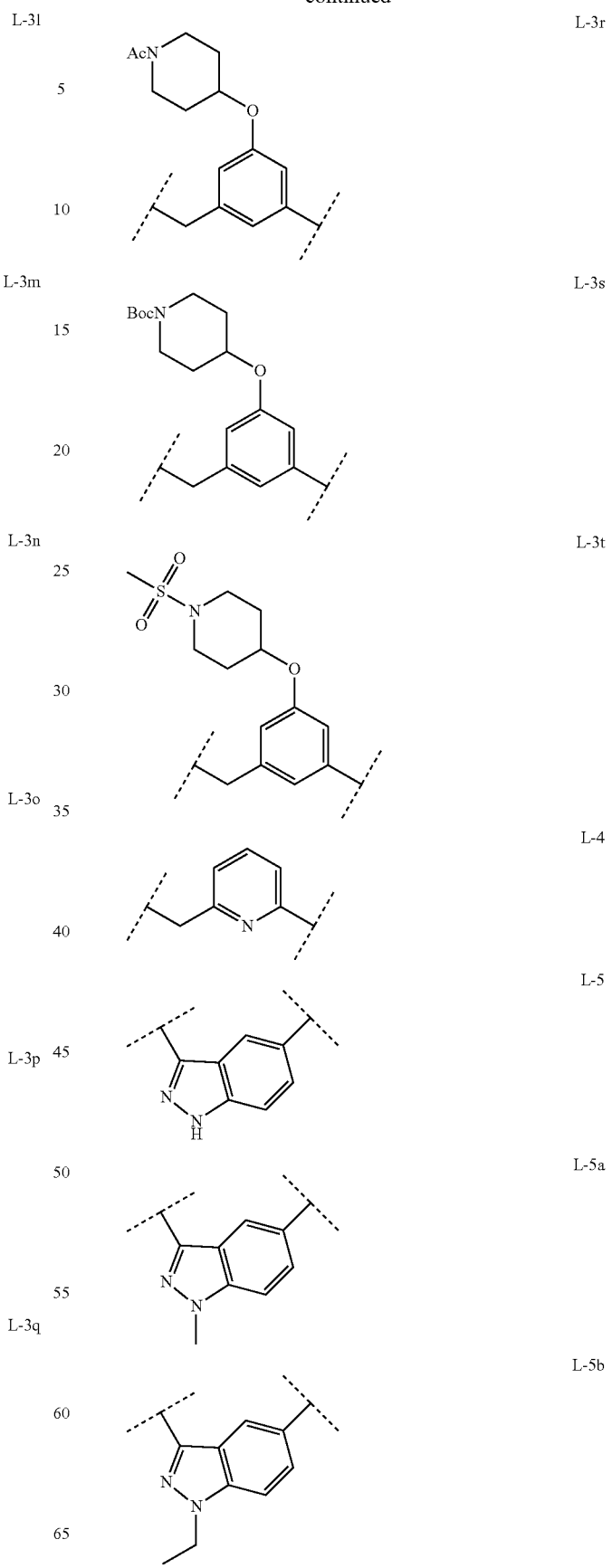

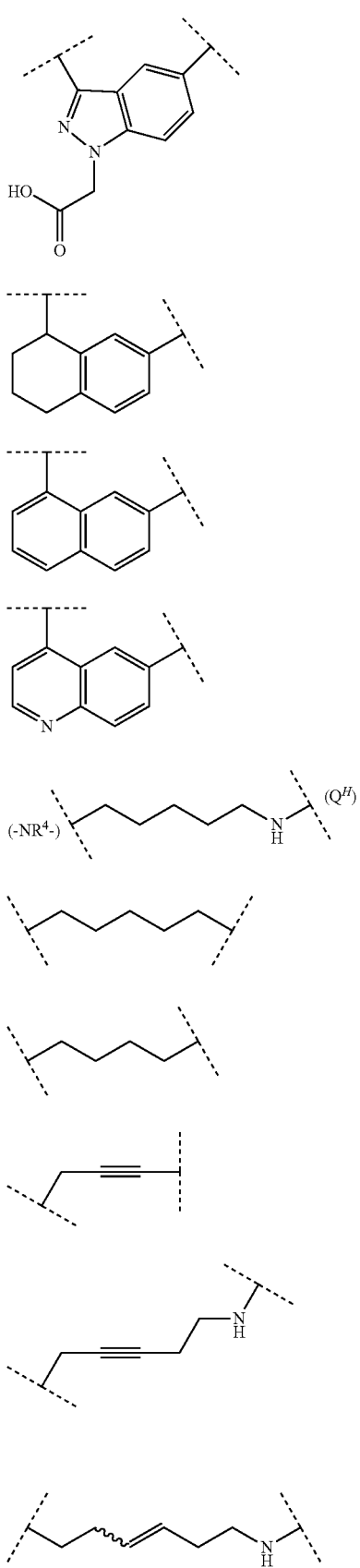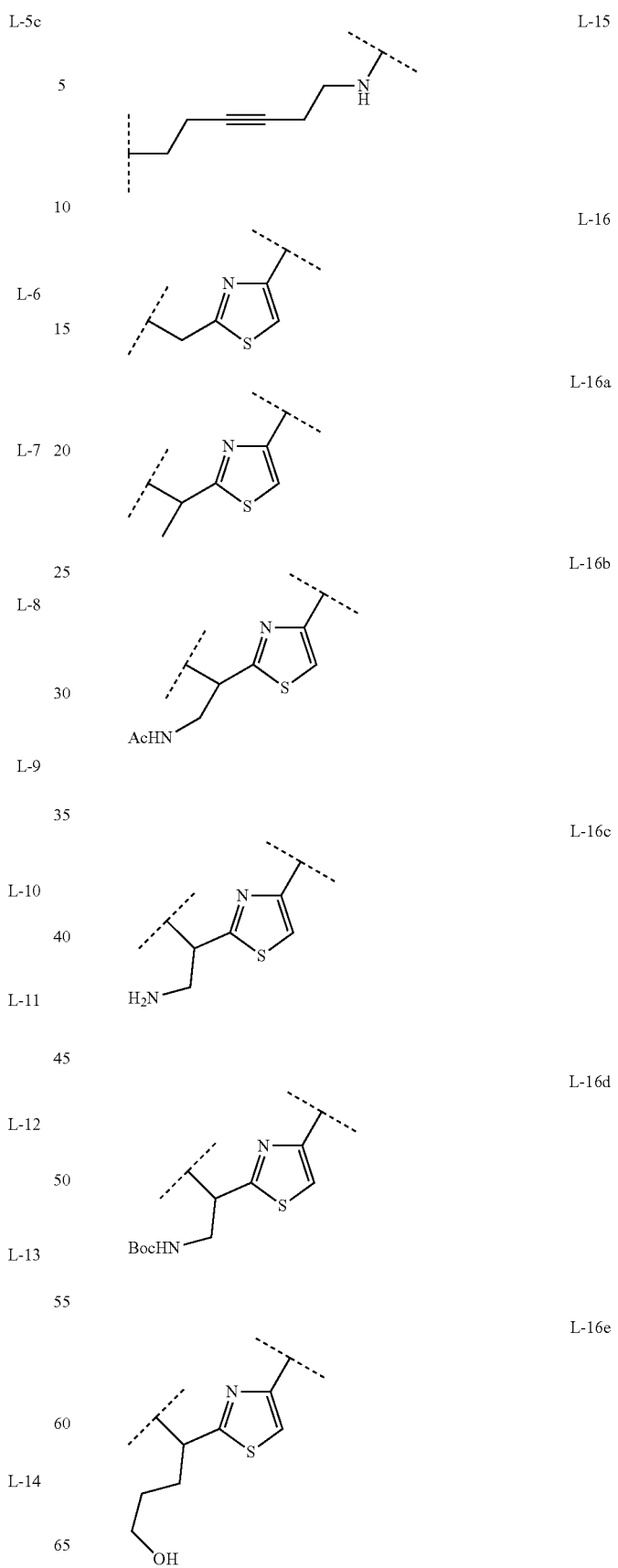

L-16f 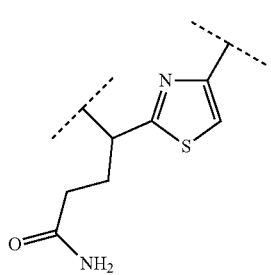
L-16g 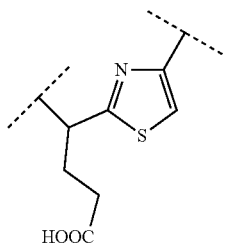
L-16h 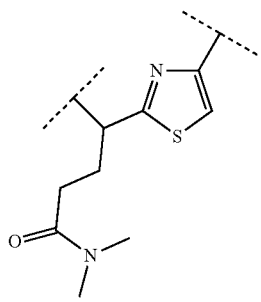
L-16i 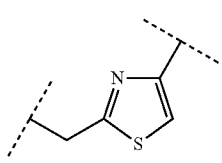
L-17 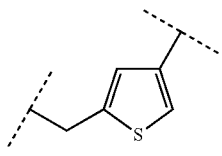
L-18 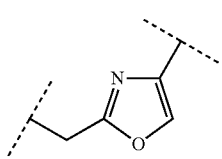
L-19 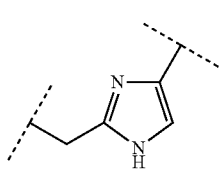
L-20 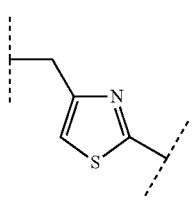
L-21 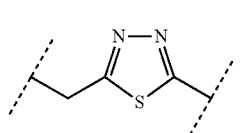
L-22 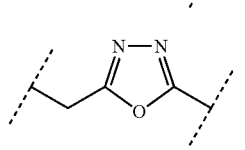
L-22a 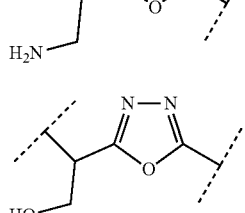
L-22b 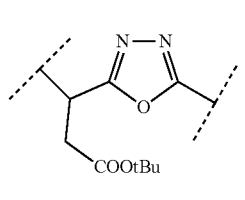
L-22c 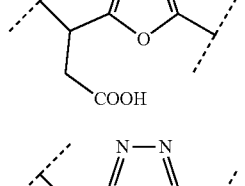
L-22d 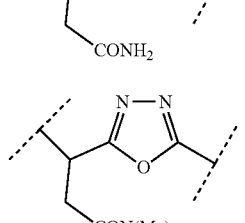
L-22e 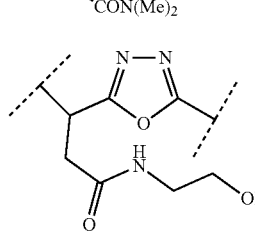
L-22f 
L-22g -continued
(-NR⁴-) 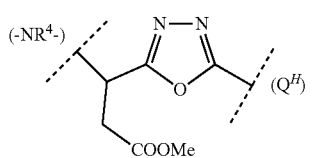 (Qᴴ)
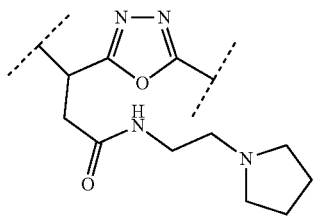
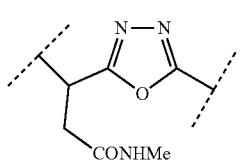
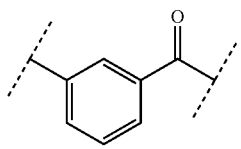
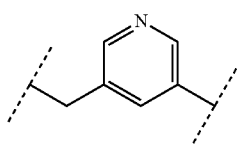
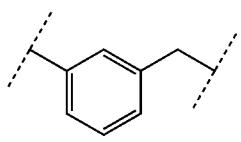
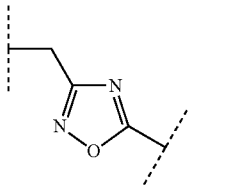
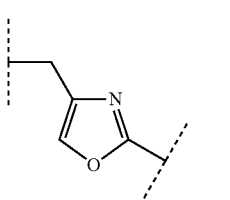
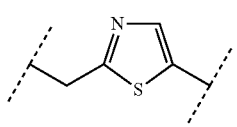
-continued
L-22h 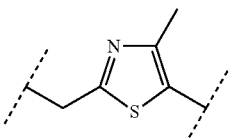 L-28a
L-22i 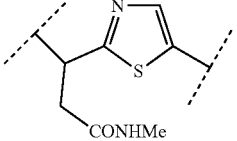 L-28b
L-22j 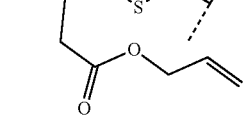 L-28c
L-23 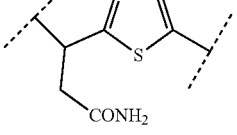 L-28d
L-24 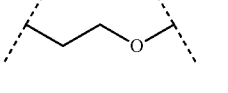 L-29
L-25 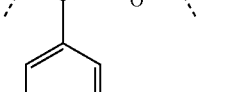 L-29a
L-26 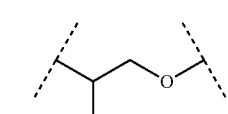 L-29b
L-27 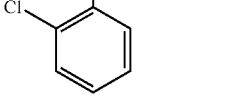 L-29c
L-28 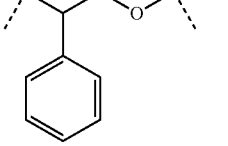 L-29d -continued
L-29e 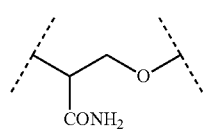
L-29f 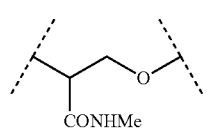
L-29g 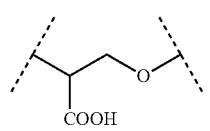
L-29h 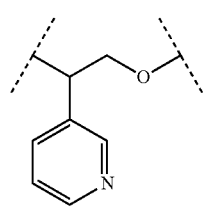
L-29i 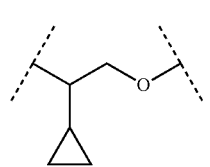
L-29j 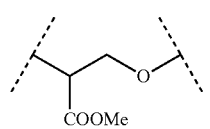
L-29k 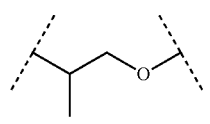
L-29l 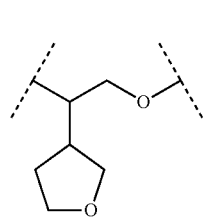
L-29m 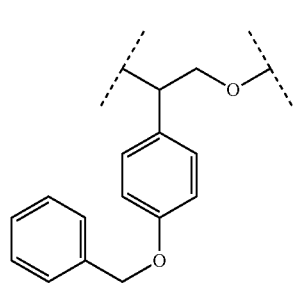
-continued
L-29n 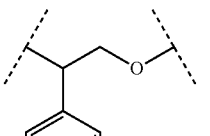
L-29o 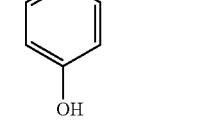
L-29p 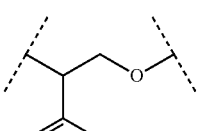
L-29q ($-NR^4-$) 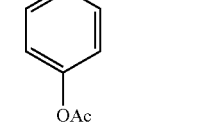 ($Q^H$)
L-29r 
L-29s 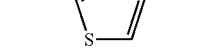
L-29t 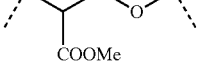
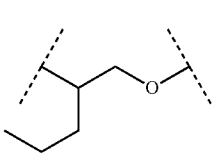
L-29u 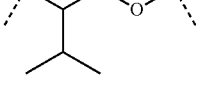
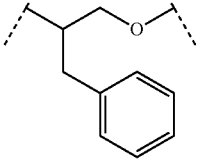
L-30 

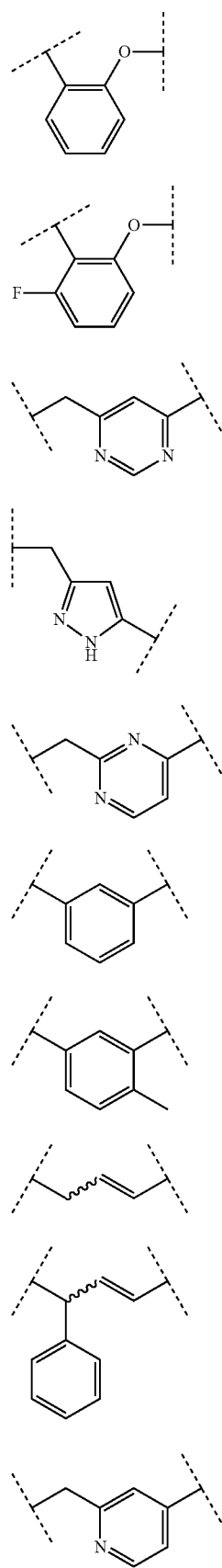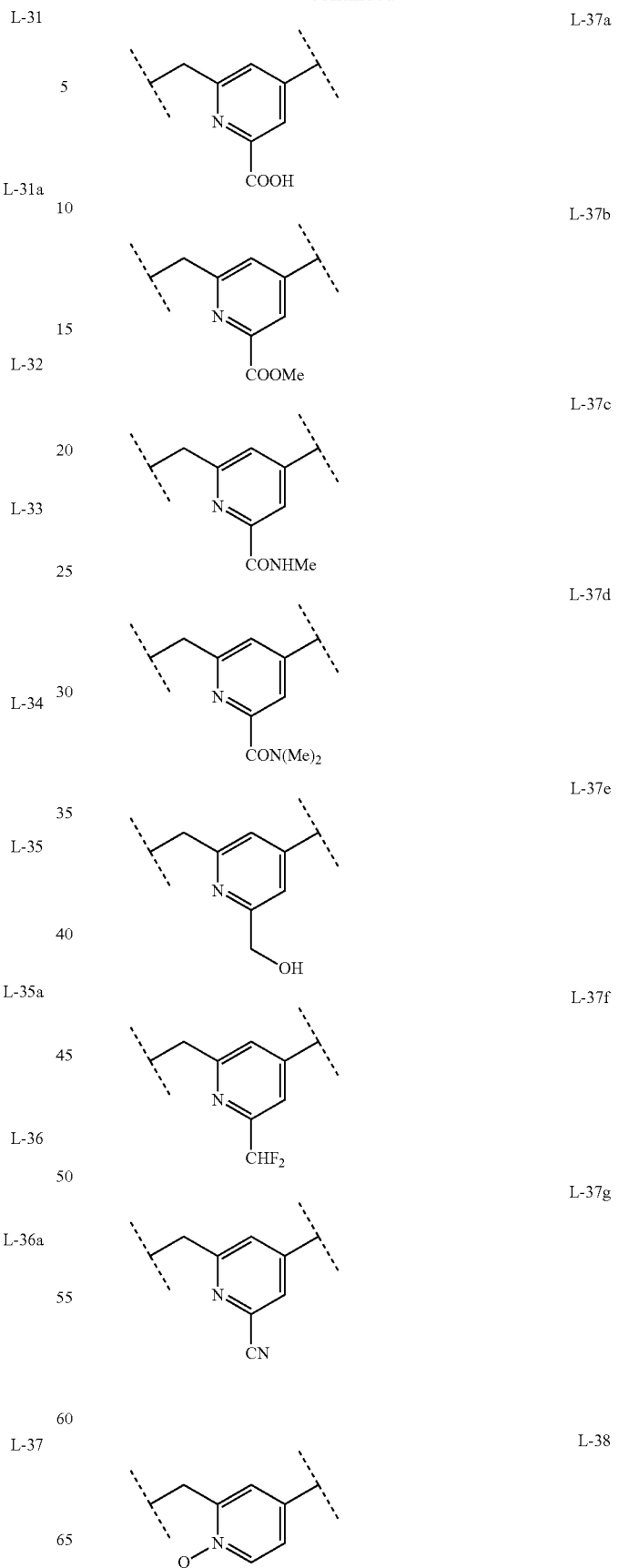

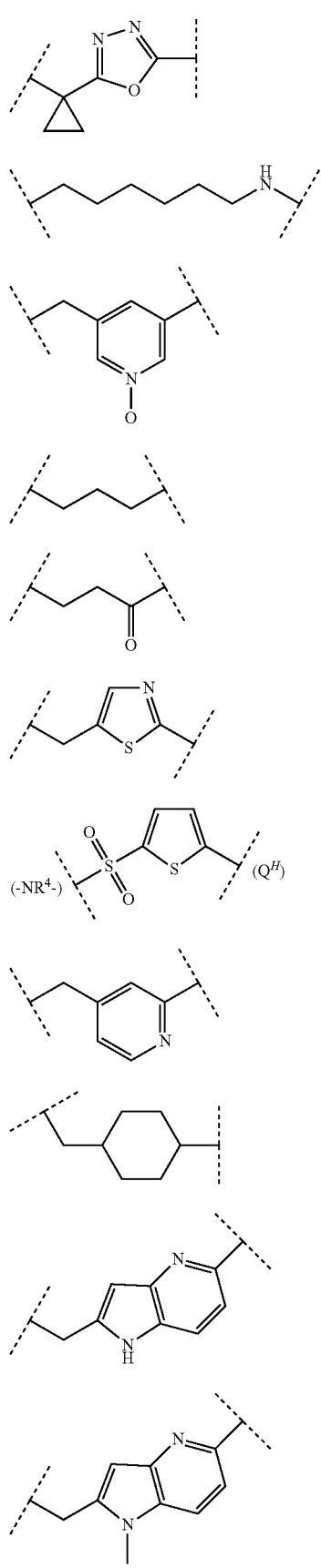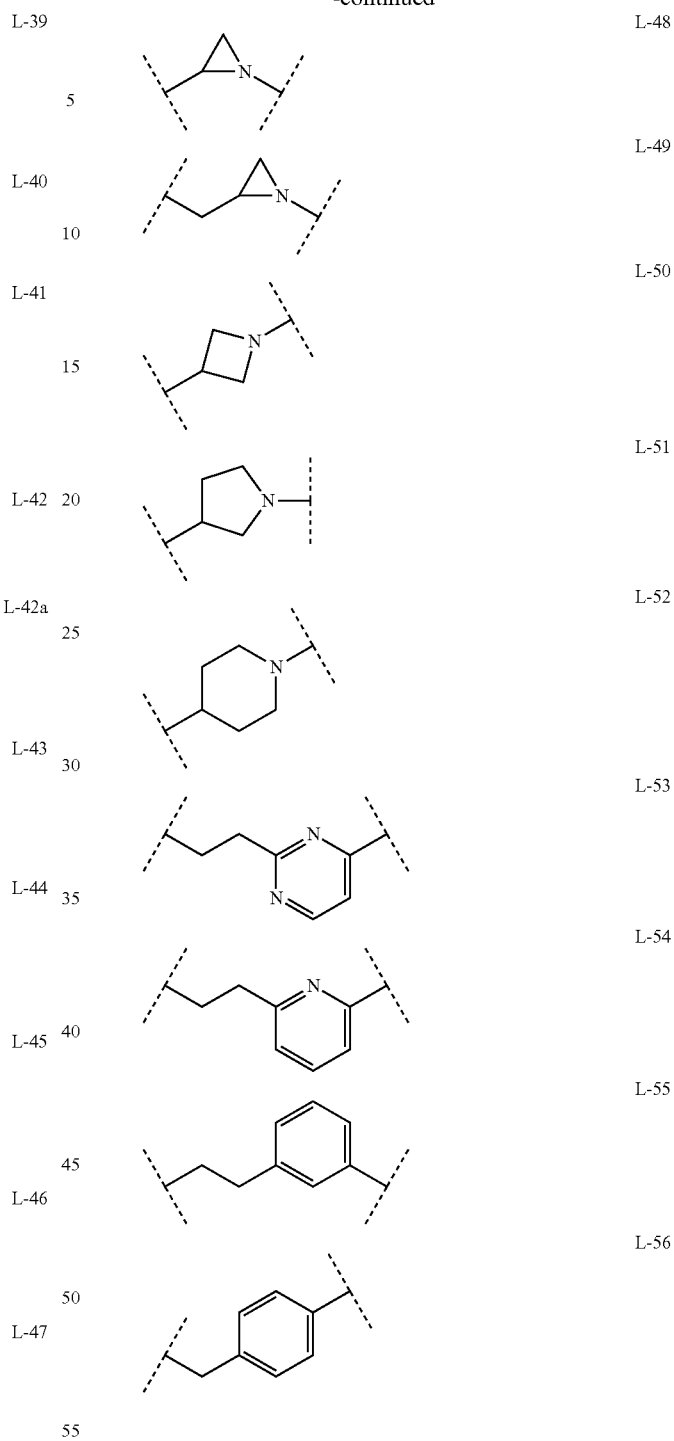
Other typical linkers L in compounds according to the invention (1) are selected from among L-1, L-2, L-2a, L-2b, L-2c, L-2d, L-2e, L-2f, L-2g, L-2h, L-2i, L-2j, L-2k, L-3, L-3a, L-3b, L-3c, L-3d, L-3e, L-3f, L-3g, L-3h, L-3i, L-3j, L-3k, L-3l, L-3m, L-3n, L-3o, L-3p, L-3q, L-3r, L-3s, L-3t, L-4, L-5, L-5a, L-5b, L-5c, L-6, L-7, L-8, L-9, L-10, L-11, L-12, L-13, L-14, L-15, L-16, L-16a, L-16b, L-16c, L-16d, L-16e; L-16f, L-16g, L-16h, L-16i, L-17, L-18, L-19, L-20, L-21, L-22, L-22a, L-22b, L-22c, L-22d, L-22e, L-22f, L-22g, L-22h, L-22i, L-22j, L-23, L-24, L-25, L-26, L-27, L-28, L-28a, L-28b, L-28c, L-28d, L-29, L-29a, L-29b, L-29c, L-29d, L-29e, L-29f, L-29g, L-29h, L-29i, L-29j, L-29k, L-29l, L-29m, L-29n, L-29o, L-29p, L-29q, L-29r, L-29s, L-29t, L-29u, L-30, L-31, L-31a, L-32, L-33, L-34, L-35, L-35a, L-36, L-36a, L-37, L-37a, L-37b, L-37c, L-37d, L-37e, L-37f, L-37g, L-38, L-39, L-40, L-41, L-42, L-42a, L-43, L-44, L-45, L-46, L-47, L-47a, l-53, L-54, L-55 and L-56.

a) Synthesis of Free Cyclic Carboxylic Acids A.1

Method for Synthesising A.1a

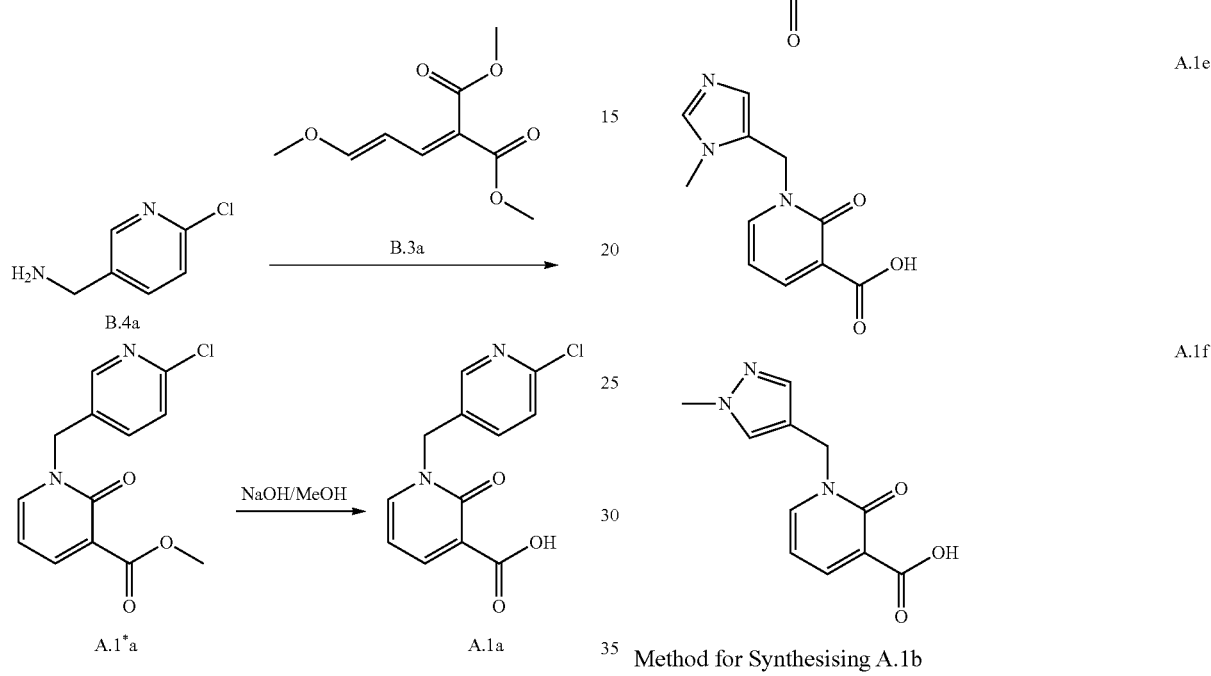

Amine B.4a (200 mg, 1.0 mmol) is taken up in 1.6 mL 2-butanol and combined with the malonic acid diester derivative B.3a (142 mg, 1.0 mmol), which is taken up in 0.4 mL 2-butanol, at 5° C. The mixture is stirred for 1 h at 20° C., diluted with another 5 mL 2-butanol and refluxed for 48 h with stirring. Then the reaction solution is combined with 0.5 mL 2 N aqueous sodium hydroxide solution and 0.5 mL 2 N methanolic sodium hydroxide solution and stirred for 2 h at 20° C. The reaction mixture is acidified with 1 N aqueous hydrochloric acid and extracted with DCM. The organic phase is dried, the solvent is eliminated in vacuo and A.1a (MS (M+H)$^+$=265/267; method FECS) is obtained.

The following carboxylic acids A.1 may also be synthesised from B.3a and the corresponding amines B.4 analogously to the synthesis of A.1a:

Method for Synthesising A.1b

Sodium hydride (60%; 28.6 mg, 0.714 mmol) is suspended in 1.5 mL DMF, combined with carboxylic acid ester B.1a (99.4 mg, 0.649 mmol) and stirred for 45 min at 20° C. Benzyl bromide B.2a (112 mg, 0.649 mmol) is metered into the suspension and it is stirred for a further 3 h at 20° C. The reaction mixture is combined with 1 N hydrochloric acid and DCM, the organic phase is separated off and extracted 2× with 1 N hydrochloric acid. Then the organic phase is dried, the solvent is eliminated in vacuo and carboxylic acid ester A.1*b (MS (M+H)$^+$=245) is obtained.

Intermediate product A.1*b is taken up in methanol and combined with 1 N sodium hydroxide solution. After 16 h at 20° C. the mixture is diluted with water and extracted with DCM. The organic phase is discarded, the aqueous phase is acidified and extracted with DCM. The organic phase is dried, the solvent is eliminated in vacuo and the free carboxylic acid A.1b (MS (M+H)$^+$=231; method FECS) is obtained.

b) Synthesis of Activated Components EWG-Q$^H$ A.4 or EWG-Q$^{H*}$ A.4*

Method for Synthesising A.4b

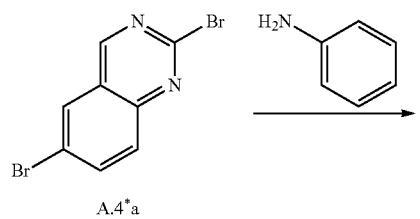

2,6-Dibromoquinazoline A.4*a (200 mg, 0.697 mmol) and aniline (97 mg, 1.045 mmol) are taken up in 1 mL dioxane and combined with dioxanic HCl (174 µL, 4 mmol/mL). The reaction mixture is stirred for 16 h at 100° C., the solvent is eliminated in vacuo, the residue is purified by RP chromatography (method prep. HPLC1; 10% acetonitrile to 60% in 10 min) and A.4b (MS (M+H)$^+$=300/302; method FECB3) is obtained.

Analogously to A.4b, A.4c may also be prepared from A.4*a and 4-dimethylaminomethylphenylamine. Generally speaking, structurally diverse anilines may be reacted with A.4*a in this way.

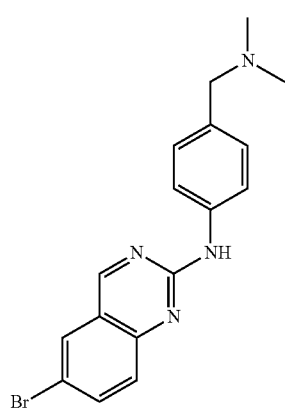

Method for Synthesising A.4d-PG and A.4f-PG

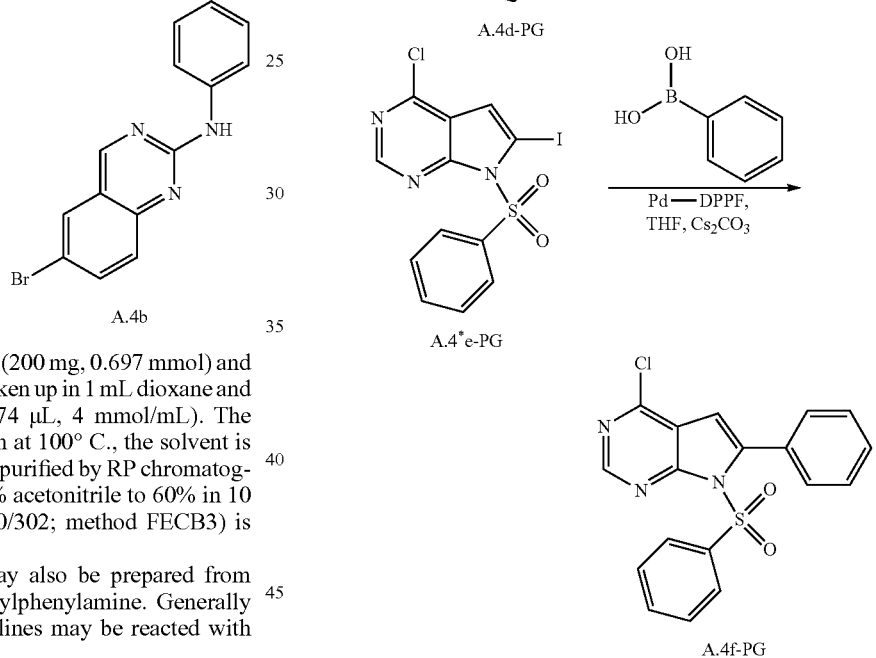

4-chloro-7H-pyrrolo[2,3-d]pyrimidine A.4d (5.00 g, 32.56 mmol) is taken up in 150 mL THF and within 5 min combined with potassium-tert-butoxide (4.60 g, 41.07 mmol). This mixture is cooled to 10° C. and within 10 min benzenesulphonyl chloride (5.40 mL, 42.31 mmol) is added thereto. The cooling is removed and the mixture is stirred at 20° C. After 3 h 10 mL water are added and the mixture is stirred for a further 10 min. Then the solvent is eliminated in vacuo, the residue is taken up in ethyl acetate and aqueous sodium chloride solution and extracted. The organic phase is dried, the solvent is eliminated in vacuo and A.4d-PG (MS (M+H)$^+$=294/296; method FECB3) is obtained.

A.4d-PG (2.50 g, 8.51 mmol) is taken up in 80 mL THF and cooled to −78° C. under an argon atmosphere. LDA dissolved in cyclohexane (8.5 mL, 12.75 mmol) is added to this mixture within 15 min. After being stirred for 1 h at −78° C. the mixture is combined with iodine (2.38 g, 9.36 mmol), which is dissolved in 20 mL THF, and stirred for a further hour at −78° C. The reaction mixture is combined with 10 mL of a 1 N hydrochloric acid solution and stirred for 1 h at 20° C. Then the solvent is removed, the residue is purified by RP-chromatography (method prep. HPLC2; 20% acetonitrile to 95% in 12 min) and A.4*e-PG (HPLC-MS: $t_{Ret.}$=2.07 min, MS(M+H)$^+$=420/422; method FECSUNFIRE) is obtained.

A.4*e-PG (300 mg, 0.715 mmol), phenylboric acid (90 mg, 0.738 mmol), caesium carbonate (348 μL, 1.72 mmol; 70% aqueous solution) and Pd-DPPF (60 mg, 0.074 mmol) are taken up in 1.2 mL THF and stirred for 16 h at 20° C. The solvent is removed, the residue is purified by RP-chromatography (method prep. HPLC2; 30% acetonitrile to 95% in 12 min) and A.4f-PG (HPLC-MS: $t_{Ret.}$=2.04 min, MS(M+H)$^+$=370/372; method FEC3) is obtained.

Method for Synthesising A.4g-PG and A.4h

The reaction mixture is stirred for 5 d at 20° C. and then combined with 10 mL EtOH, stirred for 15 min and then stirred into 250 mL water. The mixture is extracted 3× with DCM, the combined organic phases are dried and the solvent is eliminated in vacuo. The crude product is suspended in DCM and extracted 2× with 400 mL 1 N hydrochloric acid. The combined aqueous phases are adjusted to pH 5-6 with potassium carbonate, the precipitate formed is filtered off and (2-amino-5-bromo-3-methoxy-phenyl)-methanol (HPLC-MS: $t_{Ret.}$=1.41 min, MS(M+H)$^+$=232/234; method FEC3) is obtained.

(2-amino-5-bromo-3-methoxy-phenyl)-methanol (10.1 g, 43.53 mmol) is taken up in 70 mL chloroform, combined with manganese dioxide (5.99 g, 68.94 mmol) and stirred for 16 h at 20° C. The solids are filtered off, the solvent is eliminated

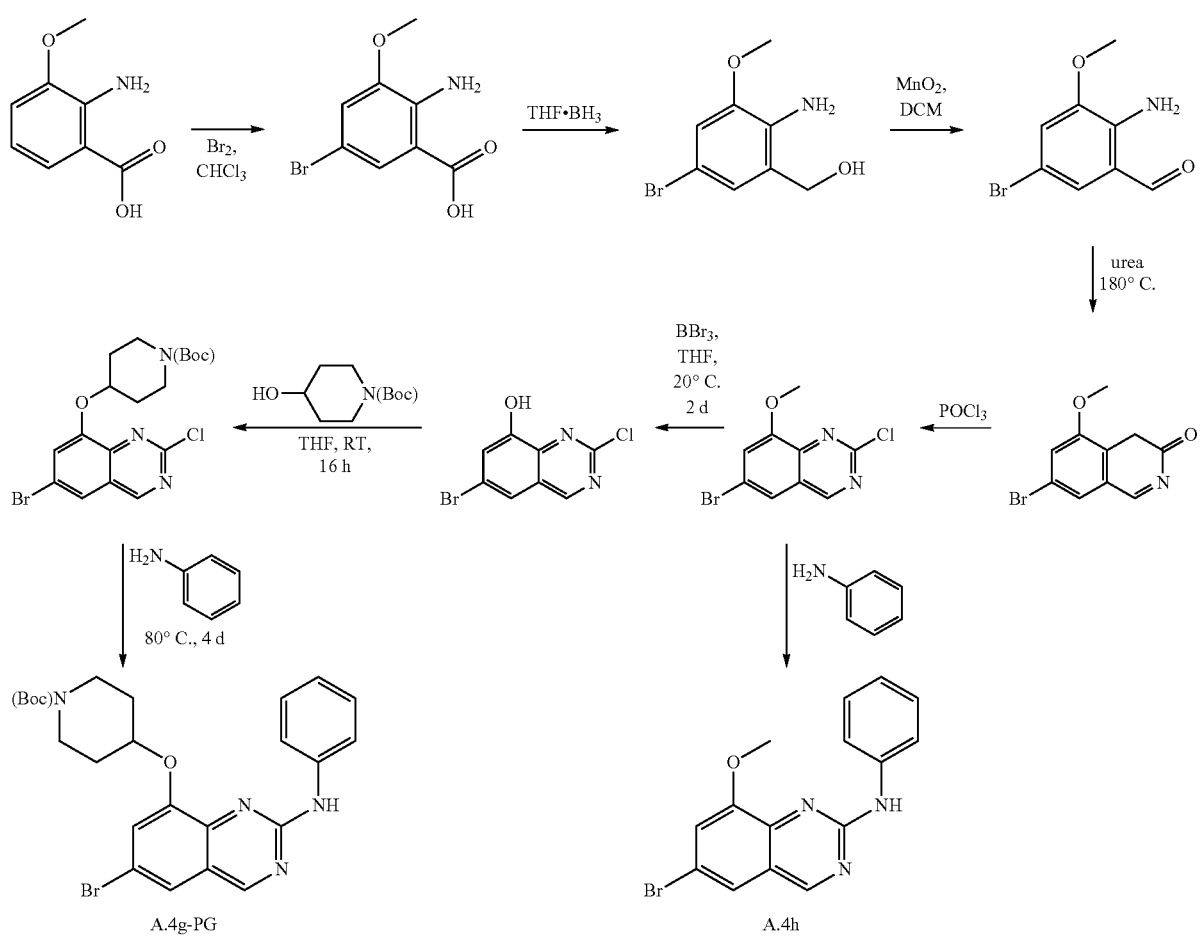

A.4g-PG or A.4h is prepared according to WO 2007/117607:

2-amino-3-methoxybenzoic acid (20.0 g, 119.64 mmol) is suspended in chloroform, cooled to 0° C. and combined with bromine (6.48 mL, 126.56 mmol), which is dissolved in 100 mL chloroform. After the addition the reaction mixture is heated to 20° C. and stirred for 16 h at this temperature. The precipitate is filtered off, dried and 2-amino-5-bromo-3-methoxybenzoic acid (HPLC-MS: $t_{Ret.}$=1.76 min, MS(M+H)$^+$=246/248; method FECS) is obtained.

2-amino-5-bromo-3-methoxybenzoic acid (20.0 g, 81.30 mmol) is suspended in 250 mL THF, cooled to 0° C. and combined with borane-THF complex (315 mL, 0.315 mol).

in vacuo and 2-amino-5-bromo-3-methoxybenzaldehyde ((HPLC-MS: $t_{Ret.}$=1.91 min MS(M+H)$^+$=230/232; method FSUN) is obtained.

2-amino-5-bromo-3-methoxybenzaldehyde (2.5 g, 10.87 mmol) is homogeneously mixed with urea and the mixture is heated to 180° C. The melt formed is kept at this temperature for 1 h. Then the reaction mixture is mixed with water, the precipitate formed is filtered off, dried and 6-bromo-8-methoxy-1H-quinazolin-2-one (HPLC-MS: $t_{Ret.}$=1.53 min MS(M+H)$^+$=255/257; method FSUN) is obtained.

6-bromo-8-methoxy-1H-quinazolin-2-one (2.62 g, 10.27 mmol) is suspended in 30 mL POCl$_3$ and refluxed for 30 min. The reaction mixture is stirred into water, while the temperature never exceeds 15° C. The aqueous phase is extracted with DCM, the organic phase is dried and 6-bromo-2-chloro-8-methoxy-quinazoline (HPLC-MS: $t_{Ret.}$=1.88 min, MS(M+H)$^+$=273/275/277; method FSUN) is obtained.

6-bromo-2-chloro-8-methoxy-quinazoline (1.24 g, 4.52 mmol) is taken up in 7 mL DCM, combined with boron tribromide (12.95 mL, 12.95 mmol) and stirred for 2 d at 20° C. Then the mixture is diluted with ice water, the precipitate formed is filtered off, dried and 6-bromo-2-chloro-quinazolin-8-ol (HPLC-MS: $t_{Ret.}$=1.77 min; method FSUN) is obtained.

Triphenylphosphine (577 mg, 2.20 mmol), di-tert-butylazodicarboxylate (506 mg, 2.20 mmol) and tert-butyl 4-hydroxy-piperidine-1-carboxylate (1.32 g, 6.62 mmol) are taken up in 6 mL THF, stirred for 15 min at 20° C. and then combined with 6-bromo-2-chloro-quinazolin-8-ol (1.16 g, 4.45 mmol). After stirring for 24 h at 20° C. the mixture is diluted with MeOH, the solvent is eliminated in vacuo, the crude product is purified by RP-chromatography (method prep. HPLC1; 20% acetonitrile to 90% in 6 min) and tert-butyl 4-(6-bromo-2-chloro-quinazolin-8-yloxy)-piperidine-1-carboxylate (HPLC-MS: $t_{Ret.}$=1.99 min; method FECB5) is obtained.

Aniline (2.00 mL, 21.48 mmol), Hünig base (142 µL, 0.88 mmol) and tert-butyl 4-(6-bromo-2-chloro-quinazolin-8-yloxy)-piperidine-1-carboxylate (195 mg, 0.44 mmol) are stirred for 4 d at 80° C. Then the mixture is combined with 1 N hydrochloric acid and extracted with DCM. The organic phase is dried and A.4g-PG (HPLC-MS: $t_{Ret.}$=2.13 min MS(M+H)$^+$=499/501; method FECB5) is obtained.

Method for Synthesising A.4i

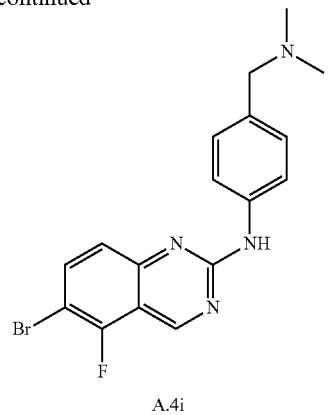

A.4i 6-bromo-2-chloro-5-fluoro-quinazoline is prepared analogously to WO 2007/117607 or to the above-mentioned synthesis of 6-bromo-2-chloro-8-methoxy-quinazoline starting from 2-amino-5-bromo-6-fluoro-benzonitrile.

4-dimethylaminomethyl-phenylamine dihydrochloride (435 mg, 1.95 mmol), and 6-bromo-2-chloro-5-fluoro-quinazoline (400 mg, 1.53 mmol) are taken up in 2.5 mL NMP, combined with 4 N dioxanic hydrochloric acid (1 mL, 4 mmol) and stirred for 24 h at 100° C. The solvent is eliminated in vacuo, the crude product is purified by RP-chromatography (method prep. HPLC2; 10% acetonitrile to 80% in 6 min) and A.4i (HPLC-MS: $t_{Ret.}$=1.44 min; MS(M+H)$^+$=375/377; method FECS1) is obtained.

Method for Synthesising A.4j

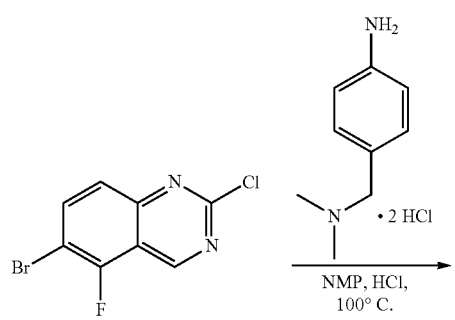

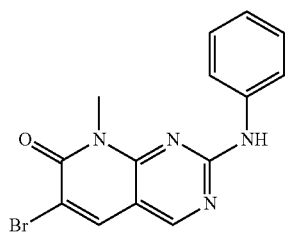

A.4j

A.4j (HPLC-MS: $t_{Ret.}$=1.92 min; MS(M+H)$^+$=331/333; method FECS1) is prepared analogously to *J. Med. Chem.* 2000, 43, 4606 or *J. Med. Chem.* 2005, 2371.

Method for Synthesising A.4k

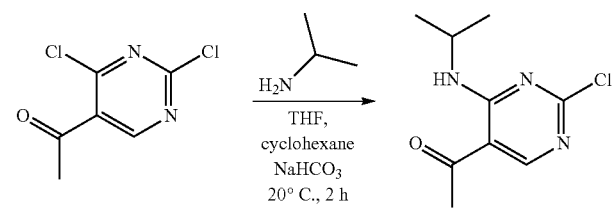

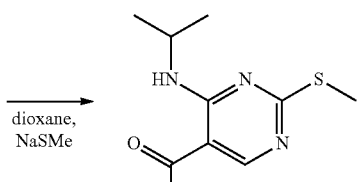

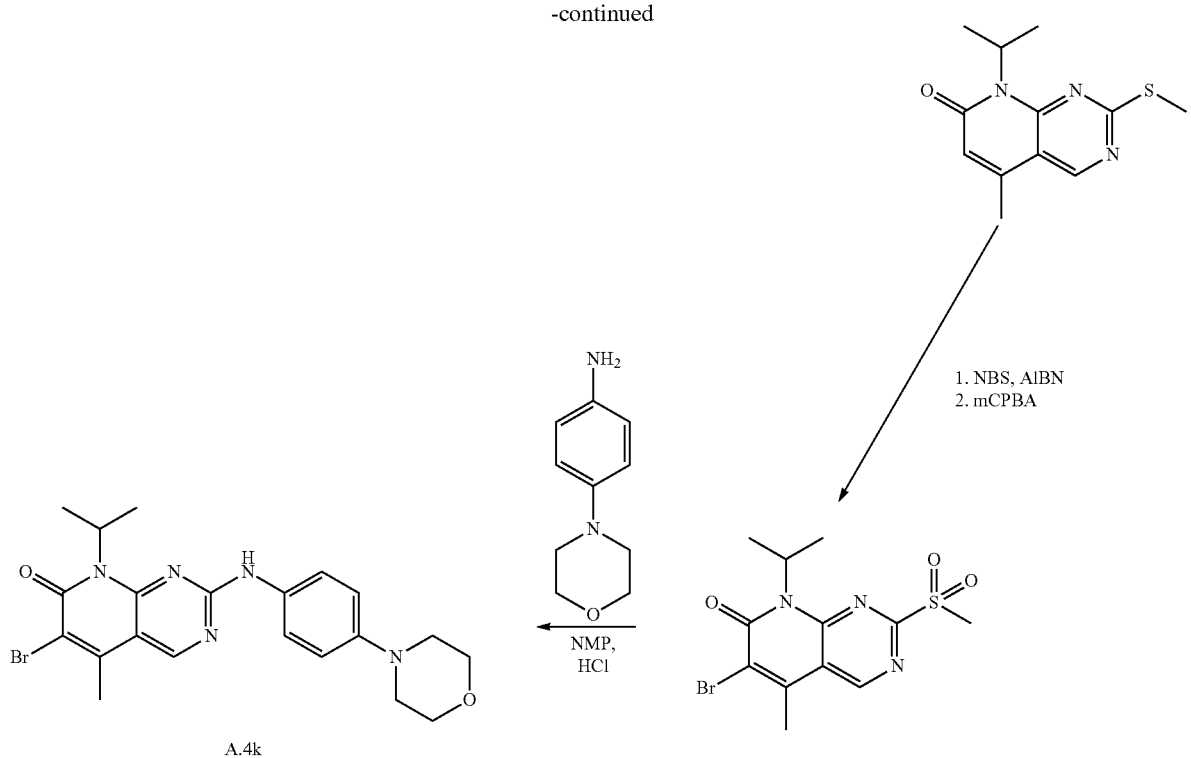

1-(2,4-dichloro-pyrimidin-5-yl)-ethanone (10 g, 0.052 mol), sodium hydrogen carbonate (19.35 g, 0.058 mol) and isopropylamine (5 mL, 0.058 mol) are taken up in 35 mL THF and 200 mL cyclohexane and stirred for 2 h at 20° C. The reaction solution is filtered through silica gel, the solvent is eliminated in vacuo and 1-(2-chloro-4-isopropylaminopyrimidin-5-yl)-ethanone (HPLC-MS: $t_{Ret.}$=1.73 min, MS(M+H)$^+$=214/216; method FECB3) is obtained.

1-(2-chloro-4-isopropylamino-pyrimidin-5-yl)-ethanone (11.1 g, 0.052 mol) and sodium thiomethoxide (5.75 g, 0.078 mol) are taken up in 100 mL dioxane and stirred for 16 h at 20° C. The solvent is eliminated in vacuo, the residue is taken up in ethyl acetate and extracted 2× with water. The organic phase is dried, the solvent is eliminated in vacuo and 1-(4-isopropylamino-2-methylsulphanyl-pyrimidin-5-yl)-ethanone (HPLC-MS: $t_{Ret.}$=1.82 min, MS(M+H)$^+$=226; method FECB3) is obtained.

Sodium hydride (16.75 g, 0.042 mol) is placed in 200 mL dioxane and combined with triethylphosphonoacetate (83.8 mL, 0.419 mmol), so that the temperature does not exceed 5° C. After the addition is complete, the mixture is heated to 20° C. and 1-(4-isopropylamino-2-methylsulphanyl-pyrimidin-5-yl)-ethanone (11.1 g, 0.049 mol) dissolved in 100 mL dioxane is added thereto. The mixture is stirred for 16 h at 90° C., then combined with 10% sodium chloride solution and extracted with ethyl acetate. The organic phase is dried, the solvent is eliminated in vacuo and the crude product is purified by normal phase chromatography (cyclohexane/ethyl acetate 90:10→50:50 in 45 min; flow 200 mL/min) and 8-isopropyl-5-methyl-2-methylsulphanyl-8H-pyrido[2,3-d]pyrimidin-7-one (HPLC-MS: $t_{Ret.}$=1.74 min; MS(M+H)$^+$=250; method FECS1) is obtained.

8-Isopropyl-5-methyl-2-methylsulphanyl-8H-pyrido[2,3-d]pyrimidin-7-one (4.88 g, 0.02 mol), NBS (6.97 g, 0.039 mol) and AIBN (250 mg, 1.524 mmol) are taken up in 30 mL DMF and stirred for 3 h at 20° C. Then the solvent is eliminated in vacuo, the residue is taken up in ethyl acetate and extracted with sodium thiosulphate solution and water. The organic phase is dried, the solvent is eliminated in vacuo and the residue is taken up in 300 mL DCM and combined with meta-chloroperbenzoic acid (7.68 g, 0.045 mol). After the mixture has been stirred for 2 h at 20° C. it is extracted with sodium thiosulphate solution and sodium hydrogen carbonate solution, dried, the solvent is eliminated in vacuo and 6-bromo-8-isopropyl-2-methanesulphonyl-5-methyl-8H-pyrido[2,3-d]pyrimidin-7-one (HPLC-MS: $t_{Ret.}$=1.62 min, MS(M+H)$^+$=362; method FECB3) is obtained.

6-bromo-8-isopropyl-2-methanesulphonyl-5-methyl-8H-pyrido[2,3-d]pyrimidin-7-one is reacted with 4-morpholin-4-yl-phenylamine under the same reaction conditions as described previously in the synthesis of A.4i and A.4k (HPLC-MS: $t_{Ret.}$=2.15 min; MS(M+H)$^+$=459; method LCMSBAS1) is obtained.

Method for Synthesising A.4l

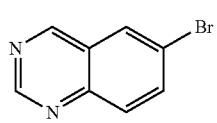

A.4l

A.4l is prepared as described in WO 2008/008821.

Method for Synthesising A.4m

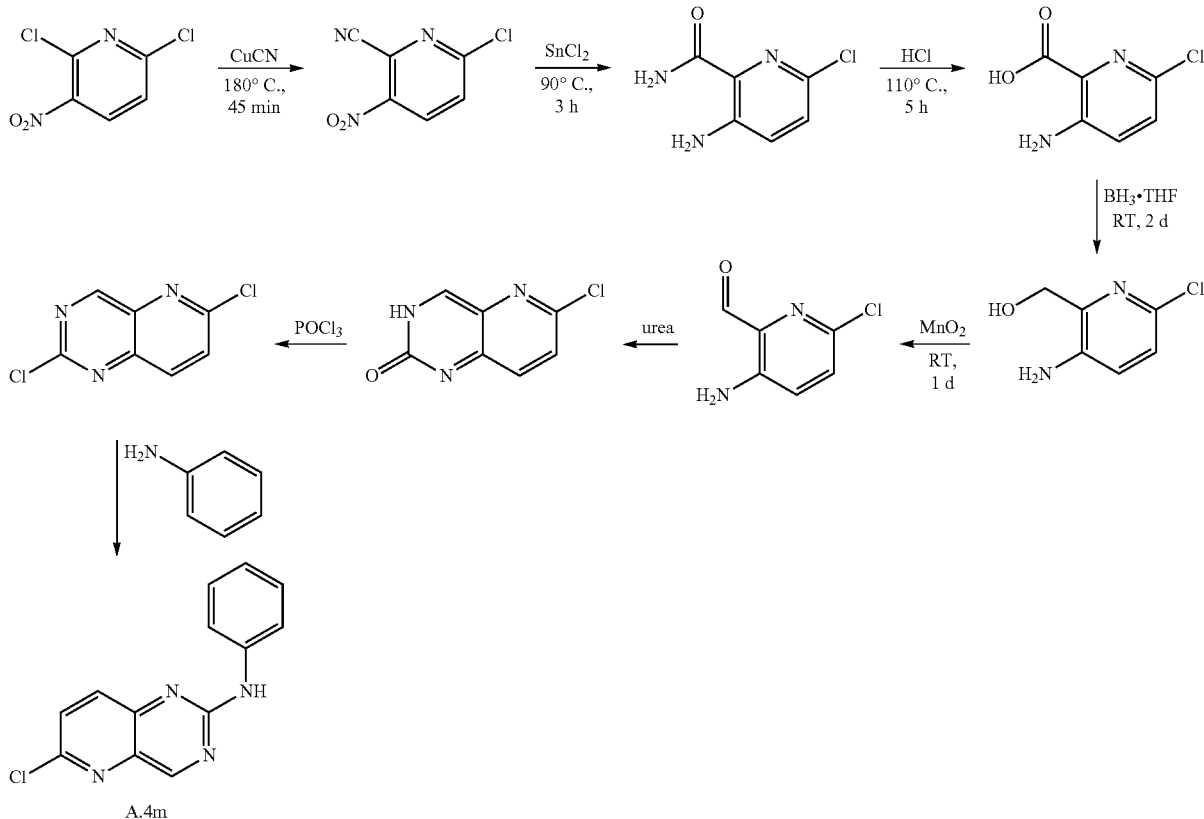

A.4m 2,6-dichloro-3-nitro-pyridine (2.5 g, 12.9 mmol) is taken up in a solvent mixture of THF and NMP (5:1, 13 mL), combined with two spatula tips of silicon carbide and CuCN (2.3 g, 26.0 mmol) and heated to 180° C. in the microwave reactor for 45 min. Then the solid obtained is suspended in $H_2O$, extracted with ethyl acetate, washed with NaCl-sln., the organic phase is dried on $MgSO_4$, the solvent is eliminated in vacuo and 6-chloro-3-nitro-pyridine-2-carbonitrile (HPLC-MS: $t_{Ret.}$=1.01 min, MS(M+H)$^+$=182, method LCMSBAS1) is obtained.

6-chloro-3-nitro-pyridine-2-carbonitrile (100 mg, 0.54 mmol) is taken up in EtOH (1 mL), combined with $SnCl_2$ (413 mg, 2.18 mmol) and heated to 90° C. for 3 h. Then the solvent is removed, the residue is taken up in ethyl acetate and first of all washed with $NaHCO_3$ to pH 7, then washed with NaOH (2 M) to pH 8-9. Then the residue is filtered through Celite®, the filtrate is extracted again with ethyl acetate and the combined organic phases are dried on $Na_2SO_4$. The solvent is eliminated in vacuo and 3-amino-6-chloro-pyridine-2-carboxylic acid amide is obtained (HPLC-MS: $t_{Ret.}$=0.78 min, MS(M+H)$^+$=172, method LCMSBAS1).

3-amino-6-chloro-pyridine-2-carboxylic acid amide (94 mg, 0.55 mmol) is taken up in conc. HCl (0.5 mL) and heated to 110° C. for 5 h. Then the solvent is removed and 3-amino-6-chloro-pyridine-2-carboxylic acid is obtained.

3-amino-6-chloro-pyridine-2-carboxylic acid (95 mg, 0.55 mmol) is taken up in THF (1 mL) and combined with $BH_3$-THF complex (2.2 mL, 2.2 mmol, 1 M in THF). The reaction mixture is stirred for 2 d at 20° C. The reaction is ended with dilute HCl and $H_2O$, then neutralised with $NaHCO_3$, extracted with EtOAc, the organic phase is dried on $MgSO_4$, the solvent is eliminated in vacuo and (3-amino-6-chloro-pyridin-2-yl)-methanol is obtained (HPLC-MS: $t_{Ret.}$=0.79 min, MS(M+H)$^+$=159; method AFEC).

(3-amino-6-chloro-pyridin-2-yl)-methanol (998 mg, 4.0 mmol) is taken up in DCM and combined with $MnO_2$ (697 mg, 8.0 mmol). After 24 h another 2 eq. $MnO_2$ are added and the mixture is stirred for further 24 h at RT. Then the reaction mixture is filtered through Celite®, the solvent is removed and 3-amino-6-chloro-pyridine-2-carbaldehyde (HPLC-MS: $t_{Ret.}$=1.88 min, MS(M+H)$^+$=157; method AFEC) is obtained.

3-amino-6-chloro-pyridine-2-carbaldehyde (3.2 g, 13.0 mmol) is mixed thoroughly with urea (7.8 g, 130 mmol) and heated to 180° C. in the preheated oil bath for 3 h. Then the reaction mixture is suspended in $H_2O$, the precipitate is filtered off and 6-chloro-3H-pyrido[3,2-d]pyrimidin-2-one is obtained.

6-chloro-3H-pyrido[3,2-d]pyrimidin-2-one (3.4 g, 5.2 mmol) are taken up in $POCl_3$ (55 mL) and the mixture is heated for 3 h to 105° C. Then the reaction mixture is added dropwise to ice water, extracted with DCM, the organic phase is dried on $MgSO_4$, the solvent is eliminated in vacuo and 2,6-dichloro-pyrido[3,2-d]pyrimidine (HPLC-MS: MS(M+H)$^+$=200; method AFEC) is obtained.

2,6-dichloro-pyrido[3,2-d]pyrimidine is reacted with aniline under the same reaction conditions as described hereinbefore for the synthesis of A.4i and A.4m (MS(M+H)$^+$=257/259; method LCMSBAS1) is obtained.

Compounds A.4n, A.4o and A.4p may be prepared analogously to A.4m starting from the corresponding carboxylic acids. 2-Amino-5-chloro-nicotinic acid is used for A.4n, while 3-amino-6-chloro-pyrazine-2-carboxylic acid is used for A.4o.

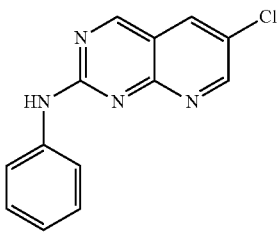

A.4n

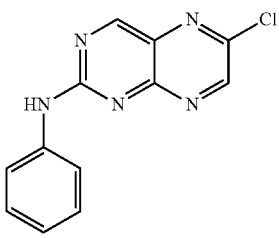

A.4o

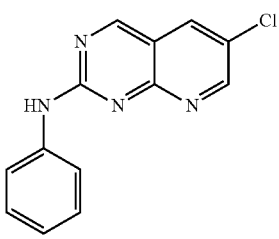

A.4p c) Synthesis of Components HR$_4$N-L-Q$^{H*}$ A.2* or HR$_4$N-L-Q$^H$A.2

Method for synthesising A.2*a

Bromoindolinone A.4*p (3.433 g, 16.19 mmol), A.3a (5.0 g, 19.43 mmol), palladium(II)acetate (363 mg, 1.619 mmol), tri-o-tolylphosphine (986 mg, 3.24 mmol) and Hünig base (5.771 mL, 34.0 mmol) are suspended in 15 mL acetonitrile and stirred for 2 h at 90° C. The reaction mixture is stirred into 0.1 N hydrochloric acid, extracted with DCM, the organic phase is dried and the solvent is eliminated in vacuo. The residue is taken up in 100 mL DCM, combined with 100 mL trifluoroacetic acid, stirred for 45 min at 20° C. and the solvent is eliminated in vacuo. The residue is purified by RP chromatography (method prep. HPLC1; 5% acetonitrile to 50% in 12 min) and the amine A.2*a (HPLC-MS: $t_{Ret.}$=1.25 min; MS(M+H)$^+$=189; method FECB3) is obtained.

A.3a may also be coupled with A.4c to form A.2b under analogous reaction conditions.

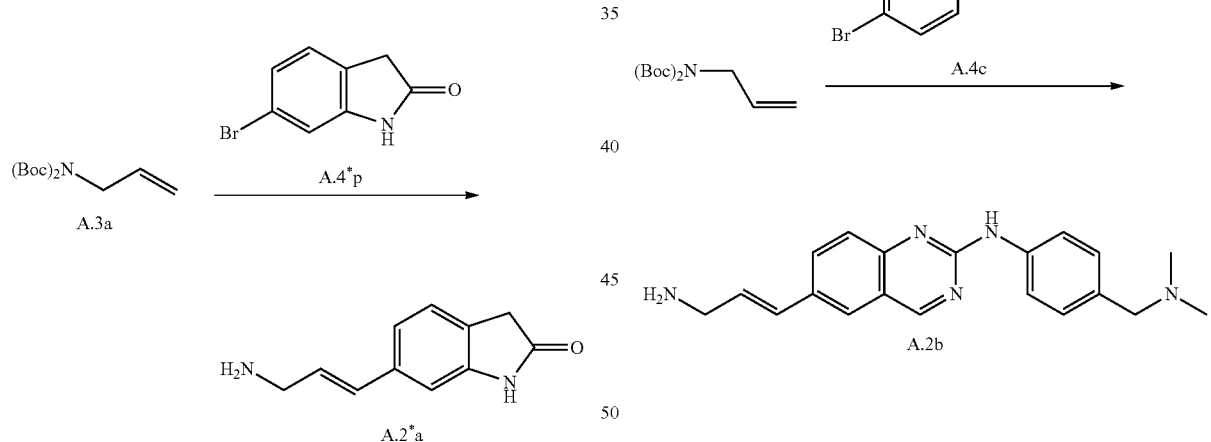

Method for Synthesising A.2c and A.2*d

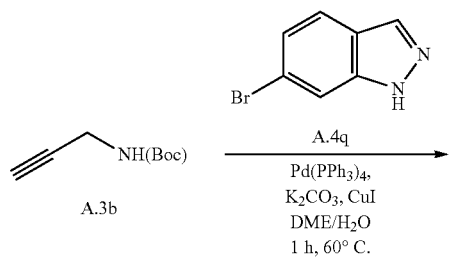

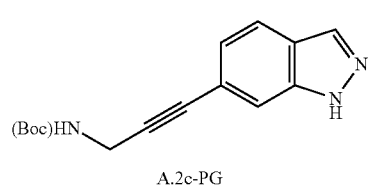

A.2c-PG

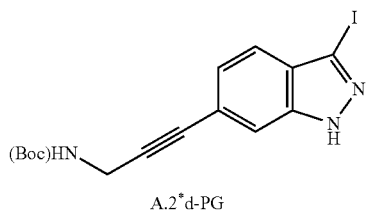

A.2*d-PG

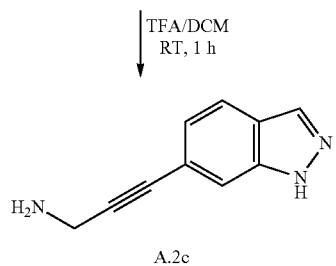

A.2c

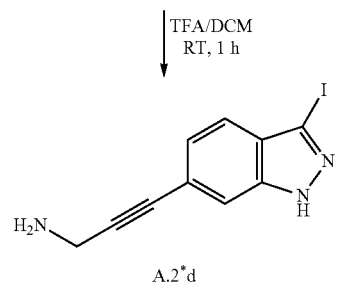

A.2*d

Bromoindazole A.4q (1.50 g, 7.61 mmol), K$_2$CO$_3$ (2.60 g, 19.0 mmol), CuI (304 mg, 1.60 mmol) and Pd(PPh$_3$)$_4$ (1.76 g, 1.60 mmol) are taken up in DME/H$_2$O (30 mL, 1:1), combined with alkyne A.3b (1.18 g, 7.61 mmol) and stirred for 1 h at 60° C. The solvent is removed, the reaction mixture is purified by column chromatography (cyclohexane/EtOAc, 10% to 70%) and A.2c-PG (HPLC-MS: t$_{Ret.}$=1.78 min; MS(M+H)$^+$=272; method LCMSBAS1) is obtained.

A.2c-PG (800 mg, 2.85 mmol) is taken up in DMF, combined with KOH (578 mg, 10.3 mmol) and heated for 2 h to 40° C. Then iodine is added (1.50 g, 5.89 mmol) and the reaction mixture is stirred for a further 30 min at 20° C. The reaction is ended with Na$_2$S$_2$O$_3$ solution, extracted with Et$_2$O, washed with NaCl, dried on MgSO$_4$, filtered off, the solvent is removed and A.2*d-PG (HPLC-MS: t$_{Ret.}$=1.96 min; MS(M−H)$^−$=396; method LCMSBAS1) is obtained.

The Boc-protective group on A.2c-PG and A.2*d-PG may be eliminated in TFA/DCM (1 h, RT) and A.2c or A.2*d is then obtained.

Under analogous S<small>ONOGASHIRA</small> conditions A.3b may also be reacted with A.4*p to form A.2*e-PG and after the Boc protective group has been cleaved A.2*e is obtained.

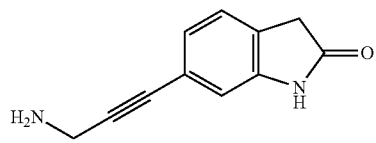

A.2*e

Method for Synthesising A.2f

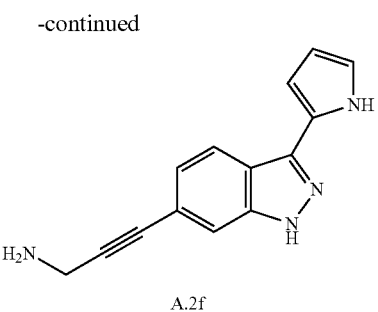

A.2f

A.2*d-PG (100 mg, 0.21 mmol) is taken up in MeOH/dioxane (1 mL, 1:1), combined with Boc-pyrrole-2-boric acid (50 mg, 0.24 mmol), K$_2$CO$_3$ (0.32 mL, 0.63 mmol, 2 M in H$_2$O) and Pd(PPh$_3$)$_4$ (12 mg, 10 mol %) and heated to 80° C. for 20 min in the microwave reactor. The reaction mixture is filtered off, purified by column chromatography (CH$_3$CN/H$_2$O, 15% auf 98%) and the A.2e provided with two Boc protective groups is obtained. This is taken up in DCM (2 mL) and slowly combined with TFA (0.1 mL). The reaction mixture is stirred for 1 h at RT, then the solvent is removed and A.2f (HPLC-MS: t$_{Ret.}$=1.41 min; MS(M+H)$^+$=237; method LCMSBAS1) is obtained.

Method for Synthesising A.2g

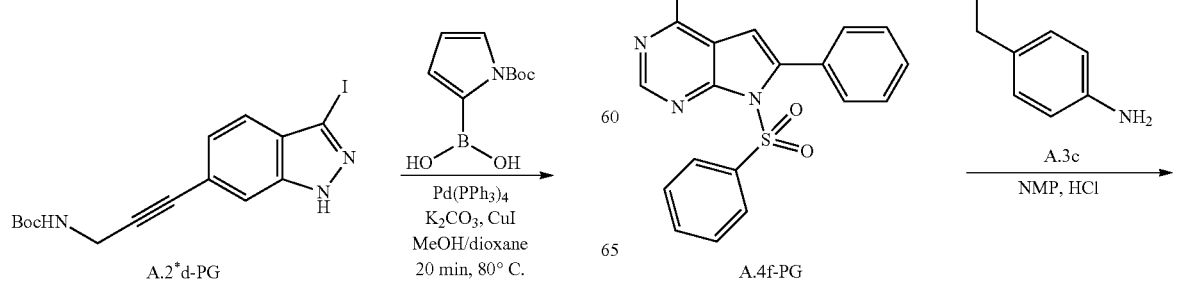

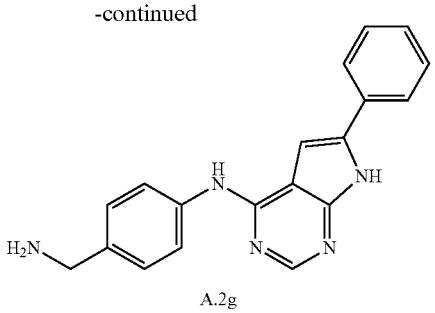

A.4f-PG (30 mg, 0.081 mmol) and 4-aminomethyl-phenylamine A.3c (20 mg, 0.164 mmol) are taken up in 0.3 mL NMP and combined with dioxanic HCl (81 µL, 4 mmol/mL). The reaction mixture is stirred for 16 h at 100° C., the solvent is eliminated in vacuo, the residue is purified by RP-chromatography (method prep. HPLC2; 3% acetonitrile to 60% in 12 min) and A.2g (HPLC-MS: $t_{Ret.}$=1.32 min, MS(M+H)$^+$=316; method FEC3) is obtained.

Method for Synthesising A.2h

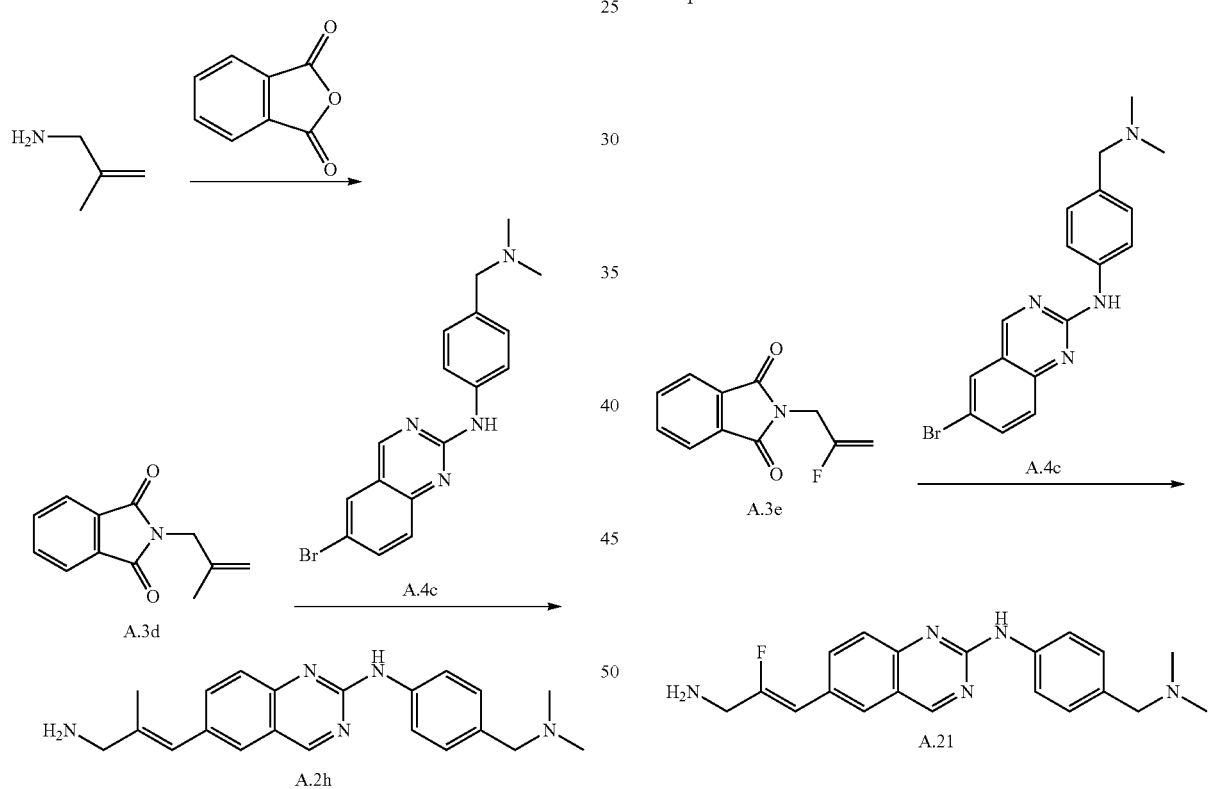

2-methyl-allylamine (1.04 g, 0.015 mol) and phthalic anhydride (2.00 g, 0.014 mol) are taken up in 50 mL acetic acid and stirred for 16 h under reflux conditions. Then the solvent is eliminated in vacuo, the residue is taken up in DCM and extracted with sodium hydrogen carbonate solution. The organic phase is dried, the solvent is eliminated in vacuo and A.3d (HPLC-MS: $t_{Ret.}$=1.85 min, MS(M+H)$^+$=202; method FECSUNFIRE) is obtained.

A.4c (200 mg, 0.56 mmol), A.3d (115 mg, 0.572 mmol), palladium(II)-acetate (14 mg, 0.063 mmol), tri-o-tolylphosphine (37 mg, 0.122 mmol) and Hünig base (0.2 mL, 1.214 mmol) are suspended in 1.5 mL THF/NMP (5:1) and the mixture is stirred for 7 h at 70° C. The reaction mixture is stirred into 0.1 N hydrochloric acid, extracted with DCM, the organic phase is dried and the solvent is eliminated in vacuo. The residue is purified by RP-chromatography (method prep. HPLC2; 5% acetonitrile to 65% in 12 min). The phthalimide-protected intermediate product thus obtained is taken up in 3 mL EtOH, combined with hydrazine hydrate (70 µL, 1.41 mmol) and stirred for 3 h at 50° C. The solvent is eliminated in vacuo and the residue is purified by normal phase chromatography (DCM/10% ammonia in methanol: 95:5→85:15 in 30 min) and A.2h (HPLC-MS: $t_{Ret.}$=1.80 min; MS(M+H)$^+$=348; method FECBM2) is obtained.

Method for Synthesising A.2i

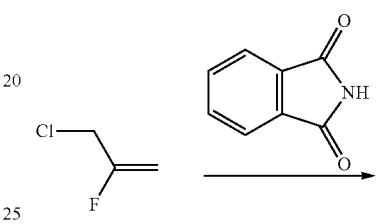

3-chloro-2-fluoro-propene (0.52 g, 5.50 mmol) and phthalimide (1.00 g, 5.40 mol) are taken up in 6 mL DMF and stirred for 16 h at 20° C. The reaction mixture is stirred into water and A.3e (HPLC-MS: $t_{Ret.}$=1.77 min, MS(M+H)$^+$=206; method FECSUNFIRE) is obtained as precipitate.

A.3e is then coupled with A.4c to form A.2i, the reaction conditions being those used in the synthesis of A.2h from A.3d and A.4c (see above). (HPLC-MS: $t_{Ret.}$=1.63 min; MS(M+H)$^+$=352; method FECB5).

Method for Synthesising A.2j

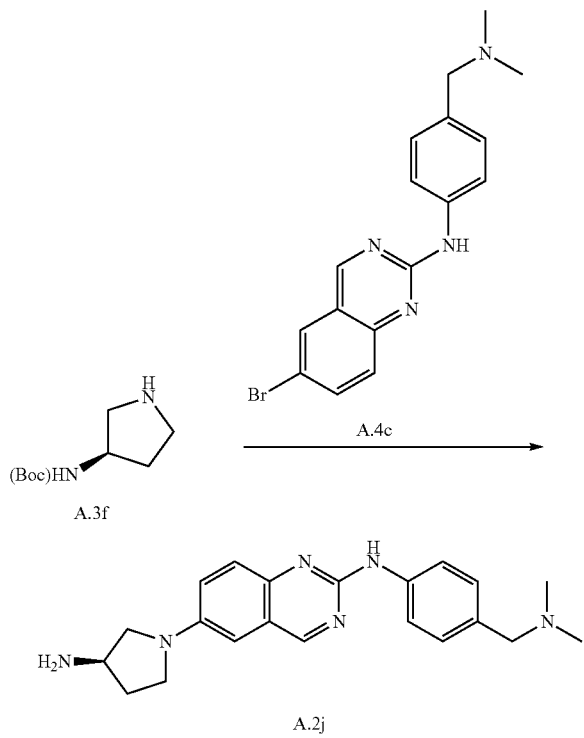

A.4c (50 mg, 0.14 mmol), A.3f (78 mg, 0.419 mmol), Pd₂dba₃ (13 mg, 0.014 mmol), X-Phos (20 mg, 0.042 mmol) and caesium carbonate (182 mg, 0.559 mmol) are suspended in 700 μL toluene and 36 μL NMP and stirred for 2 h at 115° C. The reaction mixture is stirred into 0.1 N hydrochloric acid, extracted with DCM, the organic phase is dried and the solvent is eliminated in vacuo. The residue is purified by RP-chromatography (method prep. HPLC2; 10% acetonitrile to 60% in 12 min) and the Boc-protected precursor of A.2j is obtained. This is taken up in 8 mL of a 4 N dioxanic hydrochloric acid solution and stirred for 16 h at 20° C. The solvent is eliminated in vacuo and free A.2j (HPLC-MS: $t_{Ret.}$=1.62 min; MS(M+H)⁺=363; method FECB5) is obtained.

Method for Synthesising A.2k-PG

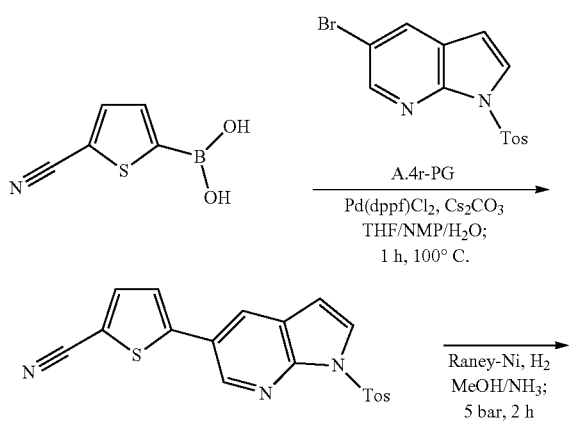

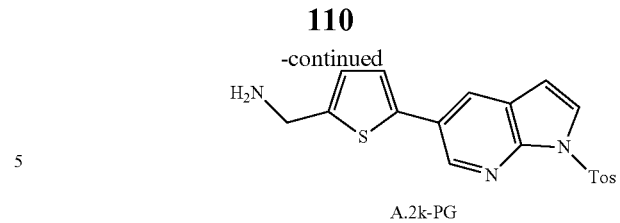

A.4r-PG (1.0 g, 2.8 mmol), 5-cyano-2-boric acid thiophene (479 mg, 3.1 mmol) and Pd(dppf)Cl₂ (232 mg, 10 mol %) are taken up in THF/NMP (7 mL, 1:1). Then Cs₂CO₃ solution (1.9 g, 5.7 mmol in 2.5 mL H₂O) is added and the reaction mixture is heated to 100 C for 1 h in the microwave reactor. The residue is taken up in H₂O, extracted with DCM, washed with NaCl-sln., the organic phase is dried on MgSO₄ and the solvent is eliminated in vacuo. The residue is purified by column chromatography (MeOH/DCM, 5% to 20%) and 5-[1-(toluene-4-sulphonyl)-1H-pyrrolo[2,3-b]pyridin-5-yl]-thiophene-2-carbonitrile (HPLC-MS: $t_{Ret.}$=2.48 min; MS(M+H)⁺=380; method AFEC) is obtained.

5-[1-(toluene-4-sulphonyl)-1H-pyrrolo[2,3-b]pyridin-5-yl]-thiophene-2-carbonitrile (155 mg, 0.41 mmol) is taken up in MeOH/NH₃ (15 mL), combined with two spatula tips of Raney nickel and hydrogenated for 2 h at 5 bar. Then the reaction mixture is filtered, the solvent is removed and A.2k-PG (HPLC-MS: $t_{Ret.}$=1.84 min; MS(M+H)⁺=384, method LCMSBAS1) is obtained.

Method for Synthesising A.2l-PG

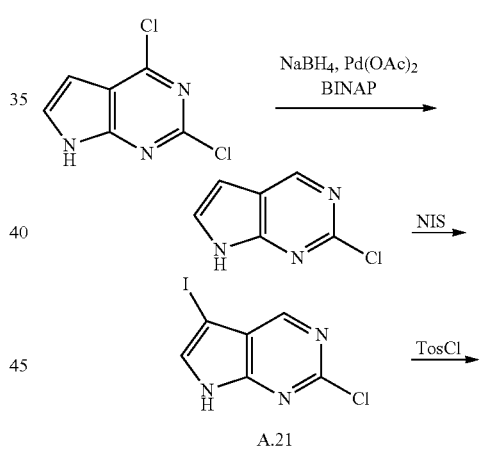

2,4-dichloro-7H-pyrrolo[2,3-d]pyrimidine (500 mg, 2.66 mmol), palladium(II)acetate (70 mg, 0.31 mmol) and BINAP (240 mg, 0.39 mmol) are dissolved in 6 mL THF and stirred for 20 min at 20° C. Then TMEDA (300 μL; 2.0 mmol) is added, the mixture is stirred for 20 min and then sodium borohydride (189 mg; 5.11 mmol) dissolved in 10 mL diglyme is added. After 1 h at 20° C. the mixture is combined with 1 N HCl and the solvent is eliminated in vacuo. The residue is purified by column chromatography (method prep. HPLC2; 3% acetonitrile to 55% in 12 min) and 2-chloro-7H- pyrrolo[2,3-d]pyrimidine (HPLC-MS: $t_{Ret.}$=1.25 min; MS(M+H)$^+$=154; method FEC3) is obtained.

2-chloro-7H-pyrrolo[2,3-d]pyrimidine (330 mg; 2.15 mmol) and N-iodosuccinimide (580 mg; 2.58 mmol) are taken up in 3.3 mL DMF and stirred for 1 h at 20° C. The reaction mixture is extracted with sodium thiosulphate solution and ethyl acetate. The combined organic phases are dried, the solvent is eliminated in vacuo and A.21 (HPLC-MS: $t_{Ret.}$=1.60 min; MS(M+H)$^+$=280; method FEC3) is obtained.

A.21 (400 mg, 1.43 mmol), benzenesulphonyl chloride (272 µL, 2.13 mmol), DMAP (18 mg, 0.15 mmol) and Hünig base (350 µL, 2.17 mmol) are taken up in 10 mL DCM and stirred for 16 h at 20° C. The solvent is eliminated in vacuo, the residue is purified by column chromatography (method prep. HPLC2; 10% acetonitrile to 95% in 12 min) and A.21-PG (HPLC-MS: $t_{Ret.}$=1.98 min; MS(M+H)$^+$=420; method FEC3) is obtained.

Method for Synthesising A.2m

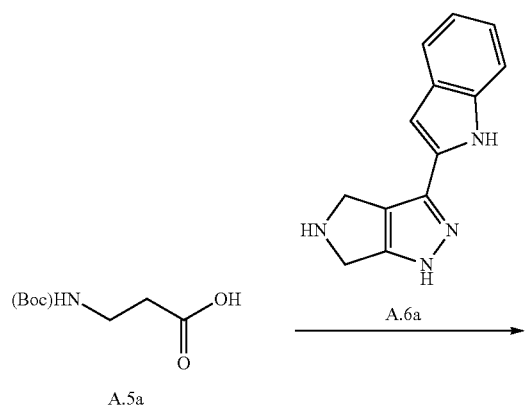

d) Synthesis of Amides A.9
Method for Synthesising A.9a

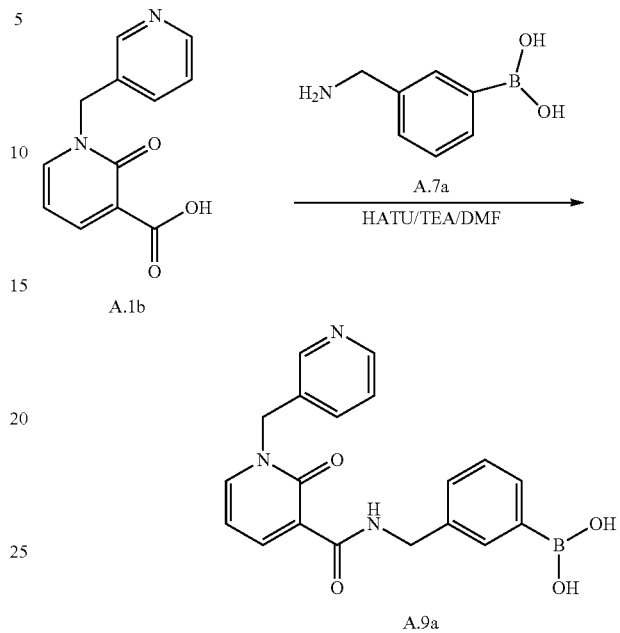

The carboxylic acid A.1b (86.5 mg, 0.376 mmol), HATU (214 mg, 0.564 mmol) and triethylamine (364 µL, 2.256 mmol) are suspended in 0.5 mL DMF and stirred for 5 min at 20° C. Then the benzylamine A.7a is added as hydrochloride (84 mg, 0.451 mmol) and the mixture is stirred for 60 min at 20° C. The solvent is eliminated in vacuo, the residue is purified by RP chromatography (method prep. HPLC1; 15% acetonitrile to 65% in 10 min) and A.9a (MS (M+H)$^+$=364; method FECB3) is obtained.

Method for Synthesising A.9b

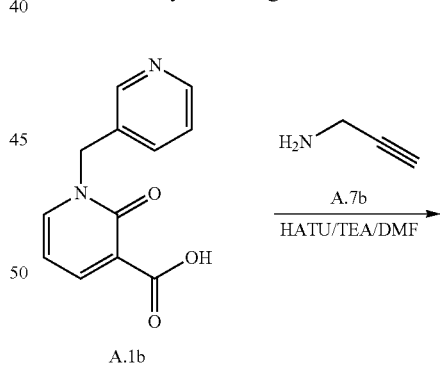

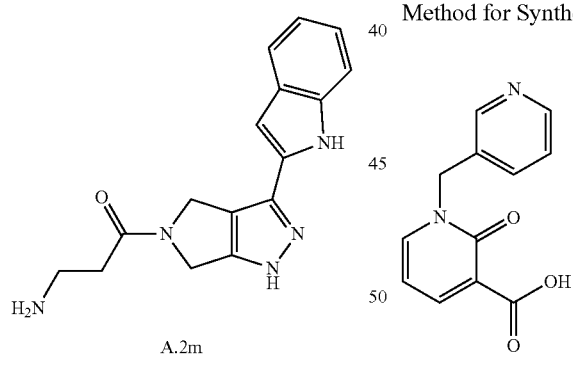

Carboxylic acid A.5a (71 mg, 0.376 mmol), HATU (214 mg, 0.564 mmol) and triethylamine (364 µL, 2.256 mmol) are suspended in 0.5 mL DMF and stirred for 5 min at 20° C. Then A.6a (101 mg, 0.451 mmol) is added and the mixture is stirred for 60 min at 20° C. It is combined with semi-saturated sodium hydrogen carbonate solution and DCM, the organic phase is separated off and the solvent is eliminated in vacuo. The residue is taken up in 5 mL DCM, combined with 5 mL trifluoroacetic acid and stirred for 4 h at 20° C. Then the solvent is eliminated in vacuo. The residue is purified by RP chromatography (method prep. HPLC1; 20% acetonitrile to 70% in 10 min) and A.2m (MS (M+H)$^+$=296; method FECB3) is obtained.

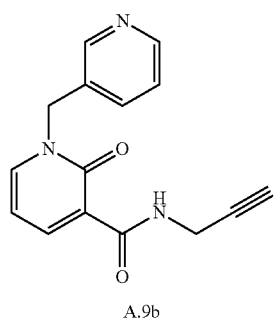

The carboxylic acid A.1b (86.5 mg, 0.376 mmol), HATU (214 mg, 0.564 mmol) and triethylamine (364 μL, 2.256 mmol) are suspended in 0.5 mL DMF and stirred for 5 min at 20° C. Then the amine A.7b (25 mg, 0.451 mmol) is added and the mixture is stirred for 60 min at 20° C. The solvent is eliminated in vacuo, the residue is purified by RP-chromatography (method prep. HPLC1; 5% acetonitrile to 50% in 10 min) and A.9b (MS (M+H)⁺=268; method FECB3) is obtained.

A.9c may also be prepared analogously to A.9b from A.1a and allylamine.

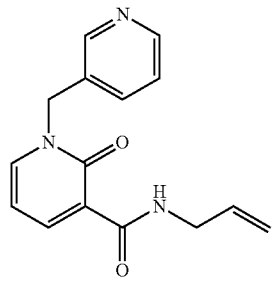

A.9c e) Synthesis of Amides C.1
Method for Synthesising C.1a

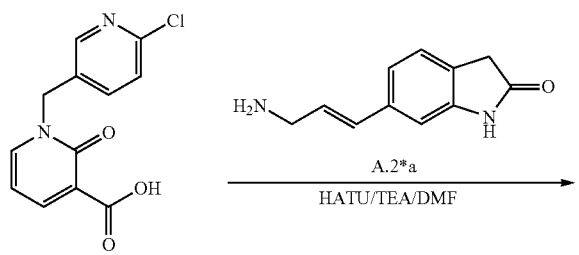

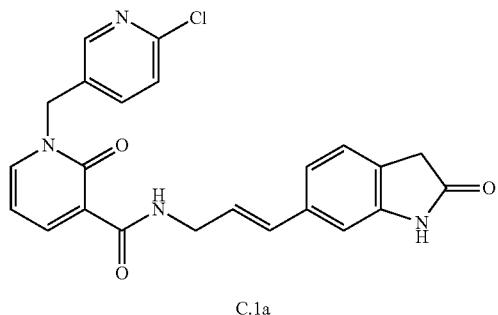

C.1a

The carboxylic acid A.1a (233 mg, 0.528 mmol), HATU (201 mg, 0.528 mmol) and triethylamine (146 μL, 1.16 mmol) are suspended in 1 mL DMF and stirred for 5 min at 20° C. Then the amine A.2*a (99 mg, 0.528 mmol) is added and the mixture is stirred for 60 min at 20 C. The reaction mixture is diluted with ethyl acetate and extracted with dilute sodium hydrogen carbonate solution. The organic phase is dried, the solvent is eliminated in vacuo and C.1a (HPLC-MS: $t_{Ret.}$=1.57 min; MS(M+H)⁺=435/437; method FECB3) is obtained.

f) Synthesis of Example Compounds of Type I
Method for Synthesising I-1

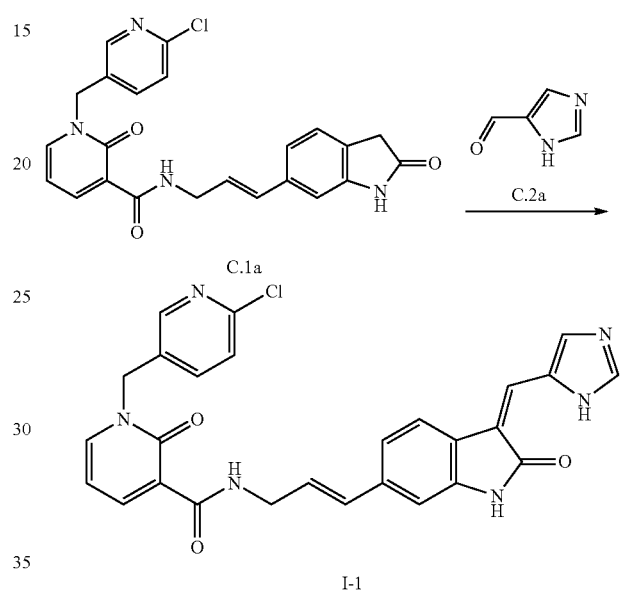

I-1

Amide C.1a (85 mg, 0.172 mmol) and imidazolecarbaldehyde C.2a (38 mg, 0.396 mmol) are taken up in 0.5 mL of a solvent mixture consisting of 2-propanol and DCM (3:1) and combined with piperidine (15 μL, 0.137 mmol). The reaction mixture is stirred for 1.5 h at 20° C., then the solvent is eliminated in vacuo, the residue is purified by RP chromatography (method prep. HPLC1; 10% acetonitrile to 60% in 10 min) and I-1 (HPLC-MS: $t_{Ret.}$=1.68 min; MS(M+H)⁺=513/515; method LCMSBAS1) is obtained.

The following Example compounds I-2 to I-27 (Table 1) are prepared analogously to I-1, by reacting the corresponding carboxylic acid A.1 first of all with component A.2*a and then with pyrrole- or imidazole-carbaldehydes C.2.

TABLE 1

| # | Structure | $t_{Ret.}$ (HPLC) [min] | MS (M + H)⁺ | HPLC-method |
|---|-----------|------|-----|--------|
| I-1 | 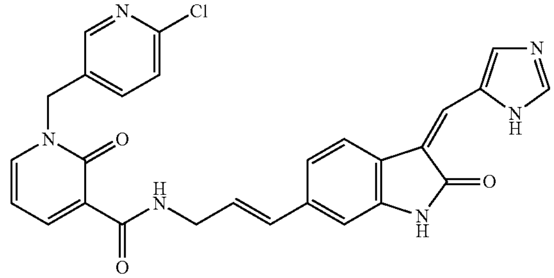 [SMILES: O=C1Nc2cc(/C=C/CNC(=O)c3cccn(Cc4ccc(Cl)nc4)c3=O)ccc2/C1=C/c1cnc[nH]1] | 1.68 | 513/515 | LCMSBAS1 |

TABLE 1-continued

| # | Structure | $t_{Ret.}$ (HPLC) [min] | MS $(M + H)^+$ | HPLC-method |
|---|---|---|---|---|
| I-2 | 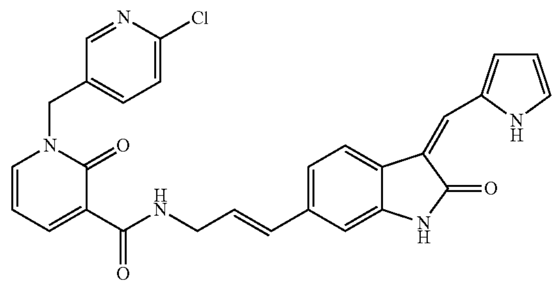 [SMILES: O=C1Nc2cc(/C=C/CNC(=O)c3cccn(Cc4ccc(Cl)nc4)c3=O)ccc2/C1=C/c1ccc[nH]1] | 1.93 | 512/514 | LCMSBAS1 |
| I-3 | 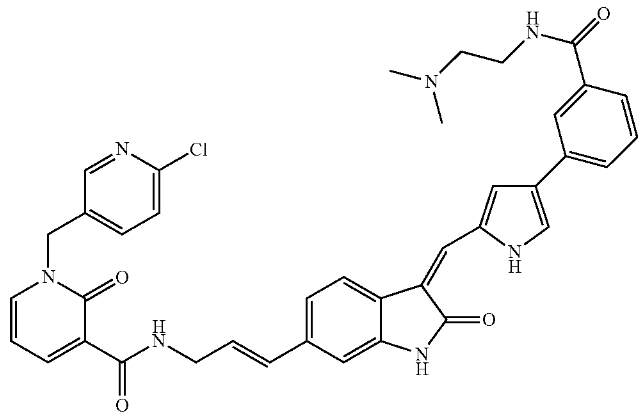 [SMILES: CN(C)CCNC(=O)c1cccc(-c2c[nH]c(/C=C3\C(=O)Nc4cc(/C=C/CNC(=O)c5cccn(Cc6ccc(Cl)nc6)c5=O)ccc43)c2)c1] | 1.86 | 702/704 | LCMSBAS1 |
| I-4 | 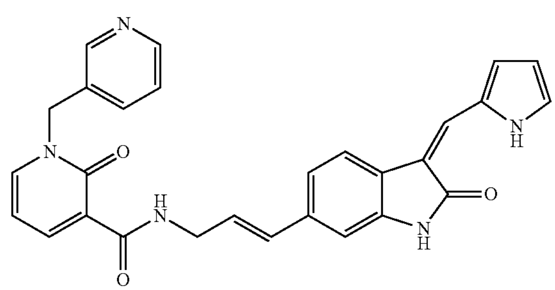 [SMILES: O=C1Nc2cc(/C=C/CNC(=O)c3cccn(Cc4cccnc4)c3=O)ccc2/C1=C/c1ccc[nH]1] | 1.69 | 478 | LCMSBAS1 |
| I-5 | 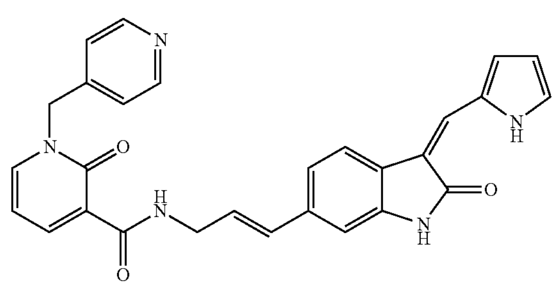 [SMILES: O=C1Nc2cc(/C=C/CNC(=O)c3cccn(Cc4ccncc4)c3=O)ccc2/C1=C/c1ccc[nH]1] | 1.67 | 478 | LCMSBAS1 |
| I-6 | 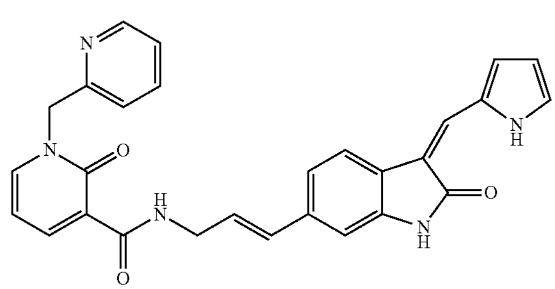 [SMILES: O=C1Nc2cc(/C=C/CNC(=O)c3cccn(Cc4ccccn4)c3=O)ccc2/C1=C/c1ccc[nH]1] | 1.76 | 478 | LCMSBAS1 |

TABLE 1-continued
| # | Structure | $t_{Ret.}$ (HPLC) [min] | MS $(M + H)^+$ | HPLC-method |
|---|---|---|---|---|
| I-7 | 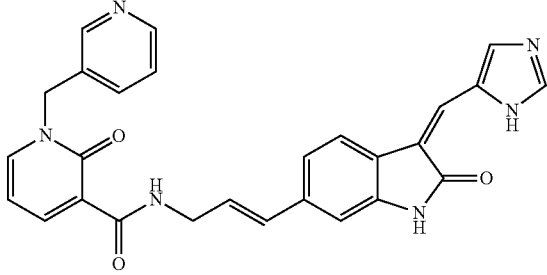 [SMILES: O=C1Nc2cc(/C=C/CNC(=O)c3cccn(Cc4cccnc4)c3=O)ccc2/C1=C/c1cnc[nH]1] | 1.24 | 479 | LCMSBAS1 |
| I-8 | 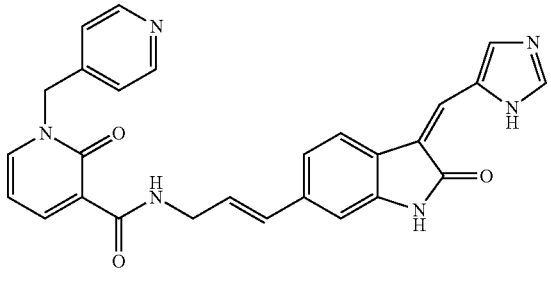 [SMILES: O=C1Nc2cc(/C=C/CNC(=O)c3cccn(Cc4ccncc4)c3=O)ccc2/C1=C/c1cnc[nH]1] | 1.42 | 479 | FECS |
| I-9 | 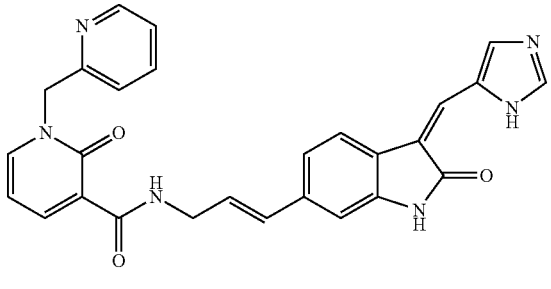 [SMILES: O=C1Nc2cc(/C=C/CNC(=O)c3cccn(Cc4ccccn4)c3=O)ccc2/C1=C/c1cnc[nH]1] | 1.24 | 479 | LCMSBAS1 |
| I-10 | 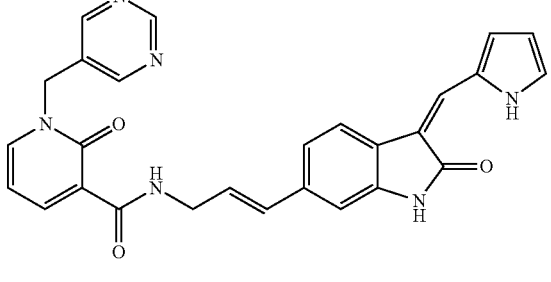 | | 479 | LCMSBAS1 |
| I-11 | 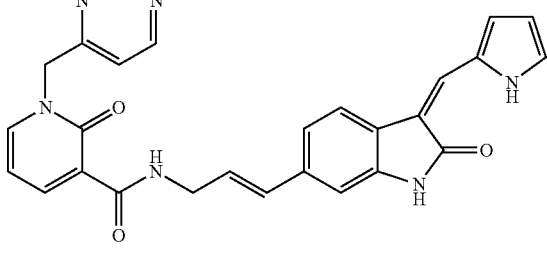 | | 479 | LCMSBAS1 |

TABLE 1-continued

| # | Structure | t$_{Ret.}$ (HPLC) [min] | MS (M + H)$^+$ | HPLC- method |
|---|---|---|---|---|
| I-12 | 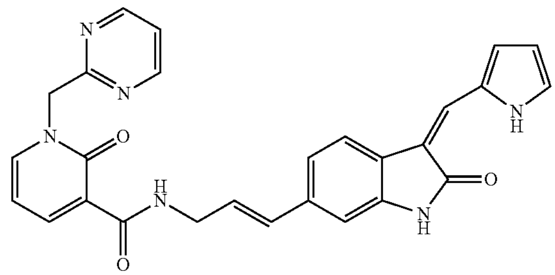 [SMILES: O=C1Nc2cc(/C=C/CNC(=O)c3cccn(Cc4ncccn4)c3=O)ccc2/C1=C/c1ccc[nH]1] | | 479 | LCMSBAS1 |
| I-13 | 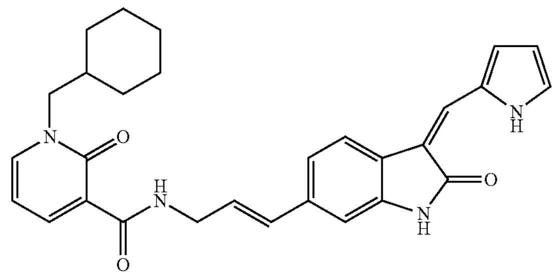 [SMILES: O=C1Nc2cc(/C=C/CNC(=O)c3cccn(CC4CCCCC4)c3=O)ccc2/C1=C/c1ccc[nH]1] | | 483 | LCMSBAS1 |
| I-14 | 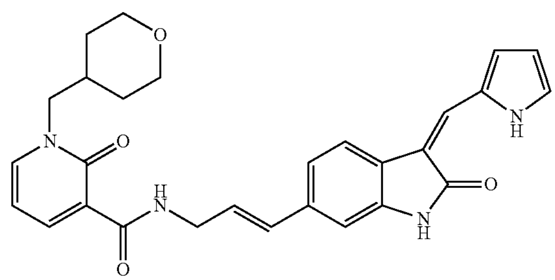 [SMILES: O=C1Nc2cc(/C=C/CNC(=O)c3cccn(CC4CCOCC4)c3=O)ccc2/C1=C/c1ccc[nH]1] | | 485 | LCMSBAS1 |
| I-15 | 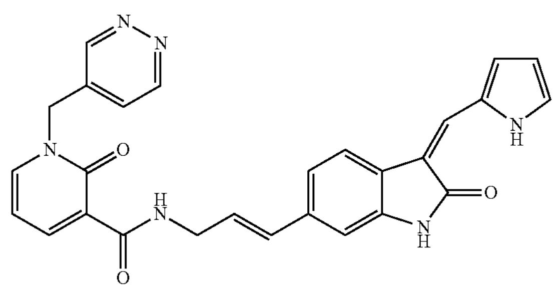 [SMILES: O=C1Nc2cc(/C=C/CNC(=O)c3cccn(Cc4ccnnc4)c3=O)ccc2/C1=C/c1ccc[nH]1] | | 479 | LCMSBAS1 |
| I-16 | 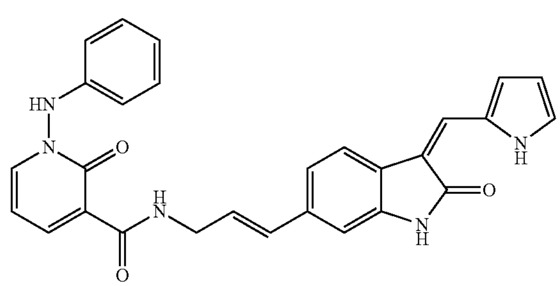 [SMILES: O=C1Nc2cc(/C=C/CNC(=O)c3cccn(Nc4ccccc4)c3=O)ccc2/C1=C/c1ccc[nH]1] | | 478 | LCMSBAS1 |

TABLE 1-continued

| # | Structure | t_Ret. (HPLC) [min] | MS (M + H)+ | HPLC-method |
|---|---|---|---|---|
| I-17 | 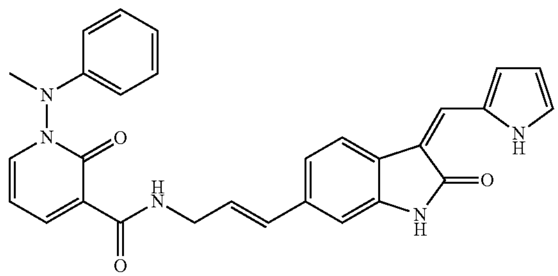 [SMILES: CN(c1ccccc1)n1cccc(C(=O)NC/C=C/c2ccc3c(c2)NC(=O)/C3=C\c2ccc[nH]2)c1=O] | | 492 | LCMSBAS1 |
| I-18 | 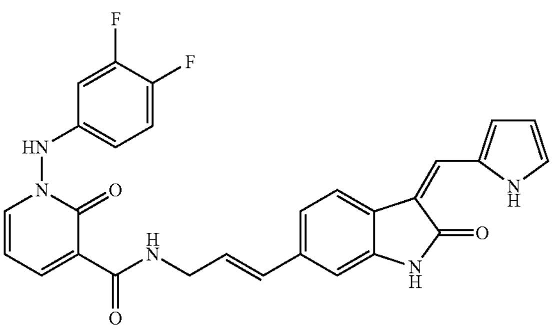 [SMILES: O=C1Nc2cc(/C=C/CNC(=O)c3cccn(Nc4ccc(F)c(F)c4)c3=O)ccc2/C1=C/c1ccc[nH]1] | | 514 | LCMSBAS1 |
| I-19 | 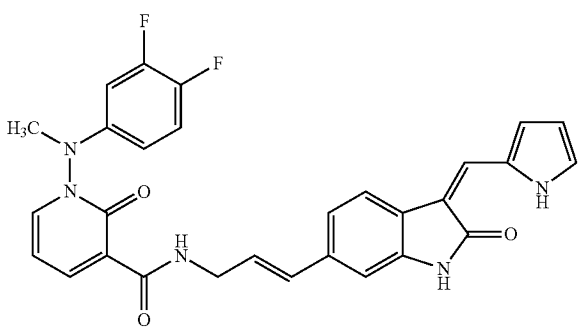 [SMILES: CN(c1ccc(F)c(F)c1)n1cccc(C(=O)NC/C=C/c2ccc3c(c2)NC(=O)/C3=C\c2ccc[nH]2)c1=O] | | 528 | LCMSBAS1 |
| I-20 | 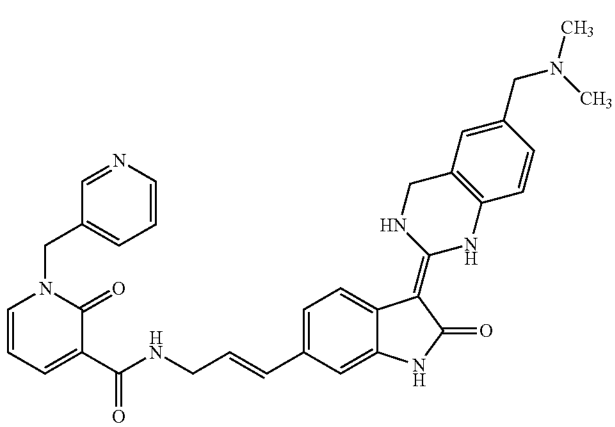 [SMILES: CN(C)Cc1ccc2c(c1)CN/C(=C1/C(=O)Nc3cc(/C=C/CNC(=O)c4cccn(Cc5cccnc5)c4=O)ccc31)N2] | | 588 | LCMSBAS1 |

TABLE 1-continued

| # | Structure | t_Ret. (HPLC) [min] | MS (M + H)+ | HPLC-method |
|---|---|---|---|---|
| I-21 | 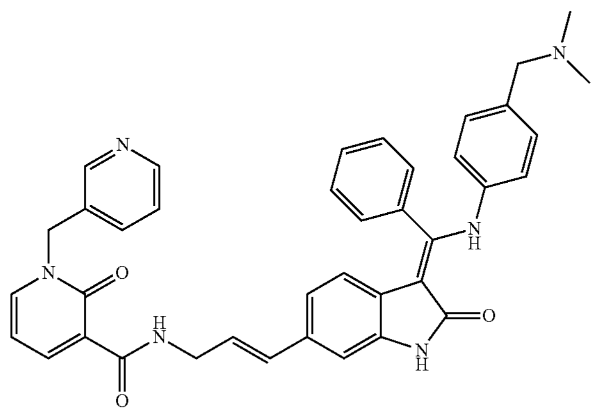 [SMILES: CN(C)Cc1ccc(N/C(=C2\C(=O)Nc3cc(/C=C/CNC(=O)c4cccn(Cc5cccnc5)c4=O)ccc32)c2ccccc2)cc1] | | 637 | LCMSBAS1 |
| I-22 | 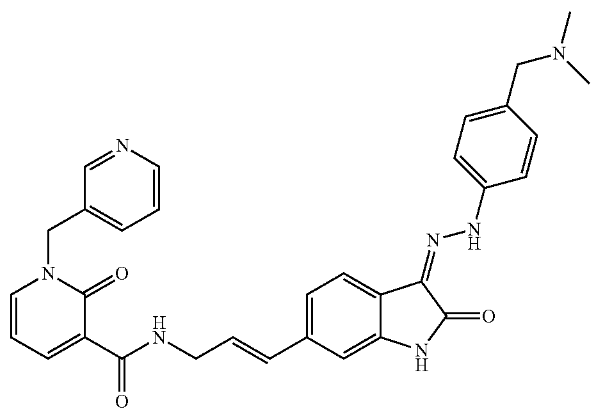 [SMILES: CN(C)Cc1ccc(N/N=C2\C(=O)Nc3cc(/C=C/CNC(=O)c4cccn(Cc5cccnc5)c4=O)ccc32)cc1] | | 562 | LCMSBAS1 |
| I-23 | 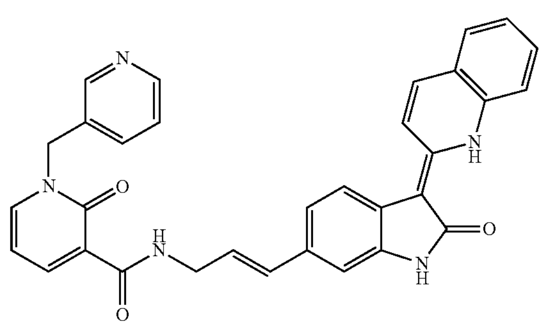 [SMILES: O=C1Nc2cc(/C=C/CNC(=O)c3cccn(Cc4cccnc4)c3=O)ccc2/C1=C1\C=Cc2ccccc2N1] | | 528 | LCMSBAS1 |
| I-24 | 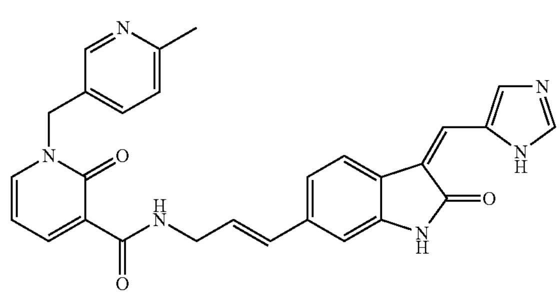 [SMILES: Cc1ccc(Cn2cccc(C(=O)NC/C=C/c3ccc4c(c3)NC(=O)/C4=C\c3cnc[nH]3)c2=O)cn1] | 1.55 | 493 | LCMSBAS1 |

TABLE 1-continued

| # | Structure | t_Ret. (HPLC) [min] | MS (M + H)+ | HPLC-method |
|---|---|---|---|---|
| I-25 | 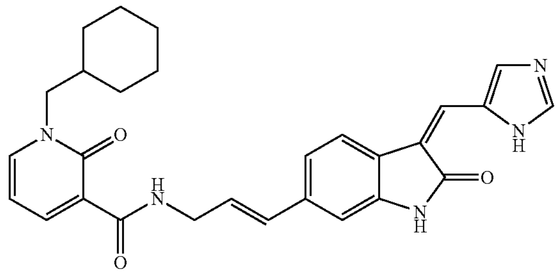 [SMILES: O=C1Nc2cc(/C=C/CNC(=O)c3cccn(CC4CCCCC4)c3=O)ccc2/C1=C/c1cnc[nH]1] | 1.93 | 484 | LCMSBAS1 |
| I-26 | 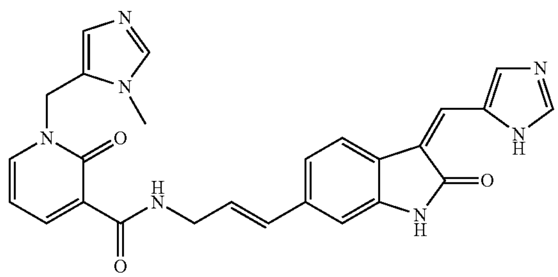 [SMILES: Cn1cncc1Cn1cccc(C(=O)NC/C=C/c2ccc3c(c2)NC(=O)/C3=C\c2cnc[nH]2)c1=O] | 1.41 | 482 | LCMSBAS1 |
| I-27 | | 1.43 | 482 | LCMSBAS1 | g) Synthesis of Example Compounds of Type II

Method for Synthesising II-1

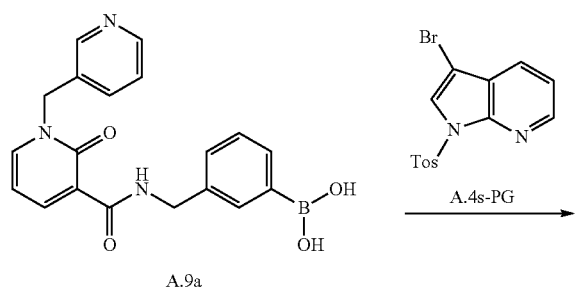

Amide A.9a (64.6 mg, 0.178 mmol), azaindole A.4s-PG (50 mg, 0.148 mmol), palladium DPPF (16 mg, 0.020 mmol) and caesium carbonate solution (72 μL, 5 mmol/mL) are suspended in 720 μL of a mixture consisting of THF/NMP (2:1) and stirred for 1 h at 100° C. The reaction mixture is diluted with water, extracted with DCM, the organic phase is dried and the solvent is eliminated in vacuo. The residue is suspended in 4 mL methanol and 1 mL water and combined with potassium carbonate (93 mg, 0.676 mmol). The reaction mixture is stirred for 1 h under reflux conditions and then freed from the solvent in vacuo. The residue is purified by RP chromatography (method prep. HPLC1; 30% acetonitrile to 80% in 8 min) and Example compound II-1 (MS (M+H)⁺=436; method FECB3) is obtained.

Method for Synthesising II-2

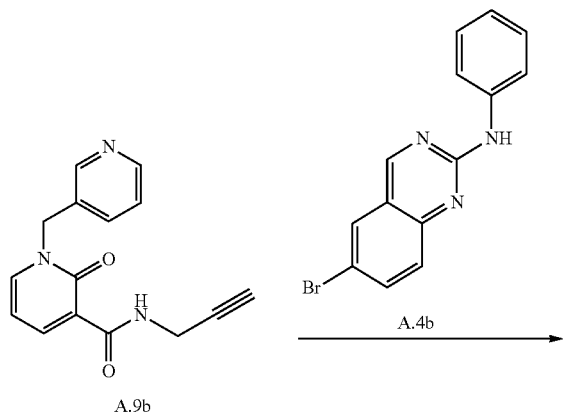

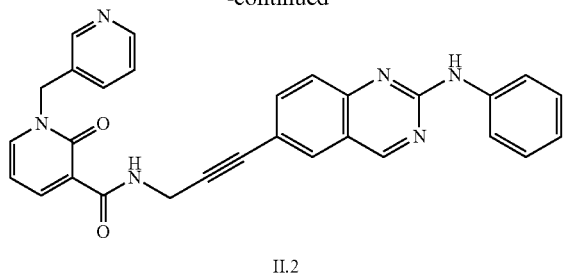

Amide A.9b (88.4 mg, 0.33 mmol), bromoquinazoline A.4b (66 mg, 0.22 mmol), dichlorobis(triphenylphosphine) palladium (15 mg, 0.022 mmol), copper(I)-iodide (4.2 mg, 0.022 mmol), triphenylphosphine (12 mg, 0.046 mmol) and diethylamine (225 mg, 3.082 mmol) are suspended in 250 µL DMF under an argon atmosphere and stirred for 1 h at 80° C. The solvents are eliminated in vacuo, the residue is purified by RP chromatography (method prep. HPLC1; 25% acetonitrile to 90% in 10 min) and the Example compound II-2 (MS (M+H)⁺=522; method FECB3) is obtained.

The following Example compounds III-3 to III-18 (Table 2) are synthesised stepwise analogously to III-1 or III-2 by SUZUKI, SONOGASHIRA or HECK cross-coupling. For this the components A.9a, A.9b, A.9c or analogues thereof are reacted with components A.4. Optionally all the Example compounds may be synthesised by synthesising corresponding amino components A.2 and coupling with carboxylic acids A.1.

TABLE 2

| # | Structure | t_Ret. (HPLC) [min] | MS (M + H)⁺ | HPLC-method |
|---|-----------|---------------------|-------------|-------------|
| II-1 | 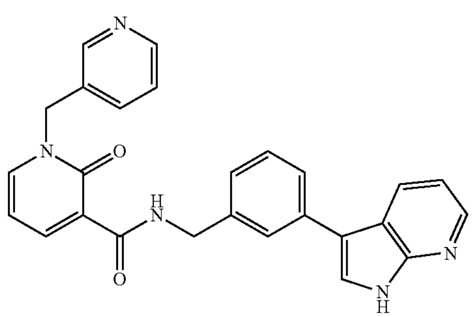 [SMILES: O=C(NCc1cccc(-c2c[nH]c3ncccc23)c1)c1cccn(Cc2cccnc2)c1=O] | | 436 | FECB3 |
| II-2 | 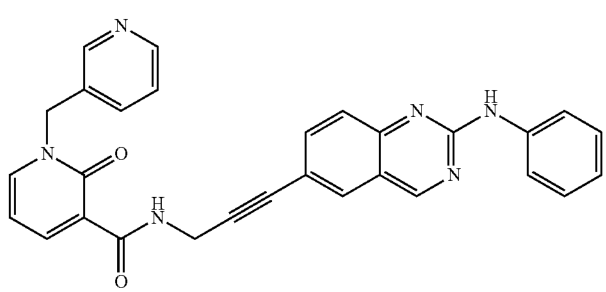 [SMILES: O=C(NCC#Cc1ccc2nc(Nc3ccccc3)ncc2c1)c1cccn(Cc2cccnc2)c1=O] | | 487 | FECB3 |

TABLE 2-continued
| # | Structure | $t_{Ret.}$ (HPLC) [min] | MS $(M+H)^+$ | HPLC-method |
|---|---|---|---|---|
| II-3 | 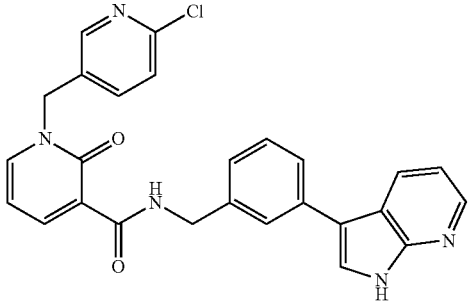 [SMILES: O=C(NCc1cccc(-c2c[nH]c3ncccc23)c1)c1cccn(Cc2ccc(Cl)nc2)c1=O] | | 470/472 | LCMSBAS1 |
| II-4 | 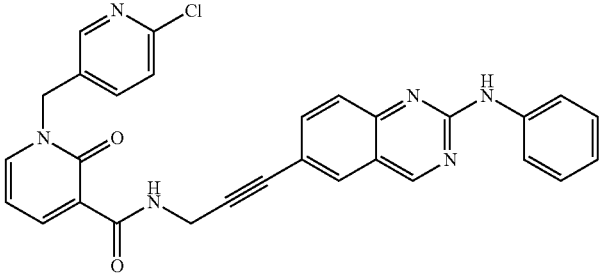 [SMILES: O=C(NCC#Cc1ccc2nc(Nc3ccccc3)ncc2c1)c1cccn(Cc2ccc(Cl)nc2)c1=O] | | 521/523 | LCMSBAS1 |
| II-5 | 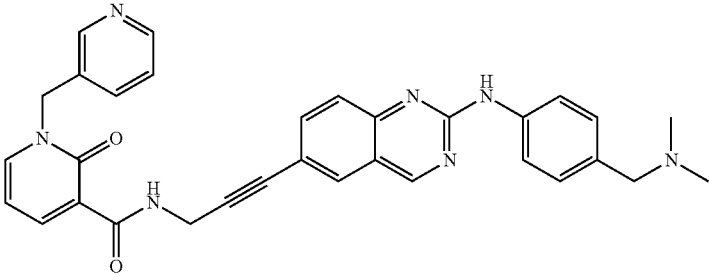 [SMILES: CN(C)Cc1ccc(Nc2ncc3cc(C#CCNC(=O)c4cccn(Cc5cccnc5)c4=O)ccc3n2)cc1] | 1.88 | 544 | LCMSBAS1 |
| II-6 | 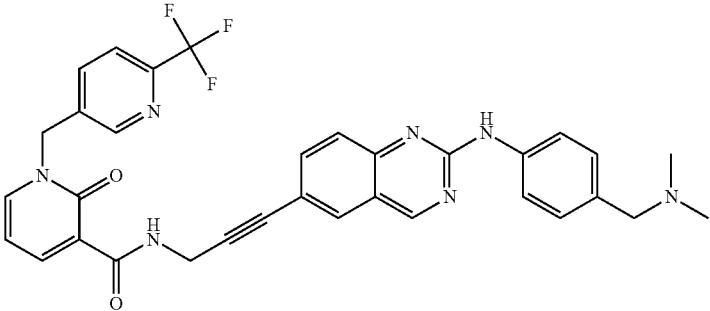 [SMILES: CN(C)Cc1ccc(Nc2ncc3cc(C#CCNC(=O)c4cccn(Cc5ccc(C(F)(F)F)nc5)c4=O)ccc3n2)cc1] | 2.06 | 612 | LCMSBAS1 |

TABLE 2-continued
| # | Structure | t_Ret. (HPLC) [min] | MS (M + H)+ | HPLC-method |
|---|---|---|---|---|
| II-7 | 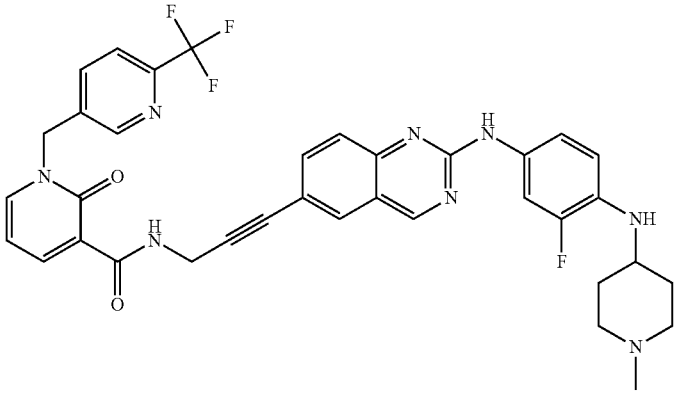 [SMILES: CN1CCC(Nc2ccc(Nc3ncc4cc(C#CCNC(=O)c5cccn(Cc6ccc(C(F)(F)F)nc6)c5=O)ccc4n3)cc2F)CC1] | 2.04 | 685 | LCMSBAS1 |
| II-8 | 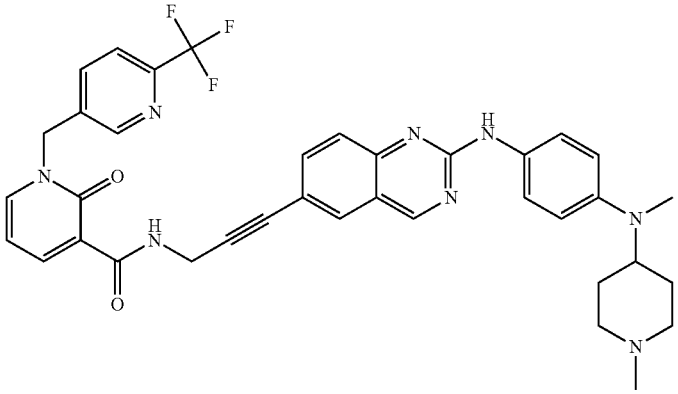 [SMILES: CN1CCC(N(C)c2ccc(Nc3ncc4cc(C#CCNC(=O)c5cccn(Cc6ccc(C(F)(F)F)nc6)c5=O)ccc4n3)cc2)CC1] | 2.09 | 681 | LCMSBAS1 |
| II-9 | 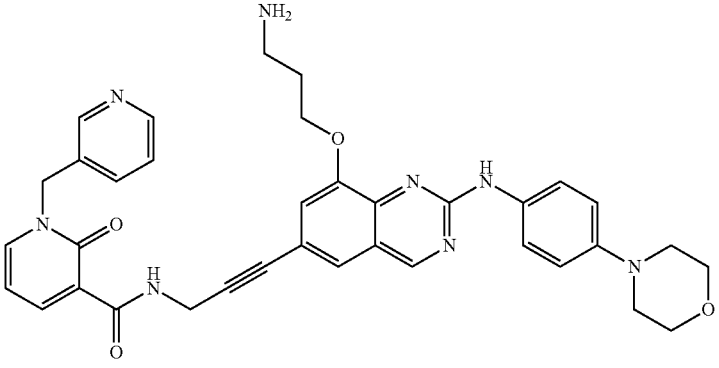 [SMILES: NCCCOc1cc(C#CCNC(=O)c2cccn(Cc3cccnc3)c2=O)cc2cnc(Nc3ccc(N4CCOCC4)cc3)nc12] |  | 645 | LCMSBAS1 |
| II-10 | 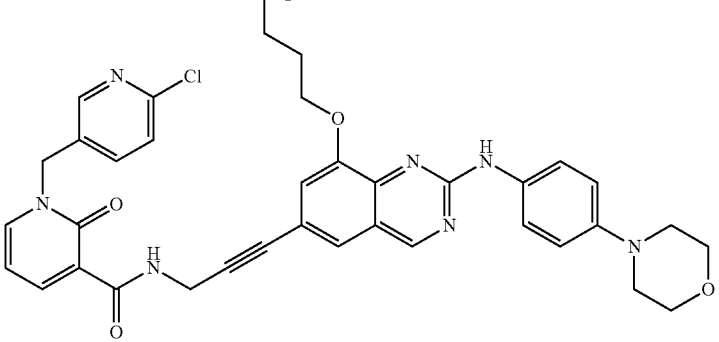 |  | 679/681 | LCMSBAS1 |

TABLE 2-continued

| # | Structure | t_Ret. (HPLC) [min] | MS (M + H)+ | HPLC-method |
|---|---|---|---|---|
| II-11 | 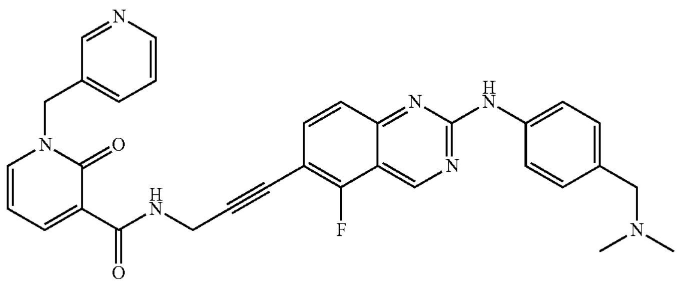 [SMILES: CN(C)Cc1ccc(Nc2ncc3c(F)c(C#CCNC(=O)c4cccn(Cc5cccnc5)c4=O)ccc3n2)cc1] | | 562 | LCMSBAS1 |
| II-12 | 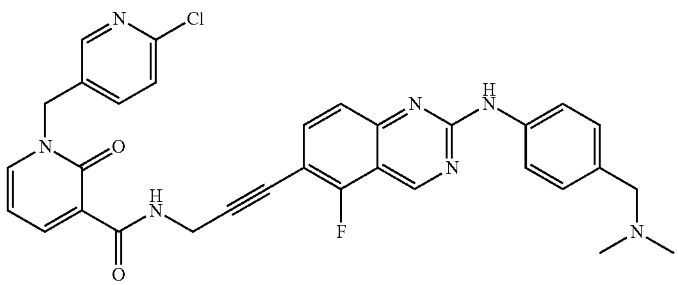 [SMILES: CN(C)Cc1ccc(Nc2ncc3c(F)c(C#CCNC(=O)c4cccn(Cc5ccc(Cl)nc5)c4=O)ccc3n2)cc1] | | 596/598 | LCMSBAS1 |
| II-13 | 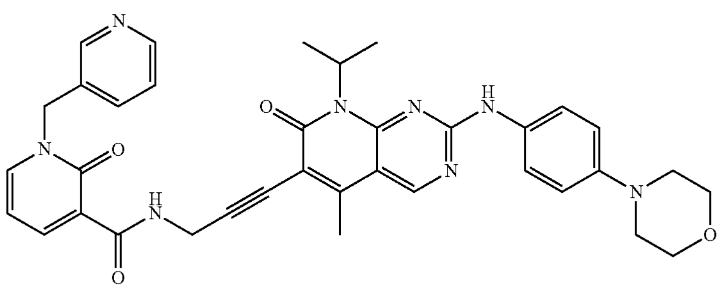 [SMILES: Cc1c(C#CCNC(=O)c2cccn(Cc3cccnc3)c2=O)c(=O)n(C(C)C)c2nc(Nc3ccc(N4CCOCC4)cc3)ncc12] | | 645 | LCMSBAS1 |
| II-14 | 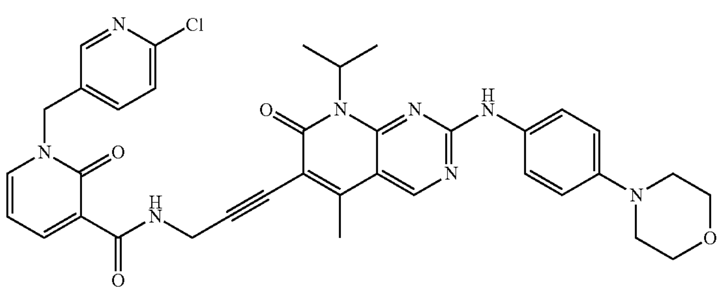 [SMILES: Cc1c(C#CCNC(=O)c2cccn(Cc3ccc(Cl)nc3)c2=O)c(=O)n(C(C)C)c2nc(Nc3ccc(N4CCOCC4)cc3)ncc12] | | 679/681 | LCMSBAS1 |
| II-15 | 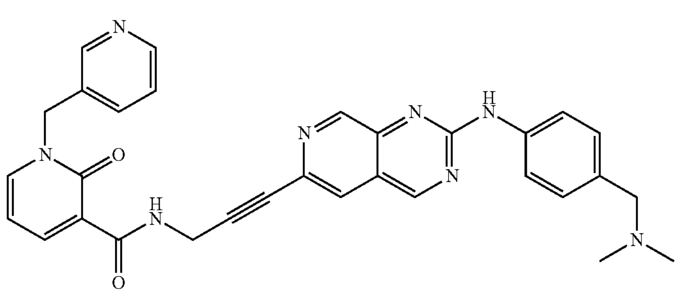 [SMILES: CN(C)Cc1ccc(Nc2ncc3cc(C#CCNC(=O)c4cccn(Cc5cccnc5)c4=O)ncc3n2)cc1] | | 545 | LCMSBAS1 |

TABLE 2-continued
| # | Structure | t_Ret. (HPLC) [min] | MS (M + H)+ | HPLC-method |
|---|---|---|---|---|
| II-16 | 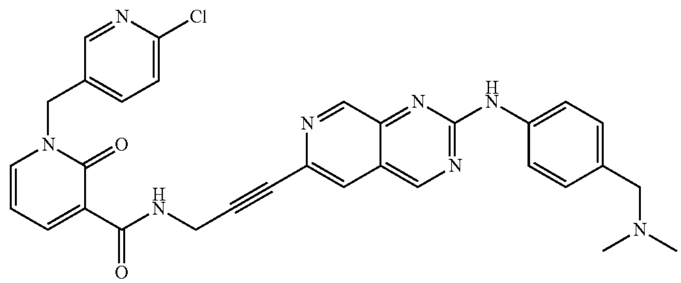 [SMILES: CN(C)Cc1ccc(Nc2ncc3cc(C#CCNC(=O)c4cccn(Cc5ccc(Cl)nc5)c4=O)ncc3n2)cc1] | | 579/581 | LCMSBAS1 |
| II-17 | 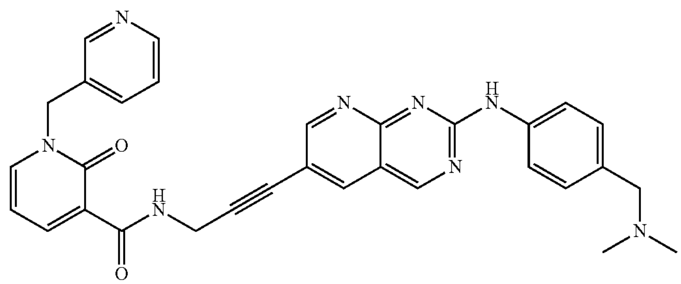 [SMILES: CN(C)Cc1ccc(Nc2ncc3cc(C#CCNC(=O)c4cccn(Cc5cccnc5)c4=O)cnc3n2)cc1] | | 545 | LCMSBAS1 |
| II-18 | 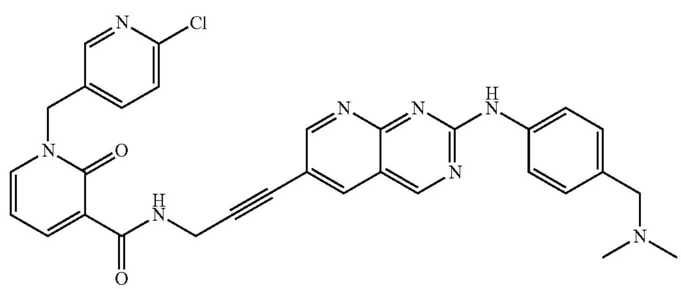 [SMILES: CN(C)Cc1ccc(Nc2ncc3cc(C#CCNC(=O)c4cccn(Cc5ccc(Cl)nc5)c4=O)cnc3n2)cc1] | | 579/581 | LCMSBAS1 |
h) Synthesis of Example Compounds of Type III
Method for Synthesising III-1
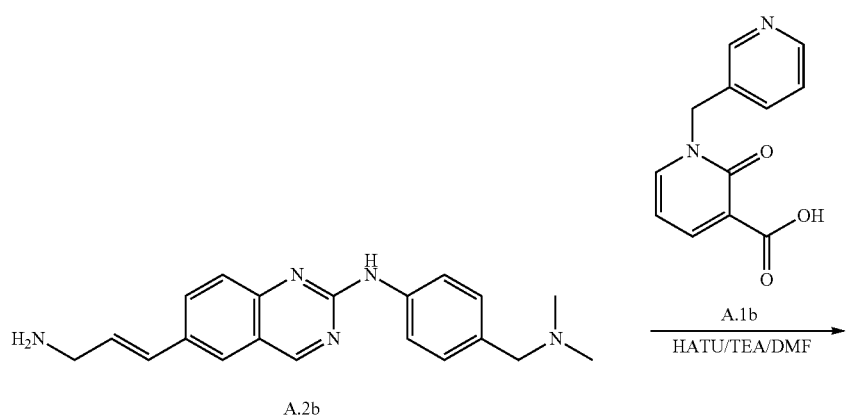

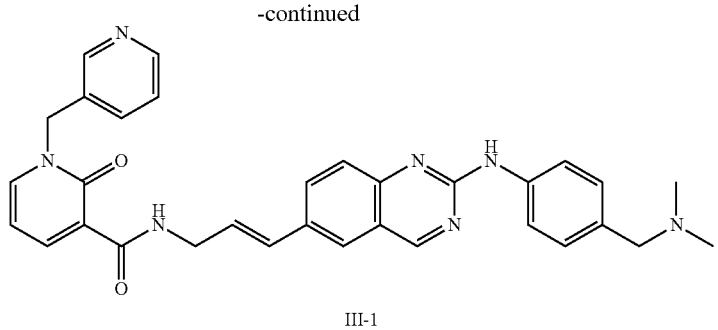

III-1

Example compound III-1 is obtained analogously to C.1a by amide coupling of A.2b and A.1b by means of HATU/TEA in DMF (MS (M+H)$^+$=546; method LCMSBAS1).

The following Example compounds III-2 to III-42 (Table 3) are synthesised analogously to the synthesis of III-1 described hereinbefore, by synthesising corresponding amino components A.2 and coupling them with carboxylic acids A.1.

TABLE 3

| # | Structure | $t_{Ret.}$ (HPLC) [min] | MS (M + H)$^+$ | HPLC-method |
|---|---|---|---|---|
| III-1 | 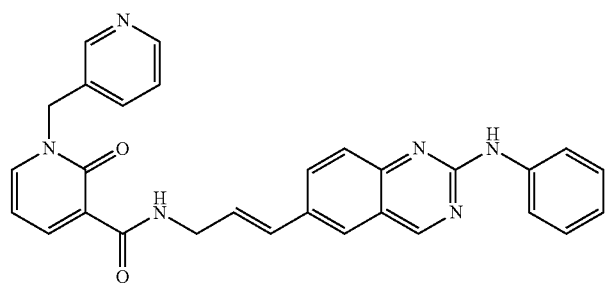 [SMILES: O=C(NC/C=C/c1ccc2nc(Nc3ccccc3)ncc2c1)c1cccn(Cc2cccnc2)c1=O] | | 489 | LCMSBAS1 |
| III-2 | 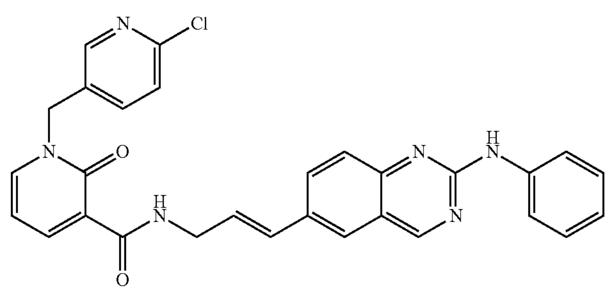 [SMILES: O=C(NC/C=C/c1ccc2nc(Nc3ccccc3)ncc2c1)c1cccn(Cc2ccc(Cl)nc2)c1=O] | | 523/525 | LCMSBAS1 |
| III-3 | 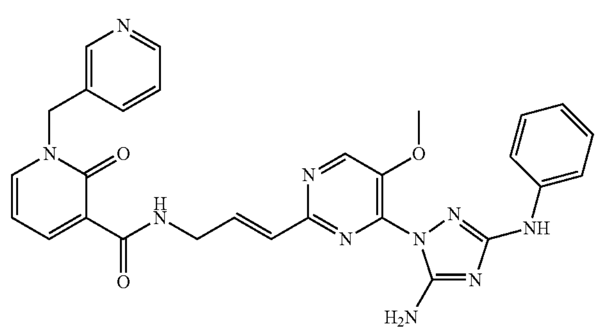 [SMILES: COc1cnc(/C=C/CNC(=O)c2cccn(Cc3cccnc3)c2=O)nc1-n1nc(Nc2ccccc2)nc1N] | | 551 | LCMSBAS1 |

TABLE 3-continued
| # | Structure | t_Ret. (HPLC) [min] | MS (M + H)+ | HPLC-method |
|---|---|---|---|---|
| III-4 | 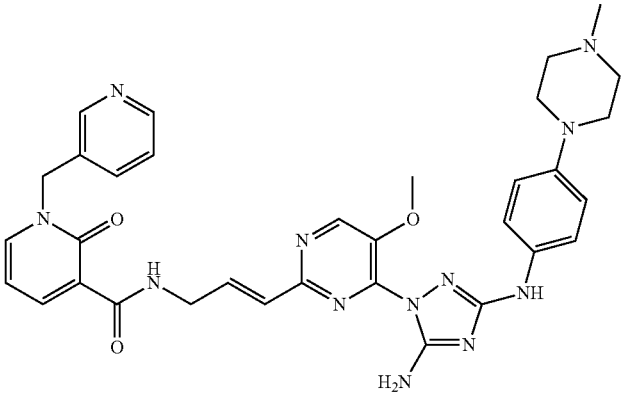 [SMILES: COc1cnc(/C=C/CNC(=O)c2cccn(Cc3cccnc3)c2=O)nc1-n1nc(Nc2ccc(N3CCN(C)CC3)cc2)nc1N] | | 649 | LCMSBAS1 |
| III-5 | 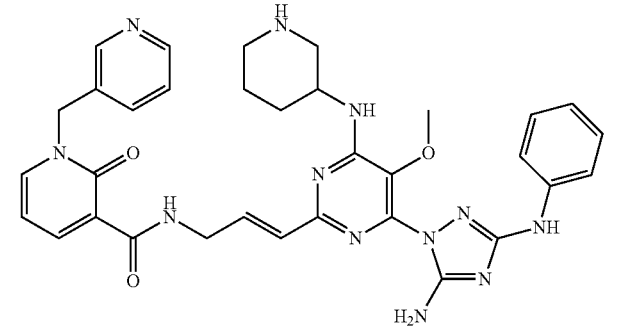 [SMILES: COc1c(NC2CCCNC2)nc(/C=C/CNC(=O)c2cccn(Cc3cccnc3)c2=O)nc1-n1nc(Nc2ccccc2)nc1N] | | 649 | LCMSBAS1 |
| III-6 | 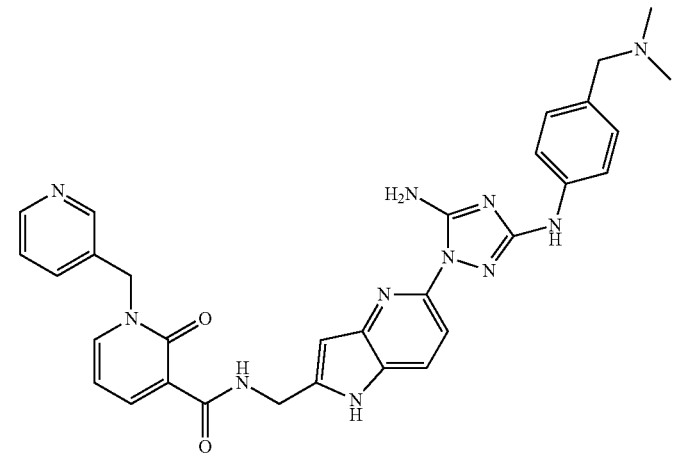 [SMILES: CN(C)Cc1ccc(Nc2nc(N)n(-c3ccc4[nH]c(CNC(=O)c5cccn(Cc6cccnc6)c5=O)cc4n3)n2)cc1] | | 590 | LCMSBAS1 |
| III-7 | 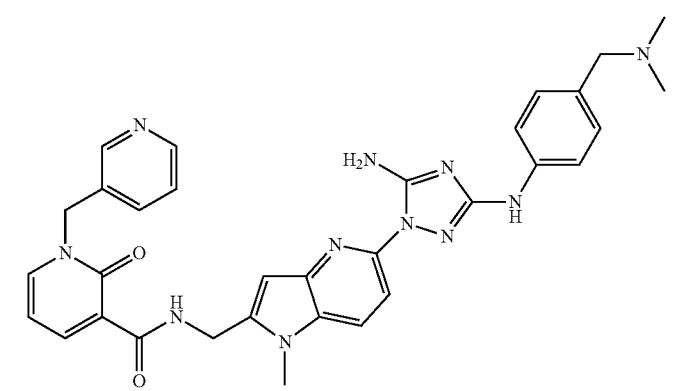 [SMILES: CN(C)Cc1ccc(Nc2nc(N)n(-c3ccc4c(cc(CNC(=O)c5cccn(Cc6cccnc6)c5=O)n4C)n3)n2)cc1] | | 604 | LCMSBAS1 |

TABLE 3-continued

| # | Structure | $t_{Ret.}$ (HPLC) [min] | MS $(M + H)^+$ | HPLC-method |
|---|---|---|---|---|
| III-8 | 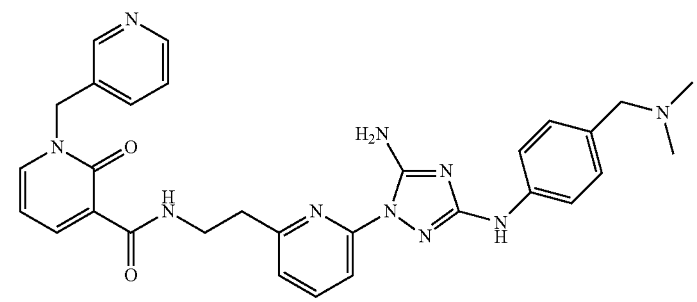 [SMILES: CN(C)Cc1ccc(Nc2nc(N)n(-c3cccc(CCNC(=O)c4cccn(Cc5cccnc5)c4=O)n3)n2)cc1] | | 565 | LCMSBAS1 |
| III-9 | 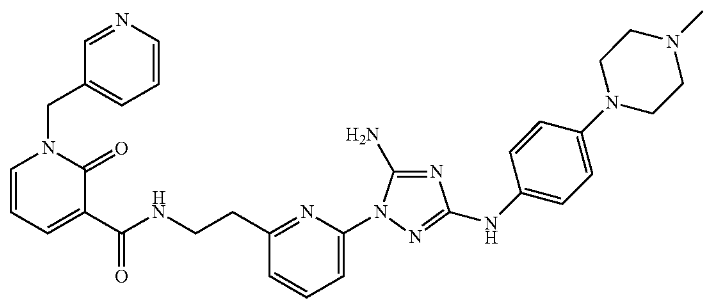 [SMILES: CN1CCN(c2ccc(Nc3nc(N)n(-c4cccc(CCNC(=O)c5cccn(Cc6cccnc6)c5=O)n4)n3)cc2)CC1] | | 606 | LCMSBAS1 |
| III-10 | 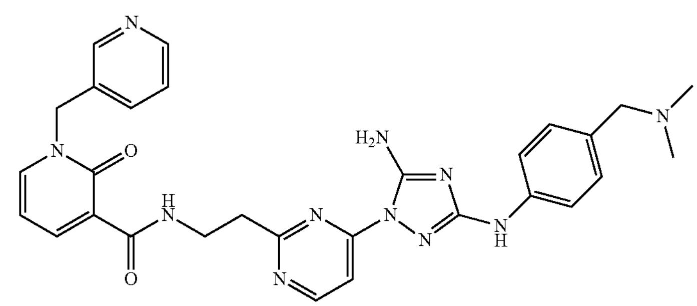 [SMILES: CN(C)Cc1ccc(Nc2nc(N)n(-c3ccnc(CCNC(=O)c4cccn(Cc5cccnc5)c4=O)n3)n2)cc1] | | 566 | LCMSBAS1 |
| III-11 | 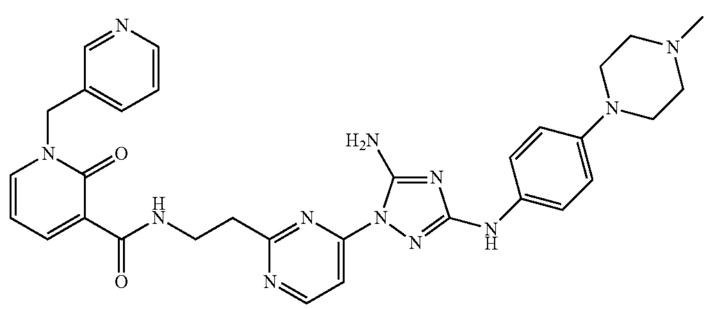 [SMILES: CN1CCN(c2ccc(Nc3nc(N)n(-c4ccnc(CCNC(=O)c5cccn(Cc6cccnc6)c5=O)n4)n3)cc2)CC1] | | 607 | LCMSBAS1 |
| III-12 | 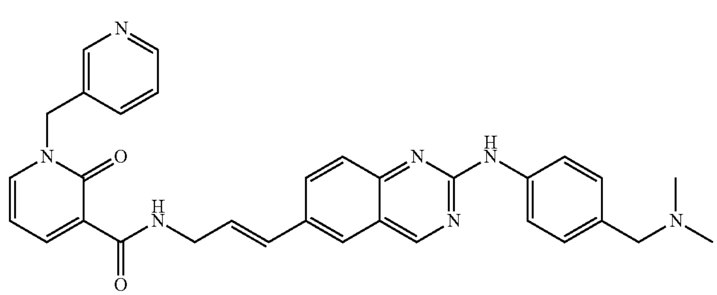 [SMILES: CN(C)Cc1ccc(Nc2ncc3cc(/C=C/CNC(=O)c4cccn(Cc5cccnc5)c4=O)ccc3n2)cc1] | 1.84 | 546 | LCMSBAS1 |

TABLE 3-continued
| # | Structure | $t_{Ret.}$ (HPLC) [min] | MS $(M + H)^+$ | HPLC-method |
|---|---|---|---|---|
| III-13 | 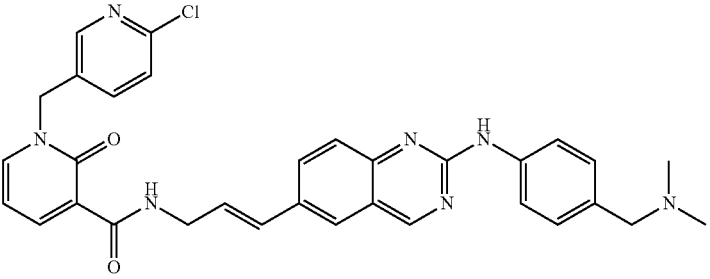 [SMILES: CN(C)Cc1ccc(Nc2ncc3cc(/C=C/CNC(=O)c4cccn(Cc5ccc(Cl)nc5)c4=O)ccc3n2)cc1] | 1.84 | 580/582 | LCMSBAS1 |
| III-14 | 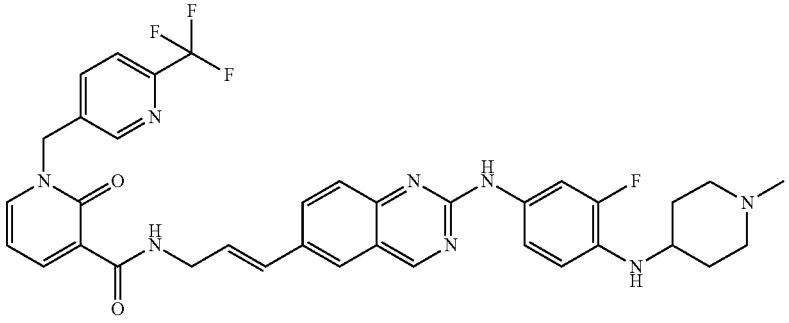 [SMILES: CN1CCC(Nc2ccc(Nc3ncc4cc(/C=C/CNC(=O)c5cccn(Cc6ccc(C(F)(F)F)nc6)c5=O)ccc4n3)cc2F)CC1] | 2.02 | 687 | LCMSBAS1 |
| III-15 | 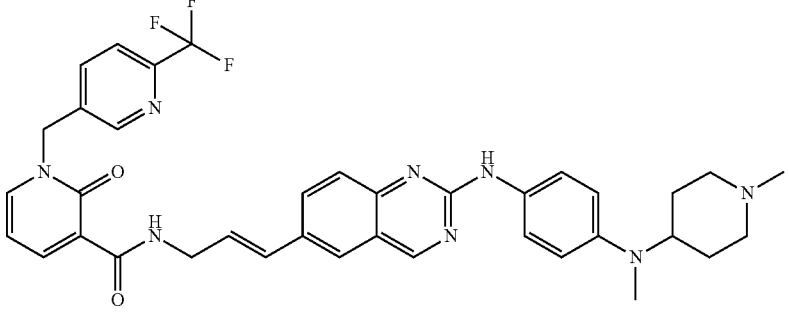 | 2.03 | 683 | LCMSBAS1 |
| III-16 | 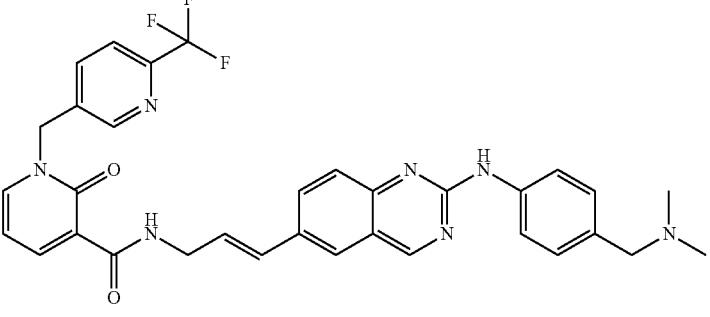 | 1.99 | 614 | LCMSBAS1 |

TABLE 3-continued

| # | Structure | t_Ret. (HPLC) [min] | MS (M + H)+ | HPLC-method |
|---|---|---|---|---|
| III-17 | 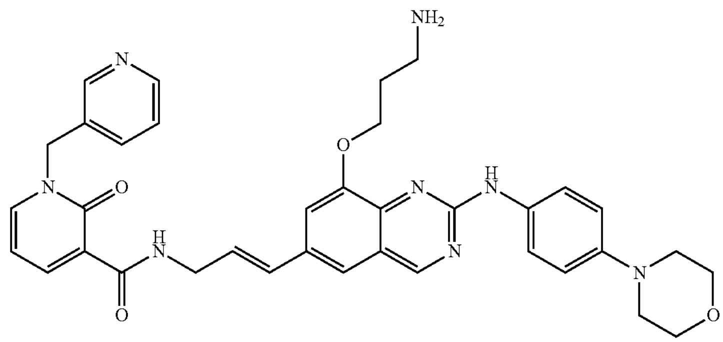 [SMILES: NCCCOc1cc(/C=C/CNC(=O)c2cccn(Cc3cccnc3)c2=O)cc2cnc(Nc3ccc(N4CCOCC4)cc3)nc12] | | 647 | LCMSBAS1 |
| III-18 | 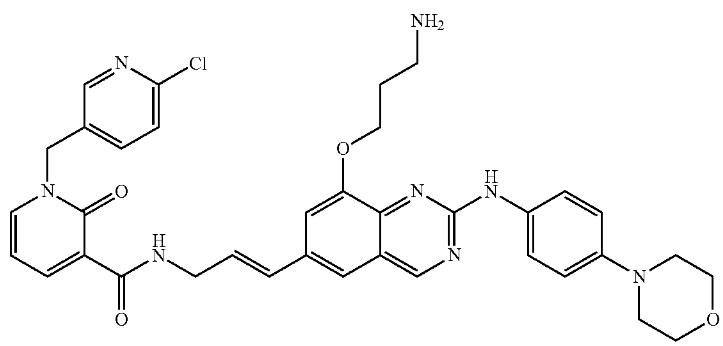 [SMILES: NCCCOc1cc(/C=C/CNC(=O)c2cccn(Cc3ccc(Cl)nc3)c2=O)cc2cnc(Nc3ccc(N4CCOCC4)cc3)nc12] | | 681/683 | LCMSBAS1 |
| III-19 | 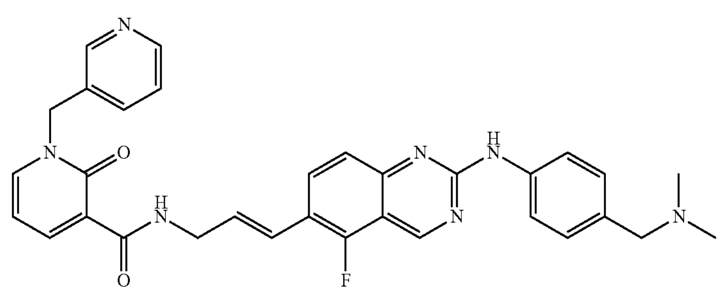 [SMILES: CN(C)Cc1ccc(Nc2ncc3c(F)c(/C=C/CNC(=O)c4cccn(Cc5cccnc5)c4=O)ccc3n2)cc1] | | 564 | LCMSBAS1 |
| III-20 | 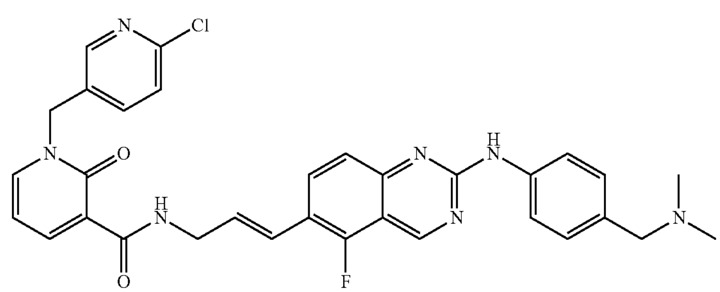 [SMILES: CN(C)Cc1ccc(Nc2ncc3c(F)c(/C=C/CNC(=O)c4cccn(Cc5ccc(Cl)nc5)c4=O)ccc3n2)cc1] | | 598/600 | LCMSBAS1 |
| III-21 | 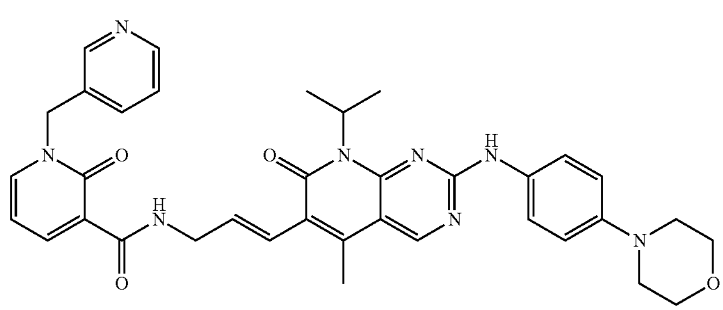 [SMILES: Cc1c(/C=C/CNC(=O)c2cccn(Cc3cccnc3)c2=O)c(=O)n(C(C)C)c2nc(Nc3ccc(N4CCOCC4)cc3)ncc12] | | 647 | LCMSBAS1 |

TABLE 3-continued

| # | Structure | t_Ret. (HPLC) [min] | MS (M + H)⁺ | HPLC-method |
|---|---|---|---|---|
| III-22 | 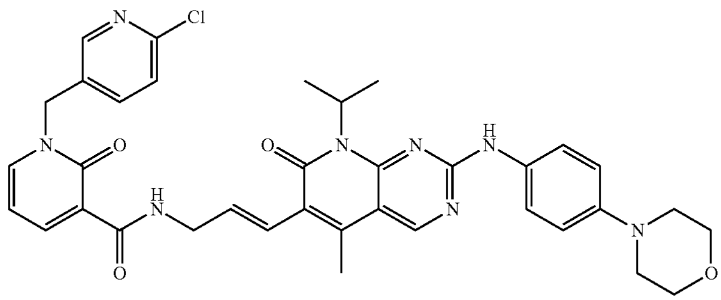 [SMILES: Cc1c(/C=C/CNC(=O)c2cccn(Cc3ccc(Cl)nc3)c2=O)c(=O)n(C(C)C)c2nc(Nc3ccc(N4CCOCC4)cc3)ncc12] | | 681/683 | LCMSBAS1 |
| III-23 | 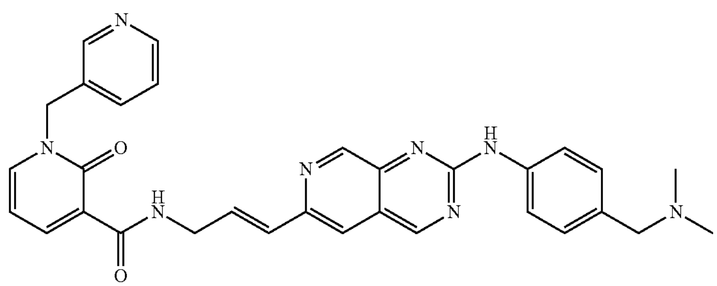 [SMILES: CN(C)Cc1ccc(Nc2ncc3cc(/C=C/CNC(=O)c4cccn(Cc5cccnc5)c4=O)ncc3n2)cc1] | | 547 | LCMSBAS1 |
| III-24 | 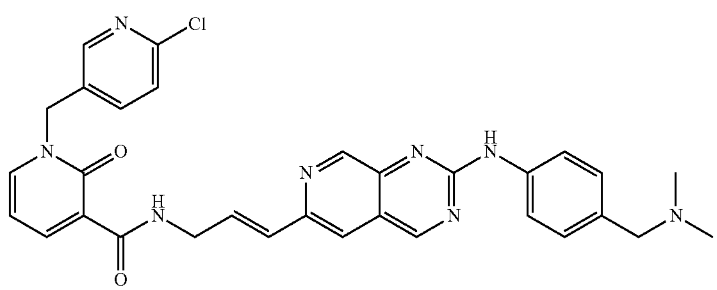 [SMILES: CN(C)Cc1ccc(Nc2ncc3cc(/C=C/CNC(=O)c4cccn(Cc5ccc(Cl)nc5)c4=O)ncc3n2)cc1] | | 581/583 | LCMSBAS1 |
| III-25 | 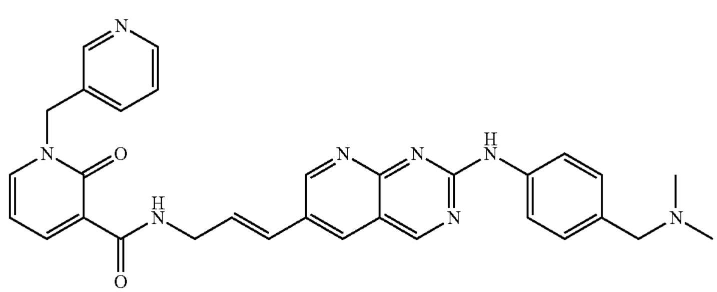 [SMILES: CN(C)Cc1ccc(Nc2ncc3cc(/C=C/CNC(=O)c4cccn(Cc5cccnc5)c4=O)cnc3n2)cc1] | | 547 | LCMSBAS1 |
| III-26 | 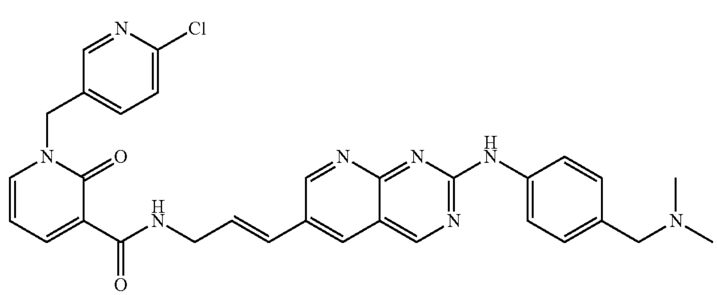 [SMILES: CN(C)Cc1ccc(Nc2ncc3cc(/C=C/CNC(=O)c4cccn(Cc5ccc(Cl)nc5)c4=O)cnc3n2)cc1] | | 581/583 | LCMSBAS1 |

TABLE 3-continued
| # | Structure | $t_{Ret.}$ (HPLC) [min] | MS $(M + H)^+$ | HPLC- method |
|---|---|---|---|---|
| III-27 | 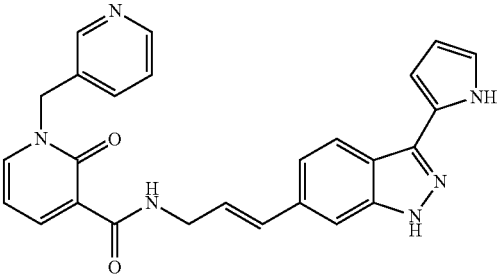 [SMILES: O=C(NC/C=C/c1ccc2c(-c3ccc[nH]3)n[nH]c2c1)c1cccn(Cc2cccnc2)c1=O] | | 451 | LCMSBAS1 |
| III-28 | 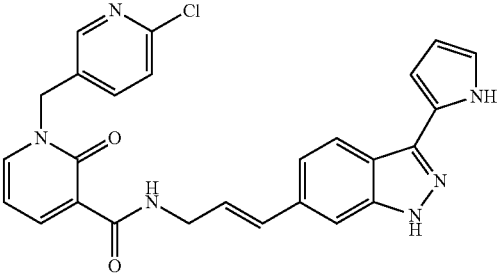 [SMILES: O=C(NC/C=C/c1ccc2c(-c3ccc[nH]3)n[nH]c2c1)c1cccn(Cc2ccc(Cl)nc2)c1=O] | | 485/487 | LCMSBAS1 |
| III-29 | 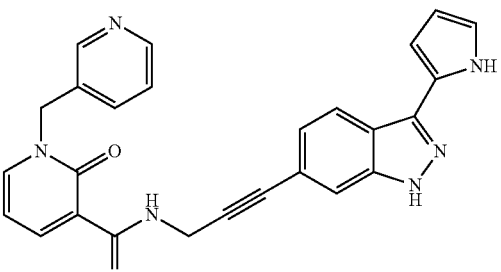 | | 449 | LCMSBAS1 |
| III-30 | 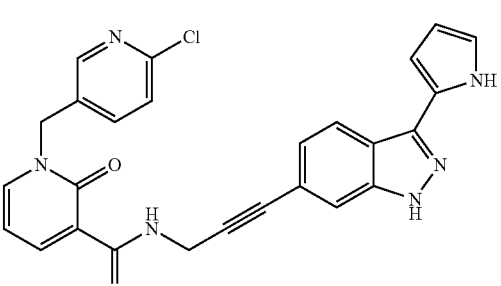 | | 483/485 | LCMSBAS1 |
| III-31 | 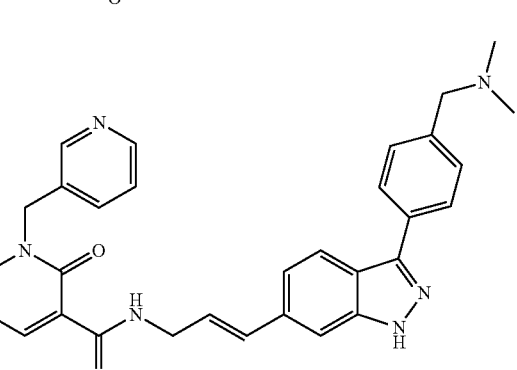 | | 519 | LCMSBAS1 |

TABLE 3-continued

| # | Structure | t_Ret. (HPLC) [min] | MS (M + H)+ | HPLC-method |
|---|---|---|---|---|
| III-32 | 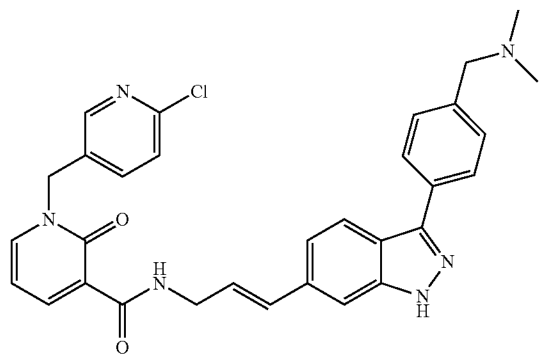 [SMILES: CN(C)Cc1ccc(-c2n[nH]c3cc(/C=C/CNC(=O)c4cccn(Cc5ccc(Cl)nc5)c4=O)ccc23)cc1] | | 553/555 | LCMSBAS1 |
| III-33 | 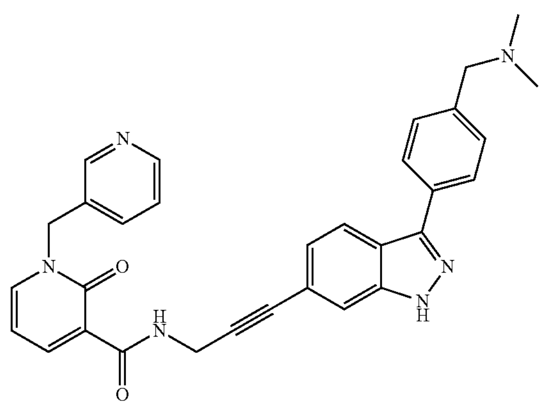 [SMILES: CN(C)Cc1ccc(-c2n[nH]c3cc(C#CCNC(=O)c4cccn(Cc5cccnc5)c4=O)ccc23)cc1] | | 517 | LCMSBAS1 |
| III-34 | 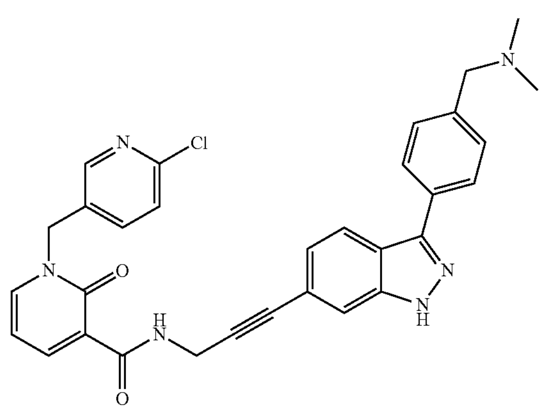 [SMILES: CN(C)Cc1ccc(-c2n[nH]c3cc(C#CCNC(=O)c4cccn(Cc5ccc(Cl)nc5)c4=O)ccc23)cc1] | | 551/553 | LCMSBAS1 |
| III-35 | 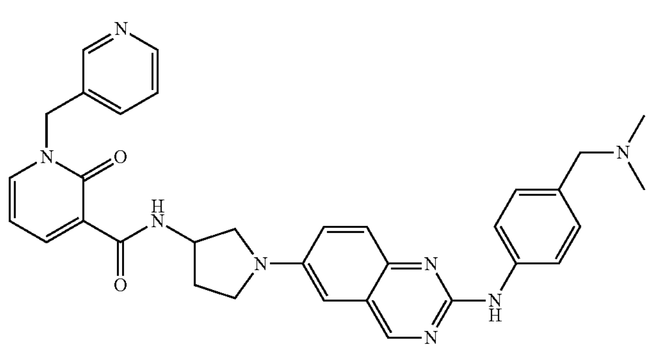 [SMILES: CN(C)Cc1ccc(Nc2ncc3cc(N4CCC(NC(=O)c5cccn(Cc6cccnc6)c5=O)C4)ccc3n2)cc1] | | 575 | LCMSBAS1 |

TABLE 3-continued

| # | Structure | $t_{Ret.}$ (HPLC) [min] | MS $(M + H)^+$ | HPLC-method |
|---|---|---|---|---|
| III-36 | 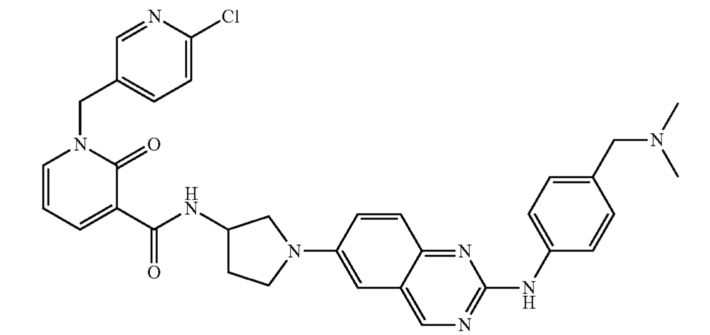 [SMILES: CN(C)Cc1ccc(Nc2ncc3cc(N4CCC(NC(=O)c5cccn(Cc6ccc(Cl)nc6)c5=O)C4)ccc3n2)cc1] | | 609/611 | LCMSBAS1 |
| III-37 | 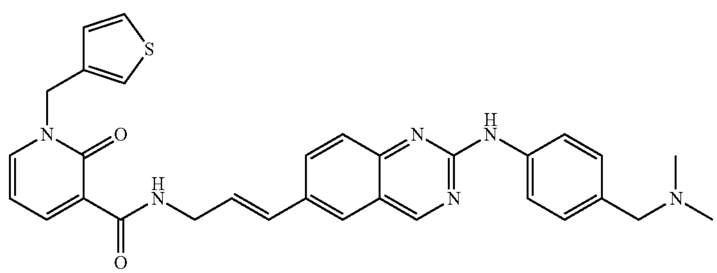 [SMILES: CN(C)Cc1ccc(Nc2ncc3cc(/C=C/CNC(=O)c4cccn(Cc5ccsc5)c4=O)ccc3n2)cc1] | | 551 | LCMSBAS1 |
| III-38 | 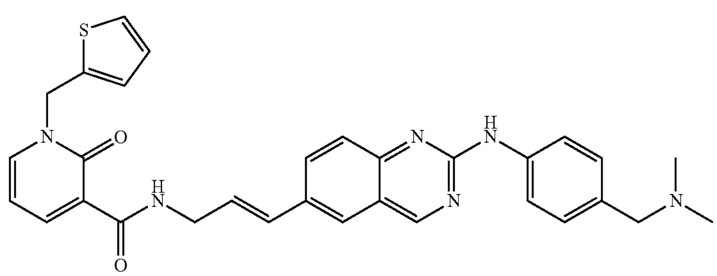 [SMILES: CN(C)Cc1ccc(Nc2ncc3cc(/C=C/CNC(=O)c4cccn(Cc5cccs5)c4=O)ccc3n2)cc1] | | 551 | LCMSBAS1 |
| III-39 | 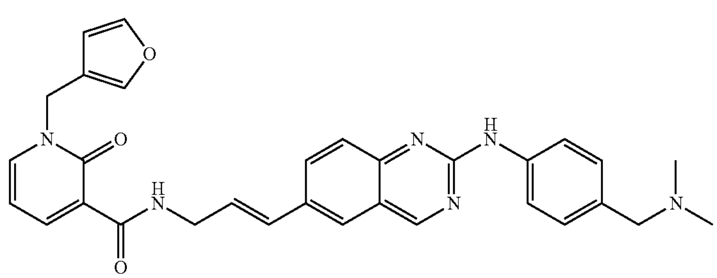 [SMILES: CN(C)Cc1ccc(Nc2ncc3cc(/C=C/CNC(=O)c4cccn(Cc5ccoc5)c4=O)ccc3n2)cc1] | | 535 | LCMSBAS1 |

TABLE 3-continued

| # | Structure | $t_{Ret.}$ (HPLC) [min] | MS $(M+H)^+$ | HPLC- method |
|---|---|---|---|---|
| III-40 | 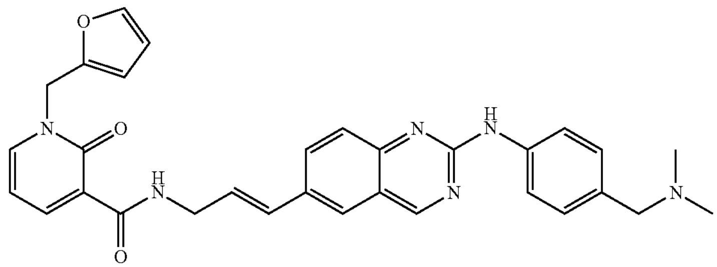 [SMILES: CN(C)Cc1ccc(Nc2ncc3cc(/C=C/CNC(=O)c4cccn(Cc5ccco5)c4=O)ccc3n2)cc1] | | 535 | LCMSBAS1 |
| III-41 | 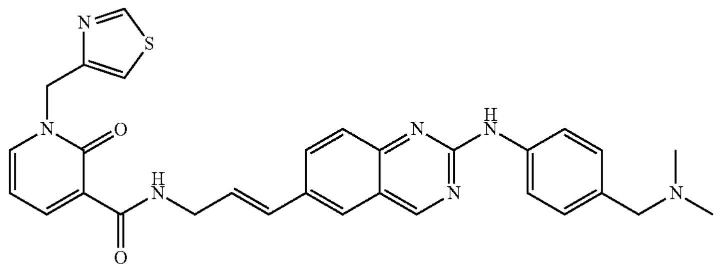 [SMILES: CN(C)Cc1ccc(Nc2ncc3cc(/C=C/CNC(=O)c4cccn(Cc5cscn5)c4=O)ccc3n2)cc1] | | 552 | LCMSBAS1 |
| III-42 | | | 549 | LCMSBAS1 | i) Synthesis of Example Compounds of Type IV

Method for Synthesising IV-1

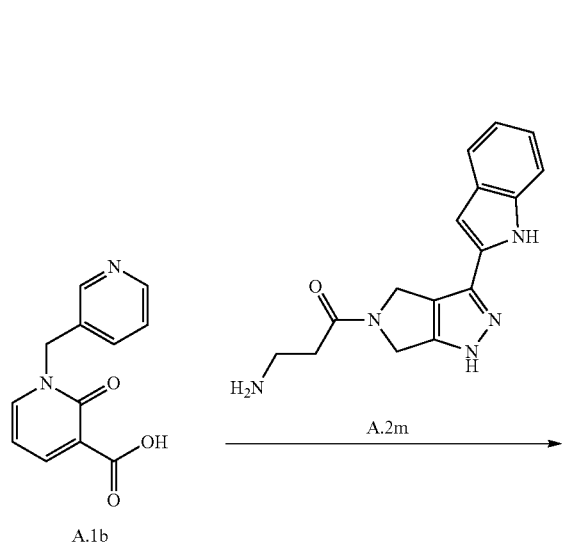

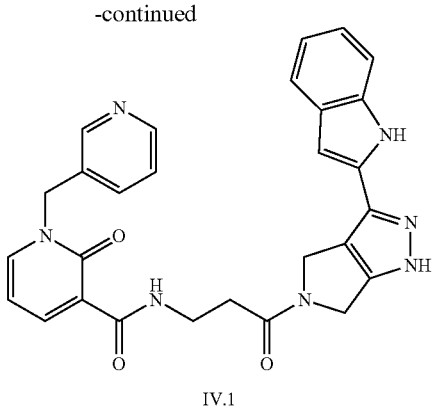

The carboxylic acid A.1b (43.2 mg, 0.188 mmol), HATU (107 mg, 0.282 mmol) and triethylamine (182 μL, 1.128 mmol) are suspended in 0.5 mL DMF and stirred for 5 min at 20° C. Then the amine A.2m (67 mg, 0.226 mmol) is added and the mixture is stirred for 60 min at 20° C. The solvent is eliminated in vacuo, the residue is purified by RP-chromatography (method prep. HPLC1; 5% acetonitrile to 50% in 10 min) and Example compound IV-1 (MS (M+H)$^+$=508; method FECB3) is obtained.

Analogously to compound IV-1 the following Example compounds IV-2 and IV-3 may be prepared (Table 4).

TABLE 4

| # | Structure | $t_{Ret.}$ (HPLC) [min] | MS $(M + H)^+$ | HPLC-method |
|---|---|---|---|---|
| IV-1 | 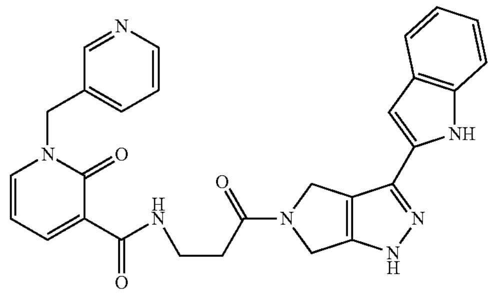 [SMILES: O=C(NCCC(=O)N1Cc2[nH]nc(-c3cc4ccccc4[nH]3)c2C1)c1cccn(Cc2cccnc2)c1=O] | | 508 | FECB3 |
| IV-2 | 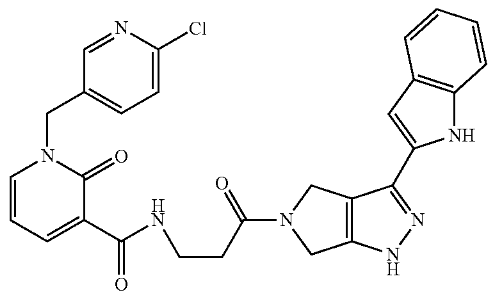 [SMILES: O=C(NCCC(=O)N1Cc2[nH]nc(-c3cc4ccccc4[nH]3)c2C1)c1cccn(Cc2ccc(Cl)nc2)c1=O] | | 542/544 | LCMSBAS1 |
| IV-3 | 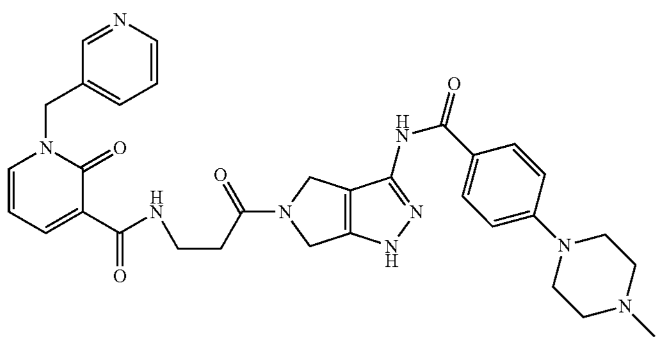 [SMILES: CN1CCN(c2ccc(C(=O)Nc3n[nH]c4c3CN(C(=O)CCNC(=O)c3cccn(Cc5cccnc5)c3=O)C4)cc2)CC1] | | 610 | LCMSBAS1 |

The following Examples describe the biological activity of the compounds according to the invention, without restricting the invention to these Examples.

Compounds of general formula (1) are characterised by their many possible applications in the therapeutic field. Particular mention should be made of those applications in which the inhibition of specific signal enzymes, particularly the inhibiting effect on the proliferation of cultivated human tumour cells but also on the proliferation of other cells such as endothelial cells, for example, are involved.

The activity of the compounds according to the invention on the kinase PDK1 which inhibits the signal transduction pathway is determined in an in vitro kinase assay with recombinantly prepared protein:

PDK1 Kinase Assay I

Recombinant human PDK1 enzyme (aa 52-556) linked at its N-terminal end to $His_6$ is isolated from baculovirus-infected insect cells. Purified enzyme may be obtained for example from the University of Dundee, Scotland. The following components are combined in a well of a 96-well round-based dish (Messrs. Greiner bio-one, No. 650101):

7.5 μL of compound to be tested in varying concentrations (e.g. Starting at 10 μM, and diluted in steps of 1:5) in 3.33% DMSO (final concentration 1% DMSO)/assay buffer (50 mM Tris pH 7.5, 0.05% β-mercaptoethanol, 10 mM Mg-acetate)

7.5 μL PDK1 (10 ng/well) and PDKtide (KTFCGTPEY-LAPEVRREPRILSEEEQEM-FRDFDYIADWC) synthesised by Pepceuticals Limited, Nottingham, United Kingdom; 25 μM final concentration); PDK1 and PDKtide are together diluted accordingly in assay buffer; PDKtide is present in this mixture as an 83.3 μM solution.

10 μL ATP solution (25 μM ATP with 0.5 μCi/well gamma-P33-ATP)

The reaction is started by adding the ATP solution and the mixture is incubated for 30 min at ambient temperature; at the start of the reaction the dishes are shaken gently. The reaction is stopped by the addition of 50 μL/well 125 mM phosphoric acid ($H_3PO_4$) and incubated for about 20 min at ambient temperature. The precipitate is transferred by harvesting onto filter plates (96-well microtitre filter plate: UniFilter GF/C;

Messrs Perkin Elmer; No. 6005174), then washed 6 times with 50 mM $H_3PO_4$ and dried at 60° C. Then the plate is stuck down with sealing tape, 25 µL/well of scintillation solution (Microscint 0; Messrs. Perkin Elmer; No. 6013611) are added and the amount of P33 precipitated is measured using the Wallac Betacounter. The measured data are evaluated using Graphpad Prism software.

PDK1 Kinase Assay II

Another assay was developed in which a shortened PDK1 enzyme (aa 51-359; Q66A mutation) is used that carries in the N-terminal position a $His_6$ tag that is cleaved during purification. (ΔPH-PDK1).

The following components are combined in a well of a 96-well round-based dish (Messrs. Greiner bio-one, No. 650101):
- 15 µL of compound to be tested in varying concentrations (e.g. Starting at 10 µM, and diluted in steps of 1:5) in 3.33% DMSO (final concentration 1% DMSO)/assay buffer (50 mM Tris pH 7.5, 0.05% β-mercaptoethanol, 10 mM Mg-acetate)
- 15 µL (ΔPH-PDK1; 12 ng/well) and PDKtide (KTFCGTPEYLAPEVRREPRILSEEE-QEMFRDFDYIADWC) synthesised by Pepceuticals Limited, Nottingham, United Kingdom; 25 µM final concentration); (ΔPH-PDK1 and PDKtide are together diluted accordingly in assay buffer; PDKtide is present in this mixture as an 83.3 µM solution. These 30 µL are incubated for 24 h at RT before ATP solution is added.
- 20 µL ATP solution (25 µM ATP with 1.0 µCi/well gamma-P33-ATP)

The reaction is started by adding the ATP solution and the mixture is incubated for 120 min at ambient temperature; at the start of the reaction the dishes are shaken gently. The reaction is stopped by the addition of 50 µL/well of 500 mM phosphoric acid ($H_3PO_4$) and incubated for about 20 min at ambient temperature. The precipitate is transferred by harvesting onto filter plates (96-well microtitre filter plate: UniFilter GF/C; Messrs Perkin Elmer; No. 6005174), then washed 6 times with 50 mM $H_3PO_4$ and dried at 60° C. Then the plate is stuck down with sealing tape, 25 µL/well of scintillation solution (Microscint 0; Messrs. Perkin Elmer; No. 6013611) are added and the amount of P33 precipitated is measured using the Wallac Betacounter. The measured data are evaluated using Graphpad Prism software.

PDK1 Kinase Assay III

Another PDK1 assay was developed which by comparison with PDK1 assay 1 additionally contains Tween 20:

The following components are combined in a well of a 96-well round-based dish (Messrs. Greiner bio-one, No. 650101):
- 15 µL of compound to be tested in varying concentrations (e.g. Starting at 10 µM, and diluted in steps of 1:5) in APT buffer (50 mM tris/C1 pH7.5; 0.05% β-mercaptoethanol; 10 mM Mg-acetate; 0.0166% Tween 20; 3.33% DMSO)
- 15 µL $His_6$-PDK1 (aa 52-556) 3.33 ng/well) and PDKtide (KTFCGTPEYLAPEVRRE PRILSEEEQEMFRDFDYIADWC), synthesised by Pepceuticals Limited, Nottingham, United Kingdom; 25 µM final concentration); $His_6$-PDK1 and PDKtide are together diluted accordingly in assay buffer (50 mM tris pH 7.5, 0.05% β-mercaptoethanol, 10 mM Mg-acetate); PDKtide is present in this mixture as an 83.3 µM solution. These 30 µL are routinely incubated for 30 min at RT.
- 20 µL ATP solution (25 µM ATP with 1.0 µCi/well gamma-P33-ATP). The final concentration of Tween 20 is 0.005%.

The reaction is started by adding the ATP solution and the mixture is incubated for 90 min at ambient temperature; at the start of the reaction the dishes are shaken gently. The reaction is stopped by the addition of 50 µL/well of 500 mM phosphoric acid ($H_3PO_4$) and incubated for about 20 min at ambient temperature. The precipitate is transferred by harvesting onto filter plates (96-well microtitre filter plate: UniFilter GF/C; Messrs Perkin Elmer; No. 6005174), then washed 6 times with 50 mM $H_3PO_4$ and dried at 60° C. Then the plate is stuck down with sealing tape, 25 µL/well of scintillation solution (Microscint 0; Messrs. Perkin Elmer; No. 6013611) are added and the amount of P33 precipitated is measured using the Wallac Betacounter. The measured data are evaluated using Graphpad Prism software.

Compounds (1) according to the invention generally exhibit good to very good inhibition in at least one of the PDK1 assays described hereinbefore, i.e. for example an $IC_{50}$ value of less than 1 µmol/L, less than 0.25 µmol/L.

To demonstrate that compounds according to the invention with different structural elements have an inhibitory activity, Table 5 shows the % CTL values of the compound examples at a concentration of 10 µM. A value of 100% indicates that there is no total inhibition with a value of 0%. The % CTL values indicate the residual activity of the enzyme after the addition of the inhibitory compound in the solvent DMSO in relation to the enzyme activity in the solvent DMSO without the addition of a compound (control). The majority of the values were determined using the PDK1 kinase assay III described hereinbefore. The values marked with an asterisk (*) were determined using the PDK1 kinase assay II described hereinbefore.

TABLE 5

| # | % CTL |
|---|---|
| I-1 | 16.8 |
| I-2 | 21.4 |
| I-3 | 18.9 |
| I-4 | 18.6 |
| I-5 | 39.6 |
| I-6 | 20.1 |
| I-7 | 14.5 |
| I-8 | 25.1 |
| I-9 | 17.7 |
| I-13 | 25.7 |
| I-24 | 20.1 |
| I-25 | 15.1 |
| I-26 | 34.1 |
| I-27 | 47.7 |
| II-5 | 15.6* |
| II-6 | 16.0 |
| II-7 | 18.6 |
| II-8 | 47.0* |
| III-12 | 18.3 |
| III-13 | 13.6 |
| III-14 | 17.2 |
| III-15 | 21.0 |
| III-16 | 19.2 |

The antiproliferative activity of the compounds according to the invention is determined in the proliferation test on cultivated human tumour cells and/or in a cell cycle analysis, for example on HCT116 or PC-3 tumour cells:

Inhibition of Proliferation on Cultivated Human Tumour Cells (HCT116)

To measure proliferation on cultivated human tumour cells, cells of the colon carcinoma line HCT116 (obtained from American Type Culture Collection (ATCC)) are cultivated in McCoy medium (Gibco) and 10% foetal calf serum (Gibco) and harvested in the log growth phase. Then the HCT116 cells are placed in 96-well flat bottomed plates (Falcon) at a density of 1000 cells per well in McCoy medium and incubated overnight in an incubator (at 37° C. and 5% $CO_2$). The active substances are added to the cells in various concentrations (dissolved in DMSO; DMSO final concentration: 0.1%). After 72 hours' incubation 20 µl AlamarBlue reagent (AccuMed International) are added to each well, and the cells are incubated for a further 5-7 hours. After incubation the colour change of the AlamarBlue reagent is determined in a Wallac Microbeta fluorescence spectrophotometer $EC_{50}$ values are calculated by means of Standard Levenburg Marquard algorithms (GraphPadPrizm).

Inhibition of Proliferation on Cultivated Human Tumour Cells (PC-3)

To measure proliferation on prostate carcinoma tumour cell line PC-3 (obtained from American Type Culture Collection (ATCC)) the cells are cultivated in Ham's F12K (Gibco) and 10% foetal calf serum (Gibco) and harvested in the log growth phase. Then the PC-3 cells are placed in 96-well plates (Costar) at a density of 2000 cells per well and incubated overnight in an incubator (at 37° C. and 5% $CO_2$), while on each plate 16 wells are used as controls (8 wells with cells to which only DMSO solution has been added (should yield 30-50% maximum value of reduced AlamarBlue), 4 wells containing only medium (medium control, after the addition of oxidised AlamarBlue reagent the background signal is obtained) and 4 wells where again only medium is added (after the addition of reduced AlamarBlue reagent it acts as a maximum value)). The active substances are added to the cells in various concentrations (dissolved in DMSO; DMSO final concentration: 0.2%) (in each case as a double or triple measurement). After 5 days' incubation 20 µl AlamarBlue reagent (Serotec) are added to each well, and the cells are incubated for a further 5-7 hours. As a control, 20 µl reduced AlamarBlue reagent is added to each of 4 wells (AlamarBlue reagent which is autoclaved for 30 min). After incubation the colour change of the AlamarBlue reagent in the individual wells is determined in a SpectraMax Photometer (Molecular Devices) (extinction 530 nm, emission 590 nm, 5 sec measuring time). The amount of AlamarBlue reagent reacted represents the metabolic activity of the cells. The relative cell activity is calculated in relation to the control (PC-3 cells without inhibitor) and the active substance concentration which inhibits the cell activity by 50% (EC50) is derived. The values are calculated from the average of two or three individual measurements.

Many of the compounds according to the invention cause inhibition of proliferation by interfering with intracellular signal transduction pathways which are important for cell survival, predominantly, but not exclusively, in cells which have become dependent on these signal pathways during their development Inhibition of these pathways induces arrest in corresponding cells in the G1 phase of the cell cyle and/or apoptosis, i.e. cell responses that can be analysed using Cellomics Array Scan or FACS analysis (see below).

The compounds according to the invention are also tested accordingly on other tumour cells. For example these compounds are effective on carcinomas of all kinds of tissue (e.g. Gliomas (U87MG; U373MG), sarcoma (e.g. MES-SA; SK-UT-1B), breast (MDA-MB468), colon (HCT116), lung (NCIH460, NCI-H520), melanoma (MALME-3M; C32), prostate (DU-145), ovary (SKOV-3)] and could be used in indications of this kind, particularly in indications which have activating changes in the PI3K-AKT-PDK1 signal pathway. This demonstrates the wide range of applications for the compounds according to the invention for the treatment of all kinds of tumour types.

Therefore cell lines such as U87MG, MALME-3M, NCI-H520, DU-145, NCI-H460, SKOV-3 etc. are analysed for inhibition of proliferation, with suitable adjustment of the number of cells seeded per well and optionally the measuring time after the addition of the substance.

Compounds (1) according to the invention generally demonstrate good activity in cell assays of this kind, i.e. for example an $EC_{50}$ value in the PC-3 or HCT116 proliferation test of less than 10 µmol/L, very often less than 2 µmol/L.

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, $1.0 \times 10^6$ PC-3 or HCT116 cells are seeded onto a 75 $cm^2$ cell culture flask, and after 24 h either 0.1% DMSO is added as control or the substance is added in various concentrations (in 0.1% DMSO). The cells are incubated for 42 h with the substance or with DMSO. Then the cells are detached with trypsin and centrifuged. The cell pellet is washed with buffered saline solution (PBS) and the cells are then fixed with 80% ethanol at −20° C. for at least 2 h. After another washing step with PBS the cells are permeabilised with Triton X-100 (Sigma; 0.25% in PBS) on ice for 5 min, then washed with PBS and incubated with a mixture of PBS and anti-cyclin B1 (FITC conjugated) antibody for 30 min at RT. This step is optional, but helps improve the identification of cells in the G2/M phase as these specifically express cyclin B1. Then the suspension is washed with PBS and the pellet is incubated in a solution of PI (Sigma; 10 µg/ml) and RNAse (Serva; 1 mg/mL1) in the ratio 9:1 for at least 20 min in the dark. The DNA measurement is carried out in a Becton Dickinson FACScalibur, with an argon laser (500 mW, emission 488 nm); data are obtained and evaluated using the DNA Cell Quest Programme (BD).

Cellomics Array Scan

PC-3 cells are cultivated in Ham's F12K (Gibco) and 10% foetal calf serum (Gibco) and harvested in the log growth phase. Then the PC-3 cells are placed in 96-well plates [FALCON black/clear bottom (#353948)] in a density of 3000 cells per well and incubated overnight in an incubator (at 37° C. and 5% $CO_2$). The active substances are added to the cells in various concentrations (dissolved in DMSO; DMSO final concentration: 0.1%). After 42 h incubation the medium is suction filtered, the cells are fixed for 10 min with 4% formaldehyde solution and Triton X-100 (1:200 in PBS) at ambient temperature and simultaneously permeabilised, and then washed twice with a 0.3% BSA solution (Calbiochem). Then the DNA is stained by the addition of 50 µL/well of 4',6-diamidino-2-phenylindole (DAPI; Molecular Probes) in a final concentration of 300 nM for 1 h at RT, in the dark. Alternatively 50 µL/well of Hoechst 33342 (Invitrogen) in PBS may be used for the DNA staining (1 h at RT, final concentration: 5 µg/mL). The preparations are then carefully washed twice with PBS, the plates are stuck down with black adhesive film and analysed in the Cellomics ArrayScan using the CellCycle BioApplication programme and visualised and evaluated using Spotfire.

Compounds (1) according to the invention generally induce G1 arrest in PC-3 cells, for example, at concentrations of less than 30 µmol/L, often less than 5 µmol/L. In HCT116 or MALME-3M cells they generally induce apoptosis at similar or lower concentrations.

Biomarker Inhibition:

The substances of the present invention bring about cellular inhibition of PDK1-substrates. Examples of the latter are Phospho-Thr308/AKT, Phospho-Ser221,227/RSK, or phosphorylation sites on p70S6 kinase (Thr229). In order to determine the inhibitory effect, the cells are treated with substance for e.g. 2 h, lysed and analysed by Western Blot and/or BioPlex analysis for phosphoproteins of this kind. Commercially obtainable phospho-specific antibodies against the above-mentioned phosphorylation sites are used.

In PC-3 or other signal pathway-mutated cell lines (see above) as a rule $EC_{50}$ values of less than 5 µmol/L, often less than 0.5 µmol/L, are achieved with the present compounds on these phosphorylation sites compared with the carrier control and after standardisation to the corresponding whole protein.

On the basis of their biological properties the compounds of general formula (1) according to the invention, their tautomers, racemates, enantiomers, diastereomers, mixtures thereof and the salts of all the above-mentioned forms are suitable for treating diseases characterised by excessive or abnormal cell proliferation or by aberrant activation of the phosphatidylinositol-3-kinase (PI3K)-PDK1-AKT signal pathway.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomuscaroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immuno cytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. Cisplatin, oxaliplatin, carboplatin); alkylation agents (e.g. Estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (1) | 100 mg |
| | lactose | 140 mg |

167

-continued

| A) | Tablets | per tablet |
|---|---|---|
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (1) | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (1) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

168

The invention claimed is:
1. A compound of formula (I)

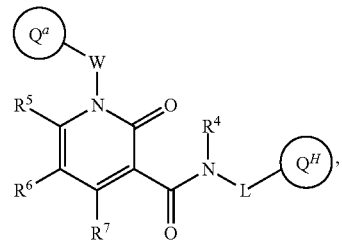

(1)

wherein:
$Q^a$ denotes pyridyl, while
this pyridyl may be substituted by up to three identical or different substituents, selected independently of one another from among methyl, trifluoromethyl, —$OCH_3$, —$NH_2$, —$NH(CH_3)$, —$N(CH_3)_2$, fluorine, chlorine and bromine, and
W is selected from among —$CH_2$— and —$CH(CH_3)$—;
$R^4$ denotes hydrogen or $C_{1-6}$-alkyl;
$R^5$, $R^6$ and $R^7$ independently of one another are selected from among $R^a$ and $R^b$;
L denotes the group -$L^1$-$L^2$-$L^3$-, wherein $L^1$ binds to the unit —$NR^4$— and $L^3$ binds to the ring system $Q^H$;
$L^1$, $L^2$ and $L^3$ are selected independently of one another from among $C_{1-6}$alkylene, 2-6 membered heteroalkylene, $C_{1-6}$haloalkylene, $C_{3-10}$cycloalkylene, $C_{6-10}$arylene, 5-12 membered heteroarylene, 3-14 membered heterocycloalkylene,
while all the above-mentioned bivalent units may each optionally be substituted independently of one another by one or more, identical or different $R^a$ and/or $R^b$, —O—, —S—, $NR^g$, $N(OR^g)$—, —C(O)—, —C(O)O—, —C(O)$NR^g$—, —OS(O)$_2$—, —OS(O)$_2NR^g$—, —OC(O)—, —OC(O)O—, —OC(O)$NR^g$—, —S(O)$_2$—, —S(O)$_2$O—, —S(O)$_2NR^g$—, —$NR^gC(O)$—, —$NR^gC(O)O$—, —$NR^gC(O)NR^g$—, —$NR^gS(O)_2$—, —$NR^gS(O)_2O$— and —$NR^gS(O)_2NR^g$—,
$L^1$, $L^2$ and $L^3$ each independently of one another denotes a bond,
while at least one of the units $L^1$, $L^2$ or $L^3$ must be other than a bond;
the ring system $Q^H$ is selected from among

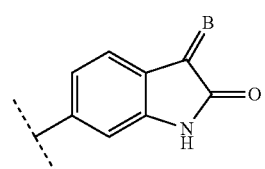

$Q^H$-1a

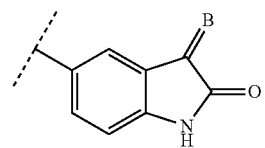

$Q^H$-1b

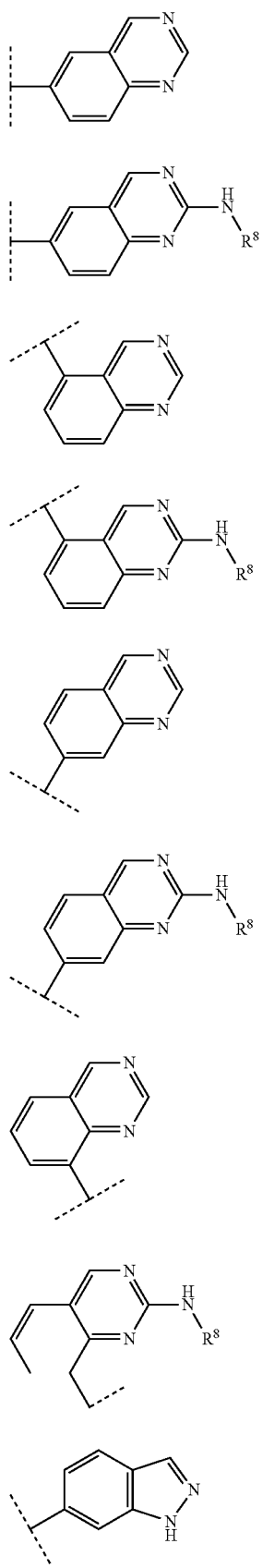

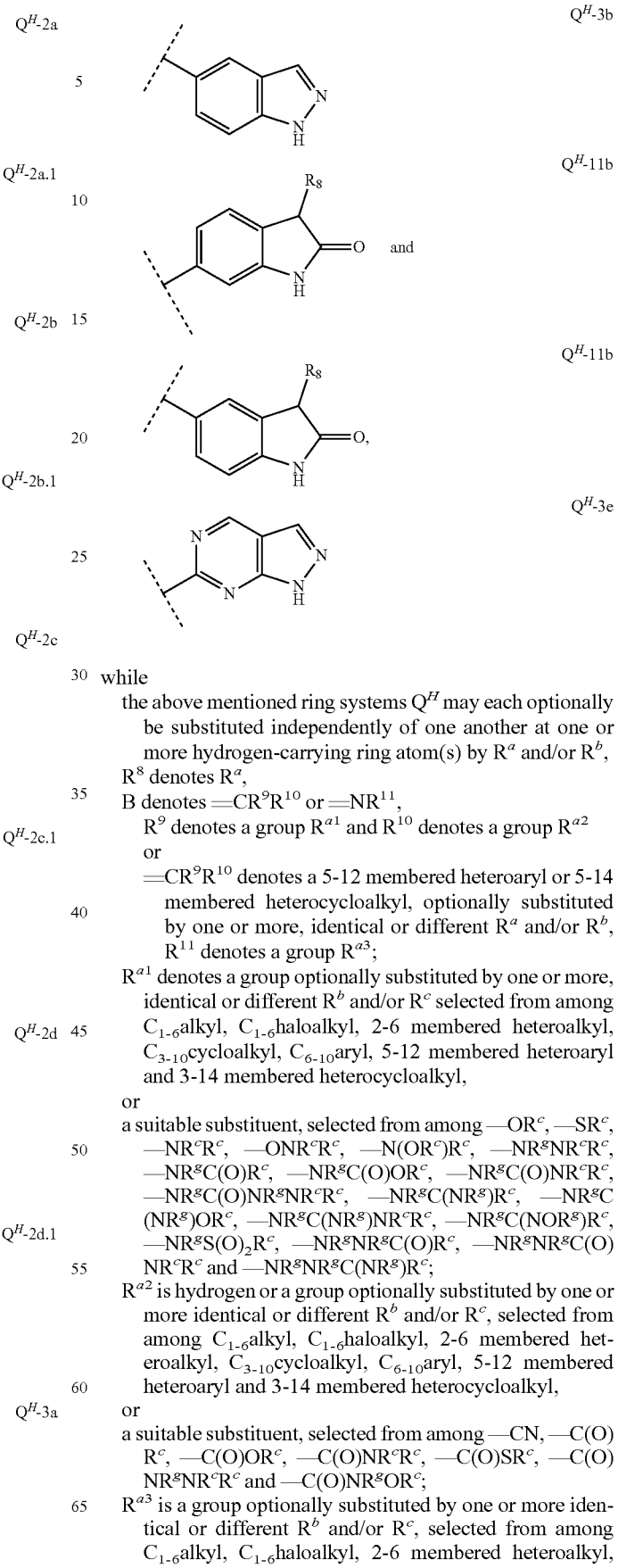

while
the above mentioned ring systems $Q^H$ may each optionally be substituted independently of one another at one or more hydrogen-carrying ring atom(s) by $R^a$ and/or $R^b$, $R^8$ denotes $R^a$, B denotes $=CR^9R^{10}$ or $=NR^{11}$, $R^9$ denotes a group $R^{a1}$ and $R^{10}$ denotes a group $R^{a2}$ or $=CR^9R^{10}$ denotes a 5-12 membered heteroaryl or 5-14 membered heterocycloalkyl, optionally substituted by one or more, identical or different $R^a$ and/or $R^b$, $R^{11}$ denotes a group $R^{a3}$;

$R^{a1}$ denotes a group optionally substituted by one or more, identical or different $R^b$ and/or $R^c$ selected from among $C_{1-6}$alkyl, $C_{1-6}$haloalkyl, 2-6 membered heteroalkyl, $C_{3-10}$cycloalkyl, $C_{6-10}$aryl, 5-12 membered heteroaryl and 3-14 membered heterocycloalkyl, or a suitable substituent, selected from among —$OR^c$, —$SR^c$, —$NR^cR^c$, —$ONR^cR^c$, —$N(OR^c)R^c$, —$NR^gNR^cR^c$, —$NR^gC(O)R^c$, —$NR^gC(O)OR^c$, —$NR^gC(O)NR^cR^c$, —$NR^gC(O)NR^gNR^cR^c$, —$NR^gC(NR^g)R^c$, —$NR^gC(NR^g)OR^c$, —$NR^gC(NR^g)NR^cR^c$, —$NR^gC(NOR^g)R^c$, —$NR^gS(O)_2R^c$, —$NR^gNR^gC(O)R^c$, —$NR^gNR^gC(O)NR^cR^c$ and —$NR^gNR^gC(NR^g)R^c$;

$R^{a2}$ is hydrogen or a group optionally substituted by one or more identical or different $R^b$ and/or $R^c$, selected from among $C_{1-6}$alkyl, $C_{1-6}$haloalkyl, 2-6 membered heteroalkyl, $C_{3-10}$cycloalkyl, $C_{6-10}$aryl, 5-12 membered heteroaryl and 3-14 membered heterocycloalkyl, or a suitable substituent, selected from among —CN, —C(O)$R^c$, —C(O)O$R^c$, —C(O)N$R^cR^c$, —C(O)S$R^c$, —C(O)N$R^gNR^cR^c$ and —C(O)N$R^gOR^c$;

$R^{a3}$ is a group optionally substituted by one or more identical or different $R^b$ and/or $R^c$, selected from among $C_{1-6}$alkyl, $C_{1-6}$haloalkyl, 2-6 membered heteroalkyl, $C_{3-10}$cycloalkyl, $C_{6-10}$aryl, 5-12 membered heteroaryl and 3-14 membered heterocycloalkyl, or a suitable substituent, selected from among —$OR^c$ and —$NR^cR^c$;

each $R^a$ independently of one another is hydrogen or a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

each $R^b$ denotes a suitable substituent and each is selected independently of one another from among —$OR^c$, —$NR^cR^c$, halogen, —CN, —$NO_2$, —$C(O)R^c$, —$C(O)OR^c$, —$C(O)NR^cR^c$, —$OC(O)R^c$, —$OC(O)OR^c$, —$OC(O)NR^cR^c$, —$S(O)_2R^c$, —$S(O)_2OR^c$, —$S(O)_2NR^cR^c$, —$NR^gC(O)R^c$, —$NR^gC(O)OR^c$, —$NR^gC(O)NR^cR^c$, —$NR^gS(O)_2R^c$, —$NR^gS(O)_2OR^c$ and —$NR^gS(O)_2NR^cR^c$, and the bivalent substituent =O, while the latter may only be a substituent in non-aromatic ring systems;

each $R^c$ independently of one another is hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

each $R^d$ is a suitable substituent and each is selected independently of one another from among —$OR^e$, —$NR^eR^e$, halogen, —CN, —$NO_2$, —$C(O)R^e$, —$C(O)OR^e$, —$C(O)NR^eR^e$, —$OC(O)R^e$, —$OC(O)OR^e$, —$OC(O)NR^eR^e$, —$S(O)_2R^e$, —$S(O)_2OR^e$, —$S(O)_2NR^eR^e$, —$NR^gC(O)R^e$, —$NR^gC(O)OR^e$, —$NR^gC(O)NR^eR^e$, —$NR^gS(O)_2R^e$, —$NR^gS(O)_2OR^e$ and —$NR^gS(O)_2NR^eR^e$, and the bivalent substituent =O, while the latter may only be a substituent in non-aromatic ring systems;

each $R^e$ independently of one another is hydrogen or a group optionally substituted by one or more identical or different $R^f$ and/or $R^g$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

each $R^f$ is a suitable substituent and each is selected independently of one another from among —$OR^g$, —$NR^gR^g$, halogen, —CN, —$NO_2$, —$C(O)R^g$, —$C(O)OR^g$, —$C(O)NR^gR^g$, —$OC(O)R^g$, —$OC(O)OR^g$, —$OC(O)NR^gR^g$, —$S(O)_2R^g$, —$S(O)_2OR^g$, —$S(O)_2NR^gR^g$, —$NR^hC(O)R^g$, —$NR^hC(O)OR^g$, —$NR^hC(O)NR^gR^g$, —$NR^hS(O)_2R^g$, —$NR^hS(O)_2OR^g$ and —$NR^hS(O)_2NR^gR^g$, and the bivalent substituent =O, while the latter may only be a substituent in non-aromatic ring systems;

each $R^g$ independently of one another is hydrogen or a group optionally substituted by one or more identical or different $R^h$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl, and each $R^h$ independently of one another is selected from among hydrogen, $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

or a tautomer thereof, a racemate thereof, an enantiomer thereof, a diastereomer thereof, or a mixture of any of the foregoing forms, or a salt of any of the above-mentioned forms.

2. The compound according to claim 1, wherein $R^4$ denotes hydrogen.

3. The compound according to claim 1, wherein $R^5$, $R^6$ and $R^7$ are selected independently of one another from among hydrogen, $C_{1-6}$alkyl, $C_{1-6}$haloalkyl, —$OR^{h2}$, —$NR^{h2}R^{h2}$, halogen, —CN, —$C(O)R^{h2}$, —$C(O)OR^{h2}$, —$C(O)NR^{h2}R^{h2}$, —$S(O)_2NR^{h2}R^{h2}$, —$NR^{h2}C(O)R^{h2}$, —$NR^{h2}C(O)OR^{h2}$, —$NR^{h2}C(O)NR^{h2}R^{h2}$ and —$NR^{h2}S(O)_2R^{h2}$ and $R^{h2}$ is selected independently of one another in each case from among hydrogen, $C_{1-6}$alkyl, 2-6 membered heteroalkyl and $C_{1-6}$haloalkyl.

4. The compound according to claim 3, wherein $R^5$, $R^6$ and $R^7$ each denote hydrogen.

5. The compound according to claim 1, wherein L is selected from among

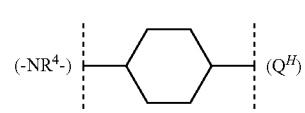

L-1

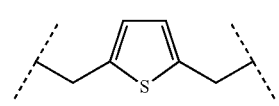

L-2

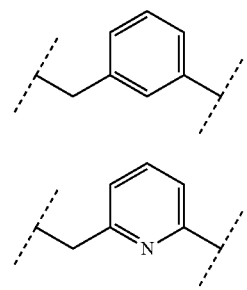

L-3

L-4

L-5

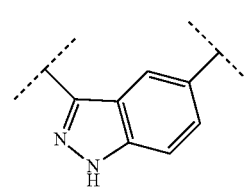

L-6

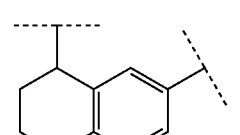

L-7

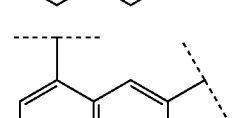

L-8

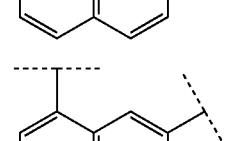

L-9

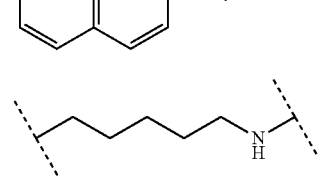

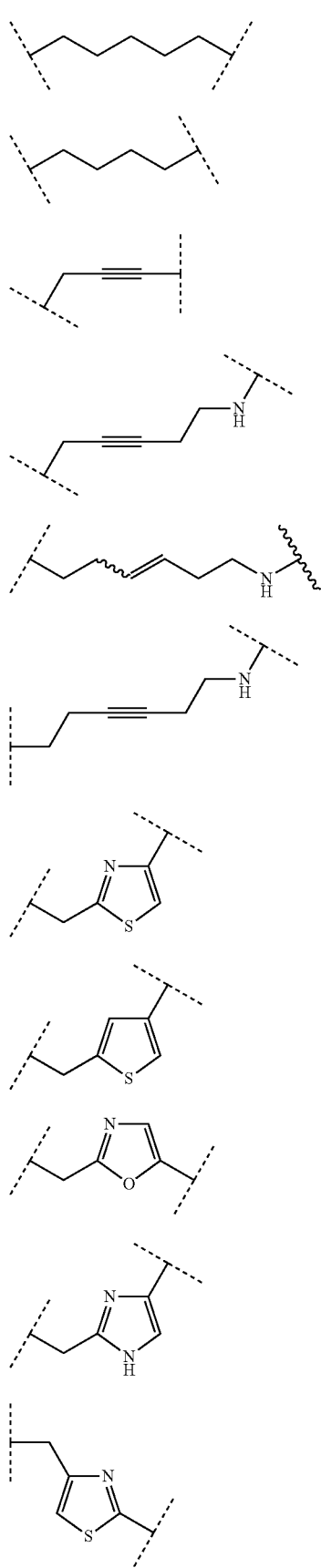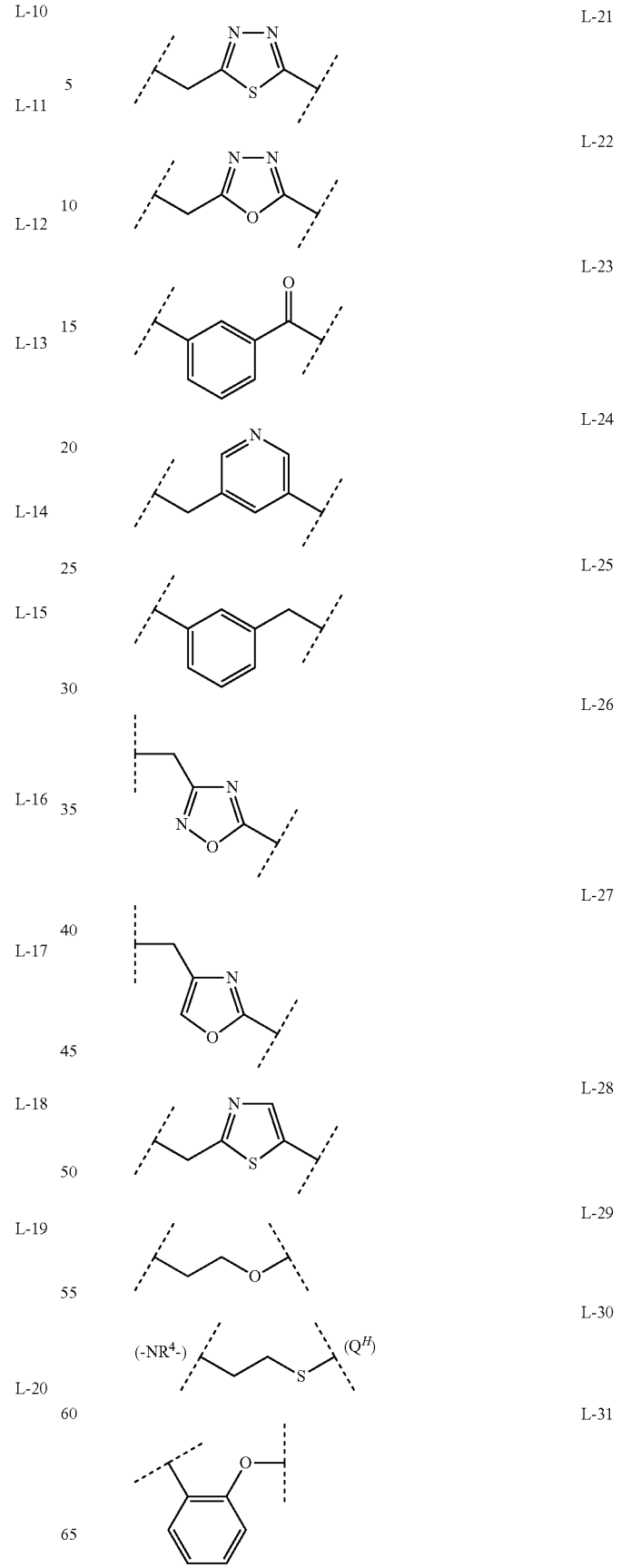

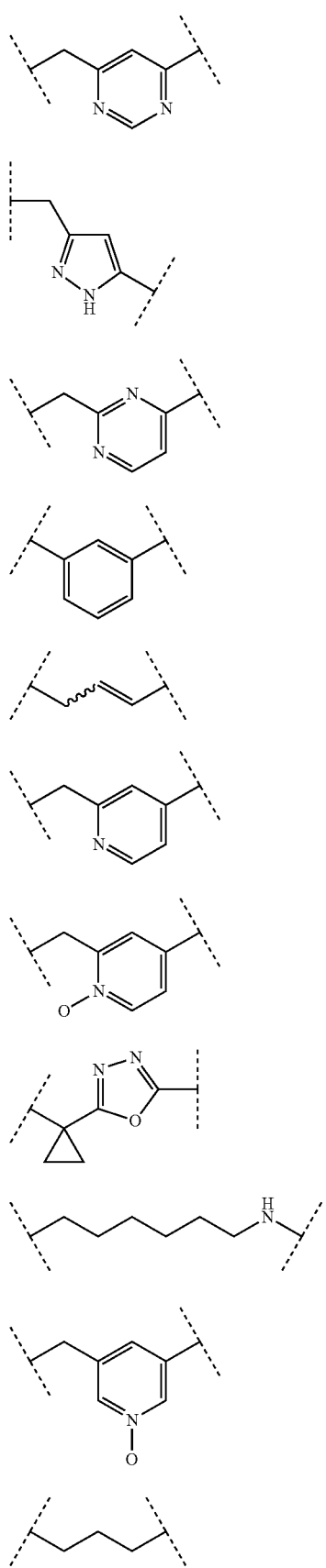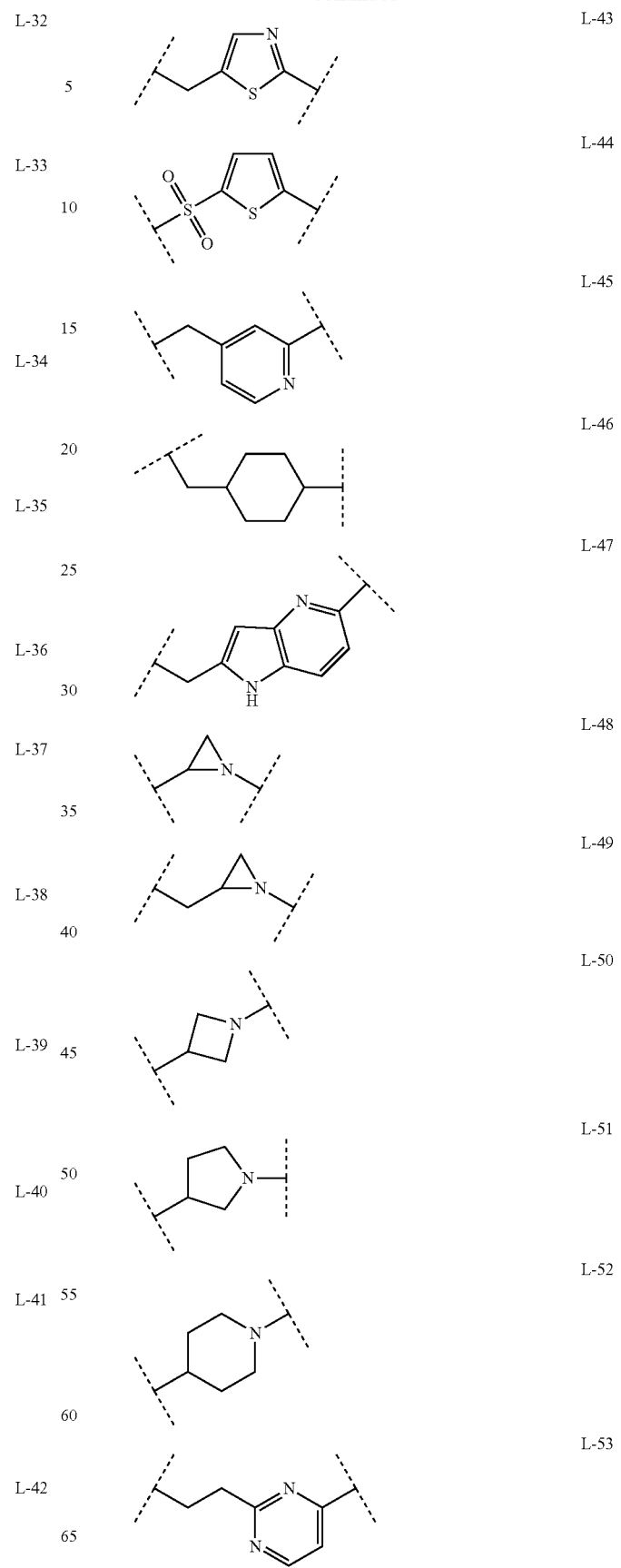

-continued

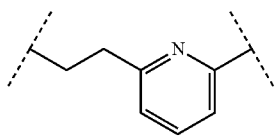

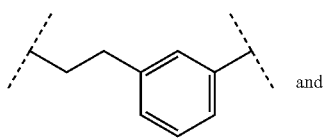 and

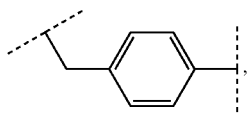

the bivalent units L shown bind on the right to the ring system $Q^H$ and on the left to the amide nitrogen —$NR^4$— according to formula (I) and may optionally each be substituted independently of one another by one or more identical or different $R^a$ and/or $R^b$.

6. The compound according to claim 1, wherein

L is selected from among

L-I

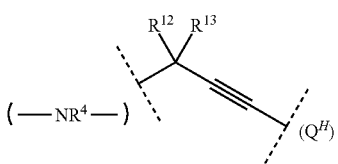

L-II

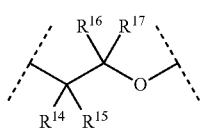

L-III

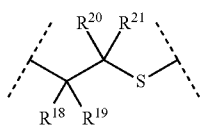

L-IV

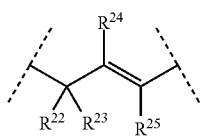

L-V

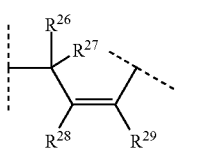

L-VI

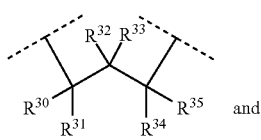

L-VII

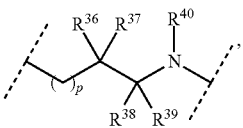

wherein the bivalent units L shown bind on the right to the ring system $Q^H$ and on the left to the amide nitrogen —$NR^4$— according to formula (I);

p denotes 0 or 1;

$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$ and $R^{39}$ is in each case selected independently of one another from among $R^a$ and $R^b$, and $R^{40}$ denotes $R^a$; or $R^{15}$ and $R^{17}$ is in each case selected independently of one another from among $R^a$ and $R^b$, $R^{14}$ and $R^{16}$ together with the carbon atoms to which they are bound form a $C_{3-7}$cycloalkylene or a 3-7 membered heterocycloalkylene, while the above-mentioned ring systems may optionally each be substituted independently of one another by one or more identical or different $R^a$ and/or $R^b$; or $R^{19}$ and $R^{21}$ is in each case selected independently of one another from among $R^a$ and $R^b$, $R^{18}$ and $R^{20}$ together with the carbon atoms to which they are bound form a $C_{3-7}$cycloalkylene or a 3-7 membered heterocycloalkylene, while the above-mentioned ring systems may optionally each be substituted independently of one another by one or more identical or different $R^a$ and/or $R^b$; or $R^{23}$ and $R^{24}$ is in each case selected independently of one another from among $R^a$ and $R^b$, $R^{22}$ and $R^{25}$ together with the carbon atoms to which they are bound form an unsaturated $C_{4-7}$cycloalkylene or an unsaturated 4-7 membered heterocycloalkylene, while the above-mentioned ring systems may optionally each be substituted independently of one another by one or more identical or different $R^a$ and/or $R^b$; or $R^{30}$, $R^{31}$, $R^{33}$ and $R^{35}$ is in each case selected independently of one another from among $R^a$ and $R^b$, $R^{32}$ and $R^{35}$ together with the carbon atoms to which they are bound form a $C_{3-7}$cycloalkylene or a 3-7 membered heterocycloalkylene, while the above-mentioned ring systems may optionally each be substituted independently of one another by one or more identical or different $R^a$ and/or $R^b$; or $R^{37}$, $R^{38}$ and $R^{39}$ are each selected independently of one another from among $R^a$ and $R^b$, $R^{36}$ and $R^{40}$ together with the atoms to which they are bound form a 3-7 membered heterocycloalkylene, while this heterocycloalkylene may optionally be substituted independently of one another in each case by one or more identical or different $R^a$ and/or $R^b$; or $R^{36}$, $R^{37}$ and $R^{39}$ are each selected independently of one another from among $R^a$ and $R^b$, $R^{38}$ and $R^{40}$ together with the atoms to which they are bound form a 3-7 membered heterocycloalkylene, while this heterocycloalkylene may optionally be substituted independently of one another in each case by one or more identical or different $R^1$ and/or $R^b$.

7. The compound according to claim 6, wherein L is selected from among

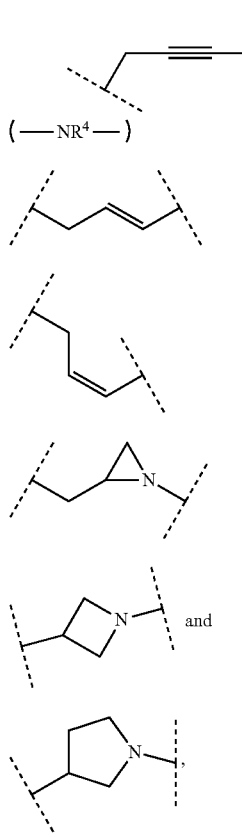

and the bivalent units L shown bind on the right to the ring system $Q^H$ and on the left to the amide nitrogen —$NR^4$— according to formula (I).

8. The compound according to claim 1, wherein $Q^H$ is

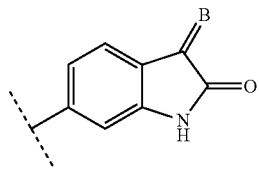

the ring systems $Q^H$ shown may optionally be substituted at one or more hydrogen-carrying carbon atom(s) by $R^a$ and/or $R^b$.

9. The compound according to claim 8, wherein
B denotes =$CR^{a1}R^{a2}$;
$R^{a1}$ denotes a group optionally substituted by one or more identical or different $R^b$ and/or $R^c$, selected from among $C_{6-10}$aryl and 5-12 membered heteroaryl; and
$R^{a2}$ is selected from among hydrogen, $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl.

10. The compound according to claim 9, wherein
$R^{a1}$ is a group optionally substituted by one or more identical or different $R^b$ and/or $R^c$, selected from among pyrrolyl, pyrazolyl and imidazolyl.

11. The compound according to claim 10, wherein
$R^{a2}$ is hydrogen, methyl or ethyl.

12. The compound according to claim 11, wherein
$R^{a1}$ is substituted by one or more, identical or different $R^{b1}$ and/or $R^{c1}$;
each $R^{b1}$ is a suitable substituent and is selected in each case independently of one another from among —$OR^c$, —$SR^c$, —$NR^cR^c$, halogen, —CN, —$NO_2$, —C(O)$R^c$, —C(O)O$R^c$, —C(O)N$R^cR^c$, —OC(O)$R^c$, —OC(O)O$R^c$, —OC(O)N$R^cR^c$, —S(O)$_2R^c$, —S(O)$_2$O$R^c$, —S(O)$_2$N$R^cR^c$, —$NR^g$C(O)$R^c$, —$NR^g$C(O)O$R^c$, —$NR^g$C(O)N$R^cR^c$, —$NR^g$S(O)$_2R^c$, —$NR^g$S(O)$_2$O$R^c$ and —$NR^g$S(O)$_2$N$R^cR^c$ and the bivalent substituent =O, while the latter may only be a substituent in non-aromatic ring systems; and
each $R^{c1}$ in each case independently of one another is a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl.

13. The compound according to claim 1, wherein
$Q^H$ is selected from among

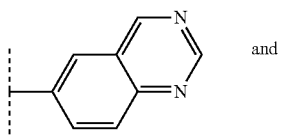

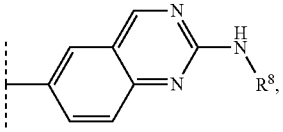

the ring systems $Q^H$ shown may each optionally be substituted independently of one another at one or more hydrogen-carrying ring atom(s) by $R^a$ and/or $R^b$.

14. The compound according to claim 13, wherein
$Q^H$ is

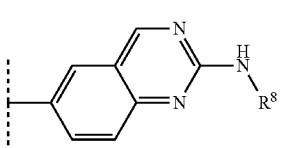

the ring system $Q^H$ shown may optionally be substituted at one or more hydrogen-carrying ring atom(s) by $R^a$ and/or $R^b$, and
$R^8$ denotes $R^c$.

15. The compound according to claim 1, wherein $Q^H$ is

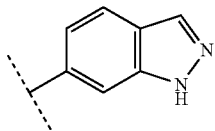

$Q^H$-3a the ring system $Q^H$ shown may optionally be substituted at one or more hydrogen-carrying ring atom(s) by $R^a$ and/or $R^b$.

16. The compound according to claim 15, wherein $Q^H$ is

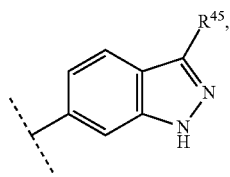

$R^{45}$ denotes hydrogen or a group optionally substituted by one or more identical or different $R^b$ and/or $R^c$, selected from among $C_{3-7}$cycloalkyl, phenyl, 5-10 membered heteroaryl and 3-10 membered heterocycloalkyl.

17. The compound according to claim 1 selected from the group consisting of the following compounds:

I-1 1-[(6-chloropyridin-3-yl)methyl]-N-{(2E)-3-[(3Z)-3-(1H-imidazol-5-ylmethylidene)-2-oxo-2,3-dihydro-1H-indol-6-yl]prop-2-en-1-yl}-2-oxo-1,2-dihydropyridine-3-carboxamide;

I-2 1-[(6-chloropyridin-3-yl)methyl]-2-oxo-N-{(2E)-3-[(3Z)-2-oxo-3-(1H-pyrrol-2-ylmethylidene)-2,3-dihydro-1H-indol-6-yl]prop-2-en-1-yl}-1,2-dihydropyridine-3-carboxamide;

I-3 1-[(6-chloropyridin-3-yl)methyl]-N-{(2E)-3-[(3Z)-3-{[4-(3-{[2-(dimethylamino)-ethyl]carbamoyl}phenyl)-1H-pyrrol-2-yl]methylidene}-2-oxo-2,3-dihydro-1H-indol-6-yl]prop-2-en-1-yl}-2-oxo-1,2-dihydropyridine-3-carboxamide;

I-4 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyridin-3-ylmethyl)-1,2-dihydropyridine-3-carboxamide;

I-5 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyridin-4-ylmethyl)-1,2-dihydropyridine-3-carboxamide;

I-6 2-oxo-N-{(2E)-3-[(3Z)-2-oxo-3-(1H-pyrrol-2-ylmethylidene)-2,3-dihydro-1H-indol-6-yl]prop-2-en-1-yl}-1-(pyridin-2-ylmethyl)-1,2-dihydropyridine-3-carboxamide;

I-7 N-{(2E)-3-[(3Z)-3-(1H-imidazol-5-ylmethylidene)-2-oxo-2,3-dihydro-1H-indol-6-yl]prop-2-en-1-yl}-2-oxo-1-(pyridin-3-ylmethyl)-1,2-dihydropyridine-3-carboxamide;

I-8 N-{(2E)-3-[(3Z)-3-(1H-imidazol-5-ylmethylidene)-2-oxo-2,3-dihydro-1H-indol-6-yl]prop-2-en-1-yl}-2-oxo-1-(pyridin-4-ylmethyl)-1,2-dihydropyridine-3-carboxamide;

I-9 N-{(2E)-3-[(3Z)-3-(1H-imidazol-5-ylmethylidene)-2-oxo-2,3-dihydro-1H-indol-6-yl]prop-2-en-1-yl}-2-oxo-1-(pyridin-2-ylmethyl)-1,2-dihydropyridine-3-carboxamide;

I-20 N-{(2E)-3-[(3Z)-3-{6-[(dimethylamino)methyl]-3,4-dihydroquinazolin-2(1H)-yliden}-2-oxo-2,3-dihydro-1H-indol-6-yl]prop-2-en-1-yl}-2-oxo-1-(pyridin-3-ylmethyl)-1,2-dihydropyridine-3-carboxamide;

I-21 N-[(2E)-3-{(3Z)-3-[({4-[(dimethylamino)methyl]phenyl}amino)(phenyl)methylidene]-2-oxo-2,3-dihydro-1H-indol-6-yl}prop-2-en-1-yl]-2-oxo-1-(pyridin-3-ylmethyl)-1,2-dihydropyridine-3-carboxamide;

I-22 N-{(2E)-3-[(3Z)-3-(2-{4-[(dimethylamino)methyl]phenyl}hydrazinyliden)-2-oxo-2,3-dihydro-1H-indol-6-yl]prop-2-en-1-yl}-2-oxo-1-(pyridin-3-ylmethyl)-1,2-dihydropyridine-3-carboxamide;

I-23 2-oxo-N-{(2E)-3-[(3Z)-2-oxo-3-(quinoline-2(1H)-yliden)-2,3-dihydro-1H-indol-6-yl]prop-2-en-1-yl}-1-(pyridin-3-ylmethyl)-1,2-dihydropyridine-3-carboxamide;

I-24 N-{(2E)-3-[(3Z)-3-(1H-imidazol-5-ylmethylidene)-2-oxo-2,3-dihydro-1H-indol-6-yl]prop-2-en-1-yl}-1-[(6-methylpyridin-3-yl)methyl]-2-oxo-1,2-dihydropyridine-3-carboxamide;

II-2 2-oxo-N-{3-[2-(phenylamino)quinazolin-6-yl]prop-2-yn-1-yl}-1-(pyridin-3-ylmethyl)-1,2-dihydropyridine-3-carboxamide;

II-4 1-[(6-chloropyridin-3-yl)methyl]-2-oxo-N-{3-[2-(phenylamino)quinazolin-6-yl]prop-2-yn-1-yl}-1,2-dihydropyridine-3-carboxamide;

II-5 N-{3-[2-({4-[(dimethylamino)methyl]phenyl}amino)quinazolin-6-yl]prop-2-yn-1-yl}-2-oxo-1-(pyridin-3-ylmethyl)-1,2-dihydropyridine-3-carboxamide;

II-6 N-{3-[2-({4-[(dimethylamino)methyl]phenyl}amino)quinazolin-6-yl]prop-2-yn-1-yl}-2-oxo-1-{[6-(trifluoromethyl)pyridin-3-yl]methyl}-1,2-dihydropyridine-3-carboxamide;

II-7 N-{3-[2-({3-fluoro-4-[(1-methylpiperidin-4-yl)amino]phenyl}amino)quinazolin-6-yl]prop-2-yn-1-yl}-2-oxo-1-{[6-(trifluoromethyl)pyridin-3-yl]methyl}-1,2-dihydropyridine-3-carboxamide;

II-8 N-{3-[2-({4-[methyl(1-methylpiperidin-4-yl)amino]phenyl}amino)quinazolin-6-yl]prop-2-yn-1-yl}-2-oxo-1-{[6-(trifluoromethyl)pyridin-3-yl]methyl}-1,2-dihydropyridine-3-carboxamide;

II-9 N-{3-[8-(3-aminopropoxy)-2-{[4-(morpholin-4-yl)phenyl]amino}quinazolin-6-yl]prop-2-yn-1-yl}-2-oxo-1-(pyridin-3-ylmethyl)-1,2-dihydropyridine-3-carboxamide;

II-10 N-{3-[8-(3-aminopropoxy)-2-{[4-(morpholin-4-yl)phenyl]amino}quinazolin-6-yl]prop-2-yn-1-yl}-1-[(6-chlorpyridin-3-yl)methyl]-2-oxo-1,2-dihydropyridine-3-carboxamide;

II-11 N-{3-[2-({4-[(dimethylamino)methyl]phenyl}amino)-5-fluoroquinazolin-6-yl]prop-2-yn-1-yl}-2-oxo-1-(pyridin-3-ylmethyl)-1,2-dihydropyridine-3-carboxamide;

II-12 1-[(6-chloropyridin-3-yl)methyl]-N-{3-[2-({4-[(dimethylamino)methyl]phenyl}amino)-5-fluoroquinazolin-6-yl]prop-2-yn-1-yl}-2-oxo-1,2-dihydropyridine-3-carboxamide;

III-1 2-oxo-N-{(2E)-3-[2-(phenylamino)quinazolin-6-yl]prop-2-en-1-yl}-1-(pyridin-3-ylmethyl)-1,2-dihydropyridine-3-carboxamide;

III-2 1-[(6-chloropyridin-3-yl)methyl]-2-oxo-N-{(2E)-3-[2-(phenylamino)quinazolin-6-yl]prop-2-en-1-yl}-1,2-dihydropyridine-3-carboxamide;

III-12 N-{(2E)-3-[2-({4-[(dimethylamino)methyl]phenyl}amino)quinazolin-6-yl]prop-2-en-1-yl}-2-oxo-1-(pyridin-3-ylmethyl)-1,2-dihydropyridine-3-carboxamide;

III-13 1-[(6-chloropyridin-3-yl)methyl]-N-{(2E)-3-[2-({4-[(dimethylamino)methyl]-phenyl}amino)quinazolin-6-yl]prop-2-en-1-yl}-2-oxo-1,2-dihydropyridine-3-carboxamide;

III-14 N-{(2E)-3-[2-({3-fluoro-4-[(1-methylpiperidin-4-yl)amino]phenyl}amino)quinazolin-6-yl]prop-2-en-1-yl}-2-oxo-1-{[6-(trifluoromethyl)pyridin-3-yl]methyl}-1,2-dihydropyridine-3-carboxamide;

III-15 N-{(2E)-3-[2-({4-[methyl(1-methylpiperidin-4-yl)amino]phenyl}amino)quinazolin-6-yl]prop-2-en-1-yl}-2-oxo-1-{[6-(trifluoromethyl)pyridin-3-yl]methyl}-1,2-dihydropyridine-3-carboxamide;

III-16 N-{(2E)-3-[2-({4-[(dimethylamino)methyl]phenyl}amino)quinazolin-6-yl]prop-2-en-1-yl}-2-oxo-1-{[6-(trifluoromethyl)pyridin-3-yl]methyl}-1,2-dihydropyridine-3-carboxamide;

III-17 N-{(2E)-3-[8-(3-aminopropoxy)-2-{[4-(morpholin-4-yl)phenyl]amino}quinazolin-6-yl]prop-2-en-1-yl}-2-oxo-1-(pyridin-3-ylmethyl)-1,2-dihydropyridine-3-carboxamide;

III-18 N-{(2E)-3-[8-(3-aminopropoxy)-2-{[4-(morpholin-4-yl)phenyl]amino}quinazolin-6-yl]prop-2-en-1-yl}-1-[(6-chlorpyridin-3-yl)methyl]-2-oxo-1,2-dihydropyridine-3-carboxamide;

III-19 N-{(2E)-3-[2-({4-[(dimethylamino)methyl]phenyl}amino)-5-fluoroquinazolin-6-yl]prop-2-en-1-yl}-2-oxo-1-(pyridin-3-ylmethyl)-1,2-dihydropyridine-3-carboxamide;

III-20 1-[(6-chloropyridin-3-yl)methyl]-N-{(2E)-3-[2-({4-[(dimethylamino)methyl]-phenyl}amino)-5-fluoroquinazolin-6-yl]prop-2-en-1-yl}-2-oxo-1,2-dihydropyridine-3-carboxamide;

III-27 2-oxo-1-(pyridin-3-ylmethyl)-N-{(2E)-3-[3-(1H-pyrrol-2-yl)-1H-indazol-6-yl]prop-2-en-1-yl}-1,2-dihydropyridine-3-carboxamide;

III-28 1-[(6-chloropyridin-3-yl)methyl]-2-oxo-N-{(2E)-3-[3-(1H-pyrrol-2-yl)-1H-indazol-6-yl]prop-2-en-1-yl}-1,2-dihydropyridine-3-carboxamide;

III-29 2-oxo-1-(pyridin-3-ylmethyl)-N-{3-[3-(1H-pyrrol-2-yl)-1H-indazol-6-yl]prop-2-yn-1-yl}-1,2-dihydropyridine-3-carboxamide;

III-30 1-[(6-chloropyridin-3-yl)methyl]-2-oxo-N-{3-[3-(1H-pyrrol-2-yl)-1H-indazol-6-yl]prop-2-yn-1-yl}-1,2-dihydropyridine-3-carboxamide;

III-31 N-[(2E)-3-(3-{4-[(dimethylamino)methyl]phenyl}-1H-indazol-6-yl)prop-2-en-1-yl]-2-oxo-1-(pyridin-3-ylmethyl)-1,2-dihydropyridine-3-carboxamide;

III-32 1-[(6-chloropyridin-3-yl)methyl]-N-[(2E)-3-(3-{4-[(dimethylamino)methyl]phenyl}-1H-indazol-6-yl)prop-2-en-1-yl]-2-oxo-1,2-dihydropyridine-3-carboxamide;

III-33 N-[3-(3-{4-[(dimethylamino)methyl]phenyl}-1H-indazol-6-yl)prop-2-yn-1-yl]-2-oxo-1-(pyridin-3-ylmethyl)-1,2-dihydropyridine-3-carboxamide;

III-34 1-[(6-chloropyridin-3-yl)methyl]-N-[3-(3-{4-[(dimethylamino)methyl]phenyl}-1H-indazol-6-yl)prop-2-yn-1-yl]-2-oxo-1,2-dihydropyridine-3-carboxamide;

III-35 N-{1-[2-({4-[(dimethylamino)methyl]phenyl}amino)quinazolin-6-yl]pyrrolidin-3-yl}-2-oxo-1-(pyridin-3-ylmethyl)-1,2-dihydropyridine-3-carboxamide;

III-36 1-[(6-chloropyridin-3-yl)methyl]-N-{1-[2-({4-[(dimethylamino)methyl]phenyl}-amino)quinazolin-6-yl]pyrrolidin-3-yl}-2-oxo-1,2-dihydropyridine-3-carboxamide;

or a salt of any of the foregoing.

* * * * *

UNITED STATES PATENT AND TRADEMARK OFFICE
CERTIFICATE OF CORRECTION

PATENT NO. : 8,637,549 B2  
APPLICATION NO. : 13/054245  
DATED : January 28, 2014  
INVENTOR(S) : Engelhardt et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 82 days.

Signed and Sealed this  
Twenty-first Day of April, 2015

Michelle K. Lee  
*Director of the United States Patent and Trademark Office*